US012466822B2

(12) United States Patent
Wu et al.

(10) Patent No.: US 12,466,822 B2
(45) Date of Patent: Nov. 11, 2025

(54) HETEROCYCLIC COMPOUNDS AS IMMUNOMODULATORS

(71) Applicant: Incyte Corporation, Wilmington, DE (US)

(72) Inventors: Liangxing Wu, Wilmington, DE (US); Neil Lajkiewicz, Bedford, MA (US); Chunhong He, Boothwyn, PA (US); Kaijiong Xiao, Clark, NJ (US); Wenyu Zhu, Media, PA (US); Zhenwu Li, Wilmington, DE (US); Chao Qi, Newark, DE (US); Leah C. Konkol, Newark, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 908 days.

(21) Appl. No.: 17/483,959

(22) Filed: Sep. 24, 2021

(65) Prior Publication Data

US 2022/0213090 A1 Jul. 7, 2022

Related U.S. Application Data

(63) Continuation of application No. 17/170,662, filed on Feb. 8, 2021, now abandoned, which is a continuation of application No. 16/913,616, filed on Jun. 26, 2020, now abandoned, which is a continuation of application No. 16/678,117, filed on Nov. 8, 2019, now abandoned, which is a continuation of application No. 16/365,234, filed on Mar. 26, 2019, now abandoned, which is a continuation of application No. 16/058,149, filed on Aug. 8, 2018, now abandoned, which is a continuation of application No. 15/850,985, filed on Dec. 21, 2017, now abandoned.

(60) Provisional application No. 62/551,011, filed on Aug. 28, 2017, provisional application No. 62/487,362, filed on Apr. 19, 2017, provisional application No. 62/438,038, filed on Dec. 22, 2016.

(51) Int. Cl.

| | |
|---|---|
| ***C07D 471/04*** | (2006.01) |
| ***A61K 31/4375*** | (2006.01) |
| ***A61P 37/00*** | (2006.01) |
| ***A61P 37/02*** | (2006.01) |
| ***C07D 401/04*** | (2006.01) |
| ***C07D 519/00*** | (2006.01) |

(52) U.S. Cl.

CPC ............ *C07D 471/04* (2013.01); *A61P 37/00* (2018.01); *A61P 37/02* (2018.01); *C07D 401/04* (2013.01); *C07D 519/00* (2013.01)

(58) Field of Classification Search

CPC ......................... C07D 471/04; A61K 31/4375; A61K 31/519; A61P 35/00; A61P 37/04

USPC ................ 546/122; 514/300, 258.1; 544/279

See application file for complete search history.

(56) References Cited

U.S. PATENT DOCUMENTS

| | | | |
|---|---|---|---|
| 3,272,781 | A | 9/1966 | Goodrow |
| 4,208,328 | A | 6/1980 | Lavallee et al. |
| 4,789,711 | A | 12/1988 | Monnier et al. |
| 5,077,164 | A | 12/1991 | Ueda et al. |
| 6,114,497 | A | 9/2000 | Tada et al. |
| 6,297,351 | B1 | 10/2001 | Murayama et al. |
| 6,372,907 | B1 | 4/2002 | Lee et al. |
| 6,521,618 | B2 | 2/2003 | Boschelli et al. |
| 6,867,200 | B1 | 3/2005 | Allen et al. |
| 7,320,989 | B2 | 1/2008 | Anderson et al. |
| 7,417,065 | B2 | 8/2008 | Mi et al. |
| 7,488,802 | B2 | 2/2009 | Collins et al. |
| 7,491,245 | B2 | 2/2009 | Glenn et al. |
| 7,691,870 | B2 | 4/2010 | Buchstaller et al. |
| 7,851,489 | B2 | 12/2010 | Borzilleri et al. |
| 7,906,522 | B2 | 3/2011 | Kishikawa et al. |
| 7,943,743 | B2 | 5/2011 | Korman et al. |

(Continued)

FOREIGN PATENT DOCUMENTS

| | | |
|---|---|---|
| CA | 2355249 | 6/2000 |
| CA | 3099994 | 11/2019 |

(Continued)

OTHER PUBLICATIONS

Abdellaoui et al., "Palladium-catalyzed non-directed C—H bond arylation of difluorobenzenes and dichlorobenzenes bearing benzoxazole or benzothiazole," Catalysis Communications, 2015, 71:13-16.

(Continued)

*Primary Examiner* — Charanjit Aulakh

(74) *Attorney, Agent, or Firm* — Fish & Richardson P.C.

(57) ABSTRACT

Disclosed are compounds of Formula (I), methods of using the compounds as immunomodulators, and pharmaceutical compositions comprising such compounds. The compounds are useful in treating, preventing or ameliorating diseases or disorders such as cancer or infections.

(I)

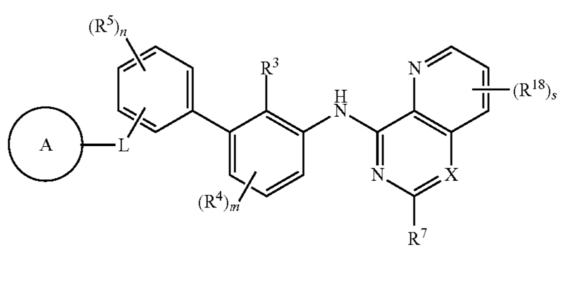

28 Claims, No Drawings

(56) References Cited

U.S. PATENT DOCUMENTS

| | | | |
|---|---|---|---|
| 8,008,449 | B2 | 8/2011 | Korman et al. |
| 8,163,743 | B2 | 4/2012 | Baldwin et al. |
| 8,168,757 | B2 | 5/2012 | Finnefrock et al. |
| 8,217,149 | B2 | 7/2012 | Irving et al. |
| 8,541,424 | B2 | 9/2013 | DeGoey et al. |
| 8,993,604 | B2 | 3/2015 | Byrd et al. |
| 9,085,576 | B2 | 7/2015 | Minatti et al. |
| 9,163,017 | B2 | 10/2015 | DeGoey et al. |
| 9,394,365 | B1 | 7/2016 | Eisenbach-Schwartz et al. |
| 9,540,322 | B2 | 1/2017 | Jorgensen et al. |
| 9,603,950 | B1 | 3/2017 | Li et al. |
| 9,611,261 | B2 | 4/2017 | Minatti et al. |
| 9,643,922 | B2 | 5/2017 | Jorgensen et al. |
| 10,017,520 | B2 | 7/2018 | Koehler et al. |
| 10,202,343 | B2 | 2/2019 | Jorgensen et al. |
| 10,308,644 | B2 | 6/2019 | Wu et al. |
| 10,618,916 | B2 | 4/2020 | Wu et al. |
| 10,669,271 | B2 | 6/2020 | Wu et al. |
| 10,793,565 | B2 | 10/2020 | Wu et al. |
| 10,800,768 | B2 | 10/2020 | Wu et al. |
| 10,806,785 | B2 | 10/2020 | Liu et al. |
| 10,906,920 | B2 | 2/2021 | Wu et al. |
| 11,124,511 | B2 | 9/2021 | Wu et al. |
| 11,339,149 | B2 | 5/2022 | Wu et al. |
| 11,401,279 | B2 | 8/2022 | Li et al. |
| 11,407,749 | B2 | 8/2022 | Wu et al. |
| 11,414,433 | B2 | 8/2022 | Wu et al. |
| 11,465,981 | B2 | 10/2022 | Wu et al. |
| 11,535,615 | B2 | 12/2022 | Lajkiewicz et al. |
| 11,566,026 | B2 | 1/2023 | Wu et al. |
| 11,572,366 | B2 | 2/2023 | Li et al. |
| 11,596,692 | B1 | 3/2023 | Wu et al. |
| 11,608,337 | B2 | 3/2023 | Li et al. |
| 11,613,536 | B2 | 3/2023 | Wu et al. |
| 11,673,883 | B2 | 6/2023 | Lu et al. |
| 11,718,605 | B2 | 8/2023 | Yu et al. |
| 11,753,406 | B2 | 9/2023 | Jia et al. |
| 11,760,756 | B2 | 9/2023 | Jia et al. |
| 11,780,836 | B2 | 10/2023 | Zhou et al. |
| 11,787,793 | B2 | 10/2023 | Wu et al. |
| 11,866,434 | B2 | 1/2024 | Wang et al. |
| 11,866,435 | B2 | 1/2024 | Lajkiewicz et al. |
| 11,866,451 | B2 | 1/2024 | Jia et al. |
| 11,879,309 | B2 | 1/2024 | Xiao et al. |
| 12,084,443 | B2 | 9/2024 | Zhou et al. |
| 12,187,746 | B2 | 1/2025 | Wu et al. |
| 12,247,026 | B2 | 3/2025 | Wu et al. |
| 12,247,038 | B2 | 3/2025 | Li et al. |
| 2002/0082266 | A1 | 6/2002 | Gallant et al. |
| 2003/0134843 | A1 | 7/2003 | Lubisch et al. |
| 2003/0191115 | A1 | 10/2003 | Pinto et al. |
| 2004/0018986 | A1 | 1/2004 | Pitlik et al. |
| 2004/0058938 | A1 | 3/2004 | Cullmann et al. |
| 2004/0063963 | A1 | 4/2004 | Ueno et al. |
| 2004/0082635 | A1 | 4/2004 | Hashimoto et al. |
| 2004/0186114 | A1 | 9/2004 | Cirillo et al. |
| 2004/0214040 | A1 | 10/2004 | Lee et al. |
| 2005/0187230 | A1 | 8/2005 | Ding et al. |
| 2005/0245536 | A1 | 11/2005 | Hao et al. |
| 2005/0260126 | A1 | 11/2005 | Kudo et al. |
| 2005/0288295 | A1 | 12/2005 | Currie et al. |
| 2006/0004010 | A1 | 1/2006 | Habashita et al. |
| 2006/0084650 | A1 | 4/2006 | Dong et al. |
| 2006/0089362 | A1 | 4/2006 | Seno et al. |
| 2006/0178367 | A1 | 8/2006 | Currie et al. |
| 2006/0183746 | A1 | 8/2006 | Currie et al. |
| 2006/0229337 | A1 | 10/2006 | Brittelli et al. |
| 2006/0270686 | A1 | 11/2006 | Kelly et al. |
| 2007/0099938 | A1 | 5/2007 | Ohmoto et al. |
| 2007/0191395 | A1 | 8/2007 | Kawakami et al. |
| 2007/0286864 | A1 | 12/2007 | Buck et al. |
| 2008/0045536 | A1 | 2/2008 | Vaccaro et al. |
| 2008/0139557 | A1 | 6/2008 | Blomgren et al. |
| 2008/0153834 | A1 | 6/2008 | Blomgren et al. |
| 2008/0280891 | A1 | 11/2008 | Kelly et al. |
| 2008/0286864 | A1 | 11/2008 | Elliott et al. |
| 2009/0163545 | A1 | 6/2009 | Goldfarb |
| 2009/0253735 | A1 | 10/2009 | Almario-Garcia et al. |
| 2009/0281075 | A1 | 11/2009 | Roughton et al. |
| 2009/0281120 | A1 | 11/2009 | Nakai et al. |
| 2009/0304821 | A1 | 12/2009 | Notoya et al. |
| 2010/0155712 | A1 | 6/2010 | Kitamura |
| 2010/0160292 | A1 | 6/2010 | Whitney et al. |
| 2010/0160303 | A1 | 6/2010 | Liu et al. |
| 2010/0249151 | A1 | 9/2010 | Klein et al. |
| 2010/0267775 | A1 | 10/2010 | Negoro et al. |
| 2010/0267778 | A1 | 10/2010 | Kusuda et al. |
| 2010/0273832 | A1 | 10/2010 | Jung et al. |
| 2010/0292227 | A1 | 11/2010 | Yoakim et al. |
| 2011/0053915 | A1 | 3/2011 | Ivaschenko et al. |
| 2011/0062858 | A1 | 3/2011 | Yersin et al. |
| 2011/0065699 | A1 | 3/2011 | De Peretti et al. |
| 2011/0065700 | A1 | 3/2011 | De Peretti et al. |
| 2011/0065745 | A1 | 3/2011 | De Peretti et al. |
| 2011/0124640 | A1 | 5/2011 | Liu et al. |
| 2011/0294781 | A1 | 12/2011 | Yamamoto et al. |
| 2011/0301145 | A1 | 12/2011 | Barbosa Jr. et al. |
| 2012/0058996 | A1 | 3/2012 | Liu et al. |
| 2012/0295884 | A1 | 11/2012 | Altmann et al. |
| 2012/0323002 | A1 | 12/2012 | Yamamoto et al. |
| 2012/0328569 | A1 | 12/2012 | McComas et al. |
| 2013/0018034 | A1 | 1/2013 | Yao et al. |
| 2013/0096118 | A1 | 4/2013 | Liu et al. |
| 2013/0131063 | A1 | 5/2013 | Castro et al. |
| 2013/0203741 | A1 | 8/2013 | Suzuki et al. |
| 2013/0203747 | A1 | 8/2013 | Yoakim et al. |
| 2013/0203754 | A1 | 8/2013 | Yang et al. |
| 2013/0253011 | A1 | 9/2013 | Jung et al. |
| 2014/0058097 | A1 | 2/2014 | Kobayashi et al. |
| 2014/0088117 | A1 | 3/2014 | Burch et al. |
| 2014/0107027 | A1 | 4/2014 | Kong et al. |
| 2014/0128382 | A1 | 5/2014 | Wu et al. |
| 2014/0243306 | A1 | 8/2014 | Heng et al. |
| 2014/0275058 | A1 | 9/2014 | Minatti et al. |
| 2014/0288094 | A1 | 9/2014 | Bennett et al. |
| 2014/0378447 | A1 | 12/2014 | Okano et al. |
| 2015/0005279 | A1 | 1/2015 | Bonafoux et al. |
| 2015/0011751 | A1 | 1/2015 | Kawakami et al. |
| 2015/0073024 | A1 | 3/2015 | Sasikumar et al. |
| 2015/0181880 | A1 | 7/2015 | Takahashi |
| 2015/0210680 | A1 | 7/2015 | Kobayashi et al. |
| 2015/0232478 | A1 | 8/2015 | Ishida et al. |
| 2015/0239868 | A1 | 8/2015 | Pais et al. |
| 2015/0252011 | A1 | 9/2015 | Minatti et al. |
| 2015/0258505 | A1 | 9/2015 | Hironaka et al. |
| 2015/0291549 | A1 | 10/2015 | Chupak et al. |
| 2015/0299227 | A1 | 10/2015 | Wolkenberg et al. |
| 2015/0307465 | A1 | 10/2015 | Scott et al. |
| 2015/0376172 | A1 | 12/2015 | Guba et al. |
| 2016/0015690 | A1 | 1/2016 | Babaoglu et al. |
| 2016/0046648 | A1 | 2/2016 | Petrukhin et al. |
| 2016/0130251 | A1 | 5/2016 | Graupe et al. |
| 2016/0194295 | A1 | 7/2016 | Sasikumar et al. |
| 2016/0229816 | A1 | 8/2016 | Sato et al. |
| 2016/0280695 | A1 | 9/2016 | Minatti et al. |
| 2017/0107216 | A1 | 4/2017 | Wu et al. |
| 2017/0145025 | A1 | 5/2017 | Li et al. |
| 2017/0174671 | A1 | 6/2017 | Wu et al. |
| 2017/0174679 | A1 | 6/2017 | Lajkiewicz et al. |
| 2017/0304282 | A1 | 10/2017 | Rocco et al. |
| 2017/0320875 | A1 | 11/2017 | Li et al. |
| 2017/0342060 | A1 | 11/2017 | Lu et al. |
| 2017/0362253 | A1 | 12/2017 | Xiao et al. |
| 2018/0016260 | A1 | 1/2018 | Yu et al. |
| 2018/0057486 | A1 | 3/2018 | Wu et al. |
| 2018/0177784 | A1 | 6/2018 | Wu et al. |
| 2018/0177870 | A1 | 6/2018 | Liu et al. |
| 2018/0179179 | A1 | 6/2018 | Wu et al. |
| 2018/0179197 | A1 | 6/2018 | Wu et al. |
| 2018/0179201 | A1 | 6/2018 | Wu et al. |
| 2018/0179202 | A1 | 6/2018 | Wu et al. |
| 2018/0271940 | A1 | 9/2018 | Triebel et al. |
| 2018/0273519 | A1 | 9/2018 | Wu et al. |
| 2019/0040082 | A1 | 2/2019 | Xiao et al. |

(56) References Cited

U.S. PATENT DOCUMENTS

| | | | |
|---|---|---|---|
| 2019/0062345 | A1 | 2/2019 | Xiao et al. |
| 2019/0071439 | A1 | 3/2019 | Li et al. |
| 2019/0144439 | A1 | 5/2019 | Wu et al. |
| 2019/0202824 | A1 | 7/2019 | Wu et al. |
| 2019/0225601 | A1 | 7/2019 | Wu et al. |
| 2019/0270706 | A1 | 9/2019 | Jorgensen et al. |
| 2019/0300524 | A1 | 10/2019 | Wu et al. |
| 2019/0345170 | A1 | 11/2019 | Wu et al. |
| 2020/0172533 | A1 | 6/2020 | Wu et al. |
| 2020/0172541 | A1 | 6/2020 | Li et al. |
| 2020/0181126 | A1 | 6/2020 | Lu et al. |
| 2020/0255424 | A1 | 8/2020 | Wu et al. |
| 2020/0277309 | A1 | 9/2020 | Wu et al. |
| 2020/0277378 | A1 | 9/2020 | Sabatos-Peyton et al. |
| 2020/0283423 | A1 | 9/2020 | Yu et al. |
| 2020/0325115 | A1 | 10/2020 | Wu et al. |
| 2020/0397893 | A1 | 12/2020 | Liu et al. |
| 2020/0407357 | A1 | 12/2020 | Lajkiewicz et al. |
| 2021/0002276 | A1 | 1/2021 | Wu et al. |
| 2021/0017164 | A1 | 1/2021 | Lu et al. |
| 2021/0017175 | A1 | 1/2021 | Li et al. |
| 2021/0040090 | A1 | 2/2021 | Jia et al. |
| 2021/0094976 | A1 | 4/2021 | Li et al. |
| 2021/0107900 | A1 | 4/2021 | Wu et al. |
| 2021/0115025 | A1 | 4/2021 | Yu et al. |
| 2021/0115068 | A1 | 4/2021 | Wu et al. |
| 2021/0139511 | A1 | 5/2021 | Jia et al. |
| 2021/0221819 | A1 | 7/2021 | Li et al. |
| 2021/0317139 | A1 | 10/2021 | Xiao et al. |
| 2021/0347771 | A1 | 11/2021 | Wu et al. |
| 2021/0363137 | A1 | 11/2021 | Wu et al. |
| 2021/0380584 | A1 | 12/2021 | Wu et al. |
| 2022/0089588 | A1 | 3/2022 | Wu et al. |
| 2022/0144830 | A1 | 5/2022 | Zhou et al. |
| 2022/0144831 | A1 | 5/2022 | Wang et al. |
| 2022/0144832 | A1 | 5/2022 | Jia et al. |
| 2022/0193050 | A1 | 6/2022 | Yang et al. |
| 2022/0194931 | A1 | 6/2022 | Wu et al. |
| 2022/0340600 | A1 | 10/2022 | Li et al. |
| 2022/0348594 | A1 | 11/2022 | Wu et al. |
| 2022/0412976 | A1 | 12/2022 | Lovat |
| 2023/0100875 | A1 | 3/2023 | Lajkiewicz et al. |
| 2023/0146129 | A1 | 5/2023 | Wu et al. |
| 2023/0149409 | A1 | 5/2023 | Geschwindt et al. |
| 2023/0181605 | A1 | 6/2023 | Mohanlal et al. |
| 2023/0192689 | A1 | 6/2023 | Lajkiewicz et al. |
| 2023/0226062 | A1 | 7/2023 | Wu et al. |
| 2023/0406852 | A1 | 12/2023 | Zhou et al. |
| 2024/0132523 | A1 | 4/2024 | Jia et al. |
| 2024/0158395 | A1 | 5/2024 | Wang et al. |
| 2024/0376106 | A1 | 11/2024 | Zhou et al. |
| 2025/0084104 | A1 | 3/2025 | Wu et al. |
| 2025/0171443 | A1 | 5/2025 | Wu et al. |

FOREIGN PATENT DOCUMENTS

| | | |
|---|---|---|
| CL | 2018001531 | 7/2018 |
| CL | 2018003734 | 2/2019 |
| CL | 2018003701 | 4/2019 |
| CL | 2018003697 | 5/2019 |
| CL | 2019001744 | 10/2019 |
| CL | 2020002511 | 9/2020 |
| CN | 1344256 | 4/2002 |
| CN | 101891895 | 11/2010 |
| CN | 101910158 | 12/2010 |
| CN | 101993415 | 3/2011 |
| CN | 103228657 A | 7/2013 |
| CN | 103403161 A | 11/2013 |
| CN | 103562204 A | 2/2014 |
| CN | 103933036 | 7/2014 |
| CN | 104045552 | 9/2014 |
| CN | 104211726 | 12/2014 |
| CN | 105073747 | 11/2015 |
| CN | 105164121 | 12/2015 |
| CN | 105705489 | 6/2016 |
| EP | 0361069 | 4/1990 |
| EP | 0644460 | 3/1995 |
| EP | 1505068 | 2/2005 |
| EP | 1644370 | 4/2006 |
| EP | 1942105 | 7/2008 |
| EP | 2233474 | 9/2010 |
| EP | 2402345 | 1/2012 |
| EP | 2871179 | 5/2015 |
| EP | 2824099 | 1/2018 |
| FR | 1425700 | 1/1966 |
| JP | H 10316853 | 12/1998 |
| JP | 2000128986 | 5/2000 |
| JP | 2000128987 | 5/2000 |
| JP | 2000212281 | 8/2000 |
| JP | 2001114893 | 4/2001 |
| JP | 2001163975 | 6/2001 |
| JP | 3461397 | 10/2003 |
| JP | 2003287634 | 10/2003 |
| JP | 2004059761 | 2/2004 |
| JP | 2004091369 | 3/2004 |
| JP | 2004294556 | 10/2004 |
| JP | 2005002330 | 1/2005 |
| JP | 2005248082 | 9/2005 |
| JP | 2005290301 | 10/2005 |
| JP | 2006290883 | 10/2006 |
| JP | 2008218327 | 9/2008 |
| JP | 2010202530 | 9/2010 |
| JP | 2010540452 | 12/2010 |
| JP | 2013084945 | 5/2013 |
| JP | 2014520866 | 8/2014 |
| JP | 2014532066 | 12/2014 |
| JP | 2015510890 | 4/2015 |
| JP | 2015155397 | 8/2015 |
| JP | 2015193612 | 11/2015 |
| JP | 2016135778 | 7/2016 |
| JP | 2016532710 | 10/2016 |
| JP | 2019523231 | 8/2019 |
| JP | 2019530732 | 10/2019 |
| JP | 2020504737 | 2/2020 |
| JP | 2020504739 | 2/2020 |
| JP | 2020514271 | 5/2020 |
| JP | 2020514272 | 5/2020 |
| JP | 6911031 | 7/2021 |
| KR | 1715090 | 3/2015 |
| KR | 1717601 | 12/2015 |
| KR | 1653560 | 2/2016 |
| MX | 2019007651 | 2/2020 |
| TW | 103143948 | 12/2014 |
| TW | 201625527 | 7/2016 |
| WO | WO 98/27108 | 6/1998 |
| WO | WO 1999/018096 | 4/1999 |
| WO | WO 99/44992 | 9/1999 |
| WO | WO 00/35886 | 6/2000 |
| WO | WO 01/07409 | 2/2001 |
| WO | WO 2001/047883 | 7/2001 |
| WO | WO 01/74815 | 10/2001 |
| WO | WO 2002/000196 | 1/2002 |
| WO | WO 02/14321 | 2/2002 |
| WO | WO 02/48147 | 6/2002 |
| WO | WO 02/066477 | 8/2002 |
| WO | WO 02/071827 | 9/2002 |
| WO | WO 02/078700 | 10/2002 |
| WO | WO 02/083672 | 10/2002 |
| WO | WO 02/088124 | 11/2002 |
| WO | WO 03/022845 | 3/2003 |
| WO | WO 03/030901 | 4/2003 |
| WO | WO 03/031587 | 4/2003 |
| WO | WO 2003/042402 | 5/2003 |
| WO | WO 2004/006906 | 1/2004 |
| WO | WO 2004/033454 | 4/2004 |
| WO | WO 2004/035588 | 4/2004 |
| WO | WO 2004/085385 | 10/2004 |
| WO | WO 2004/089940 | 10/2004 |
| WO | WO 2005/000833 | 1/2005 |
| WO | WO 2005/005429 | 1/2005 |
| WO | WO 2005/014543 | 2/2005 |
| WO | WO 2005/014599 | 2/2005 |
| WO | WO 2005/023761 | 3/2005 |
| WO | WO 2005/034869 | 4/2005 |

(56) References Cited

FOREIGN PATENT DOCUMENTS

| | | |
|---|---|---|
| WO | WO 2005/047290 | 5/2005 |
| WO | WO 2005/063710 | 7/2005 |
| WO | WO 2005/077948 | 8/2005 |
| WO | WO 2005/079802 | 9/2005 |
| WO | WO 2005/080316 | 9/2005 |
| WO | WO 2005/086808 | 9/2005 |
| WO | WO 2005/086904 | 9/2005 |
| WO | WO 2005/097751 | 10/2005 |
| WO | WO 2005/103022 | 11/2005 |
| WO | WO 2005/105798 | 11/2005 |
| WO | WO 2006/034317 | 3/2006 |
| WO | WO 2006/034337 | 3/2006 |
| WO | WO 2006/050803 | 5/2006 |
| WO | WO 2006/053121 | 5/2006 |
| WO | WO 2006/094235 | 9/2006 |
| WO | WO 2006/099075 | 9/2006 |
| WO | WO 2006/125101 | 11/2006 |
| WO | WO 2007/004954 | 1/2007 |
| WO | WO 2007/034282 | 3/2007 |
| WO | WO 2007/038314 | 4/2007 |
| WO | WO 2007/061764 | 5/2007 |
| WO | WO 2007/067711 | 6/2007 |
| WO | WO 2007/069565 | 6/2007 |
| WO | WO 2007/096764 | 8/2007 |
| WO | WO 2007/113226 | 10/2007 |
| WO | WO 2007/146712 | 12/2007 |
| WO | WO 2008/011560 | 1/2008 |
| WO | WO 2008/021745 | 2/2008 |
| WO | WO 2008/027812 | 3/2008 |
| WO | WO 2008/032171 | 3/2008 |
| WO | WO 2008/033854 | 3/2008 |
| WO | WO 2008/033857 | 3/2008 |
| WO | WO 2008/033858 | 3/2008 |
| WO | WO 2008/057254 | 5/2008 |
| WO | WO 2008/062182 | 5/2008 |
| WO | WO 2008/064317 | 5/2008 |
| WO | WO 2008/064318 | 5/2008 |
| WO | WO 2008/071944 | 6/2008 |
| WO | WO 2008/079965 | 7/2008 |
| WO | WO 2008/104077 | 9/2008 |
| WO | WO 2008/104278 | 9/2008 |
| WO | WO 2008/104279 | 9/2008 |
| WO | WO 2008/111299 | 9/2008 |
| WO | WO 2008/114002 | 9/2008 |
| WO | WO 2008/118122 | 10/2008 |
| WO | WO 2008/133274 | 11/2008 |
| WO | WO 2008/134553 | 11/2008 |
| WO | WO 2008/141249 | 11/2008 |
| WO | WO 2008/156712 | 12/2008 |
| WO | WO 2009/027733 | 3/2009 |
| WO | WO 2009/038759 | 3/2009 |
| WO | WO 2009/039397 | 3/2009 |
| WO | WO 2009/059162 | 5/2009 |
| WO | WO 2009/062059 | 5/2009 |
| WO | WO 2009/075830 | 6/2009 |
| WO | WO 2009/077197 | 6/2009 |
| WO | WO 2009/079683 | 7/2009 |
| WO | WO 2009/106539 | 9/2009 |
| WO | WO 2009/106597 | 9/2009 |
| WO | WO 2009/123986 | 10/2009 |
| WO | WO 2009/139576 | 11/2009 |
| WO | WO 2009/143156 | 11/2009 |
| WO | WO 2009/146358 | 12/2009 |
| WO | WO 2010/011837 | 1/2010 |
| WO | WO 2010/029950 | 3/2010 |
| WO | WO 2010/036959 | 4/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/080474 | 7/2010 |
| WO | WO 2010/089411 | 8/2010 |
| WO | WO 2010/104306 | 9/2010 |
| WO | WO 2010/115736 | 10/2010 |
| WO | WO 2010/119264 | 10/2010 |
| WO | WO 2010/130034 | 11/2010 |
| WO | WO 2011/002635 | 1/2011 |
| WO | WO 2011/008709 | 1/2011 |
| WO | WO 2011/018170 | 2/2011 |
| WO | WO 2011/044181 | 4/2011 |
| WO | WO 2011/047129 | 4/2011 |
| WO | WO 2011/047319 | 4/2011 |
| WO | WO 2011/050245 | 4/2011 |
| WO | WO 2009/096202 | 5/2011 |
| WO | WO 2011/066342 | 6/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2011/159877 | 12/2011 |
| WO | WO 2011/161699 | 12/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |
| WO | WO 2012/166951 | 12/2012 |
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/121085 | 8/2014 |
| WO | WO 2014/133046 | 9/2014 |
| WO | WO 2014/138484 | 9/2014 |
| WO | WO 2014/138791 | 9/2014 |
| WO | WO 2014/151634 | 9/2014 |
| WO | WO 2014/152536 | 9/2014 |
| WO | WO 2014/159959 | 10/2014 |
| WO | WO 2014/181287 | 11/2014 |
| WO | WO 2014/186035 | 11/2014 |
| WO | WO 2014/210255 | 12/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086498 | 6/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/175678 | 11/2015 |
| WO | WO 2015/197028 | 12/2015 |

(56) References Cited

FOREIGN PATENT DOCUMENTS

| | | |
|---|---|---|
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2017/223239 | 12/2017 |
| WO | WO 2018/013789 | 1/2018 |
| WO | WO 2018/026971 | 2/2018 |
| WO | WO 2018/044783 | 3/2018 |
| WO | WO 2018/045084 | 3/2018 |
| WO | WO 2016/057500 | 4/2018 |
| WO | WO 2018/116259 | 6/2018 |
| WO | WO 2018/119036 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/160882 | 8/2019 |
| WO | WO 2019/191707 | 10/2019 |
| WO | WO 2019/192506 | 10/2019 |
| WO | WO 2019/204609 | 10/2019 |
| WO | WO 2020/086556 | 4/2020 |
| WO | WO 2020/088357 | 5/2020 |
| WO | WO 2020/156323 | 8/2020 |
| WO | WO 2021/030162 | 2/2021 |
| WO | WO 2021/053207 | 3/2021 |

OTHER PUBLICATIONS

Ahmed et al., "Enantioselective Polymerization of Epoxides Using Biaryl-Linked Bimetallic Cobalt Catalysts: A Mechanistic Study," J Am Chem Soc., 2013, 135(50):18901-18911.

Alverez et al., "Structure—Activity Study of Bioisosteric Trifluoromethyl and Pentafluorosulfanyl Indole Inhibitors of the AAA ATPase p97," ACS Med Chem., 2015, 6(12):1225-1230.

Amaya et al., "Synthesis of three-dimensionally arranged bis-biphenol ligand on hexaaryl benzene scaffold and its application for cross-pinacol coupling reaction," Tetrahedron Letters, 2011, 52(35):4567-4569.

Anyika et al., "Point-to-Axial Chirality Transfer—A New Probe for "Sensing" the Absolute Configurations of Monoamines," J Am Chem Soc., 2014, 136(2):550-553.

Arkin et al., "Small-Molecule Inhibitors of Protein-Protein Interactions: Progressing toward the Reality," Chemistry & Biology, Sep. 2014, 21:1102-1114.

Arkin et al., "Small-Molecule Inhibitors of Protein-Protein Interactions: Progressing Towards the Dream," Nature Reviews, Apr. 2004, 3:301-317.

Artz et al., "Host-guest complexation. 28. Hemispherands with four self-organizing units," J Am Chem Soc., 1984, 106(7):2160-2171.

Atzrodt et al., "The Renaissance of H/D Exchange," Angew Chem Int Ed., 2007, 7744-7765.

Australian Office Action in Australian Application No. 2016358100, dated May 8, 2020, 5 pages.

Azuma et al., "B7-H1 is a ubiquitous antiapoptotic receptor on cancer cells," Blood, Apr. 1, 2018, 111(7):3635-3643.

Barakat, "Do We Need Small Molecule Inhibitors for the Immune Checkpoints?" J. Pharma. Care Health Sys., 2014, 1(4):1000e119.

Barber et al., "Restoring function in exhausted CD8 T cells during chronic viral infection," Nature, Feb. 2006, 439:682-687.

Bentley et al., "Antenna Biphenols: Development of Extended Wavelength Chiroptical Reporters," J Org Chem., 2016, 81(3):1185-1191.

Berg, "Modulation of Protein-Protein Interactions with Small Organic Molecules," Angew. Chem. Int. Ed., 2003, 42:2462-2481.

Berge et al., "Pharmaceutical Salts," J. Pharm. Sci., Jan. 1977, 66(1):1-19.

Blank et al., "PD-L1/B7H-1 Inhibits the Effector Phase of Tumor Rejection by T Cell Receptor (TCR) Transgenic CD8+ T Cells," Cancer Res., Feb. 2004, 64(3):1140-5.

Blom et al., "Optimizing Preparative LC-MS Configurations and Methods for Parallel Synthesis Purification", J. Combi. Chem., 2003, 5:670-83.

Blom et al., "Preparative LC-MS Purification: Improved Compound Specific Method Optimization", J. Combi. Chem., Nov. 2004, 6:874-883.

Blom, "Two-Pump At Column Dilution Configuration for Preparative LC-MS", K. Blom, J. Combi. Chem., 2002, 4:295-301.

Brazilian Office Action in Brazilian Application No. BR112018012756-6, dated Jan. 5, 2021, 6 pages.

Bross et al., "Radiation damage to 2-(2'-hydroxyphenyl)benzothiazoles," Radiation Physics and Chemistry, Jul. 1992, 41:379-387.

Buisman et al., "Chiral Cooperativity in Diastereomeric Diphosphite Ligands: Effects on the Rhodium-Catalyzed Enantioselective Hydroformylation of Styrene," Organometallics, 1997, 16(13):2929-2939.

Camara et al., "Multiple dermatofibromas: Dermoscopic patterns," Indian journal of dermatology, 2013, 58(3):243.

Carter et al., "PD-1:PD-L inhibitory pathway affects both CD4+ and CD8+ T cells and is overcome by IL-2," Eur. J. Immunol., 2002, 32(3):634-643.

Chang et al., "Blocking of the PD-1/PD-L1 Interaction by a d-Peptide Antagonist for Cancer Immunotherapy" Angew. Chem. Int. Ed., 2015, 26 pages; Supporting Information for 127(40):11926-11930.

Chang et al., "Blocking of the PD-1/PD-L1 Interaction by a d-Peptide Antagonist for Cancer Immunotherapy," Angew. Chem. Int. Ed., 2015, 127(40):11926-11930.

Chen et al., "Anti-PD-1/PD-L1 therapy of human cancer: past, present, and future," J. Clin. Invest., Sep. 2015, 125(9):3384-3391.

Cheng et al., "Cancer-associated fibroblasts induce PDL1+ neutrophils through the IL6-STAT3 pathway that foster immune suppression in hepatocellular carcinoma," Cell Death and Disease, 2018, 9:422.

Cheng et al., "Recent Advances in Small Molecule Based Cancer Immunotherapy," Eur J Med Chem., 2018, 157:582-598.

Cheng et al., "Structure and Interactions of the Human Programmed Cell Death 1 Receptor," J. Bio. Chem., Apr. 2013, 288(17):11771-11785.

Cheng et al., "Synthetic connections to the aromatic directed metalation reaction. Iterative ortho metalation-cross coupling tactics for the construction of polyphenyls," Tetrahedron Letters, 1978, 28(43):5097-5098.

Chilean Office Action in Chilean Application No. 201801685, dated Aug. 20, 2019, 18 pages.

Chilean Office Action in Chilean Application No. 201803701, dated Nov. 22, 2019, 18 pages.

Chilean Office Action in Chilean Application No. 201901744, dated Apr. 14, 2020, 19 pages.

Chilean Office Action in Chilean Application No. 2922-2020, dated Dec. 8, 2021, 21 pages.

Chinese Office Action in Chinese Application No. 201680077700.8, dated Jul. 2, 2021, 23 pages.

Chinese Search Report in Chinese Application No. 201780049752.9, dated Dec. 28, 2020, 5 pages.

(56) References Cited

OTHER PUBLICATIONS

Clayden et al., "Conformational Preference and Remote (1,10) Stereocontrol in Biphenyl-2,2'-dicarboxamides," Org. Lett., 2001, 3(26):4133-4136.
Colombian Office Action in Colombian Application No. NC2019/0000386, dated Sep. 25, 2020, 18 pages.
Cram et al., "Host-guest complexation. 29. Expanded hemispherands," J Am Chem Soc., 1984, 106(11):6386-3292.
Cram et al., "Host-guest complexation. 32. Spherands composed of cyclic urea and anisyl units," J Am Chem Soc., 1984, 106(23):7150-7167.
Cram et al., "Host-guest complexation. 26. Cavitands composed of fluorobenzene units bonded in their 2,6-positions to form macrocycles," J Am Chem Soc., 1984, 106(3):695-701.
Cram et al., "Spherand hosts containing cyclic urea units," J Am Chem Soc., 1982, 104(24):6828-6830.
Curis, "Overview and Path for Growth," Aurigene Strategic Collaboration, Jan. 21, 2015, 13 slides.
Database accession No. 1478989-52-4 abstract, Nov. 22, 2013, 1 page.
Database Accession No. 1568738-04-4 abstract, Mar. 14, 2014, 1 page.
Database Accession No. 1580823-55-7 abstract, Apr. 6, 2014, 1 page.
Database Accession No. 1581556-71-9 abstract, Apr. 8, 2014, 1 page.
Database Accession No. 1590700-72-3 abstract, Apr. 27, 2014, 1 page.
Database accession No. 2013:447446 abstract, 2013, 1 page.
De Lucca et al., "Small Molecule Reversible Inhibitors of Bruton's Tyrosine Kinase (BTK): Structure—Activity Relationships Leading to the Identification of 7-(2-Hydroxypropan-2-y1)-4-[2-methyl-3-(4-oxo-3,4-dihydroquinazolin-3-y1)phenyl]-9H-carbazole-1-carboxamide (BMS-935177)," Journal of Medicinal Chemistry, 2016, 59(17):7915-7935.
Dhanunjayarao et al., "Synthesis and Optical Properties of Salicylaldimine-Based Diboron Complexes," Eur J Inorg Chem., 2014, 3:539-545.
Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Differding Consulting s.p.r.l. (Belgium), Feb. 26, 2014, 12 pages.
Dolan et al., "PD-1 Pathway Inhibitors: Changing the Landscape of Cancer Immunotherapy," Cancer Control, Jul. 2014, 21(3):231-237.
Dong et al., "Tumor-associated B7-H1 promotes T-cell apoptosis: a potential mechanism of immune evasion," Nature Medicine, Aug. 2002, 8(8):793-800.
Domling et al., "Programmed Death-1: Therapeutic Success after More than 100 Years of Cancer Immunotherapy," Angew. Chem. Int. Ed., 2014, 53:2283-2288.
Ecuador Opposition in Ecuador Application No. SENADI-2019-3773, dated Oct. 10, 2019, 29 pages.
Escarcega-Bobadilla et al., "A Recyclable Trinuclear Bifunctional Catalyst Derived from a Tetraoxo Bis-Zn(salphen) Metalloligand," Chemistry—A European Journal., 2013, 19(8):2641-2648.
Escarcega-Bobadilla et al., "Metal-directed assembly of chiral bis-Zn(II) Schiff base structures," Dalton Transactions, 2012, 41(32):9766-9772.
Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.
Eurasian Office Action in Eurasian Application No. 201990074/28, dated Oct. 3, 2019, 5 pages.
European Communication in European Application No. 16805690.1, dated Jan. 22, 2020, 5 pages.
European Communication in European Application No. 16805690.1, dated Jul. 10, 2018, 6 pages.
European Communication in European Application No. 16805690.1, dated Nov. 5, 2020, 4 pages.
European Communication in European Application No. 17743174.9, dated Jan. 31, 2020, 5 pages.
Fabris et al., "Central to Axial Transfer of Chirality in Menthone or Camphor-Derived 2,2'-Biphenols," J Org Chem., 1997, 62(21):7156-7164.
FDA Report, "22 Case Studies Where Phase 2 and Phase 3 Trials Had Divergent Results," U.S. Food and Drug Administration, Jan. 2017, 44 pages.
Francisco et al., "The PD-1 Pathway in Tolerance and Autoimmunity," Immunol. Rev., Jul. 2010, 236:219-242.
Freeman et al., "Engagement of the Pd-1 Immunoinhibitory Receptor by a Novel B7 Family Member Leads to Negative Regulation of Lymphocyte Activation," J. Exp. Med., Oct. 2000, 192(7):1027-34.
Freeman, "Structures of PD-1 with its ligands: Sideways and dancing cheek to cheek," PNAS, Jul. 2008, 105(30):10275-10276.
Freindorf, M., "Vibronic couplings in an excited state of hydrogen bond dimeric systems," Acta Physica Polonica, 1990, A78(6):825-839.
Gong et al., "Rhodium(I)-catalyzed regiospecific dimerization of aromatic acids: two direct C—H bond activations in water," Angewandte Chemie, 2015, 54(19):5718-5721.
Goswami et al., "A turn on ESIPT probe for rapid and ratiometric fluorogenic detection of homocysteine and cysteine in water with live cell-imaging," Tetrahedron Letters, 2014, 55(2):490-494.
Gould et al. "Salt selection for basic drugs," Int J Pharma., 1986, 33(1-3):201-217.
Green et al., "Synthesis and investigation of the configurational stability of some dimethylammonium borate salts," J. Chem. Soc., Perkin Trans. 1, 2000, 24:4403-4408.
Greenwald et al, "The B7 Family Revisited," Annu. Rev. Immunol., 2005, 23:515-548.
Gu et al., "Undo the brake of tumour immune tolerance with antibodies, peptide mimetics and small molecule compounds targeting PD-1/PD-L1 checkpoint at different locations for acceleration of cytotoxic immunity to cancer cells," Clinical and Experimental Pharmacology and Physiology, 2019, 46(2):105-115.
Han et al., "Synthesis of binuclear phenoxyimino organoaluminum complexes and their use as the catalyst precursors for efficient ring-opening polymerisation of E-caprolactone," Dalton Transactions, 2013, 41:12346-12353.
Helgeson et al., "Host-guest complexation. 66. 18-Membered-ring spherands containing five anisyl groups," J Am Chem Soc., 1993, 1115(24):11506-11511.
Hilfiker "Relevance of Solid-state Properties for Pharmaceutical Products," Polymorphism in the Pharmaceutical Industry, Jan. 1, 2006, pp. 1-19.
Highlights Prescribing Information, "Opdivo," Revised Apr. 2019, 90 pages.
Highlights Prescribing Information, "Keytruda," Revised Feb. 2019, 66 pages.
Hu et al., "Novel highly active binuclear neutral nickel and palladium complexes as precatalysts for norbornene polymerization," Journal of Molecular Catalysis A: Chemical 253, 2006, 155-164.
Hu et al., "Syntheses and Ethylene Polymerization Behavior of Supported Salicylaldimine-Based Neutral Nickel(II) Catalysts," Organometallics, 2007, 26(10):2609-2615.
Hu et al., "Synthesis and Ethylene Polymerization Activity of a Novel, Highly Active Single-Component Binuclear Neutral Nickel(II) Catalyst," Organometallics, 2005, 24(11):2628-2632.
Huang et al, "The prognostic significance of PD-L1 in bladder cancer," Oncol. Rep., 2015, 33:3075-3084.
Huang et al., "Pharmacological treatment for keloids," Expert opinion on pharmacotherapy, 2013, 14(15):2087-2100.
Huddle et al., "Reactions of alkyl-lithium compounds with aryl halides," J Chem Soc., Perkin I, 1980, 12:2617-2625.
HuGEMM™ and HuCELL™ Models, "FactSheet," CrownBio, Oct. 2016, 8 pages.
Indian Office Action with Indian Application No. 201817026809, dated Apr. 29, 2020, 6 pages.
Indian Office Action with Indian Application No. 201917001998, dated Nov. 24, 2020, 7 pages.

(56) References Cited

OTHER PUBLICATIONS

Indian Office Action with Indian Application No. 201917028273, dated Feb. 15, 2021, 5 pages.
International Preliminary Report on Patentability in International Application No. PCT/US2017/041899, dated Jan. 15, 2019, 7 pages.
International Preliminary Report on Patentability in International Application No. PCT/US2016/057487, dated May 3, 2018, 7 pages.
International Preliminary Report on Patentability in International Application No. PCT/US2016/062730, dated May 31, 2018, 7 pages.
International Preliminary Report on Patentability in International Application No. PCT/US2016/067155, dated Jun. 19, 2018, 10 pages.
International Preliminary Report on Patentability in International Application No. PCT/US2016/067925, dated Jun. 26, 2018, 8 pages.
International Preliminary Report on Patentability in International Application No. PCT/US2017/031242, dated Nov. 6, 2018, 7 pages.
International Preliminary Report on Patentability in International Application No. PCT/US2017/034173, dated Nov. 27, 2018, 8 pages.
International Preliminary Report on Patentability in International Application No. PCT/US2017/038120, dated Dec. 25, 2018, 6 pages.
International Preliminary Report on Patentability in International Application No. PCT/US2017/048880, dated March, 5, 2019, 9 pages.
International Preliminary Report on Patentability in International Application No. PCT/US2017/067880, dated Jun. 25, 2019, 7 pages.
International Preliminary Report on Patentability in International Application No. PCT/US2017/067886, dated Jun. 25, 2019, 9 pages.
International Preliminary Report on Patentability in International Application No. PCT/US2017/067904, dated Jun. 25, 2019, 7 pages.
International Preliminary Report on Patentability in International Application No. PCT/US2017/067946, dated Jun. 25, 2019, 9 pages.
International Preliminary Report on Patentability in International Application No. PCT/US2017/067951, dated Jun. 25, 2019, 8 pages.
International Preliminary Report on Patentability in International Application No. PCT/US2017/067984, dated Jun. 25, 2019, 7 pages.
International Preliminary Report on Patentability in International Application No. PCT/US2019/025036, dated Oct. 15, 2020, 7 pages.
International Preliminary Report on Patentability in International Application No. PCT/US2019/031728, dated Nov. 17, 2020, 7 pages.
International Preliminary Report on Patentability in International Application No. PCT/US2020/045311, dated Feb. 17, 2022, 8 pages.
International Search Report and Written Opinion in International Application No. PCT/US2016/057487, dated Dec. 8, 2016, 11 pages.
International Search Report and Written Opinion in International Application No. PCT/US2016/062730, dated Feb. 9, 2017, 12 pages.
International Search Report and Written Opinion in International Application No. PCT/US2016/067155, dated Apr. 24, 2017, 26 pages.
International Search Report and Written Opinion in International Application No. PCT/US2016/067925, dated Mar. 27, 2017, 13 pages.
International Search Report and Written Opinion in International Application No. PCT/US2017/031242, dated Jun. 20, 2017, 22 pages.
International Search Report and Written Opinion in International Application No. PCT/US2017/034173, dated Aug. 8, 2017, 15 pages.
International Search Report and Written Opinion in International Application No. PCT/US2017/038120, dated Aug. 1, 2017, 14 pages.
International Search Report and Written Opinion in International Application No. PCT/US2017/041899, dated Sep. 5, 2017, 12 pages.
International Search Report and Written Opinion in International Application No. PCT/US2017/048880, dated Oct. 23, 2017, 15 pages.
International Search Report and Written Opinion in International Application No. PCT/US2017/067880, dated Mar. 21, 2018, 13 pages.
International Search Report and Written Opinion in International Application No. PCT/US2017/067886, dated Mar. 23, 2018, 24 pages.
International Search Report and Written Opinion in International Application No. PCT/US2017/067904, dated Mar. 22, 2018, 14 pages.
International Search Report and Written Opinion in International Application No. PCT/US2017/067946, dated May 22, 2018, 16 pages.
International Search Report and Written Opinion in International Application No. PCT/US2017/067951, dated Mar. 27, 2018, 15 pages.
International Search Report and Written Opinion in International Application No. PCT/US2017/067984, dated Mar. 22, 2018, 14 pages.
International Search Report and Written Opinion in International Application No. PCT/US2019/025036, dated Jul. 3, 2019, 12 pages.
International Search Report and Written Opinion in International Application No. PCT/US2019/031728, dated Jun. 25, 2019, 12 pages.
International Search Report and Written Opinion in International Application No. PCT/US2020/045311, dated Oct. 2, 2020, 14 pages.
International Search Report and Written Opinion in International Application No. PCT/US2020/059817, dated Mar. 29, 2021, 19 pages.
International Search Report in International Application No. PCT/US2020/053190, dated Jan. 29, 2021, 13 pages.
Israeli Office Action in Israeli Application No. 259,406, dated Mar. 11, 2020, 10 pages.
Israeli Office Action in Israeli Application No. 260,166, dated Jun. 2, 2020, 13 pages.
Israeli Office Action in Israeli Application No. 287,267, dated Feb. 15, 2022, 4 pages.
Iwai et al, "Involvement of PD-L1 on tumor cells in the escape from host immune system and tumor immunotherapy by PD-L1 blockade," PNAS, Sep. 2002, 99(19):12293-12297.
Japanese Office Action in Japanese Application No. 2018526213, dated Oct. 13, 2020, 10 pages.
Japanese Office Action in Japanese Application No. 2019-534122, dated Oct. 19, 2021, 10 pages.
Japanese Office Action in Japanese Application No. 2019-534195, dated Nov. 1, 2021, 8 pages.
Japanese Office Action in Japanese Application No. 2019-534196, dated Nov. 9, 2021, 8 pages.
Jiang et al., "Self-immobilizing binuclear neutral nickel catalyst for ethylene polymerization: Synthesis and catalytic studies," J Mol Cat., 2013, 380:139-143.
Kayal et al., "3,3'-Bis(triphenylsilyl)biphenoxide as a Sterically Hindered Ligand on Fe(II), Fe(III), and Cr(II)," Inorg Chem., 2002, 41(2):321-330.
Keir et al., "PD-1 and Its Ligands in Tolerance and Immunity," Annu. Rev. Immunol., 2008, 26:677-704.
Kerekes et al., "Aurora kinase inhibitors based on the imidazo[1,2-a]pyrazine core: fluorine and deuterium incorporation improve oral absorption and exposure," J Med Chem., 2011, 54(1):201-210.

(56) References Cited

OTHER PUBLICATIONS

Koch et al., "Nucleophilic reactions of pyridines and imidazoles with vinyl and aromatic halides," J Org Chem., 1993, 58(6):1409-1414.
Komiyama et al, "IL-17 Plays an Important Role in the Development of Experimental Autoimmune Encephalomyelitis," J. Immunol., Jul. 2006, 177:566-73.
Latchman et al, "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30):10483-10488.
Legon'kova et al., "Interaction of o,o-dihalo o'-hydroxy azo compounds with metallic copper. II. Preparation of oligomeric azo compounds from monoazo compounds," Mosk Khim-Tekhnol Inst im Mendeleeva., 1968, 11(11):1281-1284 Machine Translation.
Legon'kova et al., "Interaction of o,o-dihalogeno o-hydroxy azo compounds with metallic copper," Trudy Instituta—Moskovskii Khimiko-Tekhnologicheskii Institut imeni D. I. Mendeleeva, 1965, 48:120-125 Machine Translation.
Lehtonen et al., "Comparison of quaternary methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Lexico.com, "Synonyms of Enhance," Oxford Dictionary, retrieved on Dec. 9, 2021, retrieved from URL <https://www.lexico.conn/synonynns/enhance>, 4 pages.
Li et al., "A 3D Mesomeric Supramolecular Structure of a Cu(II) Coordination Polymer with 1,1'-Bipheny1-2,2',3,3'-tetracarboxylic Acid and 5,5'-Dimethyl-2,2'-bipyridine Ligands," J Inorg and Organomet Poly Mat., 2012, 22(6):1320-1324.
Li et al., "A Mini-Review for Cancer Immunotherapy: Molecular Understanding of PD-1/PD-L1 Pathway & Translational Blockade of Immune Checkpoints," Int. J. Mol. Soc., 2016, 17:1151, 22 pages.
Li et al., "Analysis of Receptor Tyrosine Kinase Internalization Using Flow Cytometry," Methods Mol. Biol., 2008, 457:305-317.
Li et al., "Asymmetric Alternating Copolymerization of Meso-epoxides and Cyclic Anhydrides: Efficient Access to Enantiopure Polyesters," J. Am. Chem. Soc., 2016, 138(36):11493-11496.
Li et al., "Discovery of peptide inhibitors targeting human programmed death 1 (PD-1) receptor," Oncotarget, Aug. 2016, 7(40):64967-64976.
Lin et al., "The PD-1/PD-L1 complex resembles the antigen-binding Fv domains of antibodies and T cell receptors," PNAS, Feb. 2008, 105(8):3011-3016.
Lipson et al., "From Discovery to Development: Blocking PD-1 and its Ligands," The Melanoma Letter, A Publication of The Skin Cancer Foundation, vol. 31, Summer 2013, 6 pages.
Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44):11594-11598.
Liu et al., "Development of amino- and dimethylcarbamate-substituted resorcinol as programmed cell death-1 (PD-1) inhibitor," Eur J Pharm Sci, 2016, 88:50-58.
Mahoney et al., "The Next Immune-Checkpoint Inhibitors:PD-1/PD-L1 Blockade in Melanoma," Clin. Therapeutics, Nov. 2015, 37(4):761-782.
Maier et al., "Effects of the stationary phase and the solvent on the stereodynamics of biphep ligands quantified by dynamic three-column HPLC," Angewante Chemie, 2012, 51(12):2985-2988.
Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.
Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.
Mexican Office Action in Mexican Application No. MX/a/2018/007774, dated Apr. 8, 2021, 5 pages.
Mexican Office Action in Mexican Application No. MX/a/2018/016273, dated Mar. 26, 2021, 5 pages.
Miyaura and Suzuki, "Palladium-Catalyzed Cross-Coupling Reactions of Organoboron Compounds," Chem Rev., 1995, 95:2457-2483.
Mochida et al., "Rhodium-Catalyzed Regioselective Olefination Directed by a Carboxylic Group," J Org Chem, 2011, 76(9):3024-3033.
Moneta et al., "Boron templated synthesis of macrocyclic hosts containing convergent hydroxy or methoxy groups," Bulletin de la Societe Chimique de France, 1988, 6:995-1004 (English Abstract).
Nallasivam et al., "Development of Unimolecular Tetrakis(piperidin-4-ol) as a Ligand for Suzuki-Miyaura Cross-Coupling Reactions: Synthesis of Incrustoporin and Preclamol," 2015, Eur J Org Chem., 2015(16):3558-3567.
Nero et al., "Oncogenic protein interfaces: small molecules, big challenges," Nature Reviews, Apr. 2014, 14:248-262.
Nishimura et al, "Autoimmune Dilated Cardiomyopathy in PD-1 Receptor-Deficient Mice," Science, Jan. 2001, 291:319-322.
Nishimura et al, "Development of Lupus-like Autoimmune Diseases by Disruption of the PD-1 Gene Encoding an ITIM Motif-Carrying Immunoreceptor," Immunity, Aug. 1999, 11:141-151.
Nishimura et al., "PD-1: an inhibitory immunoreceptor involved in peripheral tolerance," Trends in Immunology, May 2001, 22(5):265-268.
Nishino et al., "Copper-Mediated C—H/C—H Biaryl Coupling of Benzoic Acid Derivatives and 1,3-Azoles," Angew. Chem. Int. Ed., 2013, 52:4457-4461.
Normand et al., "Dinuclear vs. mononuclear complexes: accelerated, metal-dependent ring-opening polymerization of lactide," Chem. Commun., 2013, 49(99):11692-11694.
Okazaki and Honjo, "The PD-1—PD-L pathway in immunological tolerance," Trends Immunol., Apr. 2006, 4:195-201.
Okazaki et al., "A rheostat for immune responses: the unique properties of PD-1 and their advantages for clinical application," Nature Immunology, Dec. 2013, 14(12):1212-1218.
Paek et al., "Chiral host. Attempted synthesis using McMurray reaction as a final ring closure method," Bulletin of the Korean Chemical Society, 1989, 10(6):572-577.
Paek et al.., "Facile syntheses and multi-orthofunctionalizations of tertiary benzamides," Bulletin of the Korean Chemical Society, 1993, 14(6):732-739.
Pardoll, "The blockade of immune checkpoints in cancer immunotherapy," Nature, Apr. 2012, 12:252-264.
Parry et al, "CTLA-4 and PD-1 Receptors Inhibit T-Cell Activation by Distinct Mechanisms," Mol. Cell. Biol., Nov. 2005, 25(21):9543-9553.
Parsons et al., "Directed ortho metalation reactions. Expedient synthesis of 3,3'-disubstituted 1,1'-bi-(2-phenols) (BIPOLS)," Tetrahedron Letters, 1994, 35(41):7537-7540.
Pascolutti et al., "Structure and Dynamics of PD-L1 and an Ultra-High-Affinity PD-1 Receptor Mutant," Structure, Oct. 2016, 24:1719-1728.
Paulini et al., "Orthogonal Multipolar Interactions in Structural Chemistry and Biology," Angew. Chem. Int. Ed., 2005, 44:1788-1805.
Pearson et al., "The formation of complexes between aza-derivatives of crown ethers and primary alkylammonium salts. Part 5. Chiral macrocyclic diamines," J. Chem. Soc., Perkin I, 1979, 12:3113-3126.
Pfeiffer et al., "Inner complex salts of the aldimine and azo series," Journal fuer Praktische Chemie, 1937, 149:217-296 Machine Translation.
Pierre et al., "Synthesis of a new macrobicyclic siderophoric host molecule with six converging phenolate groups," Angewandte Chemie, 1991, 103(1):75-76 Machine Translation.
Postow et al, "Immune Checkpoint Blockade in Cancer Therapy," J. Clinical Oncology, Jun. 2015, 33(17):1974-1982.

(56) References Cited

OTHER PUBLICATIONS

Press Release Archive, "Boehringer Ingelheim and Yale University collaborate to investigate novel immunotherapy targets across several therapeutic areas," Boehringer Ingelheim, Jan. 13, 2015, 2 pages.
Puehlhofer et al., "SASAPOS cascades of perfluorinated aromatic carboxylic acids: low-temperature decarboxylation triggered by electrostatic effects of polycationic ligand sets," Euro J of Org Chem., 2004, 5:1002-1007.
Punniyamurthy et al., "Enantiomerically pure bicyclo[3.3.1]nona-2,6-diene as the sole source of enantioselectivity in BIPHEP-Rh asymmetric hydrogenation," Chem Comm., 2008, 41:5092-5094.
Qin et al., "The Diverse Function of PD-1/PD-L Pathway Beyond Cancer," Frontiers In Imunology, Oct. 2019, 10(2298):1-16.
Reck et al., "Pembrolizumab versus Chemotherapy for PD-L1-Positive Non-Small-Cell Lung Cancer," N Engl J Med., Nov. 10, 2016, 375(19):1823-1833.
Sabatier et al, "Prognostic and predictive value of PDL 1 expression in breast cancer," Oncotarget, Mar. 2015, 6(7):5449-5464.
Sharma et al., "Palladium-Catalyzed Decarboxylative Acylation of O-Phenyl Carbamates with Alpha-Oxocarboxylic Acids at Room Temperature," Advanced Synthesis & Catalysis, 2013, 355(4):667-672.
Sharpe et al, "The function of programmed cell death 1 and its ligands in regulating autoimmunity and infection," Nat. Immunol., Mar. 2007 8(3):239-245.
Sharpe et al., "The B7-CD28 Superfamily," Nature Reviews, Feb. 2002, 2:116-126.
Sorrell et al., "3,3'-Disubstituted 2,2'-biphenols. Synthesis of nonplanar, tetradentate chelating ligands," J Org Chem., 1985, 50(26):5765-5769.
STN Search Report dated Dec. 20, 2016, 117 pages.
STN Search Report dated Apr. 14, 2016, 79 pages.
STN Search Report dated Apr. 29, 2016, 69 pages.
STN Search Report dated Apr. 30, 2018, 8 pages.
STN Search Report dated Aug. 19, 2016, 23 pages.
STN Search Report dated Aug. 30, 2016, 4 pages.
STN Search Report dated Dec. 15, 2016, 4 pages.
STN Search Report dated Dec. 16, 2016, 25 pages.
STN Search Report dated Dec. 16, 2016, 4 pages.
STN Search Report dated Dec. 19, 2016, 11 pages.
STN Search Report dated Jul. 12, 2016, 4 pages.
STN Search Report dated Jun. 16, 2016, 8 pages.
STN Search Report dated Jun. 6, 2016, 115 pages.
STN Search Report dated Mar. 27, 2018, 4 pages.
STN Search Report dated May 24, 2016, 92 pages.
STN Search Report dated Sep. 12, 2016, 4 pages.
STN Search Report dated Sep. 12, 2016, 17 pages.
STN Search Report dated Sep. 2, 2016, 115 pages.
STN Search Report dated Sep. 27, 2017, 4 pages.
STN Search Report, dated May 1, 2016, 12 pages.
Storz, "Intellectual property issues of immune checkpoint inhibitors," mAbs, Jan. 2016, 8(1):10-26.
Suarez et al., "Inhibitors of TAM subfamily of tyrosine kinases: synthesis and biological evaluation," European Journal of Medicinal Chemistry, 2013, 61:2-25.
Sumrit et al., "Aluminum complexes containing salicylbenzoxazole ligands and their application in the ring-opening polymerization of rac-lactide and ε-caprolactone," Dalton Transactions (2016), 45(22), 9250-9266.
Sun et al., "Studies on Synthesis and Properties of Some New Dibenzocyclobromonium," Chemical Journal of Chinese Universities, 1998, 19(12), 6 pages (English Abstract).
Sznol et al., "Antagonist Antibodies to PD-1 and B7-H1 (PD-L1) in the Treatment of Advanced Human Cancer," Clin Cancer Res., Mar. 1, 2013, 19(5):1021-1034.
Taiwan Office Action in Taiwan Application No. 105133530, dated Oct. 15, 2020, 8 pages.
Taiwan Office Action in Taiwan Application No. 105137807, dated Nov. 12, 2020, 12 pages.
Taiwan Office Action in Taiwan Application No. 105141804, dated Nov. 9, 2020, 9 pages.
Tang et al., "Facile synthesis of enantioenriched phenol-sulfoxides and their aluminum complexes," Org Biomol Chem., 2016, 14(24):5580-5585.
Thiel et al., "Small-Molecule Stabilization of Protein-Protein Interactions: An Underestimated Concept in Drug Discovery?" Angew. Chem. Int. Ed., 2012, 51:2012-2018.
Tucker et al., "Host-guest complexation. 52. Bridged and chiral hemispherands," J Org Chem., 1989, 54(23):5460-5482.
Ukraine Office Action in Ukraine Application No. a 2019 00525, dated Jan. 14, 2021, 11 pages.
Unrau et al., "Directed ortho metalation. Suzuki cross coupling connections. Convenient regiospecific routes to functionalized m- and p-teraryls and m-quinquearyls," Tetrahedron Letters, 1992, 33(20):2773-2776.
Vaddepally et al., "Review of Indications of FDA-Approved Immune Checkpoint Inhibitors per NCCN Guidelines with the Level of Evidence," Cancers, 2020, 12(3):738.
Velcheti et al., "Programmed death-1/programmed death-1 ligand axis as a therapeutic target in oncology: current insights," Journal of Receptor Ligand and Channel Research, Dec. 2014, 8(23):1-7.
Wang et al, "The prognostic value of PD-L1 expression for non-small cell lung cancer patients: A meta-analysis," Eur. J. Surg. Oncol., 2015, 41:450-456.
Wang et al., "A binuclear Zn(II)-Zn(II) complex from a 2-hydroxybenzohydrazide-derived Schiff base for selective detection of pyrophosphate," Dalton Transactions, Oct. 2014, 43(37):14142-14146.
Wang et al., "Molecular Modeling and Functional Mapping of B7-H1 and B7-DC Uncouple Costimulatory Function from PD-1 Interaction," J. Exp. Med., Apr. 2013, 197(3):1083-1091.
Wei et al., "Strength of PD-1 signaling differentially affects T-cell effector functions," PNAS, Apr. 2013, E2480-E2489.
Weinmann, "Cancer Immunotherapy: Selected Targets and Small-Molecule Modulators," Chem. Med. Chem., 2016, 11:450-466.
Weiss et al., "Electrostatic activation of SNAr-reactivity by sulfonylonio substituents," Zeitschrift fuer Naturforschung, 2001, 56(12):1360-1368 English Abstract.
Weiss et al., "Electrostatics and color: Massive electrostatic perturbation of chromophores by ion cluster ligands," J Am Chem Soc., 2007, 129(3):547-553.
Weiss et al., "First-ever per(onio) substitution of benzene: the role of the counterion," Angewandte Chemie, 1995, 34(12):1319-1321.
Weiss et al., "Massive electrostatic effects on heteropolar C—C disconnections: Transforming a phenyl anion into a potent leaving group," Euro J Org Chem., 2005, 16:3530-3535.
Weiss et al., "Poly-onio substituted quinones as strong electron acceptors," Inst Org Chem., 1986, 98(10):925-926.
Weiss et al., "Sasapos, not Sisyphus: highly efficient 20-step one-pot synthesis of a discrete organic-inorganic ion cluster with a porphyrin core," Angewandte Chemie International Edition, 2002, 41(20):3815-3817.
Weiss et al., "Syntheses and Reactions of Polycationically Substituted Azido- and Diazidobenzenes," Eur J Org Chem., Nov. 2007, 31:5270-5276.
Wells et al., "Reaching for high-hanging fruit in drug discovery at protein-protein interfaces," Nature, Dec. 2007, 450:1001-1009.
Wu et al., "Targeting the BACE1 Active Site Flap Leads to a Potent Inhibitor That Elicits Robust Brain Aß Reduction in Rodents," ACS Medicinal Chemistry Letters, 2016, 7(3):271-276.
Wuts et al., "Protective Groups in Organic Synthesis," 4th Ed., 2007, 1111 pages.
www.medscape.com' [online]. "The 'Family Business' Behind the Flurry of PD-1 Inhibitors," Sep. 10, 2014. [Retrieved on Jan. 29, 2015]. Retrieved from the Internet: URL<http://www.medscape.com/viewarticle/831448_print>. 3 pages.
Xiong et al., "Biaryl-Bridged Salalen Ligands and Their Application in Titanium-Catalyzed Asymmetric Epoxidation of Olefins with Aqueous H2O2," Eur J Org Chem., 2011, 23:4289-4292.
Xu et al., "Design, synthesis and biological evaluation of deuterated nintedanib for improving pharmacokinetic properties," J Label Compd RadioPharm., Jun. 15, 2015, 58(7):308-312.

(56) References Cited

OTHER PUBLICATIONS

Xu et al., "Quantitative structure-activity relationship study on BTK inhibitors by modified multivariate adaptive regression spline and CoMSIA methods," SAR QSAR Environ Res., 2015, 26(4):279-300.
Yao et al., "PD-1 as an Immune Modulatory Receptor," Cancer J., 2014, 20(4):262-264.
Yin et al., "Strategies for Targeting Protein-Protein Interactions With Synthetic Agents," Angew. Chem. Int. Ed., 2005, 44:4130-4163.
Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.
Young et al., "Potent and selective Bruton's tyrosine kinase inhibitors: Discovery of GDC-0834," Bioorganic & Medicinal Chemistry Letters, 2015, 25(6):1333-1337.
Zak et al., "Structural basis for small molecule targeting of the programmed death ligand 1 (PD-L1)" Oncotarget, Apr. 2016, 19 pages; Supplemental Material for 2016, 7(21):30323-30335.
Zak et al., "Structural basis for small molecule targeting of the programmed death ligand 1 (PD-L1)," Oncotarget, 2016, 7(21):30323-30335.
Zak et al., "Structure of the Complex of Human Programmed Death 1, PD-1, and Its Ligand PD-L1: with Supplemental Information," Structure, Dec. 2015, 23:2341-2348.
Zang et al., "Four 2D metal-organic networks incorporating Cd-cluster SUBs: hydrothermal synthesis, structures and photoluminescent properties," CrystEngComm, 2009, 11(1):122-129.
Zarganes-Tzitzikas, "Inhibitors of programmed cell death 1 (PD-1): a patent review (2010-2015)," Expert Opinion on Therapeutic Patents, Sep. 19, 2016, 26(9):973-977.
Zhan et al., "From monoclonal antibodies to small molecules: the development of inhibitors targeting the PD-1/PD-L1 pathway," Drug Discovery Today, Apr. 2016, 10 pages.
Zhang et al., "Biaryl-Based Macrocyclic and Polymeric Chiral (Salophen)Ni(II) Complexes: Synthesis and Spectroscopic Study," J Org Chem., 2001, 66(2):481-487.
Zhang et al., "Electrospray mass spectrum of a per(onio)-substituted benzene: retention of Coulombic charge upon collisionally activated decomposition," J Am Soc. Mass. Spectrom., 1998, 9(1):15-20.
Zhang et al., "Non-symmetrical diarylcarboxylic acids via rhodium(I)-catalyzed regiospecific cross-dehydrogenation coupling of aromatic acids: twofold direct C—H bond activations in water," RSC Advances, 2016, 6(64):91617-91620.
Zhang et al., "Structural and Functional Analysis of the Costimulatory Receptor Programmed Death-1," Immunity, Mar. 2004, 20:337-347.
Zhao et al., "Design, synthesis and organocatalysis of 2,2'-biphenol-based prolinamide organocatalysts in the asymmetric direct aldol reaction in water," Synlett, 2013, 24(20):2743-2747.
Methot et al., "Exploration of the internal cavity of histone deacetylase (H DAC) with selective HDAC1/HDAC2 inhibitors (SHIT-1:2)," Bioorganic & Medicinal Chemistry Letters, 2008, 18:973-978.
Mexican Office Action in Mexican Application No. MX/a/2020/012045, dated Jul. 12, 2023, 5 pages (with English Translation).
Otter et al., "The human papillomavirus as a common pathogen in oropharyngeal, anal and cervical cancers," Clin Oncol (R Coll Radiol), Feb. 2019, 31(2):81-90.
Pajouhesh et al., "Medicinal Chemical Properties of Successful Central Nervous System Drugs," NeuroRx, 2005, 2, 541-553.
Poljak et al., "Nucleic Acid Tests for the Detection of Alpha Human Papillomaviruses," Vaccine, 2012, 30S:F100-F106.
Rowe et al., "Fumaric Acid," Handbook of pharmaceutical excipients, Jan. 1, 2009, pp. 276-277, 318-321, 663-666.
Venuti et al., "HPV Detection Methods in Head and Neck Cancer," Head and Neck Pathol, 2012, 6:S63-S74.
Argentina Office Action in Argentina Application No. 20170103634, dated Jan. 27, 2022, 7 pages.
Australian Notice of Allowance in Australian Application No. 2017382870, dated Mar. 15, 2022, 4 pages.
Bastin et al., "Salt Selection and Optimisation for Pharmaceutical New Chemical Entities," Org Proc Res Dev., dated Jan. 1, 2000, pp. 4(5):427-435.
Caira, "Crystalline Polymorphism of Organic Compounds," Topics in Current Chemistry, Jan. 1, 1998, 198:163-208.
European Communication in European Application No. 20202254.7, dated Apr. 1, 2022, 4 pages.
Indian Office Action in Indian Application No. 202017053661, dated Jun. 3, 2022, 5 pages.
International Preliminary Report on Patentability in International Application No. PCT/US2020/053190, dated Apr. 5, 2022, 7 pages.
International Preliminary Report on Patentability in International Application No. PCT/US2020/059817, dated May 17, 2022, 12 pages.
International Search Report and Written Opinion in International Application No. PCT/US2021/058268, dated Apr. 21, 2022, 22 pages.
International Search Report and Written Opinion in International Application No. PCT/US2021/058334, dated Apr. 25, 2022, 23 pages.
International Search Report and Written Opinion in International Application No. PCT/US2021/058338, dated Feb. 9, 2022, 15 pages.
International Search Report and Written Opinion in International Application No. PCT/US2021/063965, dated Apr. 12, 2022, 20 pages.
Invitation to Pay Fee's in International Application No. PCT/US2021/058268, dated Jan. 31, 2022, 16 pages.
Invitation to Pay Fee's in International Application No. PCT/US2021/058334, dated Feb. 3, 2022, 12 pages.
Rowe et al., "Fumaric Acid" Handbook of pharmaceutical excipients, Jan. 1, 2009, pp. 276-277, 309-310, 393-396.
Stahl et al., "Handbook of Pharmaceutical Salts: Properties, Selection, and Use," Wiley, 2002, p. 329-350.
Braga et al., "Crystal Polymorphism and Multiple Crystal Forms," Structure and Bonding, Feb. 2009, 132:25-50.
Canadian Office Action in Canadian Application No. 3,047,991, dated May 17, 2024, 9 pages.
Guzik et al., "Development of the inhibitors that target the PD-1/PD-L1 interaction—a brief look at progress on small molecules, peptides and macrocycles," Molecules, May 2019, 24(11):2071, 30 pages.
Menning et al., "Fumaric acid microenvironment tablet formulation and process development for crystalline cenicriviroc mesylate, a BCS IV compound," Molecular pharmaceutics, Nov. 2013, 10(11):4005-4015.
Meric-Bernstam et al., "Enhancing anti-tumour efficacy with immunotherapy combinations," The Lancet, Dec. 4, 2020, 397(10278):1010-1022, 13 pages.
Motzer et al., "Lenvatinib, everolimus, and the combination in patients with metastatic renal cell carcinoma: a randomised, phase 2, open-label, multicentre trial," Lancet Oncology, 2015, 16(15):1473-1482.
Upadhaya, "Combinations take centre stage in PD1/PDL1 inhibitor clinical trials," Nature Reviews Drug Discovery, Mar. 20, 2021, 20(3):168-169.
Yang et al., "Pembrolizumab With or Without Lenvatinib for First-Line Metastatic NSCLC With Programmed Cell Death-Ligand 1 Tumor Proportion Score of at least 1% (LEAP-007): A Randomized, Double-Blind, Phase 3 Trial," Journal of Thoracic Therapy, Dec. 29, 2023, 19(6):941-953.
Zhang et al., "The Roles of Programmed Cell Death Ligand-1/Programmed Cell Death-1 (PD-L1/PD-1) in HPV-induced Cervical Cancer and Potential for their Use in Blockade Therapy," Current Medical Chemistry, 2020, 28(5):893-909.

HETEROCYCLIC COMPOUNDS AS IMMUNOMODULATORS

CLAIM OF PRIORITY

This application is a continuation of U.S. patent application Ser. No. 17/170,662, filed on Feb. 8, 2021; which is a continuation of U.S. patent application Ser. No. 16/913,616, filed on Jun. 26, 2020; which is a continuation of U.S. patent application Ser. No. 16/678,117, filed on Nov. 8, 2019; which is a continuation of U.S. patent application Ser. No. 16/365,234, filed on Mar. 26, 2019; which is a continuation of U.S. patent application Ser. No. 16/058,149, filed on Aug. 8, 2018; which is a continuation of U.S. patent application Ser. No. 15/850,985, filed on Dec. 21, 2017; which claims the benefit of U.S. Provisional Application No. 62/551,011, filed on Aug. 28, 2017; U.S. Provisional Application No. 62/487,362, filed on Apr. 19, 2017; and U.S. Provisional Application No. 62/438,038, filed on Dec. 22, 2016, each of which is incorporated herein by reference in its entirety.

FIELD OF THE INVENTION

The present application is concerned with pharmaceutically active compounds. The disclosure provides compounds as well as their compositions and methods of use. The compounds modulate PD-1/PD-L1 protein/protein interaction and are useful in the treatment of various diseases including infectious diseases and cancer.

BACKGROUND OF THE INVENTION

The immune system plays an important role in controlling and eradicating diseases such as cancer. However, cancer cells often develop strategies to evade or to suppress the immune system in order to favor their growth. One such mechanism is altering the expression of co-stimulatory and co-inhibitory molecules expressed on immune cells (Postow et al, J. Clinical Oncology 2015, 1-9). Blocking the signaling of an inhibitory immune checkpoint, such as PD-1, has proven to be a promising and effective treatment modality.

Programmed cell death-1 (PD-1), also known as CD279, is a cell surface receptor expressed on activated T cells, natural killer T cells, B cells, and macrophages (Greenwald et al, Annu. Rev. Immunol 2005, 23:515-548; Okazaki and Honjo, Trends Immunol 2006, (4):195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, *Nat Immunol* 2007 8, 239-245; Postow et al, J. Clinical Oncol 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is upregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS2002, 99(19):12293-7; Blank et al, Cancer Res 2004, 64(3):1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7):1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-κB and AP1 pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7):1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Together, these data support the development of a therapeutic approach to block the PD-1-mediated inhibitory signaling cascade in order to augment or "rescue" T cell response. Accordingly, there is a need for new compounds that block PD-1/PD-L1 protein/protein interaction.

SUMMARY

The present disclosure provides, inter alia, a compound of Formula (I):

(I)

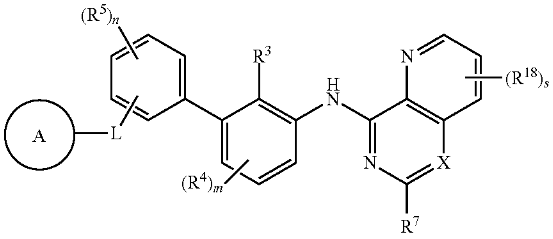

or a pharmaceutically acceptable salt or a stereoisomer thereof, wherein constituent variables are defined herein.

The present disclosure further provides a pharmaceutical composition comprising a compound disclosed herein, or a pharmaceutically acceptable salt or a stereoisomer thereof, and one or more pharmaceutically acceptable excipient or carrier.

The present disclosure further provides methods of inhibiting PD-1/PD-L1 interaction, said method comprising administering to a patient a compound disclosed herein, or a pharmaceutically acceptable salt or a stereoisomer thereof.

The present disclosure further provides methods of treating a disease or disorder associated with inhibition of PD-1/PD-L1 interaction, said method comprising administering to a patient in need thereof a therapeutically effective amount of a compound of disclosed herein, or a pharmaceutically acceptable salt or a stereoisomer thereof.

The present disclosure further provides methods of enhancing, stimulating and/or increasing the immune response in a patient, said method comprising administering to the patient in need thereof a therapeutically effective amount of a compound disclosed herein, or a pharmaceutically acceptable salt or a stereoisomer thereof.

DETAILED DESCRIPTION

I. Compounds

This disclosure provides, inter alia, a compound of Formula (I):

(I)

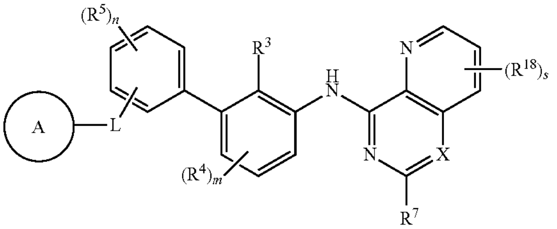

or a pharmaceutically acceptable salt or a stereoisomer thereof, wherein:

- ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from B, P, N, O and S, wherein the P, N or S atom as ring members is optionally oxidized and one or more carbon atoms as ring members are each optionally replaced by a carbonyl group; and wherein ring A is optionally substituted with 1, 2, 3, 4 or 5 $R^6$ substituents;
- L is a bond, —C(O)$NR^{13}$—, —$NR^{13}$C(O)—, —C(═S)$NR^{13}$—, —$NR^{13}$C(═S)—, —C(═$NR^{13}$)$NR^{13}$—, —$NR^{13}$C(═$NR^{13}$)—, —C(═$NOR^{13}$)$NR^{13}$—, —$NR^{13}$C(═$NOR^{13}$)—, —C(═NCN)$NR^{13}$—, —$NR^{13}$C(═NCN)—, O, —$(CR^{14}R^{15})_q$—, —$(CR^{14}R^{15})_q$—O—, —O$(CR^{14}R^{15})_q$—, —$NR^{13}$—, —$(CR^{14}R^{15})_q$—$NR^{13}$—, —$NR^{13}$—$(CR^{14}R^{15})_q$—, —CH═CH—, —C≡C—, —$SO_2NR^{13}$—, —$NR^{13}SO_2$—, —$NR^{13}SO_2NR^{13}$—, —$NR^{13}$C(O)O—, —OC(O)$NR^{13}$ or —$NR^{13}$C(O)$NR^{13}$—;
- X is N or $CR^{17}$;
- $R^3$ is methyl, halo, CN or $C_{1-4}$ haloalkyl;
- $R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}\text{ alkyl})_2$;
- $R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}\text{ alkyl})_2$;
- $R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2\ NR^aC(O)R^a$, —$P(O)R^aR^a$, —$P(O)(OR^a)(OR^a)$, —$B(OH)_2$, —$B(OR^a)_2$ and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, 3, 4 or 5 independently selected $R^b$ substituents;
- or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;
- each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}\text{ alkyl})_2$;
- $R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}\text{ alkyl})_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;
- or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 independently selected $R^q$ substituents;
- each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;
- each $R^d$ is independently selected from $C_{1-6}$ alkyl, $C_{1-6}$ haloalkyl, halo, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $C(O)NR^eS(O)_2R^e$, $OC(O)R^e$, $OC(O)NR^eR^e$, $NHR^e$, $NR^eR^e$, $NR^eC(O)R^e$, $NR^eC(=NR^e)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $S(O)_2NR^eC(O)R^e$, $NR^eS(O)_2R^e$, $NR^eS(O)_2NR^eR^e$, $-P(O)R^eR^e$, $-P(O)(OR^e)(OR^e)$, $-B(OH)_2$, $-B(OR^e)_2$ and $S(O)_2NR^eR^e$, wherein the $C_{1-6}$ alkyl, $C_{1-6}$ haloalkyl, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, $-P(O)R^cR^c$, $-P(O)(OR^c)(OR^c)$, $-B(OH)_2$, $-B(OR^c)_2$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $C(O)NR^gS(O)_2R^g$, $OC(O)R^g$, $OC(O)NR^gR^g$, $NHR^g$, $NR^gR^g$, $NR^gC(O)R^g$, $NR^gC(=NR^g)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $S(O)_2NR^gC(O)R^g$, $NR^gS(O)_2R^g$, $NR^gS(O)_2NR^gR^g$, $-P(O)R^gR^g$, $-P(O)(OR^g)(OR^g)$, $-B(OH)_2$, $-B(OR^g)_2$ and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is independently selected from $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $C(O)NR^oS(O)_2R^o$, $OC(O)R^o$, $OC(O)NR^oR^o$, $NHR^o$, $NR^oR^o$, $NR^oC(O)R^o$, $NR^oC(=NR^o)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $S(O)_2NR^oC(O)R^o$, $NR^oS(O)_2R^o$, $NR^oS(O)_2NR^oR^o$, $-P(O)R^oR^o$, $-P(O)(OR^o)(OR^o)$, $-B(OH)_2$, $-B(OR^o)_2$ and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $C(O)NR^rS(O)_2R^r$, $OC(O)R^r$, $OC(O)NR^rR^r$, $NHR^r$, $NR^rR^r$, $NR^rC(O)R^r$, $NR^rC(=NR^r)R^r$, $NR^rC$ (O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, S(O)$_2$NR$^r$C(O)R$^r$, NR$^r$S(O)$_2$R$^r$, NR$^r$S(O)$_2$NR$^r$R$^r$, —P(O)R$^r$R$^r$, —P(O)(OR$^r$)(OR$^r$), —B(OH)$_2$, —B(OR$^r$)$_2$ and S(O)$_2$NR$^r$R$^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^p$ is optionally substituted with 1, 2 or 3 independently selected R$^q$ substituents;

or any two R$^a$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected R$^h$ substituents;

each R$^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, OR$^i$, SR$^i$, NHOR$^i$, C(O)R$^i$, C(O)NR$^i$R$^i$, C(O)OR$^i$, C(O)NR$^i$S(O)$_2$R$^i$, OC(O)R$^i$, OC(O)NR$^i$R$^i$, NHR$^i$, NR$^i$R$^i$, NR$^i$C(O)R$^i$, NR$^i$C(=NR$^i$)R$^i$, NR$^i$C(O)NR$^i$R$^i$, NR$^i$C(O)OR$^i$, C(=NR$^i$)NR$^i$R$^i$, NR$^i$C(=NR$^i$)NR$^i$R$^i$, S(O)R$^i$, S(O)NR$^i$R$^i$, S(O)$_2$R$^i$, S(O)$_2$NR$^i$C(O)R$^i$, NR$^i$S(O)$_2$R$^i$, NR$^i$S(O)$_2$NR$^i$R$^i$, —P(O)R$^i$R$^i$, —P(O)(OR$^i$)(OR$^i$), —B(OH)$_2$, —B(OR$^i$)$_2$ and S(O)$_2$NR$^i$R$^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of R$^h$ are each further optionally substituted by 1, 2, or 3 independently selected R$^j$ substituents;

each R$^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, NHOR$^k$, OR$^k$, SR$^k$, C(O)R$^k$, C(O)NR$^k$R$^k$, C(O)OR$^k$, C(O)NR$^k$S(O)$_2$R$^k$, OC(O)R$^k$, OC(O)NR$^k$R$^k$, NHR$^k$, NR$^k$R$^k$, NR$^k$C(O)R$^k$, NR$^k$C(=NR$^k$)R$^k$, NR$^k$C(O)NR$^k$R$^k$, NR$^k$C(O)OR$^k$, C(=NR)NR$^k$R$^k$, NR$^k$C(=NR)NR$^k$R$^k$, S(O)R$^k$, S(O)NR$^k$R$^k$, S(O)$_2$R$^k$, S(O)$_2$NR$^k$C(O)R$^k$, NR$^k$S(O)$_2$R$^k$, NR$^k$S(O)$_2$NR$^k$R$^k$, —P(O)R$^k$R$^k$, —P(O)(OR$^k$)(OR$^k$), —B(OH)$_2$, —B(OR$^k$)$_2$ and S(O)$_2$NR$^k$R$^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$haloalkyl and $C_{1-4}$ haloalkoxy of R$^j$ are each optionally substituted with 1, 2 or 3 independently selected R$^q$ substituents;

or two R$^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two R$^c$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^e$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^g$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^i$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents, or 1, 2, or 3 independently selected R$^q$ substituents;

or any two R$^k$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents, or 1, 2, or 3 independently selected R$^q$ substituents;

or any two R$^o$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^r$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents;

each R$^i$, R$^k$, R$^o$ or R$^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of R$^i$, R$^k$, R$^o$ or R$^r$ are each optionally substituted with 1, 2 or 3 R$^q$ substituents;

each R$^q$ is independently selected from halo, OH, CN, —COOH, NH$_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of R$^q$ are each optionally substituted with 1, 2, or 3 substituents selected from halo, OH, CN, —COOH, NH$_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, or 3.

In some embodiments, provided herein is a compound of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from B, P, N, O and S, wherein the P, N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, O, —$(CR^{14}R^{15})_q$—, —$(CR^{14}R^{15})_q$—O—, —O$(CR^{14}R^{15})_q$—, —$NR^{13}$—, —$(CR^{14}R^{15})_q$—$NR^{13}$—, —$NR^{13}$—$(CR^{14}R^{15})_q$—, —CH═CH—, —C≡C—, —$SO_2NR^{13}$—, —$NR^{13}SO_2$—, —$NR^{13}SO_2NR^{13}$—, —$NR^{13}$C(O)O—, —OC(O)$NR^{13}$ or —$NR^{13}$C(O)$NR^{13}$—.

X is N or $CR^{17}$;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, —$P(O)R^aR^a$, —$P(O)(OR^a)(OR^a)$, —$B(OH)_2$, —$B(OR^a)_2$ and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 independently selected $R^q$ substituents;

each $R^a$ is independently selected from H, CN, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^r$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, —$P(O)R^eR^e$, —$P(O)(OR^e)(OR^e)$, —$B(OH)_2$, —$B(OR^e)_2$ and $S(O)_2NR^eR^e$, wherein the $C_{1-6}$ alkyl, $C_{1-6}$ haloalkyl, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, —$P(O)R^cR^c$, —$P(O)(OR^c)(OR^c)$, —$B(OH)_2$, —$B(OR^c)_2$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, $-P(O)R^gR^g$, $-P(O)(OR^g)(OR^g)$, $-B(OH)_2$, $-B(OR^g)_2$ and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is independently selected from $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, $-P(O)R^oR^o$, $-P(O)(OR^o)(OR^o)$, $-B(OH)_2$, $-B(OR^o)_2$ and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $NR^rS(O)_2R^r$, $NR^rS(O)_2NR^rR^r$, $-P(O)R^rR^r$, $-P(O)(OR^r)(OR^r)$, $-B(OH)_2$, $-B(OR^r)_2$ and $S(O)_2NR^rR^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 independently selected $R^q$ substituents;

or any two $R^a$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, $-P(O)R^iR^i$, $-P(O)(OR^i)(OR^i)$, $-B(OH)_2$, $-B(OR^i)_2$ and $S(O)_2NR^iR^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR)NR^kR^k$, $S(O)R^k$, $S(O)NR^kR^k$, $S(O)_2R^k$, $NR^kS(O)_2R^k$, $NR^kS(O)_2NR^kR^k$, $-P(O)R^kR^k$, $-P(O)(OR^k)(OR^k)$, $-B(OH)_2$, $-B(OR^k)_2$ and $S(O)_2NR^kR^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$ haloalkyl and $C_{1-4}$haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^e$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^g$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^i$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents, or 1, 2, or 3 independently selected $R^q$ substituents;

or any two $R^k$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents, or 1, 2, or 3 independently selected $R^q$ substituents;

or any two $R^o$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2, or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, or 3.

In some embodiments, provided herein is a compound of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from B, P, N, O and S, wherein the P, N or S atom as ring members is optionally oxidized and one or more carbon atoms as ring members are each optionally replaced by a carbonyl group; and wherein ring A is optionally substituted with 1, 2, 3, 4 or 5 $R^6$ substituents; L is a bond, —C(O)$NR^{13}$—, —$NR^{13}$C(O)—, O, —$(CR^{14}R^{15})_q$—, —$(CR^{14}R^{15})_q$—O—, —O$(CR^{14}R^{15})_q$—, —$NR^{13}$—, —$(CR^{14}R^{15})_q$—$NR^{13}$—, —$NR^{13}$—$(CR^{14}R^{15})_q$—, —CH═CH—, —C≡C—, —$SO_2NR^{13}$—, —$NR^{13}SO_2$—, —$NR^{13}SO_2NR^{13}$—, —$NR^{13}$C(O)O—, —OC(O)$NR^{13}$ or —$NR^{13}$C(O)$NR^{13}$—.

X is N or $CR^{17}$;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, C(O)$R^a$, C(O)$NR^aR^a$, C(O)$OR^a$, OC(O)$R^a$, OC(O)$NR^aR^a$, $NHR^a$, $NR^aR^a$, $NR^a$C(O)$R^a$, $NR^a$C(O)$OR^a$, $NR^a$C(O)$NR^aR^a$, C(═$NR^a$)$R^a$, C(═$NR^a$)$NR^aR^a$, $NR^a$C(═$NR^a$)$NR^aR^a$, $NR^a$S(O)$R^a$, $NR^a$S(O)$_2R^a$, $NR^a$S(O)$_2NR^aR^a$, S(O)$R^a$, S(O)$NR^aR^a$, S(O)$_2R^a$, —P(O)$R^aR^a$, —P(O)($OR^a$)($OR^a$), —B(OH)$_2$, —B($OR^a$)$_2$ and S(O)$_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-membered heterocycloalkyl)-$C_{1-4}$ alkyl- of $R^6$, $R^7$, $R^{17}$ and $R^{18}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —N($C_{1-4}$ alkyl)$_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 independently selected $R^q$ substituents;

each $R^a$ is independently selected from H, CN, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, —$P(O)R^eR^e$, —$P(O)(OR^e)(OR^e)$, —$B(OH)_2$, —$B(OR^e)_2$ and $S(O)_2NR^eR^e$, wherein the $C_{1-6}$ alkyl, $C_{1-6}$ haloalkyl, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2 R^c$, $NR^cS(O)_2NR^cR^c$, $S(O)R^c$, $S(O)NR^cR^c$, $S(O)_2R^c$, —$P(O)R^cR^c$, —$P(O)(OR^c)(OR^c)$, —$B(OH)_2$, —$B(OR^c)_2$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, —$P(O)R^gR^g$, —$P(O)(OR^g)(OR^g)$, —$B(OH)_2$, —$B(OR^g)_2$ and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, —$P(O)R^oR^o$, —$P(O)(OR^o)(OR^o)$, —$B(OH)_2$, —$B(OR^o)_2$ and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $NR^rS(O)_2R^r$, $NR^rS(O)_2NR^rR^r$, $—P(O)R^rR^r$, $—P(O)(OR^r)(OR^r)$, $—B(OH)_2$, $—B(OR^r)_2$ and $S(O)_2NR^rR^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 independently selected $R^q$ substituents;

or any two $R^a$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, $—P(O)R^iR^i$, $—P(O)(OR^i)(OR^i)$, $—B(OH)_2$, $—B(OR^i)_2$ and $S(O)_2NR^iR^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR)NR^kR^k$, $S(O)R^k$, $S(O)NR^kR^k$, $S(O)_2R^k$, $NR^kS(O)_2R^k$, $NR^kS(O)_2NR^kR^k$, $—P(O)R^kR^k$, $—P(O)(OR^k)(OR^k)$, $—B(OH)_2$, $—B(OR^k)_2$ and $S(O)_2NR^kR^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$ haloalkyl and $C_{1-4}$haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^e$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^g$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^i$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^k$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^o$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2, or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, or 3.

In some embodiments, provided herein is a compound of Formula (I):

(I)

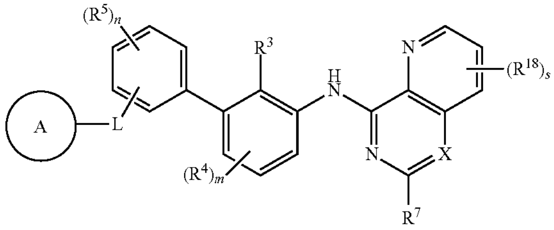

or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, O, —$(CR^{14}R^{15})_q$—, —$(CR^{14}R^{15})_q$—O—, —O$(CR^{14}R^{15})_q$—, —$NR^{13}$—, —$(CR^{14}R^{15})_q$—$NR^{13}$—, —$NR^{13}$—$(CR^{14}R^{15})_q$—, —CH═CH—, —C≡C—, —$SO_2NR^{13}$—, —$NR^{13}SO_2$—, —$NR^{13}SO_2NR^{13}$—, —$NR^{13}$C(O)O—, —OC(O)$NR^{13}$ or —$NR^{13}$C(O)$NR^{13}$—;

X is N or $CR^{17}$;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, C(O)$R^a$, C(O)$NR^aR^a$, C(O)$OR^a$, OC(O)$R^a$, OC(O)$NR^aR^a$, $NHR^a$, $NR^aR^a$, $NR^a$C(O)$R^a$, $NR^a$C(O)$OR^a$, $NR^a$C(O)$NR^aR^a$, C(═$NR^a$)$R^a$, C(═$NR^a$)$NR^aR^a$, $NR^a$C(═$NR^a$)$NR^aR^a$, $NR^a$S(O)$R^a$, $NR^aS(O)_2R^a$, $NR^aS(O)_2NR^aR^a$, S(O)$R^a$, S(O)$NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 independently selected $R^q$ substituents;

each $R^a$ is independently selected from H, CN, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, C(O)$R^e$, C(O)$NR^eR^e$, C(O)$OR^e$, OC(O)$R^e$, OC(O)$NR^eR^e$, $NHR^e$, $NR^eR^e$, $NR^e$C(O)$R^e$, $NR^e$C(O)$NR^eR^e$, $NR^e$C(O)$OR^e$, C(═$NR^e$)$NR^eR^e$, $NR^e$C(═$NR^e$)$NR^eR^e$, $NR^e$C(═NOH)$NR^eR^e$, $NR^e$C(═NCN)$NR^eR^e$, S(O)$R^e$, S(O)$NR^eR^e$, $S(O)_2R^e$, $NR^eS(O)_2R^e$, $NR^eS(O)_2NR^eR^e$, and $S(O)_2NR^eR^e$, wherein the $C_{1-6}$ alkyl, $C_{1-6}$ haloalkyl, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of $R^f$ are each optionally substituted with 1, 2, 3, 4, or independently selected $R^n$ substituents;

each $R^n$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $NR^rS(O)_2R^r$, $NR^rS(O)_2NR^rR^r$ and $S(O)_2NR^rR^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 independently selected $R^q$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 independently selected $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(═NR$^k$)NR$^k$R$^k$, NR$^k$C(═NR)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$ haloalkyl and $C_{1-4}$haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the nitrogen atom to which they are attached form a4-, 5-, 6-, 7-, 8-, 9- or 10-membered heterocycloalkyl group optionally substituted with 1, 2, or 3 independently selected $R^h$ substituents;

or any two $R^e$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^g$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^i$ substituents together with the nitrogen atom to which they are attached form a4-, 5-, 6-, 7-, 8-, 9- or 10-membered heterocycloalkyl group optionally substituted with 1, 2, or 3 independently selected $R^h$ substituents, or 1, 2, or 3 independently selected $R^q$ substituents;

or any two $R^k$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents, or 1, 2, or 3 independently selected $R^q$ substituents;

or any two $R^o$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 $R^q$ substituents;

each $R^q$ is independently selected from halo, OH, CN, —COOH, NH$_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2, or 3 substituents selected from halo, OH, CN, —COOH, NH$_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, or 3.

In some embodiments, provided herein is a compound of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)NR$^{13}$—, —NR$^{13}$C(O)—, O, —(CR$^{14}$R$^{15}$)$_q$—, —(CR$^{14}$R$^{15}$)$_q$—O—, —O(CR$^{14}$R$^{15}$)$_q$ —, —NR$^{13}$—, —(CR$^{14}$R$^{15}$)$_q$—NR$^{13}$—, —NR$^{13}$—(CR$^{14}$R$^{15}$)$_q$—, —CH═CH—, —C≡C—, —SO$_2$NR$^{13}$—, —NR$^{13}$SO$_2$—, —NR$^{13}$SO$_2$NR$^{13}$—, —NR$^{13}$C(O)O—, —OC(O)NR$^{13}$ or —NR$^{13}$C(O)NR$^{13}$—.

X is N or CR$^{17}$;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl or —N($C_{1-4}$ alkyl)$_2$;

$R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(═NR$^a$)R$^a$, C(═NR$^a$)NR$^a$R$^a$, NR$^a$C(═NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, and S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 independently selected $R^q$ substituents;

each $R^a$ is independently selected from H, CN, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-6}$ alkyl, $C_{1-6}$ haloalkyl, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2 R^c$, $NR^cS(O)_2NR^cR^c$, $S(O)R^c$, $S(O)NR^cR^c$, $S(O)_2 R^c$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of $R^f$ are each optionally substituted with 1, 2, 3, 4, or independently selected $R^n$ substituents;

each $R^n$ is independently selected from $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, and S(O)$_2$NR$^o$R$^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of R$^n$ are each optionally substituted with 1, 2 or 3 independently selected R$^q$ substituents;

each R$^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^g$ are each optionally substituted with 1, 2, or 3 independently selected R$^p$ substituents;

each R$^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ and S(O)$_2$NR$^r$R$^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^p$ is optionally substituted with 1, 2 or 3 independently selected R$^q$ substituents;

or any two R$^a$ substituents together with the nitrogen atom to which they are attached form a 4-, 5-, 6-, 7-, 8-, 9- or 10-membered heterocycloalkyl group optionally substituted with 1, 2 or 3 independently selected R$^h$ substituents;

each R$^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, OR$^i$, SR$^i$, NHOR$^i$, C(O)R$^i$, C(O)NR$^i$R$^i$, C(O)OR$^i$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR$^i$)NR$^i$R$^i$, S(O)R$^i$, S(O)NR$^i$R$^i$, S(O)$_2$R$^i$, NR$^i$S(O)$_2$R$^i$, NR$^i$S(O)$_2$NR$^i$R$^i$, and S(O)$_2$NR$^i$R$^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of R$^h$ are each further optionally substituted by 1, 2, or 3 independently selected R$^j$ substituents;

each R$^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$ haloalkyl and $C_{1-4}$haloalkoxy of R$^j$ are each optionally substituted with 1, 2 or 3 independently selected R$^q$ substituents;

or two R$^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two R$^c$ substituents together with the nitrogen atom to which they are attached form a4-, 5-, 6-, 7-, 8-, 9- or 10-membered heterocycloalkyl group optionally substituted with 1, 2, or 3 independently selected R$^h$ substituents;

or any two R$^c$ substituents together with the nitrogen atom to which they are attached form a4-, 5-, 6-, 7-, 8-, 9- or 10-membered heterocycloalkyl group optionally substituted with 1, 2, or 3 independently selected R$^h$ substituents;

or any two R$^g$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^i$ substituents together with the nitrogen atom to which they are attached form a4-, 5-, 6-, 7-, 8-, 9- or 10-membered heterocycloalkyl group optionally substituted with 1, 2, or 3 independently selected R$^h$ substituents;

or any two R$^k$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^o$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^r$ substituents together with the nitrogen atom to which they are attached form a 4-, 5-, 6-, 7-, 8-, 9- or 10-membered heterocycloalkyl group optionally substituted with 1, 2, or 3 independently selected R$^h$ substituents;

each R$^i$, R$^k$, R$^o$ or R$^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2, or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, or 3.

In some embodiments, provided herein is a compound of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-14}$ cycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, O, —$(CR^{14}R^{15})_q$—, —$(CR^{14}R^{15})_q$—O—, —O$(CR^{14}R^{15})_q$—, —$NR^{13}$—, —$(CR^{14}R^{15})_q$—$NR^{13}$—, —$NR^{13}$—$(CR^{14}R^{15})_q$—, —CH═CH—, —C≡C—, —$SO_2NR^{13}$—, —$NR^{13}SO_2$—, —$NR^{13}SO_2NR^{13}$—, —$NR^{13}$C(O)O—, —OC(O)$NR^{13}$ or —$NR^{13}$C(O)$NR^{13}$—.

X is N or $CR^{17}$;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, C(O)$R^a$, C(O)$NR^aR^a$, C(O)$OR^a$, OC(O)$R^a$, OC(O)$NR^aR^a$, $NHR^a$, $NR^aR^a$, $NR^a$C(O)$R^a$, $NR^a$C(O)$OR^a$, $NR^a$C(O)$NR^aR^a$, C(═$NR^a$)$R^a$, C(═$NR^a$)$NR^aR^a$, $NR^a$C(═$NR^a$)$NR^aR^a$, $NR^a$S(O)$R^a$, $NR^a$S(O)$_2R^a$, $NR^a$S(O)$_2NR^aR^a$, S(O)$R^a$, S(O)$NR^aR^a$, S(O)$_2R^a$, and S(O)$_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, 3, 4 or 5 independently selected $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —N($C_{1-4}$ alkyl)$_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 independently selected $R^q$ substituents;

each $R^a$ is independently selected from H, CN, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, C(O)$R^e$, C(O)$NR^eR^e$, C(O)$OR^e$, OC(O)$R^e$, OC(O)$NR^eR^e$, $NHR^e$, $NR^eR^e$, $NR^e$C(O)$R^e$, $NR^e$C(O)$NR^eR^e$, $NR^e$C(O)$OR^e$, C(═$NR^e$)$NR^eR^e$, $NR^e$C(═$NR^e$)$NR^eR^e$, $NR^e$C(═NOH)$NR^eR^e$, $NR^e$C(═NCN)$NR^eR^e$, S(O)$R^e$, S(O)$NR^eR^e$, S(O)$_2R^e$, $NR^e$S(O)$_2R^e$, $NR^e$S(O)$_2NR^eR^e$, and S(O)$_2NR^eR^e$, wherein the $C_{1-6}$ alkyl, $C_{1-6}$ haloalkyl, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of $R^f$ are each optionally substituted with 1, 2, 3, 4, or independently selected $R^n$ substituents;

each $R^n$ is independently selected from $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^9$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $NR^rS(O)_2R^r$, $NR^rS(O)_2NR^rR^r$ and $S(O)_2NR^rR^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 independently selected $R^q$ substituents;

or any two $R^a$ substituents together with the nitrogen atom to which they are attached form a4-, 5-, 6-, 7-, 8-, 9- or 10-membered heterocycloalkyl group optionally substituted with 1, 2 or 3 independently selected $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$ haloalkyl and $C_{1-4}$haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the nitrogen atom to which they are attached form a4-, 5-, 6-, 7-, 8-, 9- or 10-membered heterocycloalkyl group optionally substituted with 1, 2, or 3 independently selected $R^h$ substituents;

or any two $R^c$ substituents together with the nitrogen atom to which they are attached form a4-, 5-, 6-, 7-, 8-, 9- or 10-membered heterocycloalkyl group optionally substituted with 1, 2, or 3 independently selected $R^h$ substituents;

or any two $R^g$ substituents together with the nitrogen atom to which they are attached form a4-, 5-, 6-, 7-, 8-, 9- or 10-membered heterocycloalkyl group optionally substituted with 1, 2, or 3 independently selected $R^h$ substituents;

or any two $R^i$ substituents together with the nitrogen atom to which they are attached form a4-, 5-, 6-, 7-, 8-, 9- or 10-membered heterocycloalkyl group optionally substituted with 1, 2, or 3 independently selected $R^q$ substituents;

or any two $R^k$ substituents together with the nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^o$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2, or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, or 3.

In some embodiments, provided herein is a compound of Formula (I), or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-10}$ cycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 independently selected $R^6$ substituents;

L is a bond, —C(O)$NR^{13}$—, —$NR^{13}$C(O)—, O, —$(CR^{14}R^{15})_q$—, —$(CR^{14}R^{15})_q$—O—, —O$(CR^{14}R^{15})_q$ —, —$NR^{13}$—, —$(CR^{14}R^{15})_q$—$NR^{13}$—, —$NR^{13}$—$(CR^{14}R^{15})_q$, —CH═CH—, —C≡C—, —$SO_2NR^{13}$—, —$NR^{13}SO_2$—, —$NR^{13}SO_2NR^{13}$—, —$NR^{13}$C(O)O— or —$NR^{13}$C(O)$NR^{13}$—;

X is N or $CR^{17}$;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl or —N($C_{1-4}$ alkyl)$_2$;

$R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, 3, 4 or 5 independently selected $R^b$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl and —N($C_{1-4}$ alkyl)$_2$;

$R^{14}$ and $R^{15}$ are each independently selected from H, halo, CN, OH, —COOH, $C_{1-4}$ alkyl, $C_{1-4}$ alkoxy, —NH$C_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 independently selected $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^a$ are each optionally substituted with 1, 2, 3, 4, or 5 independently selected $R^d$ substituents;

each $R^d$ is independently selected from $C_{1-6}$ alkyl, $C_{1-6}$ haloalkyl, halo, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, and S(O)$_2$NR$^e$R$^e$, wherein the $C_{1-6}$ alkyl, $C_{1-6}$ haloalkyl, $C_{6-10}$ aryl, 5-14 membered heteroaryl, $C_{3-10}$ cycloalkyl, 4-14 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^q$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^q$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$ R$^c$, NR$^c$S(O)$_2$NR$^c$R$^c$, S(O)R$^c$, S(O)NR$^c$R$^c$, S(O)$_2$ R$^c$ and S(O)$_2$NR$^c$R$^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 independently selected $R^d$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 independently selected $R^h$ substituents;

or any two $R^c$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^e$ substituents together with the nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, OR$^i$, SR$^i$, NHOR$^i$, C(O)R$^i$, C(O)NR$^i$R$^i$, C(O)OR$^i$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR$^i$)NR$^i$R$^i$, S(O)R$^i$, S(O)NR$^i$R$^i$, S(O)$_2$R$^i$, NR$^i$S(O)$_2$R$^i$, NR$^i$S(O)$_2$NR$^i$R$^i$, and S(O)$_2$NR$^i$R$^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C({=}NR^k)NR^kR^k$, $NR^kC({=}NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$, wherein the $C_{1-4}$ alkyl, $C_{3-6}$ cycloalkyl, $C_{6-10}$ aryl, 5- or 6-membered heteroaryl, 4-6 membered heterocycloalkyl, $C_{2-4}$ alkenyl, $C_{2-4}$ alkynyl, $C_{1-4}$haloalkyl, and $C_{1-4}$haloalkoxy of $R_j$ are each optionally substituted with 1, 2 or 3 independently selected $R^q$ substituents;

each of $R^i$ and $R^k$ is independently selected from H, $C_{1-4}$ alkyl, $C_{3-6}$ cycloalkyl, $C_{6-10}$ aryl, or 6-membered heteroaryl, 4-7 membered heterocycloalkyl, $C_{1-6}$ haloalkyl, $C_{1-6}$ haloalkoxy, $C_2$-4 alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$ or $R^k$ are each optionally substituted with 1, 2 or 3 independently selected $R^q$ substituents;

each $R^q$ is independently selected from halo, OH, CN, —COOH, $NH_2$, —NH—$C_{1-6}$ alkyl, —N($C_{1-6}$ alky$)_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2, or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, or 3.

In some embodiments, provided herein is a compound of Formula (I), or a pharmaceutically acceptable salt or a stereoisomer thereof, wherein:

ring A is 5- to 10-membered heteroaryl, 4- to 11-membered heterocycloalkyl, $C_{6-10}$ aryl or $C_{3-10}$ cycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, O, —$(CR^{14}R^{15})_q$—, —$(CR^{14}R^{15})_q$—O—, —O$(CR^{14}R^{15})_q$—, —$NR^{13}$—, —$(CR^{14}R^{15})_q$—$NR^{13}$—, —$NR^{13}$—$(CR^{14}R^{15})_q$—, —CH═CH—, —C≡C—, —$SO_2NR^{13}$—, —$NR^{13}SO_2$—, —$NR^{13}$C(O)O— or —$NR^{13}$C(O)$NR^{13}$—;

X is N or $CR^{17}$;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl$)_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl$)_2$;

$R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C({=}NR^a)R^a$, $C({=}NR^a)NR^aR^a$, $NR^aC({=}NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, 3, 4 or 5 $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —N($C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —N($C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C({=}NR^e)NR^eR^e$, $NR^eC({=}NR^e)NR^eR^e$, $NR^eC({=}NOH)NR^eR^e$, $NR^eC({=}NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C({=}NR^c)NR^cR^c$, $NR^cC({=}NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C({=}NR^g)NR^gR^g$, $NR^gC({=}NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of $R^f$ are each optionally substituted with 1, 2, 3, 4, or 5 $R^n$ substituents;

each $R^n$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C({=}NR^o)NR^oR^o$, $NR^oC({=}NR^o)NR^oR^o$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^rC(O)OR^r$, $C({=}NR^r)NR^rR^r$, $NR^rC({=}NR^r)NR^rR^r$, $NR^rC({=}NOH)NR^rR^r$, $NR^rC({=}NCN)NR^rR^r$, $S(O)R^r$, $S(O)NR^rR^r$, $S(O)_2R^r$, $NR^rS(O)_2R^r$, $NR^rS(O)_2NR^rR^r$ and $S(O)_2NR^rR^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 $R^q$ substituents;

or any two $R^a$ substituents together with the nitrogen atom to which they are attached form a4-, 5-, 6-, 7-, 8-, 9- or 10-membered heterocycloalkyl group optionally substituted with 1, 2 or 3 $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR)NR^iR^i$, $NR^iC(=NR)NR^iR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$, wherein the $C_{1-4}$ alkyl, $C_{3-6}$ cycloalkyl, $C_{6-10}$ aryl, 5- or 6-membered heteroaryl, 4-6 membered heterocycloalkyl, $C_{2-4}$ alkenyl, $C_{2-4}$ alkynyl, $C_{1-4}$haloalkyl, and $C_{1-4}$haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents, or 1, 2, or 3 independently selected $R^q$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents, or 1, 2, or 3 independently selected $R^q$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents;

or any two $R^r$ substituents together with the nitrogen atom to which they are attached form a 4-, 5-, 6-, or 7-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2, or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript s is an integer of 1, 2, or 3.

In some embodiments, provided herein is a compound of Formula (I) or a pharmaceutically acceptable salt or a stereoisomer thereof, wherein:

ring A is 5- to 10-membered heteroaryl, 4- to 11-membered heterocycloalkyl, $C_{6-10}$ aryl or $C_{3-10}$ cycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, 4 or 5 $R^6$ substituents;

L is a bond, —C(O)$NR^{13}$—, —$NR^{13}$C(O)—, O, —$(CR^{14}R^{15})_q$, —$(CR^{14}R^{15})_q$—O—, —O$(CR^{14}R^{15})_q$, —$NR^{13}$—, —$(CR^{14}R^{15})_q$—$NR^{13}$—, —$NR^{13}$—$(CR^{14}R^{15})_q$, —CH═CH—, —C≡C—, —$SO_2NR^{13}$—, $NR^{13}SO_2$, —$NR^{13}$C(O)O— or —$NR^{13}$C(O)$NR^{13}$—;

X is N or $CR^{17}$;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$ are each optionally substituted with 1, 2, 3, 4 or 5 $R^b$ substituents;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 $R^q$ substituents;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR)NR^cR^c$, $NR^cC(=NR)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of $R^f$ are each optionally substituted with 1, 2, 3, 4, or 5 $R^n$ substituents;

each $R^n$ is independently selected from $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, and S(O)$_2$NR$^o$R$^o$, wherein the $C_{1-4}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^9$ are each optionally substituted with 1, 2, or 3 $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ and S(O)$_2$NR$^r$R$^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 $R^q$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 $R^h$ substituents;

each $R^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, OR$^i$, SR$^i$, NHOR$^i$, C(O)R$^i$, C(O)NR$^i$R$^i$, C(O)OR$^i$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR)NR$^i$R$^i$, S(O)R$^i$, S(O)NR$^i$R$^i$, S(O)$_2$R$^i$, NR$^i$S(O)$_2$R$^i$, NR$^i$S(O)$_2$NR$^i$R$^i$, and S(O)$_2$NR$^i$R$^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$, wherein the $C_{1-4}$ alkyl, $C_{3-6}$ cycloalkyl, $C_{6-10}$ aryl, 5- or 6-membered heteroaryl, 4-6 membered heterocycloalkyl, $C_{2-4}$ alkenyl, $C_{2-4}$ alkynyl, $C_{1-4}$haloalkyl, and $C_{1-4}$haloalkoxy of $R^j$ are each optionally substituted with 1, 2 or 3 independently selected $R^q$ substituents; or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents, or 1, 2, or 3 independently selected $R^q$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents, or 1, 2, or 3 independently selected $R^q$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents;

or any two $R^r$ substituents together with the nitrogen atom to which they are attached form a 4-, 5-, 6-, or 7-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^p$ are each optionally substituted with 1, 2 or 3 $R^q$ substituents;

each $R^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2, or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

the subscript p is an integer of 1, 2, 3 or 4;

each subscript q is independently an integer of 1, 2, 3 or 4; and the subscript s is an integer of 1, 2, or 3.

In some embodiments, any two $R^i$ substituents together with the nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^k$ substituents together with the nitrogen atom to which they are attached form a 4-, 5-, 6-, 7-, 8-, 9- or 10-membered heterocycloalkyl group optionally substituted with 1, 2, or 3 independently selected $R^q$ substituents.

In some embodiments, provided herein is a compound of Formula (I) or a pharmaceutically acceptable salt or a stereoisomer thereof, wherein (1) when L is —C(O)NH—, ring A is not 4,5,6,7-tetrahydro-1H-imidazo[4,5-c]pyridin-2-yl; (2) when L is a bond, ring A is not [1,2,4]triazolo[1,5-a]pyridin-2-yl; (3) when L is a bond, ring A is not 2-benzoxazolyl; and (4) when L is —C(O)NH—, ring A is not 2-pyridyl.

In some embodiments, provided herein is a compound of Formula (I) or a pharmaceutically acceptable salt or a stereoisomer thereof, wherein (1) when L is —C(O)NH—, ring A is not 4,5,6,7-tetrahydro-1H-imidazo[4,5-c]pyridin-2-yl; (2) when L is a bond, ring A is not [1,2,4]triazolo[1,5-a]pyridin-2-yl; (3) when L is a bond, ring A is not 2-benzoxazolyl; or (4) when L is —C(O)NH—, ring A is not 2-pyridyl.

In some embodiments, provided herein is a compound of Formula (Ia):

(Ia)

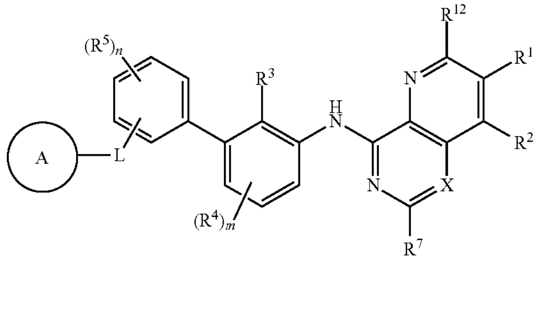

or a pharmaceutically acceptable salt or a stereoisomer thereof, wherein:

$R^{17}$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl or —N($C_{1-4}$ alkyl)$_2$, wherein the $C_{1-4}$ alkyl and $C_{1-4}$ alkoxy are each optionally substituted with 1 or 2 substituents independently selected from CN, halo and —C(O)$NH_2$;

one of $R^1$ and $R^2$ is —$(CR^8R^9)_p$—$NR^{10}R^{11}$ and the other is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl or —N($C_{1-4}$ alkyl)$_2$, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, OH, —COOH, —C(O)$NH_2$, $NH_2$, —NH$C_{1-4}$ alkyl and —N($C_{1-4}$ alkyl)$_2$;

$R^7$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl or —N($C_{1-4}$ alkyl)$_2$, wherein the $C_{1-4}$ alkyl and $C_{1-4}$ alkoxy are each optionally substituted with 1 or 2 substituents independently selected from CN, halo or —C(O)$NH_2$;

$R^8$ and $R^9$ are each independently selected from H, halo, CN, OH, —COOH, $C_{1-4}$ alkyl, $C_{1-4}$ alkoxy, —NH$C_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^8$ or $R^9$ are each optionally substituted with 1, 2 or 3 independently selected $R^q$ substituents;

or $R^8$ and $R^9$ taken together with the carbon atom to which they are attached form 3-, 4-, 5- or 6-membered cycloalkyl or 4-, 5-, 6- or 7-membered heterocycloalkyl, each of which is optionally substituted with 1 or 2 $R^q$ substituents;

or $R^8$ and $R^{10}$ taken together with the atoms to which they are attached form 4-, 5-, 6- or 7-membered heterocycloalkyl, having zero to one additional heteroatoms as ring members selected from O, N or S, wherein the 4-, 5-, 6- or 7-membered heterocycloalkyl formed by $R^8$ and $R^{10}$ are each optionally substituted with 1 or 2 $R^q$ substituents;

$R^{10}$ and $R^{11}$ are each independently selected from H, $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-6}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, —C(O)$R^g$, —C(O)O$R^g$, —C(O)$NR^gR^g$, —$SO_2R^g$ and —$SO_2NR^gR^g$, wherein the $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-6}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^{10}$ or $R^{11}$ are each optionally substituted with 1, 2, or 3 independently selected $R^d$ substituents;

or $R^{10}$ and $R^{11}$ taken together with the nitrogen atom to which they are attached form 4-, 5-, 6-, 7-, 8-, 9-, 10-, or 11-membered heterocycloalkyl, wherein the 4-11 membered heterocycloalkyl is each optionally substituted with 1, 2 or 3 $R^f$ substituents;

$R^{12}$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —NH$C_{1-4}$ alkyl or —N($C_{1-4}$ alkyl)$_2$; and the subscript p is an integer of 1, 2, 3 or 4.

In some embodiments, provided herein is a compound of Formula (Ia), or a pharmaceutically acceptable salt or a stereoisomer thereof, wherein:

$R^{17}$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$, wherein the $C_{1-4}$ alkyl and $C_{1-4}$ alkoxy are each optionally substituted with 1 or 2 substituents independently selected from CN, halo and —$C(O)NH_2$;

one of $R^1$ and $R^2$ is —$(CR^8R^9)_p$—$NR^{10}R^{11}$ and the other is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, OH, —COOH, —$C(O)NH_2$, $NH_2$, —$NHC_{1-4}$ alkyl and —$N(C_{1-4}$ alkyl$)_2$;

$R^7$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$, wherein the $C_{1-4}$ alkyl and $C_{1-4}$ alkoxy are each optionally substituted with 1 or 2 substituents independently selected from CN, halo or —$C(O)NH_2$;

$R^8$ and $R^9$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$haloalkoxy, $C_{3-6}$ cycloalkyl, phenyl, 5-6 membered heteroaryl and 4-6 membered heterocycloalkyl of $R^8$ or $R^9$ are each optionally substituted with 1, 2 or 3 independently selected $R^q$ substituents;

or $R^8$ and $R^9$ taken together with the carbon atom to which they are attached form 3-, 4-, 5- or 6-membered cycloalkyl or 4-, 5-, 6- or 7-membered heterocycloalkyl, each of which is optionally substituted with 1 or 2 $R^q$ substituents;

or $R^8$ and $R^{10}$ taken together with the atoms to which they are attached form 4-, 5-, 6- or 7-membered heterocycloalkyl, having zero to one additional heteroatoms as ring members selected from O, N or S, wherein the 4-, 5-, 6- or 7-membered heterocycloalkyl formed by R$ and $R^{10}$ are each optionally substituted with 1 or 2 $R^q$ substituents;

$R^{10}$ and $R^{11}$ are each independently selected from H, $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-6}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, —$C(O)R^g$, —$C(O)OR^g$, —$C(O)NR^gR^g$, —$SO_2R^g$ and —$SO_2NR^gR^g$, wherein the $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-6}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^{10}$ or $R^{11}$ are each optionally substituted with 1, 2, or 3 independently selected $R^d$ substituents;

or $R^{10}$ and $R^{11}$ taken together with the nitrogen atom to which they are attached form 4-, 5-, 6-, 7-, 8-, 9-, 10-, or 11-membered heterocycloalkyl, wherein the 4-11 membered heterocycloalkyl is each optionally substituted with 1, 2 or 3 $R^f$ substituents; and $R^{12}$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$.

In some embodiments, the compound provided herein is a compound having Formula (II):

(II)

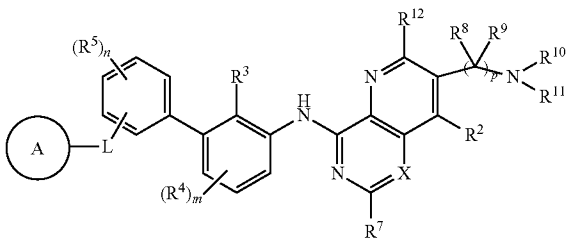

or a pharmaceutically acceptable salt or a stereoisomer thereof.

In some embodiments, the compound provided herein is a compound having Formula (IIa):

(IIa)

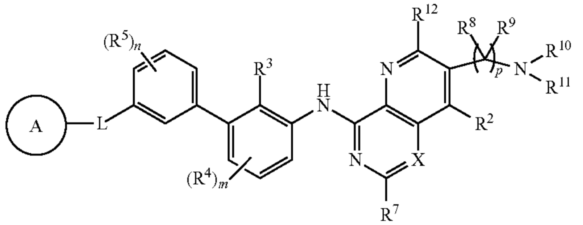

or a pharmaceutically acceptable salt or a stereoisomer thereof.

In some embodiments, the compound provided herein is a compound having Formula (IIa-1):

(IIa-1)

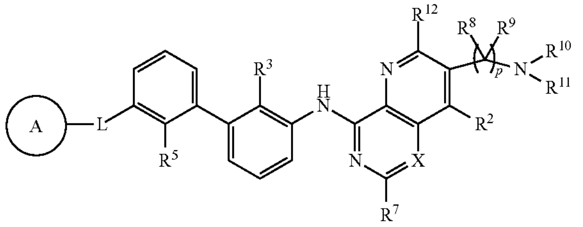

or a pharmaceutically acceptable salt or a stereoisomer thereof, wherein:

ring A is 5- to 10-membered heteroaryl, 4- to 11-membered heterocycloalkyl or $C_{6-10}$ aryl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2 or 3 $R^6$ substituents; L is a bond, —C(O)NH—, —NH— or —$OCH_2$—, wherein the carbonyl group in the —C(O)NH— linkage or the oxygen atom in the $—OCH_2—$ linkage is attached to ring A; and X is CH or N.

In some embodiments, the compound provided herein is a compound having Formula (IIa-2):

(IIa-2)

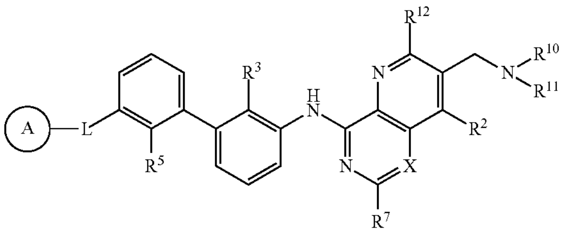

or a pharmaceutically acceptable salt or a stereoisomer thereof.

In some embodiments, the compound provided herein is a compound having Formula (IIb):

(IIb)

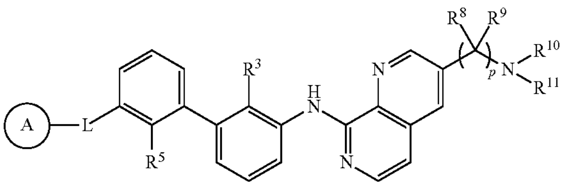

or a pharmaceutically acceptable salt or a stereoisomer thereof.

In some embodiments, the compound provided herein is a compound having Formula (IIc):

(IIc)

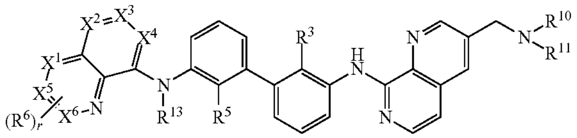

or a pharmaceutically acceptable salt or a stereoisomer thereof, wherein:

$X^1$, $X^2$, $X^3$, $X^4$, $X^5$ and $X^6$ are each independently N or CH, with the proviso that $X^1$, $X^5$ and $X^6$ are not simultaneously N;

$R^{13}$ is H or $C_{1-4}$ alkyl; and the subscript r is an integer of 1, 2 or 3.

In some embodiments, the compound provided herein is a compound having Formula (IIc-1):

(IIc-1)

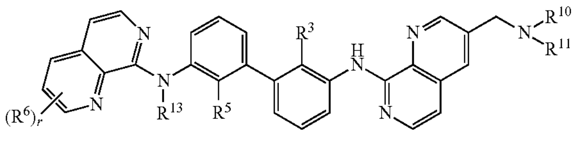

or a pharmaceutically acceptable salt or a stereoisomer thereof.

In some embodiments, $R^{13}$ is H.

In some embodiments, the compound provided herein is a compound having Formula (IId):

(IId)

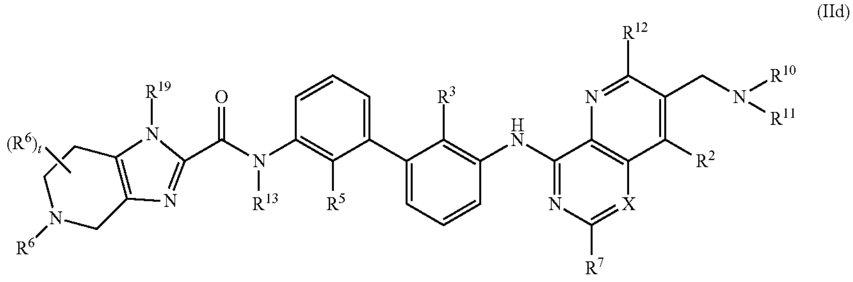

or a pharmaceutically acceptable salt or a stereoisomer thereof, wherein:

$R^{13}$ is H or $C_{1-4}$ alkyl;

$R^{19}$ is H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, or (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^{18}$ are each optionally substituted with 1, 2, or 3 $R^b$ substituents; and the subscript t is an integer of 0, 1 or 2.

In some embodiments, the compound provided herein is a compound having Formula (IId-1):

(IId-1)

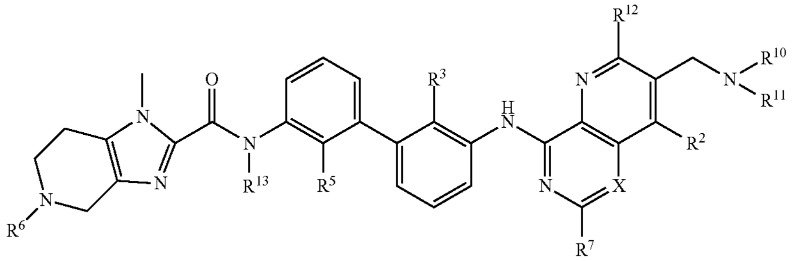

or a pharmaceutically acceptable salt or a stereoisomer thereof.

In some embodiments, the compound provided herein is a compound having Formula (IIe):

(IIe)

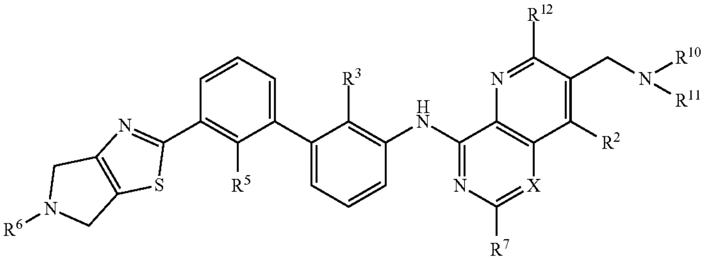

or a pharmaceutically acceptable salt or a stereoisomer thereof.

In some embodiments, the compound provided herein is a compound having Formula (IIf):

(IIf)

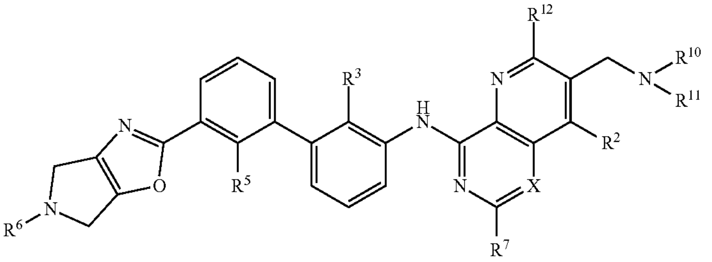

or a pharmaceutically acceptable salt or a stereoisomer thereof.

In some embodiments, the compound provided herein is a compound having Formula (III):

(III)

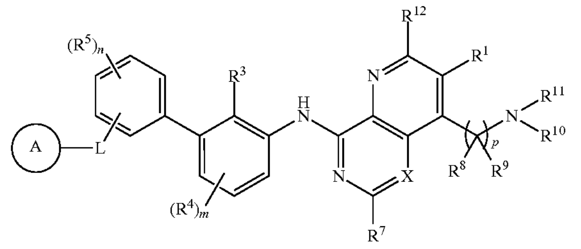

or a pharmaceutically acceptable salt or a stereoisomer thereof.

In some embodiments, the compound provided herein is a compound having Formula (IIIa):

(IIIa)

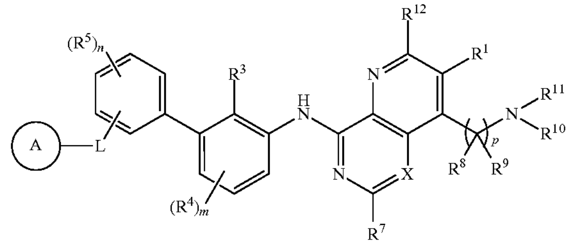

or a pharmaceutically acceptable salt or a stereoisomer thereof.

In some embodiments, the compound provided herein is a compound having Formula (IIb):

(IIIb)

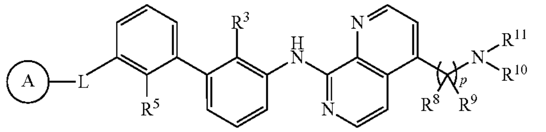

or a pharmaceutically acceptable salt or a stereoisomer thereof.

In some embodiments, provided herein are compounds having Formula (IV):

(IV)

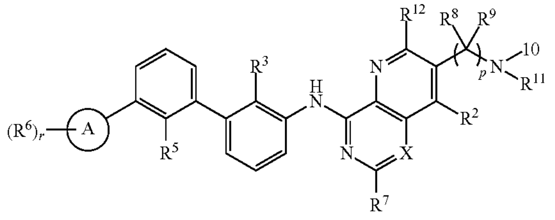

or a pharmaceutically acceptable salt or a stereoisomer thereof, wherein the subscript r is 1, 2, 3, 4 or 5. In some embodiments, X is N or CH. In one embodiment, ring A is pyridyl, for example, 2-pyridyl. In some embodiments, the subscript n is 0, 1 or 2 and each $R^5$ is independently $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$. In certain instances, $R^5$ is halo or $C_{1-4}$ alkyl. In some embodiments, the subscript m is 0. In some embodiments, the subscript r is 1 or 2. In some embodiments, $R^{12}$ is H, $C_{1-4}$ alkyl, $C_{1-4}$ alkoxy, $C_{1-4}$ haloalkyl, $C_{1-4}$ haloalkoxy, CN, halo, —COOH, $NH_2$, —$NHC_{1-4}$ alkyl or —$N(C_{1-4}$ alkyl$)_2$. In one embodiment, $R^2$ is H. In some embodiments, the subscript p is 1 and $R^8$ and $R^9$ are each H. In one embodiment, $R^{10}$ is H. In some embodiments, $R^8$ and $R^{10}$ taken together form 4- to 6-membered heterocycloalkyl, optionally substituted with 1 or 2 $R^q$ substituents. In some embodiments, $R^{10}$ and $R^{11}$ taken together form 4- to 6-membered heterocycloalkyl, optionally substituted with 1 or 2 $R^q$ substituents.

In some embodiments, provided herein are compounds having Formula (V):

(V)

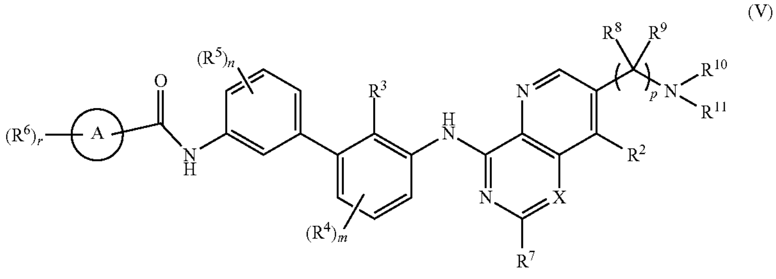

or a pharmaceutically acceptable salt or a stereoisomer thereof, wherein the subscript r is 1, 2, 3, 4 or 5, the other variables of Formula (V) are as defined in any embodiment disclosed herein. In some embodiments, the subscript r is 1 or 2.

In some embodiments, provided herein are compounds having Formula (VI):

(VI)

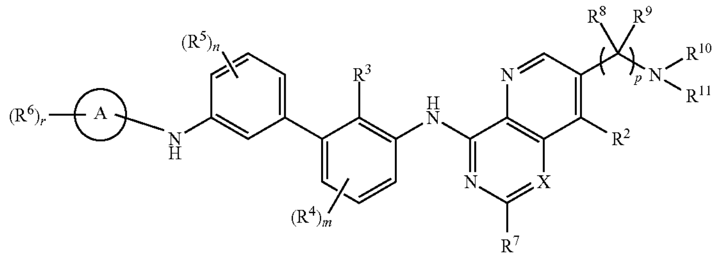

or a pharmaceutically acceptable salt or a stereoisomer thereof, wherein the subscript r is 1, 2, 3, 4 or 5, the other variables of Formula (VI) are as defined in any embodiment disclosed herein. In some embodiments, the subscript r is 1 or 2.

In some embodiments, provided herein are compounds having Formula (VIIa) or (VIIb):

(VIIa)

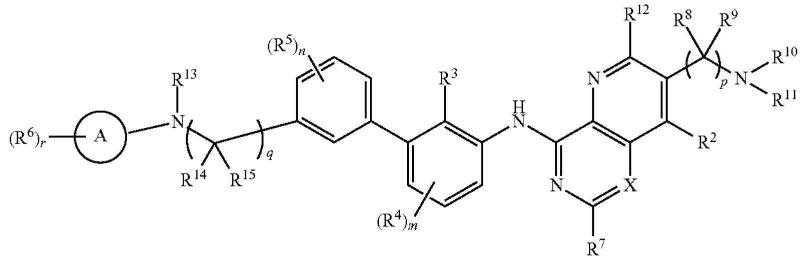

(VIIb)

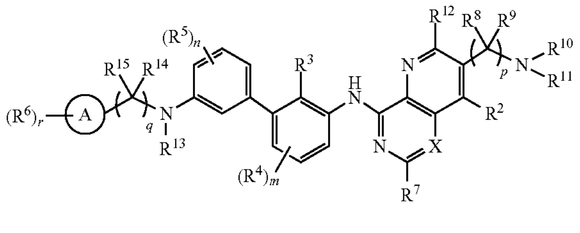

or a pharmaceutically acceptable salt or a stereoisomer thereof, wherein the subscript r is 1, 2, 3, 4 or 5, the other variables of Formula (VIIa) or (VIIb) are as defined in any embodiment disclosed herein. In some embodiments, the subscript r is 1 or 2.

In some embodiments, provided herein are compounds having Formula (VIIIa) or (VIIIb):

(VIIIa)

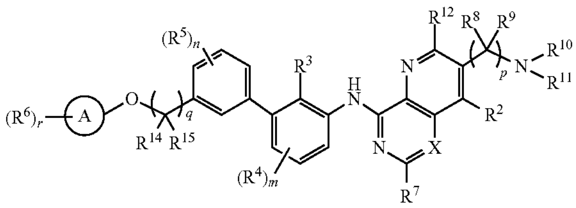

(VIIIb)

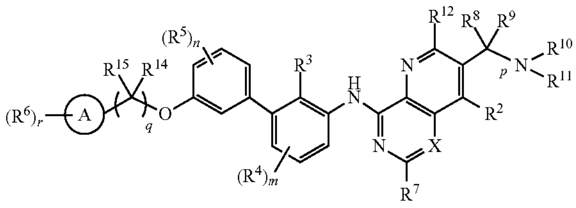

or a pharmaceutically acceptable salt or a stereoisomer thereof, wherein the subscript r is 1, 2, 3, 4 or 5, the other variables of Formula (VIIIa) or (VIIIb) are as defined in any embodiment disclosed herein. In some embodiments, the subscript r is 1 or 2.

In some embodiments, ring A is 5- to 14-membered heteroaryl, 4- to 14-membered heterocycloalkyl or $C_{6-10}$ aryl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, 3, or 4 $R^6$ substituents. In some embodiments, ring A is 5- to 14-membered heteroaryl or 4- to 14-membered heterocycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^6$ substituents. In some embodiments, ring A is 5- to 14-membered heteroaryl, wherein the 5- to 14-membered heteroaryl has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^6$ substituents. In some embodiments, ring A is 4- to 14-membered heterocycloalkyl, wherein the 4- to 14-membered heterocycloalkyl has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^6$ substituents.

In some embodiments, ring A is selected from:

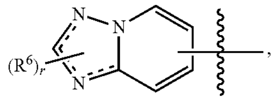,
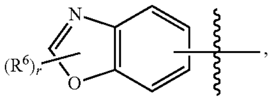,
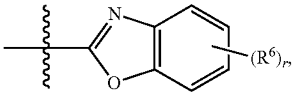,
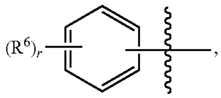,
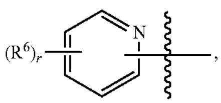,
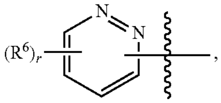,
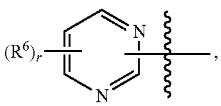,
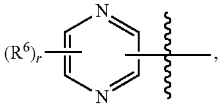,
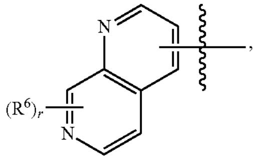,
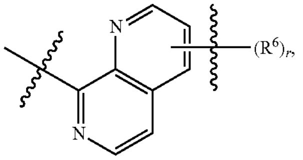,
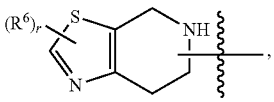,
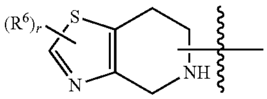, -continued

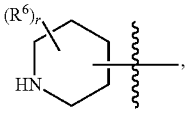,
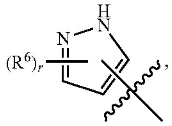,
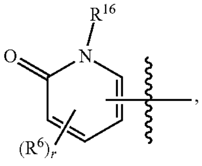,
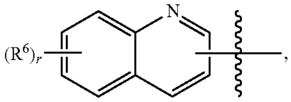,
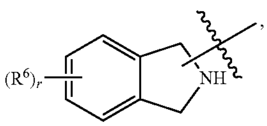,
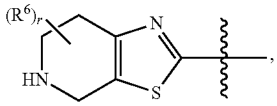,
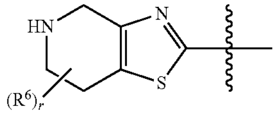 and
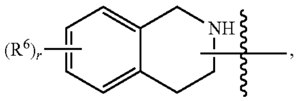, wherein each subscript r is an integer of 1, 2, 3, 4 or 5; $R^{16}$ is $C_{1-6}$ alkyl; and the wavy line indicates the point of attachment to L.

In some embodiments, ring A is selected from:

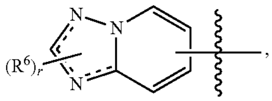,
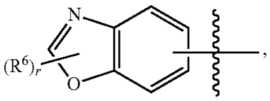,
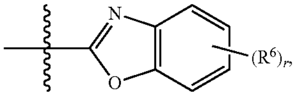,
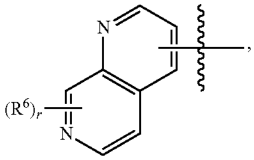,
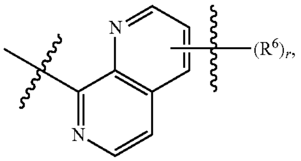,
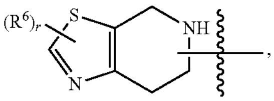,
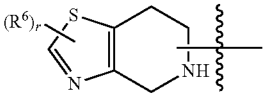,
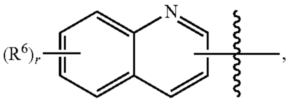,
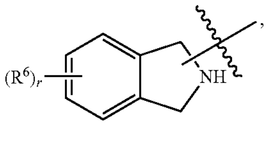,
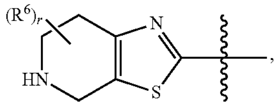, -continued

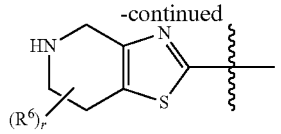

and

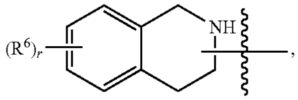

wherein each subscript r is an integer of 1, 2, 3, 4 or 5; and the wavy line indicates the point of attachment to L.

In some embodiments, ring A is selected from:

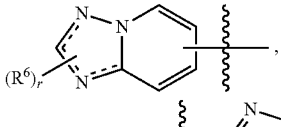
,
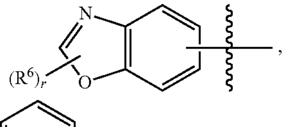
,
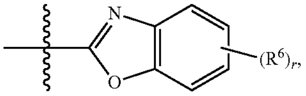
,
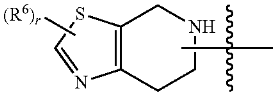
,
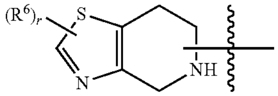
,
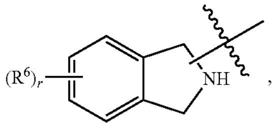
,
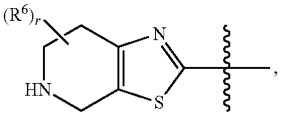
, and
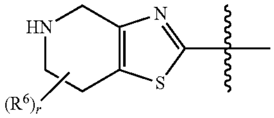

wherein each subscript r is an integer of 1, 2, 3, 4 or 5; and the wavy line indicates the point of attachment to L.

In some embodiments, ring A is selected from:

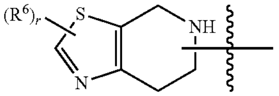
,
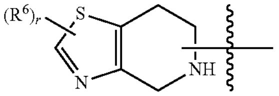
,
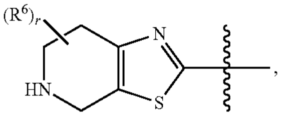
, and
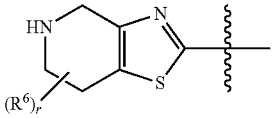

wherein each subscript r is an integer of 1, 2, 3, 4 or 5; and the wavy line indicates the point of attachment to L.

In some embodiments, ring A is

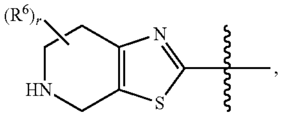
, wherein each subscript r is an integer of 1, 2, 3, 4 or 5; and the wavy line indicates the point of attachment to L.

In some embodiments, ring A is selected from:

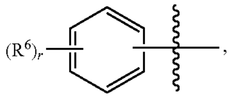
,
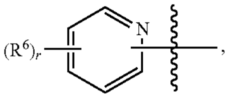
,
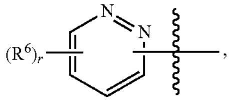
,
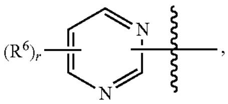
,
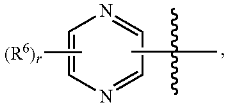
,
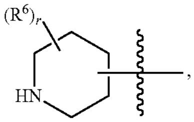
,
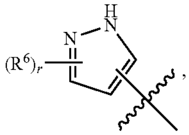
, and
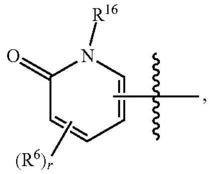
, wherein each subscript r is an integer of 1, 2, 3, 4 or 5; $R^{16}$ is $C_{1-6}$ alkyl; and the wavy line indicates the point of attachment to L.

In some embodiments, ring A is selected from:

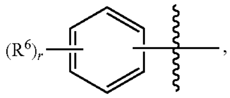
,
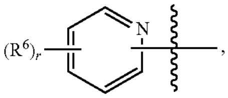
,
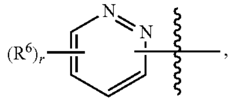
,
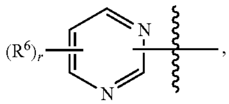
, and
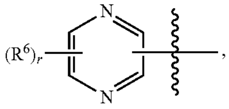
, wherein each subscript r is an integer of 1, 2, 3, 4 or 5; and the wavy line indicates the point of attachment to L.

In some embodiments, ring A is

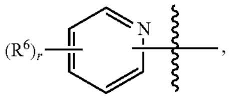
, wherein each subscript r is an integer of 1, 2, 3, 4 or 5; and the wavy line indicates the point of attachment to L.

In some embodiments, ring A is 2-pyridyl, optionally substituted with 1, 2, 3, or 4 independently selected $R^6$ substituents.

In some embodiments, ring A is

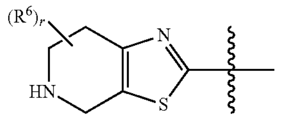

or

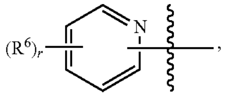

, wherein each subscript r is an integer of 1, 2, 3, 4 or 5; and the wavy line indicates the point of attachment to L.

In some embodiments, ring A is selected from:

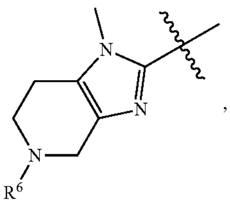

,

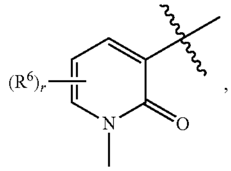

,

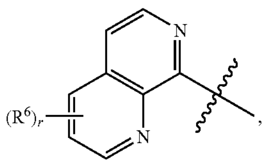

,

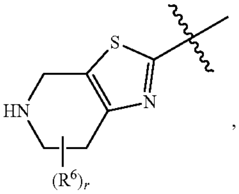

,

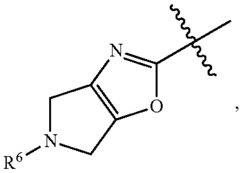

,

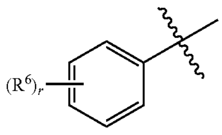

and

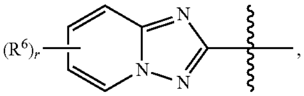

, wherein each subscript r is an integer of 1, 2 or 3.

In some embodiments, ring A is selected from:

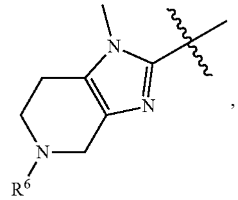

,

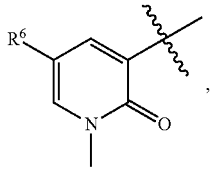

,

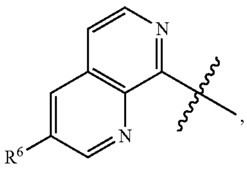

,

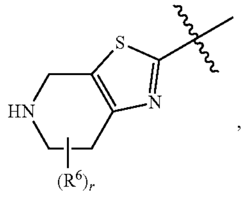

,

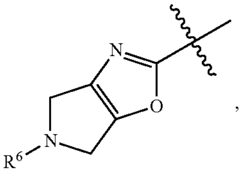

,

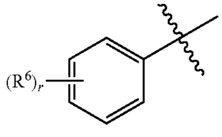

and

-continued

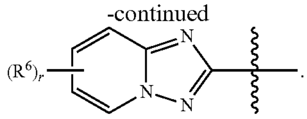

.

In some embodiments, L is a bond, —C(O)NR$^{13}$—, —NR$^{13}$C(O)—, —(CR$^{14}$R$^{15}$)$_q$—O—, —O(CR$^{14}$R$^{15}$)$_q$—, —NR$^{13}$—, or —CH═CH—. In some embodiments, L is a bond, —C(O)NR$^{13}$—, —NR$^{13}$C(O)—, —(CR$^{14}$R$^{15}$)$_q$—O—, —O(CR$^{14}$R$^{15}$)$_q$—, or —NR$^{13}$—. In some embodiments, L is —C(O)NR$^{13}$—, —NR$^{13}$C(O)—, —(CR$^{14}$R$^{15}$)$_q$—O—, —O(CR$^{14}$R$^{15}$)$_q$—, or —NR$^{13}$—. In some embodiments, L is a bond, —C(O)NR$^{13}$—, —NR$^{13}$C(O)—, —NR$^{13}$—, or —CH═CH—. In some embodiments, L is a bond, —NH—, —CH═CH— or —C(O)NH—, wherein the carbonyl group in the —C(O)NH— linkage is attached to ring A. In some embodiments, L is a bond. In some embodiments, L is —C(O)NR$^{13}$— (e.g., —C(O)NH—), wherein the carbonyl group is attached to ring A. In some embodiments, L is a bond, —NR$^{13}$—, —(CR$^{14}$R$^{15}$)$_q$O—, —O(CR$^{14}$R$^{15}$)$_q$—, —(CR$^{14}$R$^{15}$)$_q$NR$^{13}$— or —NR$^{13}$—(CR$^{14}$R$^{15}$)$_q$—, wherein the subscript q is 1, 2 or 3. In certain instances, R$^{14}$ and R$^{15}$ are each independently H or C$_{1-4}$ alkyl. In other instances, R$^{14}$ and R$^{15}$ taken together form C$_{3-6}$ cycloalkyl or 4-6-membered heterocycloalkyl, each of which is optionally substituted with 1 or 2 R$^q$ substituents.

In some embodiments, L is a bond.

In some embodiments, L is —NR$^{13}$—. In certain instances, R$^{13}$ is H or C$_{1-4}$ alkyl.

In some embodiments, L is —CH$_2$O— or —OCH$_2$—.

In some embodiments, L is —NR$^{13}$CH$_2$— or —CH$_2$NR$^{13}$. In certain instances, R$^{13}$ is H or C$_{1-4}$ alkyl.

In some embodiments, L is —C(O)NH—.

In some embodiments, L is —NH—.

In some embodiments, the subscript m is 0, 1, or 2. In some embodiments, the subscript m is 0 or 1. In some embodiments, the subscript m is 0.

In some embodiments, R$^5$ is C$_{1-4}$ alkyl, C$_{1-4}$ alkoxy, C$_{1-4}$ haloalkyl, C$_{1-4}$ haloalkoxy, CN, halo, or OH. In some embodiments, R$^5$ is C$_{1-4}$ alkyl, C$_{1-4}$ alkoxy, CN, halo, or OH. In some embodiments, R$^5$ is C$_{1-4}$ alkyl or halo. In some embodiments, R$^5$ is C$_{1-4}$ alkyl (e.g., methyl). In some embodiments, R$^5$ is halo (e.g., Cl).

In some embodiments, the subscript n is an integer of 0, 1, or 2. In some embodiments, the subscript n is an integer of 1 or 2. In some embodiments, the subscript n is an integer of 1.

In some embodiments, the subscript n is 1 and R$^5$ is halo or C$_{1-4}$ alkyl. In some embodiments, the subscript n is 1 and R$^5$ is halo. In some embodiments, the subscript n is 1 and R$^5$ is C$_{1-4}$ alkyl.

In some embodiments, R$^3$ is methyl, halo, or CN. In some embodiments, R$^3$ is methyl. In some embodiments, R$^3$ is halo (e.g., Cl). In some embodiments, R$^3$ is CN. In some embodiments, R$^3$ is methyl, CN or Cl.

In some embodiments, R$^{12}$ is H, C$_{1-4}$ alkyl, C$_{1-4}$ alkoxy, C$_{1-4}$ haloalkyl, C$_{1-4}$ haloalkoxy, CN, halo, or OH. In some embodiments, R$^{12}$ is H, halo, CN, C$_{1-4}$ alkyl or C$_{1-4}$ alkoxy. In some embodiments, R$^{12}$ is H, halo, or C$_{1-4}$ alkoxy. In some embodiments, R$^{12}$ is H.

In some embodiments, R$^7$ is H, C$_{1-4}$ alkyl, C$_{1-4}$ alkoxy, C$_{1-4}$ haloalkyl, C$_{1-4}$ haloalkoxy, CN, halo, or OH, wherein the C$_{1-4}$ alkyl and C$_{1-4}$ alkoxy are each optionally substituted with 1 or 2 substituents independently selected from CN, halo and —C(O)NH$_2$. In some embodiments, R$^7$ is H, halo, CN, $C_{1-4}$ alkyl, $C_{1-4}$ alkoxy or $C_{1-4}$ haloalkoxy, wherein the $C_{1-4}$ alkyl and $C_{1-4}$ alkoxy of $R^7$ are each optionally substituted with CN. In some embodiments, $R^7$ is H, halo, CN, or $C_{1-4}$ alkyl. In some embodiments, $R^7$ is H or $C_{1-4}$ alkyl. In some embodiments, $R^7$ is H.

In some embodiments, one of $R^1$ and $R^2$ is —$(CR^8R^9)_p$—$NR^{10}R^{11}$ and the other is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, and OH. In some embodiments, one of $R^1$ and $R^2$ is —$(CR^8R^9)_p$—$NR^{10}R^{11}$ and the other is H, $C_{1-4}$ alkyl, $C_{1-4}$ alkoxy, $C_{1-4}$ haloalkyl, or $C_{1-4}$ haloalkoxy. In some embodiments, one of $R^1$ and $R^2$ is —$(CR^8R^9)_p$—$NR^{10}R^{11}$ and the other is H or $C_{1-4}$ alkyl. In some embodiments, one of $R^1$ and $R^2$ is —$(CR^8R^9)_p$—$NR^{10}R^{11}$ and the other is H.

In some embodiments, $R^2$ is H.

In some embodiments, $R^1$ is H.

In some embodiments, $R^2$, $R^7$ and $R^{12}$ are each H.

In some embodiments, $R^3$ and $R^5$ are each independently halo, methyl or CN.

In some embodiments, the subscript p is an integer of 1, 2, or 3. In some embodiments, the subscript p is an integer of 1 or 2. In some embodiments, the subscript p is 1.

In some embodiments, $R^8$ and $R^9$ are each independently selected from H, halo, CN, OH, —COOH, $C_{1-4}$ alkyl, $C_{1-4}$ alkoxy, —NH$C_{1-4}$ alkyl, —N($C_{1-4}$ alkyl)$_2$, $C_{1-4}$ haloalkyl, and $C_{1-4}$ haloalkoxy, wherein the $C_{1-4}$ alkyl, $C_{1-4}$ alkoxy, $C_{1-4}$haloalkyl, and $C_{1-4}$haloalkoxy of $R^8$ or $R^9$ are each optionally substituted with 1 or 2 independently selected $R^q$ substituents. In some embodiments, $R^8$ and $R^9$ are each independently selected from H, halo, CN, $C_{1-4}$ alkyl, and $C_{1-4}$ alkoxy, wherein the $C_{1-4}$ alkyl and $C_{1-4}$ alkoxy of $R^8$ or $R^9$ are each optionally substituted with 1 or 2 independently selected $R^q$ substituents. In some embodiments, $R^8$ and $R^9$ are each independently selected from H and $C_{1-4}$ alkyl. In some embodiments, $R^8$ is H. In some embodiments, $R^9$ is H.

In some embodiments, $R^8$ and $R^9$ are each H.

In some embodiments, $R^{10}$ and $R^{11}$ are each independently selected from H, $C_{1-6}$ alkyl, and $C_{1-6}$ haloalkyl, wherein the $C_{1-6}$ alkyl and $C_{1-6}$ haloalkyl of $R^{10}$ or $R^{11}$ are each optionally substituted with 1, 2, or 3 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents.

In some embodiments, $R^{10}$ and $R^{11}$ are each independently selected from H and $C_{1-6}$ alkyl optionally substituted with 1 or 2 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents.

In some embodiments, $R^{10}$ and $R^{11}$ are each independently selected from H and $C_{1-6}$ alkyl optionally substituted with 1 or 2 independently selected $R^f$ substituents. In some embodiments, $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents.

In some embodiments, $R^{10}$ is H.

In some embodiments, $R^{11}$ is 2-hydroxyethyl, [1-(hydroxymethyl)cyclopropyl]methyl, [1-(hydroxymethyl)cyclobutyl]methyl or 2-(dimethylamino)-2-oxo-ethyl.

In some embodiments, $R^{11}$ is 1-hydroxy-2-propyl, 2-carboxyethyl, or 2-hydroxycyclopentyl.

In some embodiments, —$NR^{10}R^{11}$ is (2-hydroxyethyl)amino, 3-hydroxypyrrolidin-1-yl, (R)-3-hydroxypyrrolidin-1-yl, (S)-3-hydroxypyrrolidin-1-yl, 3-carboxypyrrolidin-1-yl, (R)-3-carboxypyrrolidin-1-yl, (S)-3-carboxypyrrolidin-1-yl, 3-carboxyazetidin-1-yl, (S)-3-carboxyazetidin-1-yl, (R)-3-carboxyazetidin-1-yl, 2-carboxy-1-piperidinyl, (R)-2-carboxy-1-piperidinyl, (S)-2-carboxy-1-piperidinyl, 2-oxooxazolidin-3-yl, [1-(hydroxymethyl)cyclopropyl]methylamino, [1-(hydroxymethyl)cyclobutyl]methylamino, [2-(dimethylamino)-2-oxo-ethyl]amino, 3-(dimethylaminocarbonyl)pyrrolidin-1-yl, (R)-3-(dimethylaminocarbonyl)pyrrolidin-1-yl, (S)-3-(dimethylaminocarbonyl)pyrrolidin-1-yl, 2-hydroxypropylamino, 2-hydroxy-2-methylpropylamino, or 3-methyl-3-carboxypyrrolidin-1-yl.

In some embodiments, —$NR^{10}R^{11}$ is (2-hydroxyethyl)amino, 3-hydroxypyrrolidin-1-yl, 3-carboxypyrrolidin-1-yl, 3-carboxyazetidin-1-yl, (S)-3-carboxyazetidin-1-yl, (R)-3-carboxyazetidin-1-yl, 2-carboxy-1-piperidinyl, 2-oxooxazolidin-3-yl, [1-(hydroxymethyl)cyclopropyl]methylamino, [1-(hydroxymethyl)cyclobutyl]methylamino or [2-(dimethylamino)-2-oxo-ethyl]amino.

In some embodiments, —$NR^{10}R^{11}$ is (2-hydroxyethyl)amino, 3-hydroxypyrrolidin-1-yl, 3-carboxypyrrolidin-1-yl, 3-carboxyazetidin-1-yl, (S)-3-carboxyazetidin-1-yl, (R)-3-carboxyazetidin-1-yl, 2-carboxy-1-piperidinyl, 2-oxooxazolidin-3-yl, [1-(hydroxymethyl)cyclopropyl]methylamino, [1-(hydroxymethyl)cyclobutyl]methylamino, [2-(dimethylamino)-2-oxo-ethyl]amino, 3-(dimethylaminocarbonyl)pyrrolidin-1-yl, 2-hydroxypropylamino, 2-hydroxy-2-methylpropylamino, or 3-methyl-3-carboxypyrrolidin-1-yl.

In some embodiments, —$NR^{10}R^{11}$ is (2-hydroxyethyl)amino, 3-hydroxypyrrolidin-1-yl, 3-carboxypyrrolidin-1-yl, 3-carboxyazetidin-1-yl, 2-carboxy-1-piperidinyl, 2-oxooxazolidin-3-yl, [1-(hydroxymethyl)cyclopropyl]methylamino, [1-(hydroxymethyl)cyclobutyl]methylamino or [2-(dimethylamino)-2-oxo-ethyl]amino.

In some embodiments, —$NR^{10}R^{11}$ is 1-pyrrolidinyl, (3-carboxy-3-methyl)pyrrolidin-1-yl, (R)-(3-carboxy-3-methyl)pyrrolidin-1-yl, (S)-(3-carboxy-3-methyl)pyrrolidin-1-yl, (1-hydroxy-2-propyl)amino, (R)-(1-hydroxy-2-propyl)amino, (S)-(1-hydroxy-2-propyl)amino, (3-hydroxy-3-methyl)pyrrolidin-1-yl, (R)-(3-hydroxy-3-methyl)pyrrolidin-1-yl, (S)-(3-hydroxy-3-methyl)pyrrolidin-1-yl, (2-hydroxycyclopentyl)amino, ((1R,2S)-2-hydroxycyclopentyl)amino, ((1R,2R)-2-hydroxycyclopentyl)amino, ((1S,2S)-2-hydroxycyclopentyl)amino, ((1S,2R)-2-hydroxycyclopentyl)amino, 2-carboxyethylamino, 3-(carboxymethyl)pyrrolidin-1-yl, or 5-carboxy-2-azabicyclo[2.2.1]heptan-2-yl.

In some embodiments, X is N or $CR^{17}$, wherein $R^{17}$ is H, $C_{1-4}$ alkyl, $C_{1-4}$ alkoxy, $C_{1-4}$ haloalkyl, $C_{1-4}$ haloalkoxy, CN, or halo. In some embodiments, X is N or $CR^{17}$, wherein $R^{17}$ is H or $C_{1-4}$ alkyl. In some embodiments, X is N or CH. In some embodiments, X is N. In some embodiments, X is $CR^{17}$ (e.g., CH).

In some embodiments, $R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $OR^a$, $C(O)R^a$, $C(O)NR^aR^a$, $C(O)OR^a$, $OC(O)R^a$, $OC(O)NR^aR^a$ $NHR^a$, $NR^aR^a$, $NR^aC(O)R^a$, and $NR^aC(O)OR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ $_{aryl\text{-}C1\text{-}4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, or 3 independently selected $R^b$ substituents.

In some embodiments, $R^6$, $R^7$, $R^{17}$ and $R^{18}$ are each independently selected from H, halo, $C_{1-6}$ alkyl, $C_{2-6}$ alkenyl, $C_{2-6}$ alkynyl, $C_{1-6}$ haloalkyl, $C_{1-6}$haloalkoxy, 5-14 membered heteroaryl, 4-10 membered heterocycloalkyl, (5-14 membered heteroaryl)-$C_{1-4}$ alkyl-, (4-10 membered heterocycloalkyl)-$C_{1-4}$ alkyl-, CN, $OR^a$, $C(O)R^a$, $C(O)NR^aR^a$, $C(O)OR^a$, $NHR^a$, $NR^aR^a$, $NR^aC(O)R^a$, and $NR^aC(O)OR^a$, wherein the $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, or 3 independently selected $R^b$ substituents.

In some embodiments, $R^6$, $R^7$, $R^{17}$ and $R^{18}$ are each independently selected from H, halo, $C_{1-6}$ alkyl, (5-14 membered heteroaryl)-$C_{1-4}$ alkyl-, (4-10 membered heterocycloalkyl)-$C_{1-4}$ alkyl-, CN, $OR^a$, and $C(O)R^a$, wherein the $C_{1-6}$ alkyl, (5-14 membered heteroaryl)-$C_{1-4}$ alkyl- and (4-10 membered heterocycloalkyl)-$C_{1-4}$ alkyl- of $R^6$, $R^7$, $R^{17}$ and $R^{18}$ are each optionally substituted with 1, 2, or 3 independently selected $R^b$ substituents.

In some embodiments, $R^6$ is H, $C_{1-6}$ alkyl, (3-carboxypyrrolidin-1-yl)methyl, (R)-(3-carboxypyrrolidin-1-yl)methyl, (S)-(3-carboxypyrrolidin-1-yl)methyl, (3-hydroxypyrrolidin-1-yl)methyl, (R)-(3-hydroxypyrrolidin-1-yl)methyl, (S)-(3-hydroxypyrrolidin-1-yl)methyl, (2-hydroxyethylamino)methyl, (2-hydroxy-2-methylpropylamino)methyl, 2-(dimethylamino)ethanoyl, 2-(3-carboxyazetidin-1-yl)ethanoyl, (R)-2-(3-carboxyazetidin-1-yl)ethanoyl, (S)-2-(3-carboxyazetidin-1-yl)ethanoyl, 2-(2-carboxypiperidin-1-yl)ethanoyl, (R)-2-(2-carboxypiperidin-1-yl)ethanoyl, (S)-2-(2-carboxypiperidin-1-yl)ethanoyl, 2-(3-carboxypyrrolidin-1-yl)ethanoyl, (S)-2-(3-carboxypyrrolidin-1-yl)ethanoyl, (R)-2-(3-carboxypyrrolidin-1-yl)ethanoyl, (5-cyanopyridin-3-yl)methoxy, halo or CN.

In some embodiments, $R^6$ is (4-carboxycyclohexyl)methyl, trans-(4-carboxycyclohexyl)methyl, cis-(4-carboxycyclohexyl)methyl, 1-carboxy-2-propyl, (R)-1-carboxy-2-propyl, (S)-1-carboxy-2-propyl, (4-carboxy-4-methylcyclohexyl)methyl, 2-pyrrolidinyl, 2-(3-hydroxypyrrolidin-1-yl)acetyl, 2-((R)-3-hydroxypyrrolidin-1-yl)acetyl, 2-((S)-3-hydroxypyrrolidin-1-yl)acetyl, 2-(3-hydroxyazetidin-1-yl)acetyl, 2-((2-hydroxyethyl)(methyl)amino)acetyl, (4-carboxycyclohexyl)ethyl, 4-carboxycyclohexyl, 4-carboxy-4-methylcyclohexyl, dimethylglycyl, or N-ethyl-N-methylglycyl.

In some embodiments, each $R^a$ is independently selected from H, CN, $C_{1-6}$ alkyl, $C_{1-4}$ haloalkyl, $C_{2-6}$ alkenyl, $C_{2-6}$ alkynyl, 5-14 membered heteroaryl, 4-14 membered heterocycloalkyl, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, 5-14 membered heteroaryl, 4-14 membered heterocycloalkyl, (5-14 membered heteroaryl)-$C_{1-4}$ alkyl- and (4-14 membered heterocycloalkyl)-$C_{1-4}$ alkyl- of $R^a$ are each optionally substituted with 1, 2, or 3 independently selected $R^d$ substituents. In some embodiments, each $R^a$ is independently selected from H, CN, $C_{1-6}$ alkyl, 5-14 membered heteroaryl, 4-14 membered heterocycloalkyl, (5-14 membered heteroaryl)-$C_{1-4}$ alkyl-, and (4-14 membered heterocycloalkyl)-$C_{1-4}$ alkyl-, wherein the $C_{1-6}$ alkyl, 5-14 membered heteroaryl, 4-14 membered heterocycloalkyl, (5-14 membered heteroaryl)-$C_{1-4}$ alkyl- and (4-14 membered heterocycloalkyl)-$C_{1-4}$ alkyl- of $R^a$ are each optionally substituted with 1 or 2 independently selected $R^d$ substituents. In some embodiments, each $R^a$ is independently selected from H, CN, $C_{1-6}$ alkyl, (5-14 membered heteroaryl)-$C_{1-4}$ alkyl-, and (4-14 membered heterocycloalkyl)-$C_{1-4}$ alkyl-, wherein the $C_{1-6}$ alkyl, (5-14 membered heteroaryl)-$C_{1-4}$ alkyl- and (4-14 membered heterocycloalkyl)-$C_{1-4}$ alkyl- of $R^a$ are each optionally substituted with 1 or 2 independently selected $R^d$ substituents.

In some embodiments, each $R^d$ is independently selected from $C_{1-6}$ alkyl, $C_{1-6}$ haloalkyl, halo, CN, $NH_2$, $OR^e$, $C(O)R^e$, $C(O)NR^eR^e$, $C(O)OR^e$, $OC(O)R^e$, $OC(O)NR^eR^e$, $NHR^e$, $NR^eR^e$, and $NR^eC(O)R^e$, wherein the $C_{1-6}$ alkyl of $R^d$ are each optionally substituted with 1 or 2 independently selected $R^f$ substituents. In some embodiments, each $R^d$ is independently selected from $C_{1-6}$ alkyl, CN, $NH_2$, $OR^e$, $C(O)R^e$, $C(O)NR^eR^e$, $C(O)OR^e$, $NHR^e$, or $NR^eR^e$.

In some embodiments, each $R^e$ is independently selected from H, $C_{1-6}$ alkyl, $C_{1-6}$ haloalkyl, $C_{2-6}$ alkenyl, and $C_{2-6}$ alkynyl. In some embodiments, each $R^e$ is independently selected from H and $C_{1-6}$ alkyl.

In some embodiments, each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $OR^c$, $C(O)R^c$, $C(O)NR^cR^c$, $C(O)OR^c$, $OC(O)R^c$, $OC(O)NR^cR^c$, $NHR^c$, $NR^cR^c$, and $NR^cC(O)R^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-membered heterocycloalkyl)-$C_{1-4}$ alkyl- of $R^b$ are each further optionally substituted with 1 or 2 independently selected $R^d$ substituents. In some embodiments, each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, CN, OH, $NH_2$, $OR^c$, $C(O)R^c$, $C(O)NR^cR^c$, $C(O)OR^c$, $NHR^c$, and $NR^cR^c$; wherein the $C_{1-6}$ alkyl, $C_{1-6}$ haloalkyl, $C_{1-6}$ haloalkoxy, $C_{2-6}$ alkenyl, and $C_{2-6}$ alkynyl of $R^b$ are each further optionally substituted with 1 or 2 independently selected $R^d$ substituents. In some embodiments, each $R^b$ substituent is independently selected from halo, $C_{1-6}$ alkyl, $C_{2-6}$ alkenyl, $C_{2-6}$ alkynyl, CN, OH, $NH_2$, $OR^c$, $C(O)R^c$, $C(O)NR^cR^c$, $C(O)OR^c$, $NHR^c$, and $NR^cR^c$; wherein the $C_{1-6}$ alkyl, $C_{2-6}$ alkenyl, and $C_{2-6}$ alkynyl of $R^b$ are each further optionally substituted with 1 or 2 independently selected $R^d$ substituents.

In some embodiments, each $R^c$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of R are each optionally substituted with 1 or 2 independently selected $R^f$ substituents. In some embodiments, each $R^c$ is independently selected from H and $C_{1-6}$ alkyl optionally substituted with 1 or 2 independently selected $R^f$ substituents.

In some embodiments, each $R^f$ is independently selected from $C_{1-4}$ alkyl, $C_{1-4}$ haloalkyl, $C_{2-6}$ alkenyl, $C_{2-6}$ alkynyl, halo, CN, $OR^g$, $C(O)R^g$, $C(O)NR^gR^g$, $C(O)OR^g$, $OC(O)R^g$, $OC(O)NR^gR^g$, $NHR^g$, $NR^gR^g$, and $NR^gC(O)R^g$; wherein the $C_{1-4}$ alkyl, $C_{1-4}$ haloalkyl, $C_{2-6}$ alkenyl, and $C_{2-6}$ alkynyl of $R^f$ are each optionally substituted with 1 or 2 independently selected $R^n$ substituents. In some embodiments, each $R^f$ is independently selected from $C_{1-4}$ alkyl, halo, CN, $OR^g$, $C(O)R^g$, $NHR^g$, and $NR^gR^g$; wherein the $C_{1-4}$ alkyl is optionally substituted with 1 or 2 independently selected $R^n$ substituents. In some embodiments, each $R^f$ is independently selected from $C_{1-4}$ alkyl, halo, and $OR^g$.

In some embodiments, each $R^g$ is independently selected from H, $C_{1-6}$ alkyl, $C_{1-4}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^g$ are each optionally substituted with 1 or 2 independently selected $R^p$ substituents. In some embodiments, each $R^g$ is independently selected from H and $C_{1-6}$ alkyl.

In some embodiments, provided herein is a compound of Formula (I) or (Ia), or a pharmaceutically acceptable salt or a stereoisomer thereof, wherein:

ring A is 5- to 10-membered heteroaryl, 4- to 11-membered heterocycloalkyl, or $C_{6-10}$ aryl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2 or 3 $R^6$ substituents;

L is a bond, —$C(O)NR^{13}$—, —$NR^{13}C(O)$—, —$(CR^{14}R^{15})_q$—O—, —$O(CR^{14}R^{15})_q$, —$NR^{13}$—, or CH═CH—;

X is N or $CR^{17}$, wherein $R^{17}$ is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy are each optionally substituted with 1 or 2 substituents independently selected from CN, halo and —$C(O)NH_2$;

one of $R^1$ and $R^2$ is —$(CR^8R^9)_p$—$NR^{10}R^{11}$ and the other is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, and OH;

$R^3$ is methyl, halo, CN or $C_{1-4}$ haloalkyl;

$R^4$ is $C_{1-4}$ alkyl, $C_{1-4}$ alkoxy, or $C_{1-4}$ haloalkyl;

$R^5$ is $C_{1-4}$ alkyl, $C_{1-4}$ alkoxy, $C_{1-4}$ haloalkyl, $C_{1-4}$ haloalkoxy, CN, halo, or OH;

each $R^6$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, 5-14 membered heteroaryl, 4-10 membered heterocycloalkyl, (5-14 membered heteroaryl)-$C_{1-4}$ alkyl-, (4-10 membered heterocycloalkyl)-$C_{1-4}$ alkyl-, CN, $NO_2$, $OR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, or $NR^aC(O)OR^a$, wherein the $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl- and (4-10 membered heterocycloalkyl)-$C_{1-4}$ alkyl- of $R^6$ are each optionally substituted with 1, 2, or 3 $R^b$ substituents;

$R^7$ is H, $C_{1-4}$ alkyl, $C_{1-4}$ alkoxy, $C_{1-4}$ haloalkyl, $C_{1-4}$ haloalkoxy, CN, halo, or OH;

$R^8$ and $R^9$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, and $C_{1-4}$ haloalkyl;

$R^{10}$ and $R^{11}$ are each independently selected from H, $C_{1-6}$ alkyl, $C_{1-6}$ haloalkyl, —$C(O)R^g$, —$C(O)OR^g$, and —$C(O)NR^gR^g$, wherein the $C_{1-6}$ alkyl and $C_{1-6}$ haloalkyl of $R^{10}$ or $R^{11}$ are each optionally substituted with 1 or 2 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents;

$R^{12}$ is H, $C_{1-4}$ alkyl, $C_{1-4}$ alkoxy, $C_{1-4}$ haloalkyl, $C_{1-4}$ haloalkoxy, CN, halo, or OH;

each $R^{13}$ is independently H, $C_{1-6}$ haloalkyl or $C_{1-6}$ alkyl;

$R^{14}$ and $R^{15}$ are each independently selected from H, halo, or $C_{1-4}$ alkyl;

each $R^a$ is independently selected from H, CN, $C_{1-6}$ alkyl, $C_{1-4}$haloalkyl, $C_{2-6}$ alkenyl, $C_{2-6}$ alkynyl, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, (5-14 membered heteroaryl)-$C_{1-4}$ alkyl- and (4-14 membered heterocycloalkyl)-$C_{1-4}$ alkyl- of $R^a$ are each optionally substituted with 1, 2, 3 or independently selected $R^d$ substituents;

each $R^d$ is independently selected from $C_{1-6}$ alkyl, $C_{1-6}$ haloalkyl, halo, CN, $NH_2$, $OR^e$, $C(O)R^e$, $C(O)NR^eR^e$, $C(O)OR^e$, $OC(O)R^e$, $OC(O)NR^eR^e$, $NHR^e$, $NR^eR^e$, and $NR^eC(O)R^e$;

each $R^e$ is independently selected from H, $C_{1-6}$ alkyl, $C_{1-6}$ haloalkyl, $C_{2-6}$ alkenyl, and $C_{2-6}$ alkynyl;

each $R^b$ substituent is independently selected from halo, $C_{1-6}$ alkyl, $C_{1-6}$ haloalkyl, $C_{1-6}$ haloalkoxy, CN, OH, $NH_2$, $NO_2$, $OR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR)NR^cR^c$, $NHR^c$, $NR^cR^c$, $NR^cC(O)R^c$, and $NR^cC(O)OR^c$; wherein the $C_{1-4}$ alkyl, $C_{1-4}$ haloalkyl, and $C_{1-4}$haloalkoxy of $R^b$ are each further optionally substituted with 1 or 2 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, $C_{6-10}$ aryl-$C_{1-4}$ alkyl-, and $C_{3-10}$ cycloalkyl-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, $C_{6-10}$ aryl-$C_{1-4}$ alkyl-, and $C_{3-10}$ cycloalkyl-$C_{1-4}$ alkyl- of $R^c$ are each optionally substituted with 1, 2, or 3 $R^f$ substituents;

each $R^f$ is independently selected from $C_{1-4}$ alkyl, $C_{1-4}$ haloalkyl, $C_{2-6}$ alkenyl, $C_{2-6}$ alkynyl, halo, CN, $OR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, and $NR^gC(O)OR^g$;

each $R^g$ is independently selected from H, $C_{1-6}$ alkyl, $C_{1-4}$ haloalkyl, $C_{2-6}$ alkenyl, and $C_{2-6}$ alkynyl;

each $R^h$ is independently selected from $C_{1-6}$ alkyl, $C_{1-6}$ haloalkyl, $C_{1-6}$ haloalkoxy, $C_{2-6}$ alkenyl, $C_{2-6}$ alkynyl, halo, CN, $OR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, and $NR^iC(O)OR^i$, wherein the $C_{1-6}$ alkyl, $C_{2-6}$ alkenyl, and $C_{2-6}$ alkynyl of $R^h$ are each further optionally substituted by 1, 2, or 3 $R^j$ substituents;

each $R^j$ is independently selected from $C_{2-4}$ alkenyl, $C_{2-4}$ alkynyl, halo, $C_{1-4}$ alkyl, $C_{1-4}$ haloalkyl, and CN;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

each $R^i$ is independently selected from H, $C_{1-4}$ alkyl, $C_{1-6}$ haloalkyl, $C_{1-6}$ haloalkoxy, $C_{2-4}$ alkenyl, and $C_{2-4}$ alkynyl;

the subscript m is an integer of 0, 1, or 2;

the subscript n is an integer of 0, 1, or 2; and the subscript p is an integer of 1, 2, or 3.

In some embodiments, provided herein is a compound of Formula (I) or (Ia), or a pharmaceutically acceptable salt or a stereoisomer thereof, wherein:

ring A is 5- to 10-membered heteroaryl or 4- to 11-membered heterocycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2 or 3 $R^6$ substituents;

L is a bond, —C(O)$NR^{13}$—, —$NR^{13}$C(O)—, —$NR^{13}$—, or CH═CH—;

X is N or $CR^{17}$, wherein $R^{17}$ is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy are each optionally substituted with 1 or 2 substituents independently selected from CN, halo and —C(O)$NH_2$;

one of $R^1$ and $R^2$ is —$(CR^8R^9)_p$—$NR^{10}R^{11}$ and the other is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, and OH;

$R^3$ is methyl, halo, CN or $C_{1-4}$ haloalkyl;

$R^4$ is $C_{1-4}$ alkyl, $C_{1-4}$ alkoxy, or $C_{1-4}$ haloalkyl;

$R^5$ is $C_{1-4}$ alkyl, $C_{1-4}$ alkoxy, $C_{1-4}$ haloalkyl, $C_{1-4}$ haloalkoxy, CN, halo, or OH;

each $R^6$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, 5-14 membered heteroaryl, 4-10 membered heterocycloalkyl, (5-14 membered heteroaryl)-$C_{1-4}$ alkyl-, (4-10 membered heterocycloalkyl)-$C_{1-4}$ alkyl-, CN, $NO_2$, $OR^a$, C(O)$R^a$, C(O)$NR^aR^a$, C(O)$OR^a$, OC(O)$R^a$, OC(O)$NR^aR^a$, $NHR^a$, $NR^aR^a$, $NR^a$C(O)$R^a$, or $NR^a$C(O)$OR^a$, wherein the $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl- and (4-10 membered heterocycloalkyl)-$C_{1-4}$ alkyl- of $R^6$ are each optionally substituted with 1, 2, or 3 $R^b$ substituents;

$R^7$ is H, $C_{1-4}$ alkyl, $C_{1-4}$ alkoxy, $C_{1-4}$ haloalkyl, $C_{1-4}$ haloalkoxy, CN, halo, or OH;

$R^8$ and $R^9$ are each independently selected from H, halo, CN, OH, —COOH, $C_{1-4}$ alkyl, $C_{1-4}$ alkoxy, —NH$C_{1-4}$ alkyl, —N($C_{1-4}$ alkyl)$_2$, and $C_{1-4}$ haloalkyl;

$R^{10}$ and $R^{11}$ are each independently selected from H, $C_{1-6}$ alkyl, $C_{1-6}$ haloalkyl, —C(O)$R^g$, —C(O)$OR^g$, and —C(O)$NR^gR^g$, wherein the $C_{1-6}$ alkyl and $C_{1-6}$ haloalkyl of $R^{10}$ or $R^{11}$ are each optionally substituted with 1 or 2 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents;

$R^{12}$ is H, $C_{1-4}$ alkyl, $C_{1-4}$ alkoxy, $C_{1-4}$ haloalkyl, $C_{1-4}$ haloalkoxy, CN, halo, or OH;

each $R^{13}$ is independently H, $C_{1-6}$ haloalkyl or $C_{1-6}$ alkyl;

each $R^a$ is independently selected from H, CN, $C_{1-6}$ alkyl, $C_{1-4}$ haloalkyl, $C_{2-6}$ alkenyl, and $C_{2-6}$ alkynyl;

each $R^d$ is independently selected from $C_{1-6}$ alkyl, $C_{1-6}$ haloalkyl, halo, CN, $NH_2$, $OR^e$, C(O)$R^e$, C(O)$NR^eR^e$, C(O)$OR^e$, OC(O)$R^e$, OC(O)$NR^eR^e$, $NHR^e$, $NR^eR^e$, and $NR^e$C(O)$R^e$;

each $R^e$ is independently selected from H, $C_{1-6}$ alkyl, $C_{1-6}$ haloalkyl, $C_{2-6}$ alkenyl, and $C_{2-6}$ alkynyl;

each $R^b$ substituent is independently selected from halo, $C_{1-6}$ alkyl, $C_{1-6}$ haloalkyl, $C_{1-6}$ haloalkoxy, CN, OH, $NH_2$, $NO_2$, $OR^c$, C(O)$R^c$, C(O)$NR^cR^c$, C(O)$OR^c$, OC(O)$R^c$, OC(O)$NR^cR^c$, C(═NR)$NR^cR^c$, $NR^c$C(═NR)$NR^cR^c$, $NHR^c$, $NR^cR^c$, $NR^c$C(O)$R^c$, and $NR^c$C(O)$OR^c$; wherein the $C_{1-4}$ alkyl, $C_{1-4}$ haloalkyl, and $C_{1-4}$haloalkoxy of $R^b$ are each further optionally substituted with 1 or 2 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, $C_{6-10}$ aryl-$C_{1-4}$ alkyl-, and $C_{3-10}$ cycloalkyl-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, $C_{6-10}$ aryl-$C_{1-4}$ alkyl-, and $C_{3-10}$ cycloalkyl-$C_{1-4}$ alkyl- of $R^c$ are each optionally substituted with 1, 2, or 3 $R^f$ substituents;

each $R^f$ is independently selected from $C_{1-4}$ alkyl, $C_{1-4}$ haloalkyl, $C_{2-6}$ alkenyl, $C_{2-6}$ alkynyl, halo, CN, $OR^g$, C(O)$R^g$, C(O)$NR^gR^g$, C(O)$OR^g$, OC(O)$R^g$, OC(O)$NR^gR^g$, $NHR^g$, $NR^gR^g$, $NR^g$C(O)$R^g$, and $NR^g$C(O)$OR^g$;

each $R^g$ is independently selected from H, $C_{1-6}$ alkyl, $C_{1-4}$ haloalkyl, $C_{2-6}$ alkenyl, and $C_{2-6}$ alkynyl;

each $R^h$ is independently selected from $C_{1-6}$ alkyl, $C_{1-6}$ haloalkyl, $C_{1-6}$ haloalkoxy, $C_{2-6}$ alkenyl, $C_{2-6}$ alkynyl, halo, CN, $OR^i$, C(O)$R^i$, C(O)$NR^iR^i$, C(O)$OR^i$, OC(O)$R^i$, OC(O)$NR^iR^i$, $NHR^i$, $NR^iR^i$, $NR^i$C(O)$R^i$, and $NR^i$C(O)$OR^i$, wherein the $C_{1-6}$ alkyl, $C_{2-6}$ alkenyl, and $C_{2-6}$ alkynyl of $R^h$ are each further optionally substituted by 1, 2, or 3 $R^j$ substituents;

each $R^j$ is independently selected from $C_{2-4}$ alkenyl, $C_{2-4}$ alkynyl, halo, $C_{1-4}$ alkyl, $C_{1-4}$ haloalkyl, and CN;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

each $R^i$ is independently selected from H, $C_{1-4}$ alkyl, $C_{1-6}$ haloalkyl, $C_{1-6}$ haloalkoxy, $C_{2-4}$ alkenyl, and $C_{2-4}$ alkynyl;

the subscript m is an integer of 0, 1, or 2;

the subscript n is an integer of 0, 1, or 2; and the subscript p is an integer of 1, 2, or 3.

In some embodiments provided herein is a compound of Formula (I) or (Ia), or a pharmaceutically acceptable salt or a stereoisomer thereof, wherein:

ring A is 5- to 10-membered heteroaryl or 4- to 11-membered heterocycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2 or 3 $R^6$ substituents;

L is a bond, —C(O)$NR^{13}$— or —$NR^{13}$C(O)—;

X is $CR^{17}$, wherein $R^{17}$ is H or $C_{1-4}$ alkyl;

one of $R^1$ and $R^2$ is —$(CR^8R^9)_p$—$NR^{10}R^{11}$ and the other is H, $C_{1-4}$ alkyl, or $C_{1-4}$ alkoxy;

$R^3$ is methyl, or halo;

$R^4$ is $C_{1-4}$ alkyl or $C_{1-4}$ alkoxy;

$R^5$ is $C_{1-4}$ alkyl, $C_{1-4}$ alkoxy, or halo;

each $R^6$ is independently selected from H, halo, $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl- and (4-10 membered heterocycloalkyl)-$C_{1-4}$ alkyl- of $R^6$ are each optionally substituted with 1, 2, or 3 $R^b$ substituents;

$R^7$ is H or $C_{1-4}$ alkyl;

$R^8$ and $R^9$ are each independently selected from H and $C_{1-4}$ alkyl;

$R^{10}$ and $R^{11}$ are each independently selected from H and $C_{1-6}$ alkyl optionally substituted with 1 or 2 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents;

$R^{12}$ is H or $C_{1-4}$ alkyl;

each $R^{13}$ is independently H or $C_{1-6}$ alkyl;

each $R^b$ substituent is independently selected from halo, $C_{1-6}$ alkyl, OH, $NH_2$, $C(O)OR^c$, $NHR^c$, and $NR^cR^c$;

each $R^c$ is independently selected from H, $C_{1-6}$ alkyl, $C_{2-6}$ alkenyl, $C_{2-6}$ alkynyl, $C_{3-10}$ cycloalkyl, and $C_{3-10}$ cycloalkyl-$C_{1-4}$ alkyl-, wherein the $C_{1-6}$ alkyl, $C_{2-6}$ alkenyl, $C_{2-6}$ alkynyl, $C_{3-10}$ cycloalkyl, and $C_{3-10}$ cycloalkyl-$C_{1-4}$ alkyl- of $R^c$ are each optionally substituted with 1 or 2 $R^f$ substituents;

each $R^f$ is independently selected from $C_{1-4}$ alkyl, $C_{2-6}$ alkenyl, $C_{2-6}$ alkynyl, halo, $OR^g$, and $C(O)OR^g$;

each $R^g$ is independently selected from H and $C_{1-6}$ alkyl;

each $R^h$ is independently selected from $C_{1-6}$ alkyl, $C_{2-6}$ alkenyl, $C_{2-6}$ alkynyl, halo, CN, $OR^i$, and $C(O)OR^i$;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

each $R^i$ is independently selected from H and $C_{1-4}$ alkyl;

the subscript m is an integer of 0 or 1;

the subscript n is an integer of 0 or 1; and the subscript p is an integer of 1 or 2.

In some embodiments provided herein is a compound of Formula (I) or (Ia), or a pharmaceutically acceptable salt or a stereoisomer thereof, wherein:

ring A is 5- to 10-membered heteroaryl, wherein the 5- to 10-membered heteroaryl has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1 or 2 $R^6$ substituents;

L is a bond, —$C(O)NR^{13}$— or —$NR^{13}C(O)$—;

X is $CR^{17}$, wherein $R^{17}$ is H;

one of $R^1$ and $R^2$ is —$(CR^8R^9)_p$—$NR^{10}R^{11}$ and the other is H;

$R^3$ is methyl, or halo;

$R^4$ is $C_{1-4}$ alkyl or $C_{1-4}$ alkoxy;

$R^5$ is $C_{1-4}$ alkyl or halo;

each $R^6$ is independently selected from H, $C_{1-6}$ alkyl, and (4-10 membered heterocycloalkyl)-$C_{1-4}$ alkyl-, wherein the $C_{1-6}$ alkyl and (4-10 membered heterocycloalkyl)-$C_{1-4}$ alkyl- of $R^6$ are each optionally substituted with 1 or 2 $R^b$ substituents;

$R^7$ is H;

$R^8$ and $R^9$ are each independently selected from H and $C_{1-4}$ alkyl;

$R^{10}$ and $R^{11}$ are each independently selected from H and $C_{1-6}$ alkyl optionally substituted with 1 or 2 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents;

$R^{12}$ is H;

$R^{13}$ is H;

each $R^b$ substituent is independently selected from OH, $C(O)OR^c$, $NHR^c$, and $NR^cR^c$;

each $R^c$ is independently selected from H, $C_{1-6}$ alkyl, and $C_{3-10}$ cycloalkyl, wherein the $C_{1-6}$ alkyl, and $C_{3-10}$ cycloalkyl of $R^c$ are each optionally substituted with 1 or 2 $R^f$ substituents;

each $R^f$ is independently selected from $OR^g$, and $C(O)OR^g$;

$R^g$ is H;

each $R^h$ is independently selected from $OR^i$ and $C(O)OR^i$;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

$R^i$ is H;

the subscript m is an integer of 0 or 1;

the subscript n is an integer of 0 or 1; and the subscript p is an integer of 1 or 2.

In some embodiments provided herein is a compound of Formula (I) or (Ia), or a pharmaceutically acceptable salt or a stereoisomer thereof, wherein:

ring A is 5- to 10-membered heteroaryl or 4- to 11-membered heterocycloalkyl, wherein the 5- to 10-membered heteroaryl and 4- to 11-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2 or 3 $R^6$ substituents;

L is a bond, —$C(O)NR^{13}$—, —$NR^{13}$—, or —$NR^{13}C(O)$—;

X is $CR^{17}$, wherein $R^{17}$ is H or $C_{1-4}$ alkyl;

one of $R^1$ and $R^2$ is —$(CR^8R^9)_p$—$NR^{10}R^{11}$ and the other is H, $C_{1-4}$ alkyl, or $C_{1-4}$ alkoxy;

$R^3$ is methyl, or halo;

$R^4$ is $C_{1-4}$ alkyl or $C_{1-4}$ alkoxy;

$R^5$ is $C_{1-4}$ alkyl, $C_{1-4}$ alkoxy, or halo;

each $R^6$ is independently selected from H, halo, $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl- and (4-10 membered heterocycloalkyl)-$C_{1-4}$ alkyl- of $R^6$ are each optionally substituted with 1, 2, or 3 $R^b$ substituents;

$R^7$ is H or $C_{1-4}$ alkyl;

$R^8$ and $R^9$ are each independently selected from H and $C_{1-4}$ alkyl;

$R^{10}$ and $R^{11}$ are each independently selected from H and $C_{1-6}$ alkyl optionally substituted with 1 or 2 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents;

$R^{12}$ is H or $C_{1-4}$ alkyl;

each $R^{13}$ is independently H or $C_{1-6}$ alkyl;

each $R^b$ substituent is independently selected from halo, $C_{1-6}$ alkyl, OH, $NH_2$, $C(O)OR^c$, $NHR^c$, and $NR^cR^c$;

each $R^c$ is independently selected from H, $C_{1-6}$ alkyl, $C_{2-6}$ alkenyl, $C_{2-6}$ alkynyl, $C_{3-10}$ cycloalkyl, and $C_{3-10}$ cycloalkyl-$C_{1-4}$ alkyl-, wherein the $C_{1-6}$ alkyl, $C_{2-6}$ alkenyl, $C_{2-6}$ alkynyl, $C_{3-10}$ cycloalkyl, and $C_{3-10}$ cycloalkyl-$C_{1-4}$ alkyl- of $R^c$ are each optionally substituted with 1 or 2 $R^f$ substituents;

each $R^f$ is independently selected from $C_{1-4}$ alkyl, $C_{2-6}$ alkenyl, $C_{2-6}$ alkynyl, halo, $OR^g$, and $C(O)OR^g$;

each $R^g$ is independently selected from H and $C_{1-6}$ alkyl;

each $R^h$ is independently selected from $C_{1-6}$ alkyl, $C_{2-6}$ alkenyl, $C_{2-6}$ alkynyl, halo, CN, $OR^i$, and $C(O)OR^i$;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

each $R^i$ is independently selected from H and $C_{1-4}$ alkyl;

the subscript m is an integer of 0 or 1;

the subscript n is an integer of 0 or 1; and the subscript p is an integer of 1 or 2.

In some embodiments provided herein is a compound of Formula (I) or (Ia), or a pharmaceutically acceptable salt or a stereoisomer thereof, wherein:

ring A is 5- to 10-membered heteroaryl, wherein the 5- to 10-membered heteroaryl has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1 or 2 $R^6$ substituents;

L is a bond, —C(O)$NR^{13}$—, —$NR^{13}$—, or —$NR^{13}$C(O)—;

X is $CR^{17}$, wherein $R^{17}$ is H;

one of $R^1$ and $R^2$ is —$(CR^8R^9)_p$—$NR^{10}R^{11}$ and the other is H;

$R^3$ is methyl, or halo;

$R^4$ is $C_{1-4}$ alkyl or $C_{1-4}$ alkoxy;

$R^5$ is $C_{1-4}$ alkyl or halo;

each $R^6$ is independently selected from H, $C_{1-6}$ alkyl, and (4-10 membered heterocycloalkyl)-$C_{1-4}$ alkyl-, wherein the $C_{1-6}$ alkyl and (4-10 membered heterocycloalkyl)-$C_{1-4}$ alkyl- of $R^6$ are each optionally substituted with 1 or 2 $R^b$ substituents;

$R^7$ is H;

$R^8$ and $R^9$ are each independently selected from H and $C_{1-4}$ alkyl;

$R^{10}$ and $R^{11}$ are each independently selected from H and $C_{1-6}$ alkyl optionally substituted with 1 or 2 independently selected $R^h$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents;

$R^{12}$ is H;

$R^{13}$ is H;

each $R^b$ substituent is independently selected from OH, $C(O)OR^c$, $NHR^c$, and $NR^cR^c$;

each $R^c$ is independently selected from H, $C_{1-6}$ alkyl, and $C_{3-10}$ cycloalkyl, wherein the $C_{1-6}$ alkyl, and $C_{3-10}$ cycloalkyl of $R^c$ are each optionally substituted with 1 or 2 $R^f$ substituents;

each $R^f$ is independently selected from $OR^g$, and $C(O)OR^g$;

$R^g$ is H;

each $R^h$ is independently selected from $OR^i$ and $C(O)OR^i$;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

$R^i$ is H;

the subscript m is an integer of 0 or 1;

the subscript n is an integer of 0 or 1; and the subscript p is an integer of 1 or 2.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$-includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl," employed alone or in combination with other terms, refers to a saturated hydrocarbon group that may be straight-chained or branched. The term "$C_{n-m}$ alkyl," refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl," employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl," employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene," employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl and the like.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "alkylthio," employed alone or in combination with other terms, refers to a group of formula —S-alkyl, wherein the alkyl group is as defined above. The term "$C_{n-m}$ alkylthio" refers to an alkylthio group, the alkyl group of which has n to m carbons. Example alkylthio groups include methylthio, ethylthio, etc. In some embodiments, the alkyl group of the alkylthio group has 1 to 6, 1 to 4, or 1 to 3 carbon atoms.

The term "amino," employed alone or in combination with other terms, refers to a group of formula $—NH_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl," employed alone or in combination with other terms, refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, indanyl, indenyl and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroatom" used herein is meant to include boron, phosphorus, sulfur, oxygen and nitrogen.

The term "heteroaryl" or "heteroaromatic," employed alone or in combination with other terms, refers to a monocyclic or polycyclic aromatic heterocycle having at least one heteroatom ring member selected from boron, phosphorus, sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-14, or 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, benzothiophenyl, benzofuranyl, benzisoxazolyl, imidazo[1,2-b]thiazolyl, purinyl, and the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6, 7, 8, 9, 10, 11, 12, 13, or 14 ring-forming carbons ($C_{3-14}$). In some embodiments, the cycloalkyl group has 3 to 14 members, 3 to 10 members, 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from boron, nitrogen, sulfur oxygen and phosphorus, and which has 4-14 ring members, 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic or polycyclic (e.g., having two or three fused or bridged rings) ring systems or spirorcycles. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, tetrahydrothiazolopyridinyl (e.g., 4,5,6,7-tetrahydrothiazolo[5,4-c]pyridin-2-yl) and thiomorpholino.

The term "arylalkyl," employed alone or in combination with other terms, refers to an aryl-(alkylene)- group where aryl and alkylene are as defined herein. An example arylalkyl group is benzyl.

The term "heteroarylalkyl," employed alone or in combination with other terms, refers to an heteroaryl-(alkylene)- group, where heteroaryl and alkylene are as defined herein. An example heteroarylalkyl group is pyridylmethyl.

The term "cycloalkylalkyl," employed alone or in combination with other terms, refers to a cycloalkyl-(alkylene)- group, where cycloalkyl and alkylene are as defined herein. An example cycloalkylalkyl group is cyclopropylmethyl.

The term "heterocycloalkylalkyl," employed alone or in combination with other terms, refers to a heterocycloalkyl-(alkylene)- group, where heterocycloalkyl and alkylene are as defined herein. An example heterocycloalkylalkyl group is azetidinylmethyl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art.

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences,* 17th Ed., (Mack Publishing Company, Easton, 1985), p. 1418, Berge et al., *J. Pharm. Sci.,* 1977, 66(1), 1-19 and in Stahl et al., *Handbook of Pharmaceutical Salts: Properties, Selection, and Use*, (Wiley, 2002). In some embodiments, the compounds described herein include the N-oxide forms.

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure,* 6th Ed. (Wiley, 2007); Petursson et al., "Protecting Groups in Carbohydrate Chemistry," *J Chem. Educ.,* 1997, 74(11), 1297; and Wuts et al., *Protective Groups in Organic Synthesis,* 4th Ed., (Wiley, 2006).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula I can be synthesized using a process shown in Scheme 1. In Scheme 1, a suitable halo ($Hal^1$)-substituted [4.4.0] aromatic heterocycle 1-1 is reacted with a suitable halo ($Hal^2$)-substituted aniline 1-2 to produce compound 1-3 under standard $S_NAr$ conditions using an acid such as, but not limited to, sulfuric acid, or base such as, but not limited to, potassium tert-butoxide. Compounds of formula 1-3 may also be synthesized under standard metal catalyzed cross-coupling reaction conditions (such as Buchwald-Hartwig coupling reaction, e.g., in the presence of a palladium catalyst (e.g., [(4,5-bis(diphenylphosphino)-9,9-dimethylxanthene)-2-(2'-amino-1,1'-biphenyl)]palladium(II) methanesulfonate) and a base (e.g., cesium carbonate)). Then the aromatic halide 1-3 can be reacted with a suitable coupling reagent 1-4 (where M is, e.g., —$B(OH)_2$) to provide the product of formula I under standard metal catalyzed cross-coupling reaction conditions (such as Suzuki coupling reaction, e.g., in the presence of a palladium catalyst (e.g., [1,1'-bis(diphenylphosphino)ferrocene]dichloropalladium(II)) and a base (e.g., a bicarbonate or a carbonate base)).

Scheme 1

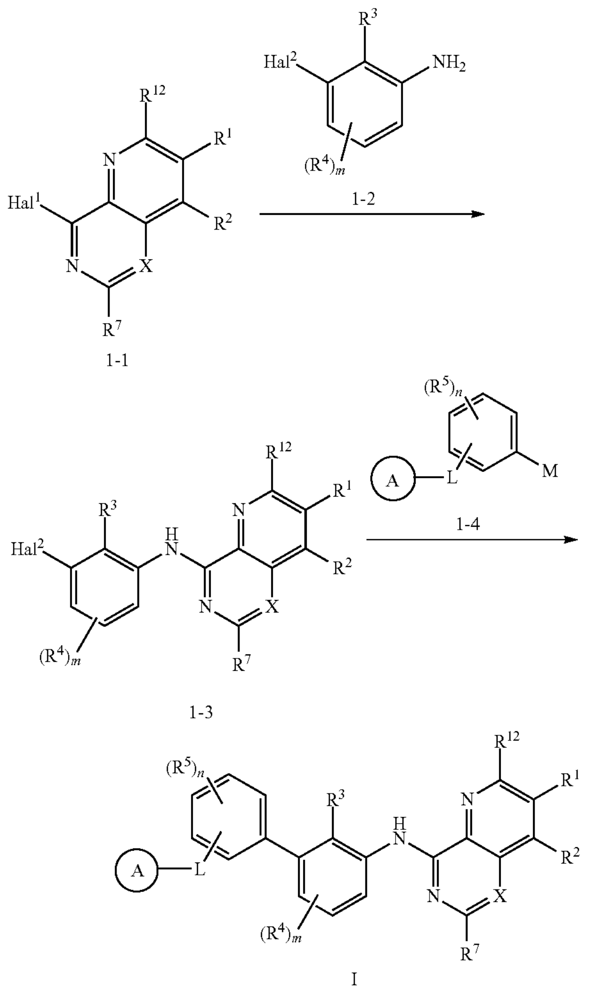

1-1

1-2

1-3

1-4

I

Compounds of formula II can be synthesized using a process shown in Scheme 2. A suitable halo ($Hal^1$)-substituted [4.4.0] aromatic heterocycle 2-1 can be reacted with a suitable halo ($Hal^2$)-substituted aniline 2-2 to produce formula 2-3 under $S_NAr$ conditions using an acid such as, but not limited to, sulfuric acid, or base such as, but not limited to, potassium tert-butoxide. Compounds of formula 2-3 may also be synthesized under standard metal catalyzed cross-coupling reaction conditions (such as Buchwald-Hartwig coupling reaction, e.g., in the presence of a palladium catalyst (e.g., [(4,5-bis(diphenylphosphino)-9,9-dimethylxanthene)-2-(2'-amino-1,1'-biphenyl)]palladium(II) methanesulfonate) and a base (e.g., cesium carbonate)). Then the aromatic halide 2-3 is reacted with a suitable coupling reagent 2-4 (where M is, e.g., —$B(OH)_2$) to form the bi-aryl bond of formula 2-5 under standard metal catalyzed cross-coupling reaction conditions (such as Suzuki coupling reaction, e.g., in the presence of a palladium catalyst (e.g., [1,1'-bis(diphenylphosphino)ferrocene]dichloropalladium (II)) and a base (e.g., a bicarbonate or a carbonate base)). The vinyl group in compound 2-5 can be oxidatively cleaved to afford an aldehyde in the presence of suitable reagents such as, but not limited to, $OsO_4$ and $NaIO_4$. Then the compound of formula II can be obtained by a reductive amination between the aldehyde derivative and a suitable amine 2-6 in a proper solvent such as THF or DCM using a reducing agent such as, but not limited to, sodium triacetoxyborohydride, optionally in the presence of an acid such as acetic acid or a base such as DIPEA.

Scheme 2

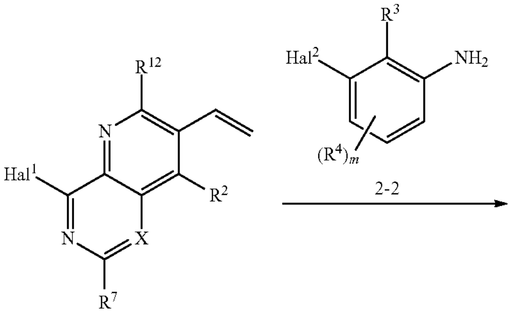

2-1

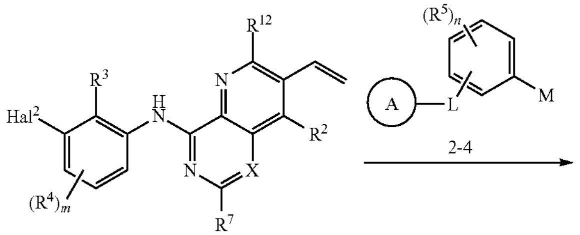

2-3

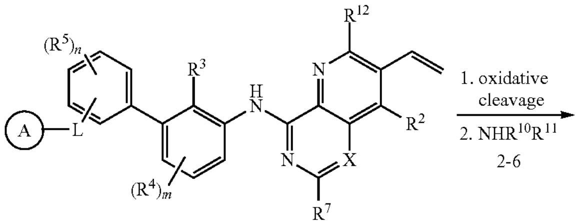

2-5

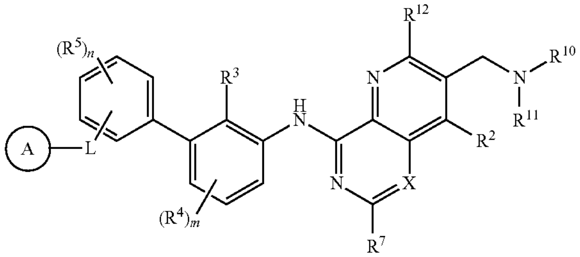

II

Compounds of formula II can be alternatively synthesized using a process shown in Scheme 3. The vinyl group of a suitable halo (Hal$^1$)-substituted [4.4.0] aromatic heterocycle 3-1 can be oxidatively cleaved to afford an aldehyde in the presence of suitable reagents such as, but not limited to, $OsO_4$ and $NaIO_4$. Then the compound of formula 3-3 can be obtained by a reductive amination between the aldehyde derivative and a suitable amine 3-2 in a proper solvent such as THF or DCM using a reducing agent such as, but not limited to, sodium triacetoxyborohydride, optionally in the presence of an acid such as acetic acid or a base such as DIPEA. The compound of formula 3-5 can be synthesized by reacting formula 3-3 with a suitable halo (Hal$^2$)-substituted aniline 3-4 under standard $S_NAr$ conditions using an acid such as, but not limited to, sulfuric acid, or base such as, but not limited to, potassium tert-butoxide. Compounds of formula 3-5 may also be synthesized under standard metal catalyzed cross-coupling reaction conditions (such as Buchwald-Hartwig coupling reaction, e.g., in the presence of a palladium catalyst (e.g., [(4,5-bis(diphenylphosphino)-9,9-dimethylxanthene)-2-(2'-amino-1,1'-biphenyl)]palladium (II) methanesulfonate) and a base (e.g., cesium carbonate)). Then the aromatic halide 3-5 is reacted with a suitable coupling reagent 3-6 (where M is, e.g., $—B(OH)_2$) to provide compounds of formula II under standard metal catalyzed cross-coupling reaction conditions (such as Suzuki coupling reaction, e.g., in the presence of a palladium catalyst (e.g., [1,1'-bis(diphenylphosphino)ferrocene] dichloropalladium(II)) and a base (e.g., a bicarbonate or a carbonate base)).

Scheme 3

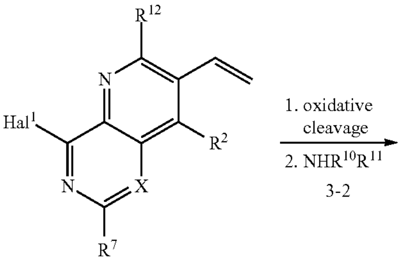

3-1

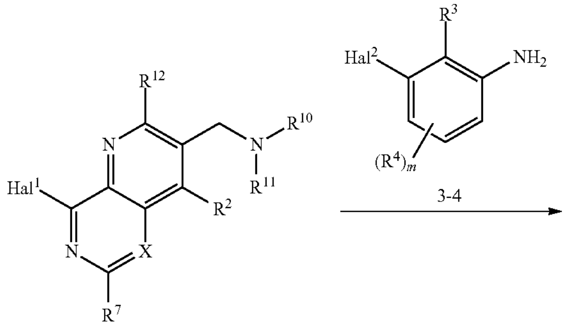

3-3

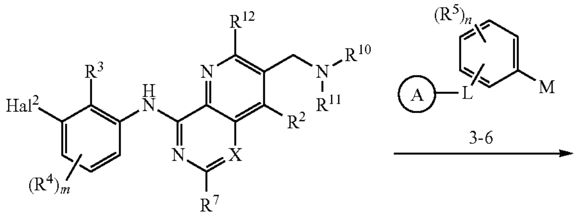

3-5

-continued

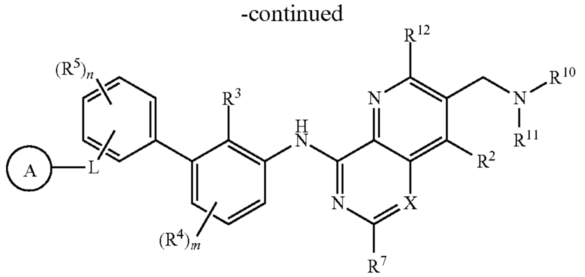

II

Compounds of formula III can be synthesized using a process shown in Scheme 4. A suitable halo ($Hal^1$)-substituted [4.4.0] aromatic heterocycle 4-1 can be reacted with a suitable halo ($Hal^2$)-substituted aniline 4-2 to produce a compound of formula 4-3 under standard $S_NAr$ conditions using an acid such as, but not limited to, sulfuric acid, or base such as, but not limited to, potassium tert-butoxide. Compounds of formula 4-3 may also be synthesized under standard metal catalyzed cross-coupling reaction conditions (such as Buchwald-Hartwig coupling reaction, e.g., in the presence of a palladium catalyst (e.g., [(4,5-bis(diphenylphosphino)-9,9-dimethylxanthene)-2-(2'-amino-1,1'-biphenyl)]palladium(II) methanesulfonate) and a base (e.g., cesium carbonate)). Then the aromatic halide 4-3 can be reacted with a suitable coupling reagent 4-4 (where M is, e.g., —$B(OH)_2$) to form the bi-aryl bond of formula 4-5 under standard metal catalyzed cross-coupling reaction conditions (such as Suzuki coupling reaction, e.g., in the presence of a palladium catalyst (e.g., [1,1'-bis(diphenylphosphino)ferrocene]dichloropalladium(II)) and a base (e.g., a bicarbonate or a carbonate base)). The vinyl group in compound 4-5 can be oxidatively cleaved to afford an aldehyde in the presence of suitable reagents such as, but not limited to, $OsO_4$ and $NaIO_4$. Then the compound of formula III is obtained by a reductive amination between the aldehyde derivative and a suitable amine 4-6 in a proper solvent such as THF or DCM using a reducing agent such as, but not limited to, sodium triacetoxyborohydride, optionally in the presence of an acid such as acetic acid or abase such as DIPEA.

Scheme 4

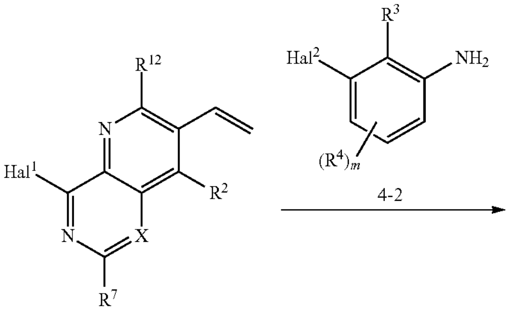

4-1

-continued

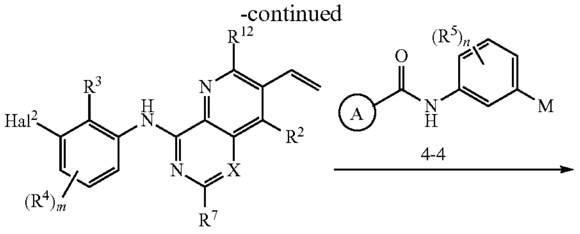

4-3

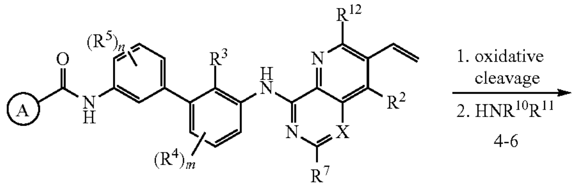

4-5

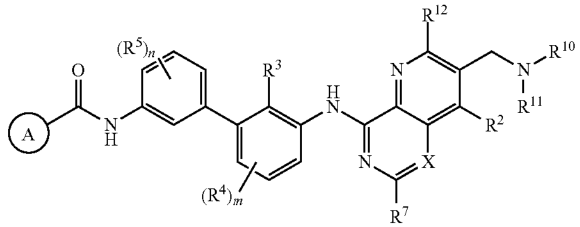

III

Compounds of formula III can be alternatively synthesized using a process shown in Scheme 5. The vinyl group of a suitable halo ($Hal^1$)-substituted [4.4.0] aromatic heterocycle 5-1 can be oxidatively cleaved to afford an aldehyde in the presence of suitable reagents such as, but not limited to, $OsO_4$ and $NaIO_4$. Then the compound of formula 5-3 is obtained by a reductive amination between the aldehyde derivative and a suitable amine 5-2 in a proper solvent such as THF or DCM using a reducing agent such as, but not limited to, sodium triacetoxyborohydride, optionally in the presence of an acid such as acetic acid or a base such as DIPEA. The compound of formula 5-5 can be synthesized by reacting formula 5-3 with a suitable halo ($Hal^2$)-substituted aniline 5-4 under standard $S_NAr$ conditions using an acid such as, but not limited to, sulfuric acid, or base such as, but not limited to, potassium tert-butoxide. Compounds of formula 5-5 may also be synthesized under standard metal catalyzed cross-coupling reaction conditions (such as Buchwald-Hartwig coupling reaction, e.g., in the presence of a palladium catalyst (e.g., [(4,5-bis(diphenylphosphino)-9,9-dimethylxanthene)-2-(2'-amino-1,1'-biphenyl)]palladium (II) methanesulfonate) and abase (e.g., cesium carbonate)). Then the aromatic halide 5-5 is reacted with a suitable coupling reagent 5-6 (where M is, e.g., —$B(OH)_2$) to provide compounds of formula II under standard metal catalyzed cross-coupling reaction conditions (such as Suzuki coupling reaction, e.g., in the presence of a palladium catalyst (e.g., [1,1'-bis(diphenylphosphino)ferrocene] dichloropalladium(II)) and a base (e.g., a bicarbonate or a carbonate base)).

Scheme 5

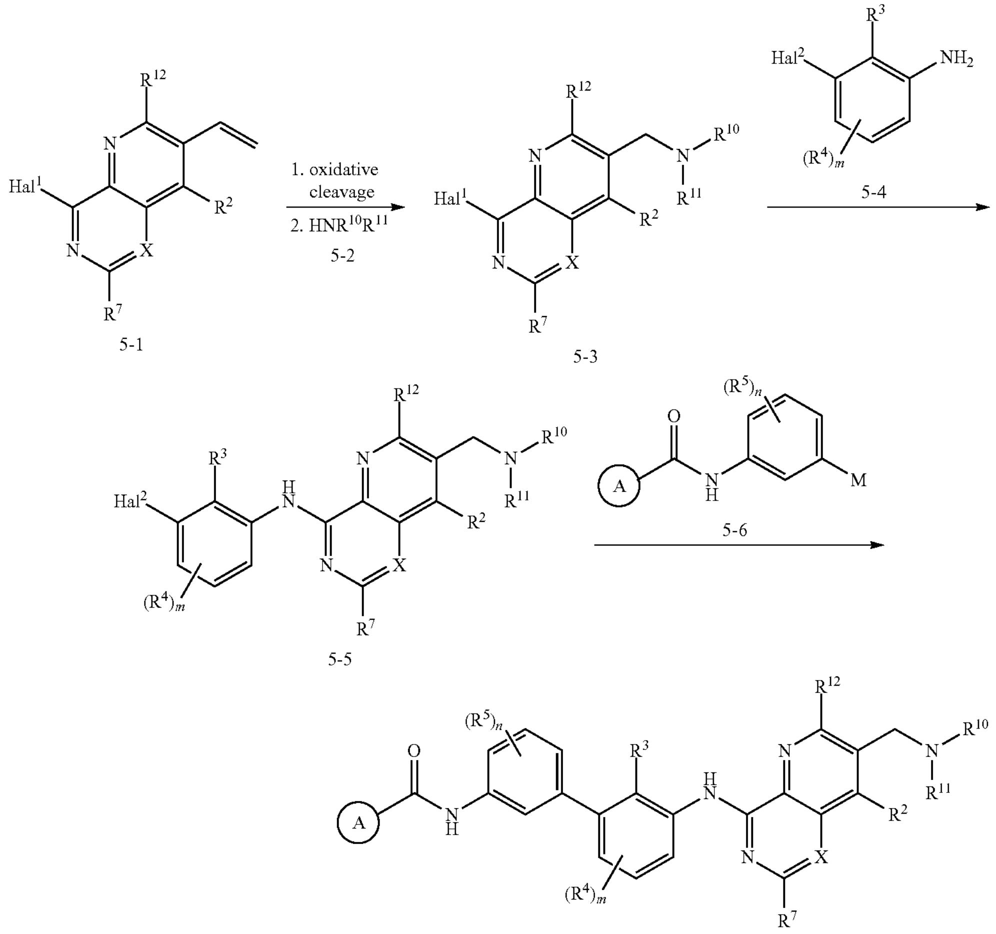

5-1 5-3 5-5

III

III. Uses of the Compounds

Compounds of the present disclosure can inhibit the activity of PD-1/PD-L1 protein/protein interaction and, thus, are useful in treating diseases and disorders associated with activity of PD-1 and the diseases and disorders associated with PD-L1 including its interaction with other proteins such as PD-1 and B7-1 (CD80). In certain embodiments, the compounds of the present disclosure, or pharmaceutically acceptable salts or stereoisomers thereof, are useful for therapeutic administration to enhance immunity in cancer, chronic infection or sepsis, including enhancement of response to vaccination. In some embodiments, the present disclosure provides a method for inhibiting the PD-1/PD-L1 protein/protein interaction. The method includes administering to an individual or a patient a compound of Formula (I) or of any of the formulas as described herein, or of a compound as recited in any of the claims and described herein, or a pharmaceutically acceptable salt or a stereoisomer thereof. The compounds of the present disclosure can be used alone, in combination with other agents or therapies or as an adjuvant or neoadjuvant for the treatment of diseases or disorders, including cancer or infection diseases. For the uses described herein, any of the compounds of the disclosure, including any of the embodiments thereof, may be used.

The compounds of the present disclosure inhibit the PD-1/PD-L1 protein/protein interaction, resulting in a PD-1 pathway blockade. The blockade of PD-1 can enhance the immune response to cancerous cells and infectious diseases in mammals, including humans. In some embodiments, the present disclosure provides treatment of an individual or a patient in vivo using a compound of Formula (I) or a salt or stereoisomer thereof such that growth of cancerous tumors is inhibited. A compound of Formula (I) or of any of the formulas as described herein, or a compound as recited in any of the claims and described herein, or a salt or stereoisomer thereof, can be used to inhibit the growth of cancerous tumors. Alternatively, a compound of Formula (I) or of any of the formulas as described herein, or a compound as recited in any of the claims and described herein, or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound of Formula (I) or of any of the formulas as described herein, or of a compound as recited in any of the claims and described herein, or of a salt or stereoisomer thereof. In another embodiment, the present disclosure provides a method for inhibiting growth of tumor cells in an individual or a patient. The method includes administering to the individual or patient in need thereof a therapeutically effective amount of a compound of Formula (I) or of any of the formulas as described herein, or of a compound as recited in any of the claims and described herein, or a salt or a stereoisomer thereof.

In some embodiments, provided herein is a method for treating cancer. The method includes administering to a patient in need thereof, a therapeutically effective amount of a compound of Formula (I) or any of the formulas as described herein, a compound as recited in any of the claims and described herein, or a salt thereof. Examples of cancers include those whose growth may be inhibited using compounds of the disclosure and cancers typically responsive to immunotherapy.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express PD-L1.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, colon cancer, lung cancer (e.g. non-small cell lung cancer and small cell lung cancer), squamous cell head and neck cancer, urothelial cancer (e.g. bladder and cancers with high microsatellite instability ($MSI^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, the compounds of the present disclosure can be used to treat sickle cell disease and sickle cell anemia.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

PD-1 pathway blockade with compounds of the present disclosure can also be used for treating infections such as viral, bacteria, fungus and parasite infections. The present disclosure provides a method for treating infections such as viral infections. The method includes administering to a patient in need thereof, a therapeutically effective amount of a compound of Formula (I) or any of the formulas as described herein, a compound as recited in any of the claims and described herein, a salt thereof. Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

The present disclosure provides a method for treating bacterial infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic bacteria causing infections treatable by methods of the disclosure include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum.*

The present disclosure provides a method for treating parasite infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic parasites causing infections treatable by methods of the disclosure include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

It is believed that compounds of Formula (I), or any of the embodiments thereof, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer or infections. Examples of diseases and indications treatable with combination therapies include those as described herein. Examples of cancers include solid tumors and liquid tumors, such as blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFPR, PI3K (alpha, beta, gamma, delta), CSFIR, KIT, FLK-II, KDR/FLK-1, FLK-4, flt-1, FGFR1, FGFR2, FGFR3, FGFR4, c-Met, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, BMS-986205), an LSD1 inhibitor (e.g., INCB59872 and INCB60003), a TDO inhibitor, a PI3K-delta inhibitor (e.g., INCB50797 and INCB50465), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, an histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), a poly ADP ribose polymerase (PARP) inhibitor such as rucaparib, olaparib, niraparib, veliparib, or talazoparib, an arginase inhibitor (INCB01158), and an adenosine receptor antagonist or combinations thereof.

Compounds of the present disclosure can be used in combination with one or more immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab. In some embodiments, the anti PD-1 antibody is SHR-1210.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MED14736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016, LAG525 or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Other anti-cancer agent(s) include antibody therapeutics such as trastuzumab (Herceptin), antibodies to costimulatory molecules such as CTLA-4 (e.g., ipilimumab), 4-1BB (e.g. urelumab, utomilumab), antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

In some embodiments, the anti-cancer agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of Formula (I) or any of the formulas as described herein, a compound as recited in any of the claims and described herein, or salts, stereoisomers thereof can be used in combination with an immune checkpoint inhibitor for the treatment of cancer and viral infections.

Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MED14736, MPDL3280A (also known as RG7446), or MSB0010718C. In some embodiments, the anti-PD-L1 monoclonal antibody is MPDL3280A or MED14736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MED16383.

The compounds of the present disclosure can further be used in combination with one or more anti-inflammatory agents, steroids, immunosuppressants or therapeutic antibodies.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia*, Malaria, *Leishmania, Staphylococcus aureus, Pseudomonas aeruginosa.*

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum.*

Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

When more than one pharmaceutical agent is administered to a patient, they can be administered simultaneously, separately, sequentially, or in combination (e.g., for more than two agents).

IV. Formulation, Dosage Forms and Administration

When employed as pharmaceuticals, the compounds of the present disclosure can be administered in the form of pharmaceutical compositions. Thus the present disclosure provides a composition comprising a compound of Formula (I) or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™) in some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the present disclosure can further be useful in investigations of biological processes in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating PD-1 or PD-L1 protein in tissue samples, including human, and for identifying PD-L1 ligands by inhibition binding of a labeled compound. Accordingly, the present invention includes PD-1/PD-L1 binding assays that contain such labeled compounds.

The present invention further includes isotopically-substituted compounds of the disclosure. An "isotopically-substituted" compound is a compound of the invention where one or more atoms are replaced or substituted by an atom having the same atomic number but different atomic mass or mass number e.g., a different atomic mass or mass number from the atomic mass or mass number typically found in nature (i.e., naturally occurring). It is to be understood that a "radio-labeled" compound is a compound that has incorporated at least one isotope that is radioactive (e.g., radionuclide). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro PD-L1 protein labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}$Br. Synthetic methods for incorporating radio-isotopes into organic compounds are applicable to compounds provided herein and are well known in the art.

A radio-labeled compound of the invention can be used in a screening assay to identify and/or evaluate compounds. In general terms, a newly synthesized or identified compound (i.e., test compound) which is labeled can be evaluated for its ability to bind a PD-L1 protein by monitoring its concentration variation when contacting with the PD-L1 protein, through tracking of the labeling. For example, a test compound (radio-labeled) can be evaluated for its ability to reduce binding of another compound which is known to bind to a PD-L1 protein (i.e., standard compound). Accordingly, the ability of a test compound to compete with the standard compound for binding to the PD-L1 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of diseases or disorders associated with the activity of PD-L1 including its interaction with other proteins such as PD-1 and B7-1 (CD80), such as cancer or infections, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of PD-1/PD-L1 protein/protein interaction according to at least one assay described herein.

EXAMPLES

Experimental procedures for compounds of the invention are provided below. Open Access Preparative LCMS Purification of some of the compounds prepared was performed on Waters mass directed fractionation systems. The basic equipment setup, protocols and control software for the operation of these systems have been described in detail in literature. See, e.g., Blom, "Two-Pump At Column Dilution Configuration for Preparative LC-MS", K. Blom, *J Combi. Chem.,* 2002, 4, 295-301; Blom et al., "Optimizing Preparative LC-MS Configurations and Methods for Parallel Synthesis Purification", *J. Combi. Chem.,* 2003, 5, 670-83; and Blom et al., "Preparative LC-MS Purification: Improved Compound Specific Method Optimization", *J. Combi. Chem.,* 2004, 6, 874-883.

Example 1: 2-(((8-((2-chloro-2'-methyl-3'-(4,5,6,7-tetrahydrothiazolo[5,4-c]pyridin-2-yl)-[1,1'-biphenyl]-3-yl)amino)-1,7-naphthyridin-3-yl)methyl)amino)ethan-1-ol

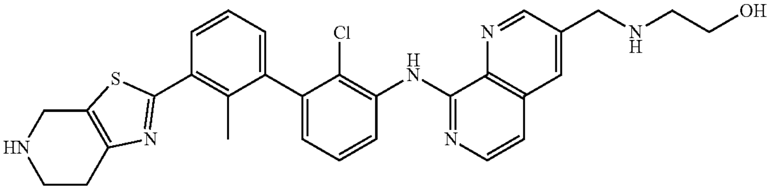 [SMILES: Cc1c(-c2nc3c(s2)CNCC3)cccc1-c1cccc(Nc2nccc3cc(CNCCO)cnc23)c1Cl]

Step 1: 8-chloro-3-vinyl-1,7-naphthyridine

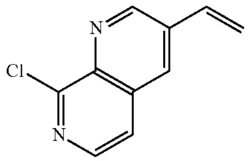

A mixture of 3-bromo-8-chloro-1,7-naphthyridine (PharmaBlock, cat #PBLJ2743: 0.200 g, 0.821 mmol), 4,4,5,5-tetramethyl-2-vinyl-1,3,2-dioxaborolane (Aldrich, cat #663348: 153 μL, 0.904 mmol), sodium carbonate (0.174 g, 1.64 mmol) and [1,1'-bis(di-cyclohexylphosphino)ferrocene]dichloropalladium(II) (Aldrich, cat #701998: 6.2 mg, 0.0082 mmol) in tert-butyl alcohol (5.91 mL, 61.8 mmol) and water (6 mL, 300 mmol) was degassed and sealed. It was stirred at 110° C. for 2 h. The reaction mixture was cooled then extracted with ethyl acetate (3×20 mL). The combined organic layers were washed with brine, dried over $MgSO_4$, filtered and concentrated under reduced pressure. The crude residue was used directly in the next step without further purification. LC-MS calculated for $C_{10}H_8ClN_2$ $(M+H)^+$: m/z=191.0; found 191.0.

Step 2: 8-chloro-1,7-naphthyridine-3-carbaldehyde

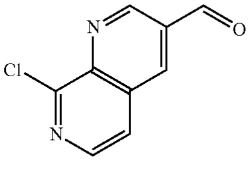 [SMILES: O=Cc1cnc2c(Cl)nccc2c1]

A flask was charged with 8-chloro-3-vinyl-1,7-naphthyridine (391. mg, 2.05 mmol), 1,4-dioxane (40. mL), a stir bar and water (40. mL). To this suspension was added a 4% w/w mixture of osmium tetraoxide in water (0.84 mL, 0.132 mmol). The reaction was stirred for 5 min then sodium periodate (3.23 g, 15.11 mmol) was added and stirred for 3 h. The mixture was diluted with water (20 mL) and EtOAc (20 mL). The layers were separated and the aqueous layer was further extracted with EtOAc (2×20 mL). The combined organic extracts were washed with brine, dried over sodium sulfate, filtered, and concentrated in vacuo. The crude aldehyde was purified by silica gel chromatography (0→60% EtOAc/hexanes). LC-MS calculated for $C_9H_6ClN_2O$ $(M+H)^+$: m/z=193.0; found 192.9.

Step 3: 2-{[(8-chloro-1,7-naphthyridin-3-yl)methyl]amino}ethanol

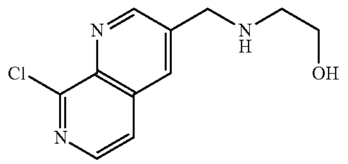 [SMILES: OCCNCc1cnc2c(Cl)nccc2c1]

A mixture of 8-chloro-1,7-naphthyridine-3-carbaldehyde (0.160 g, 0.831 mmol) and ethanolamine (Aldrich, cat #398136: 251 μL, 4.15 mmol) in methylene chloride (6 mL, 100 mmol) and N,N-diisopropylethylamine (868 μL, 4.98 mmol) was stirred at rt for 1 h. Sodium triacetoxyborohydride (0.528 g, 2.49 mmol) was carefully added in portions. The reaction was stirred at rt for 2 h. To the mixture was then carefully added sodium tetrahydroborate (157 mg, 4.15 mmol) and methanol (1 mL) and the reaction mixture was stirred overnight under nitrogen. The reaction was quenched with a saturated aqueous solution of sodium bicarbonate. The mixture was then extracted with a 3:1 mixture of chloroform/isopropyl alcohol. The combined organic layers were washed with brine, dried over sodium sulfate, then concentrated in vacuo. The crude residue was purified by column chromatography (0→50% methanol/DCM) and was obtained as an off white solid. LC-MS calculated for $C_{11}H_{13}ClN_3O$ $(M+H)^+$: m/z=238.1; found 238.1.

Step 4: 2-(((8-((3-bromo-2-chlorophenyl)amino)-1,7-naphthyridin-3-yl)methyl)amino)ethan-1-ol

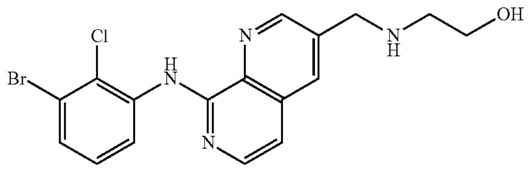 [SMILES: OCCNCc1cnc2c(Nc3cccc(Br)c3Cl)nccc2c1]

To a vial was added 3-bromo-2-chloroaniline (Enamine, cat #EN300-105778: 0.021 g, 0.101 mmol) and 2-(((8-chloro-1,7-naphthyridin-3-yl)methyl)amino)ethan-1-ol (0.020 g, 0.084 mmol). The solids were suspended in isopropanol (0.421 ml). Sulfuric acid (4.48 μl, 0.084 mmol) was added to the reaction mixture and then heated to 100° C. for 1 h. After cooling, the mixture was quenched with a saturated aqueous sodium bicarbonate solution, and extracted with 3:1 chloroform/isopropyl alcohol. The combined organic extracts were dried over magnesium sulfate, filtered, and concentrated in vacuo. The crude residue was purified using silica gel chromatography (1:1 DCM/MeOH) to afford a yellow solid. LC-MS calculated for $C_{17}H_{17}BrClN_4O$ $(M+H)^+$: m/z=407.0; found 407.2.

Step 5: tert-butyl 2-(3-chloro-2-methylphenyl)-6,7-dihydrothiazolo[5,4-c]pyridine-5(4H)-carboxylate

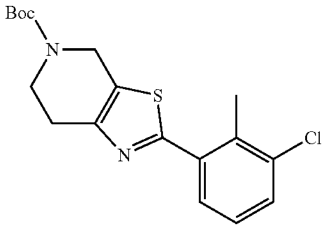 [SMILES: Cc1c(Cl)cccc1-c1nc2c(s1)CN(C(=O)OC(C)(C)C)CC2]

To a vial was added (3-chloro-2-methylphenyl)boronic acid (Combi-blocks, cat #BB-2035: 640 mg, 3.76 mmol), tert-butyl 2-bromo-6,7-dihydro[1,3]thiazolo[5,4-c]pyridine-5(4H)-carboxylate (AstaTech, cat #AB1021: 1000. mg, 3.133 mmol), sodium carbonate (996 mg, 9.40 mmol), tert-butyl alcohol (160 mmol), water (600 mmol) [1,1'-bis(di-cyclohexylphosphino)ferrocene]dichloropalladium(II) (Aldrich, cat #701998: 240 mg, 0.31 mmol). The mixture was sparged with nitrogen, then heated at 105° C. for 1.5 h. The mixture was concentrated, dissolved with DCM, and purified using silica gel chromatography (40% EtOAc/hexanes). LC-MS calculated for $C_{18}H_{22}ClN_2O_2S$ $(M+H)^+$: m/z=365.1; found 365.1.

Step 6: tert-butyl 2-(2-methyl-3-(4,4,5,5-tetramethyl-1,3,2-dioxaborolan-2-yl)phenyl)-6,7-dihydrothiazolo[5,4-c]pyridine-5(4H)-carboxylate

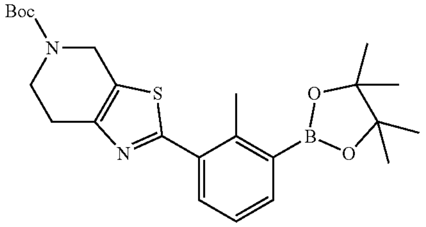 [SMILES: Cc1c(B2OC(C)(C)C(C)(C)O2)cccc1-c1nc2c(s1)CN(C(=O)OC(C)(C)C)CC2]

A mixture of tert-butyl 2-(3-chloro-2-methylphenyl)-6,7-dihydro[1,3]thiazolo[5,4-c]pyridine-5(4H)-carboxylate (261 mg, 0.715 mmol), 4,4,5,5,4',4',5',5'-octamethyl-[2,2']bi[[1,3,2]dioxaborolanyl] (Aldrich, cat #473294: 545 mg, 2.14 mmol), palladium acetate (6.42 mg, 0.0286 mmol), $K_3PO_4$ (455 mg, 2.14 mmol) and 2-(dicyclohexylphosphino)-2',6'-dimethoxy-1,1'-biphenyl (Strem Chemicals, cat #15-1143: 29.4 mg, 0.0715 mmol) in 1,4-Dioxane was degassed and stirred at rt for 16 h. The mixture was diluted with DCM, and washed with water. The organic layer was concentrated in vacuo and purified by silica-gel chromatography (5% EtOAc/DCM). LC-MS calculated for $C_{24}H_{34}BN_2O_4S$ $(M+H)^+$: m/z=457.2; found 457.3.

Step 7: tert-butyl 2-(2'-chloro-3'-(3-((2-hydroxyethylamino)methyl)-1,7-naphthyridin-8-ylamino)-2-methylbiphenyl-3-yl)-6,7-dihydrothiazolo[5,4-c]pyridine-5(4H)-carboxylate

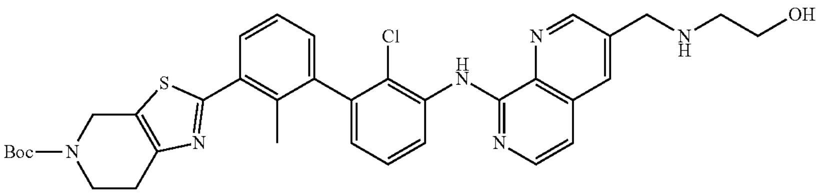 [SMILES: Cc1c(-c2nc3c(s2)CN(C(=O)OC(C)(C)C)CC3)cccc1-c1cccc(Nc2nccc3cc(CNCCO)cnc23)c1Cl]

To a vial was added tert-butyl 2-(2-methyl-3-(4,4,5,5-tetramethyl-1,3,2-dioxaborolan-2-yl)phenyl)-6,7-dihydrothiazolo[5,4-c]pyridine-5(4H)-carboxylate (0.013 g, 0.029 mmol), 2-(((8-((3-bromo-2-chlorophenyl)amino)-1,7-naphthyridin-3-yl)methyl)amino)ethan-1-ol (0.008 g, 0.020 mmol), sodium carbonate (6.24 mg, 0.059 mmol), [1,1'-bis(diphenylphosphino)ferrocene]dichloropalladium(II) (1.436 mg, 1.962 μmol), 1,4-dioxane (0.346 ml), and water (0.046 ml). The mixture was degassed, sealed, and heated to 90° C. whilst stirring for 4 h. After cooling, the mixture was diluted with DCM and water. The layers were separated and the aqueous layer was further extracted. The combined organic layers were dried over magnesium sulfate, filtered, concentrated in vacuo, and purified by silica gel chromatography (MeOH/DCM). LC-MS calculated for $C_{35}H_{38}ClN_6O_3S$ $(M+H)^+$: m/z=657.2; found 657.5.

Step 8: 2-(((8-((2-chloro-2'-methyl-3'-(4,5,6,7-tetrahydrothiazolo[5,4-c]pyridin-2-yl)-[1,1'-biphenyl]-3-yl)amino)-1,7-naphthyridin-3-yl)methyl)amino)ethan-1-ol A vial was charged with tert-butyl 2-(2'-chloro-3'-(3-((2-hydroxyethylamino)methyl)-1,7-naphthyridin-8-ylamino)-2-methylbiphenyl-3-yl)-6,7-dihydrothiazolo[5,4-c]pyridine-5(4H)-carboxylate (13 mg, 0.020 mmol), DCM (0.4 mL) and TFA (0.010 mL, 1 mmol). The resulting mixture was stirred for 1 h, open to air. The mixture was then dissolved in MeOH and purified by prep HPLC (pH=2, acetonitrile/water+TFA) to provide the compound as the TFA salt. LC-MS calculated for $C_{30}H_{30}ClN_6OS$ $(M+H)^+$: m/z=557.2; found 557.3.

Example 2: 1-(((6-(2-fluoro-3'-(3-((2-hydroxyethylamino)methyl)-1,7-naphthyridin-8-ylamino)-2'-methylbiphenyl-3-ylcarbamoyl)pyridin-3-yl)methyl)amino)cyclobutanecarboxylic acid

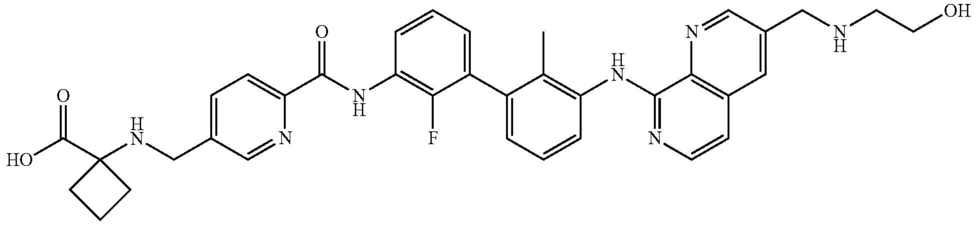 [SMILES: Cc1c(Nc2nccc3cc(CNCCO)cnc23)cccc1-c1cccc(NC(=O)c2ccc(CNC3(C(=O)O)CCC3)cn2)c1F]

Step 1: 2-(((8-((3-bromo-2-methylphenyl)amino)-1,7-naphthyridin-3-yl)methyl)amino)ethan-1-ol

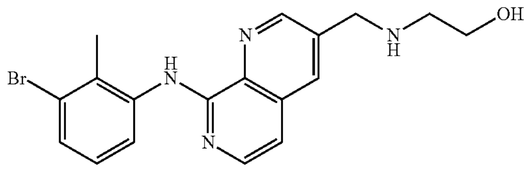 [SMILES: Cc1c(Br)cccc1Nc1nccc2cc(CNCCO)cnc12]

This compound was prepared using a similar procedure as described for Example 1, Step 4 with 3-bromo-2-methylaniline (Aldrich, cat #530018) replacing 3-bromo-2-chloroaniline. The crude compound was purified using column chromatography (0→50% MeOH/DCM). LC-MS calculated for $C_{18}H_{20}BrN_4O$ $(M+H)^+$: m/z=387.1; found 387.2.

Step 2: 5-(dimethoxymethyl)-N-(2-fluoro-3-(4,4,5,5-tetramethyl-1,3,2-dioxaborolan-2-yl)phenyl)picolinamide

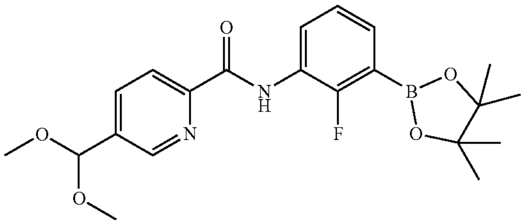

To a solution of 2-fluoro-3-(4,4,5,5-tetramethyl-1,3,2-dioxaborolan-2-yl)aniline (Combi-Blocks, cat #PN-5021: 200 mg, 0.844 mmol) and methyl 5-(dimethoxymethyl)picolinate (Combi-Blocks, cat #QY-1318: 196 mg, 0.928 mmol) in THF (8436 μl) was added 1.0 M potassium tert-butoxide in THF (1265 μl, 1.265 mmol) at rt. The mixture was stirred at rt for 2 h. Water and EtOAc were added, and the layers were separated. The aqueous layer was further extracted with ethyl acetate, and the combined organic layers were washed with brine, dried over magnesium sulfate, filtered, and concentrated in vacuo. The crude residue was purified using silica gel chromatography (30% EtOAc/hexanes). LC-MS calculated for $C_{21}H_{27}BFN_2O_5$ $(M+H)^+$: m/z=417.2; found 417.3.

Step 3: 5-(dimethoxymethyl)-N-(2-fluoro-3'-((3-(((2-hydroxyethyl)amino)methyl)-1,7-naphthyridin-8-yl)amino)-2'-methyl-[1,1'-biphenyl]-3-yl)picolinamide

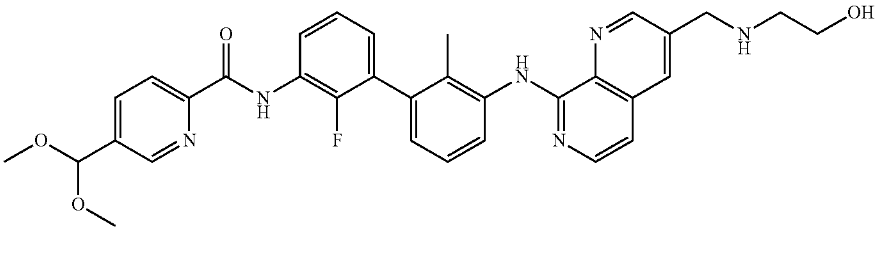 [SMILES: COC(OC)c1ccc(C(=O)Nc2cccc(-c3cccc(Nc4nccc5cc(CNCCO)cnc45)c3C)c2F)nc1]

To a vial was added 5-(dimethoxymethyl)-N-(2-fluoro-3-(4,4,5,5-tetramethyl-1,3,2-dioxaborolan-2-yl)phenyl)picolinamide (0.161 g, 0.387 mmol), 2-(((8-((3-bromo-2-methylphenyl)amino)-1,7-naphthyridin-3-yl)methyl)amino)ethan-1-ol (0.10 g, 0.258 mmol), sodium carbonate (0.041 g, 0.387 mmol), [1,1'-bis(diphenylphosphino)ferrocene]dichloropalladium(II) (0.019 g, 0.026 mmol), 1,4-dioxane (4.56 ml), and water (0.608 ml). The mixture was degassed, sealed, and heated to 90° C. whilst stirring for 4 h. After cooling, the mixture was diluted with DCM and water, and the layers were separated. The aqueous layer was further extracted with DCM, and the combined organic layers were dried over magnesium sulfate, filtered, and concentrated in vacuo. The crude residue was purified by silica gel chromatography (20% MeOH/DCM) to provide the desired product. LC-MS calculated for $C_{33}H_{34}FN_6O_4(M+H)^+$: m/z=597.3; found 597.2.

Step 4: N-(2-fluoro-3'-((3-(((2-hydroxyethyl)amino)methyl)-1,7-naphthyridin-8-yl)amino)-2'-methyl-[1,1'-biphenyl]-3-yl)-5-formylpicolinamide

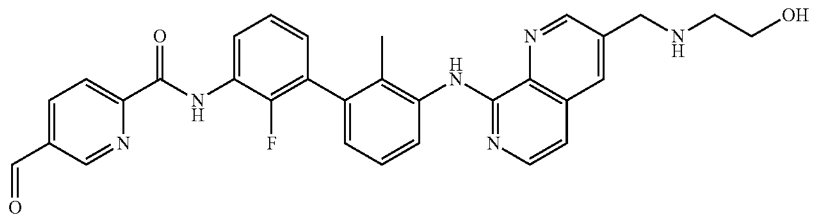

To a solution of 5-(dimethoxymethyl)-N-(2-fluoro-3'-((3-(((2-hydroxyethyl)amino)methyl)-1,7-naphthyridin-8-yl)amino)-2'-methyl-[1,1'-biphenyl]-3-yl)picolinamide (0.068 g, 0.114 mmol) in DCM (1.899 ml) was added TFA (0.439 ml, 5.70 mmol). The mixture was stirred at for 2 h. The mixture was concentrated and the residue was dissolved in DCM, and washed with a saturated aqueous $NaHCO_3$ solution. The layers were separated and the aqueous layer was further extracted with DCM. The combined organic layers were dried over magnesium sulfate, filtered and concentrated in vacuo. The crude product was used directly in the next step without further purification. LC-MS calculated for $C_{31}H_{28}FN_6O_3(M+H)^+$: m/z=551.2; found 551.2.

Step 5: 1-(((6-(2-fluoro-3'-(3-((2-hydroxyethylamino)methyl)-1,7-naphthyridin-8-ylamino)-2'-methylbiphenyl-3-ylcarbamoyl)pyridin-3-yl)methyl)amino)cyclobutanecarboxylic acid To a vial was added N-(2-fluoro-3'-((3-(((2-hydroxyethyl)amino)methyl)-1,7-naphthyridin-8-yl)amino)-2'-methyl-[1,1'-biphenyl]-3-yl)-5-formylpicolinamide (0.030 g, 0.054 mmol), 1-aminocyclobutane-1-carboxylic acid (Aldrich, cat #652369: 0.019 g, 0.163 mmol), dichloromethane (0.893 ml) and triethylamine (0.016 ml, 0.115 mmol). The reaction was stirred at rt for 2 h, then sodium triacetoxyborohydride (0.058 g, 0.272 mmol) and acetic acid (9.36 μl, 0.163 mmol) were added. The reaction was stirred for 2 h, then the mixture was diluted with methanol and purified by prep HPLC (pH=2, acetonitrile/water+TFA) to provide the desired compound as the TFA salt. LC-MS calculated for $C_{36}H_{37}FN_7O_4(M+H)^+$: m/z=650.3; found 650.3

Example 3: (S)-1-((6-((2-fluoro-3'-((3-(((2-hydroxyethyl)amino)methyl)-1,7-naphthyridin-8-yl)amino)-2'-methyl-[1,1'-biphenyl]-3-yl)carbamoyl)pyridin-3-yl)methyl)piperidine-2-carboxylic acid

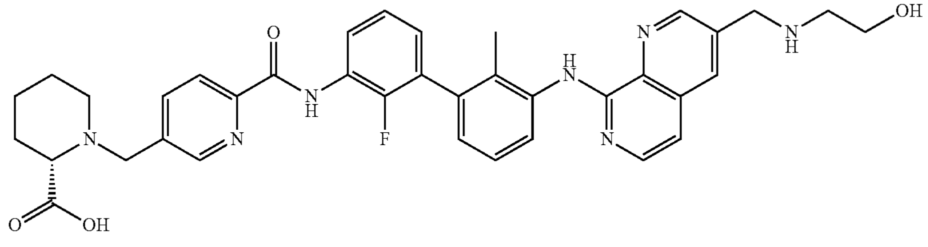 [SMILES: Cc1c(Nc2nccc3cc(CNCCO)cnc23)cccc1-c1cccc(NC(=O)c2ccc(CN3CCCC[C@H]3C(=O)O)cn2)c1F]

This compound was prepared using a similar procedure as described for Example 2, Step 5 with L-pipecolinic acid (Alfa Aesar, cat #L15373) replacing 1-aminocyclobutane-1-carboxylic acid. LC-MS calculated for $C_{37}H_{39}FN_7O_4$(M+H)$^+$: m/z=664.3; found 664.3.

Example 4: N-(2-fluoro-3'-((3-(((2-hydroxyethyl)amino)methyl)-1,7-naphthyridin-8-yl)amino)-2'-methyl-[1,1'-biphenyl]-3-yl)-5-(((2-hydroxyethyl)amino)methyl)picolinamide

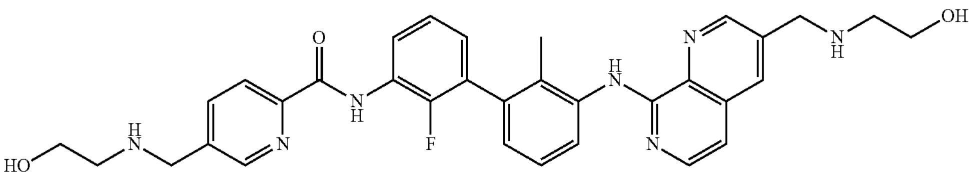

This compound was prepared using a similar procedure as described for Example 2, Step 5 with ethanolamine (Aldrich, cat #398136) replacing 1-aminocyclobutane-1-carboxylic acid. LC-MS calculated for $C_{33}H_{35}FN_7O_3$(M+H)$^+$: m/z=596.3; found 596.2.

Example 5: N-(2-chloro-3'-((3-(((2-hydroxyethyl)amino)methyl)-1,7-naphthyridin-8-yl)amino)-2'-methyl-[1,1'-biphenyl]-3-yl)-5-(((2-hydroxyethyl)amino)methyl)picolinamide

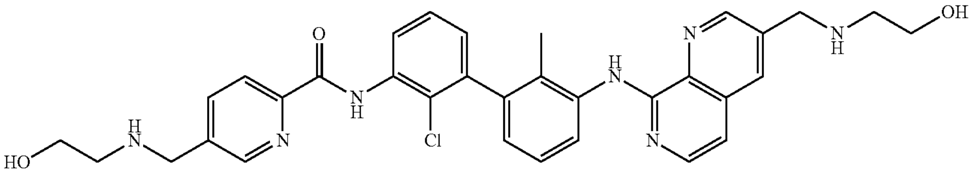 [SMILES: Cc1c(Nc2nccc3cc(CNCCO)cnc23)cccc1-c1cccc(NC(=O)c2ccc(CNCCO)cn2)c1F]

Step 1: 2-chloro-3-(4,4,5,5-tetramethyl-1,3,2-dioxaborolan-2-yl)aniline

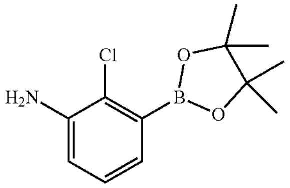 [SMILES: CC1(C)OB(c2cccc(N)c2Cl)OC1(C)C]

4,4,5,5,4',4',5',5'-Octamethyl-[2,2']bi[[1,3,2]dioxaborolanyl] (1.48 g, 5.81 mmol), potassium acetate (0.428 g, 4.36 mmol), 3-bromo-2-chloroaniline (Enamine, cat #EN300-105778: 0.300 g, 1.453 mmol), 1,4-dioxane (7.27 ml) and [1,1'-bis(diphenylphosphino)ferrocene] dichloropalladium (II) (0.053 g, 0.073 mmol) was stirred in a closed vial flushed with argon at 110° C. for 2 h. The mixture was cooled, diluted with EtOAc, and filtered over celite. The filtrate was concentrated and purified by silica gel chromatography (20% EtOAc/hexanes). LC-MS calculated for $C_{12}H_{11}BClNO_2$ (M+H)$^+$: m/z=254.1; found 254.1.

Step 2: N-(2-chloro-3-(4,4,5,5-tetramethyl-1,3,2-dioxaborolan-2-yl)phenyl)-5-(dimethoxymethyl)picolinamide

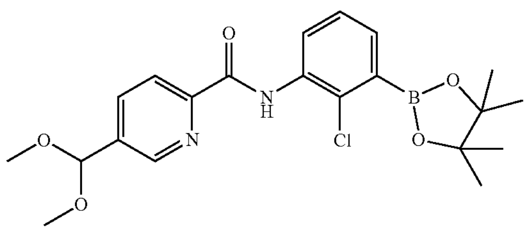

This compound was prepared using a similar procedure as described for Example 2, Step 2 with 2-chloro-3-(4,4,5,5-tetramethyl-1,3,2-dioxaborolan-2-yl)aniline replacing 2-fluoro-3-(4,4,5,5-tetramethyl-1,3,2-dioxaborolan-2-yl)aniline. LC-MS calculated for $C_{21}H_{27}BClN_2O_5$(M+H)$^+$: m/z=433.2; found 433.1.

Step 3: N-(2-chloro-3'-((3-(((2-hydroxyethyl)amino)methyl)-1,7-naphthyridin-8-yl)amino)-2'-methyl-[1,1'-biphenyl]-3-yl)-5-(dimethoxymethyl)picolinamide

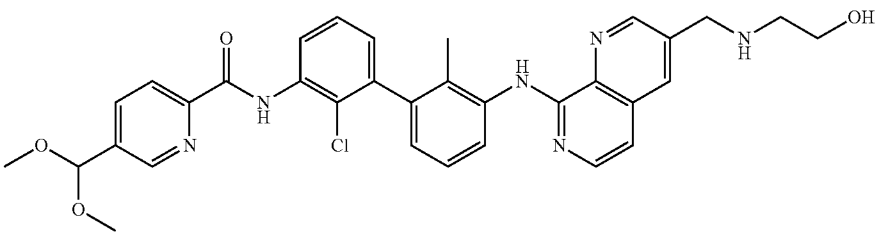 [SMILES: COC(OC)c1ccc(C(=O)Nc2cccc(-c3cccc(Nc4nccc5cc(CNCCO)cnc45)c3C)c2Cl)nc1]

This compound was prepared using a similar procedure as described for Example 2, Step 3 with N-(2-chloro-3-(4,4,5,5-tetramethyl-1,3,2-dioxaborolan-2-yl)phenyl)-5-(dimethoxymethyl)picolinamide replacing 5-(dimethoxymethyl)-N-(2-fluoro-3-(4,4,5,5-tetramethyl-1,3,2-dioxaborolan-2-yl)phenyl)picolinamide. LC-MS calculated for $C_{33}H_{34}ClN_6O_4(M+H)^+$: m/z=613.2; found 613.2.

Step 4: N-(2-chloro-3'-((3-(((2-hydroxyethyl)amino)methyl)-1,7-naphthyridin-8-yl)amino)-2'-methyl-[1,1'-biphenyl]-3-yl)-5-formylpicolinamide

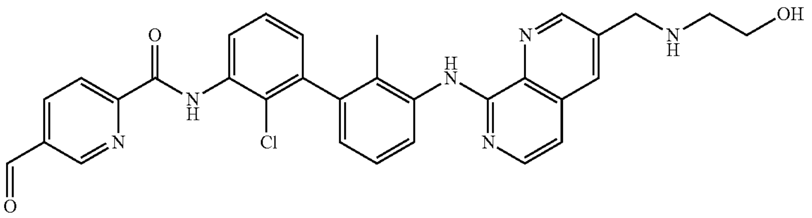 [SMILES: Cc1c(Nc2nccc3cc(CNCCO)cnc23)cccc1-c1cccc(NC(=O)c2ccc(C=O)cn2)c1Cl]

This compound was prepared using a similar procedure as described for Example 2, Step 4 with N-(2-chloro-3'-((3-(((2-hydroxyethyl)amino)methyl)-1,7-naphthyridin-8-yl)amino)-2'-methyl-[1,1'-biphenyl]-3-yl)-5-(dimethoxymethyl)picolinamide replacing 5-(dimethoxymethyl)-N-(2-fluoro-3'-((3-(((2-hydroxyethyl)amino)methyl)-1,7-naphthyridin-8-yl)amino)-2'-methyl-[1,1'-biphenyl]-3-yl)picolinamide. LC-MS calculated for $C_{31}H_{28}ClN_6O_3$ $(M+H)^+$: m/z=567.2; found 567.2.

Step 5: N-(2-chloro-3'-((3-(((2-hydroxyethyl)amino)methyl)-1,7-naphthyridin-8-yl)amino)-2'-methyl-[1,1'-biphenyl]-3-yl)-5-(((2-hydroxyethyl)amino)methyl)picolinamide To a vial was added N-(2-chloro-3'-((3-(((2-hydroxyethyl)amino)methyl)-1,7-naphthyridin-8-yl)amino)-2'-methyl-[1,1'-biphenyl]-3-yl)-5-formylpicolinamide (0.015 g, 0.026 mmol), ethanolamine (Aldrich, cat #398136: 0.0049 g, 0.163 mmol), dichloromethane (0.893 ml) and N,N-diisopropylethylamine (0.028 mL, 0.159 mmol). The reaction was stirred at rt for 2 h, then sodium triacetoxyborohydride (0.058 g, 0.272 mmol) was added. The reaction was stirred for 2 h, then the mixture was diluted with methanol and purified by prep HPLC (pH=2, acetonitrile/water+TFA; then pH=10, acetonitrile/water+$NH_4OH$). LC-MS calculated for $C_{33}H_{35}ClN_7O_3(M+H)^+$: m/z=612.2; found 612.2.

Example 6: N-(2-chloro-3'-((3-(((R)-3-hydroxypyrrolidin-1-yl)methyl)-1,7-naphthyridin-8-yl)amino)-2'-methyl-[1,1'-biphenyl]-3-yl)-5-(((R)-3-hydroxypyrrolidin-1-yl)methyl)picolinamide

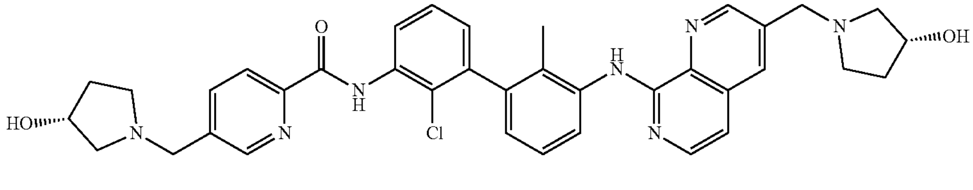 [SMILES: Cc1c(Nc2nccc3cc(CN4CC[C@@H](O)C4)cnc23)cccc1-c1cccc(NC(=O)c2ccc(CN3CC[C@@H](O)C3)cn2)c1Cl]

Step 1: N-(3-bromo-2-methylphenyl)-3-vinyl-1,7-naphthyridin-8-amine

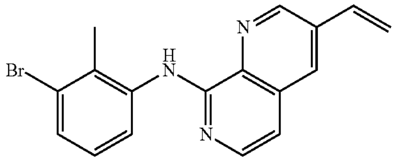 [SMILES: C=Cc1cnc2c(Nc3cccc(Br)c3C)nccc2c1]

In a vial, 3-bromo-2-methylaniline (Aldrich, cat #530018: 0.931 ml, 7.55 mmol) and 8-chloro-3-vinyl-1,7-naphthyridine (Example 1, Step 1: 1.20 g, 6.29 mmol) were suspended in isopropanol (31.5 ml). Sulfuric acid (0.336 ml, 6.29 mmol) was added to the reaction mixture. The resulting mixture was heated to 100° C. for 1 h whilst stirring. The mixture was cooled, quenched with aqueous saturated sodium bicarbonate, and diluted with DCM. The layers were separated and the water layer was further extracted with DCM. The combined organic layers were dried over magnesium sulfate, filtered and concentrated in vacuo. The crude solid was purified by column chromatography (0→1% Methanol/DCM) to provide the desired compound as a yellow solid. LC-MS calculated for $C_{17}H_{15}BrN_3$ $(M+H)^+$: m/z=340.0; found 340.1.

Step 2: 2'-chloro-2-methyl-N3-(3-vinyl-1,7-naphthyridin-8-yl)-[1,1'-biphenyl]-3,3'-diamine

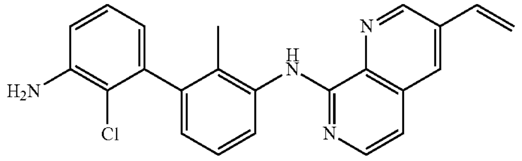 [SMILES: C=Cc1cnc2c(Nc3cccc(-c4cccc(N)c4Cl)c3C)nccc2c1]

To a flask was added 2-chloro-3-(4,4,5,5-tetramethyl-1,3,2-dioxaborolan-2-yl)aniline (Example 5, Step 1: 1.414 g, 5.58 mmol), N-(3-bromo-2-methylphenyl)-3-vinyl-1,7-naphthyridin-8-amine (1.2646 g, 3.72 mmol), sodium carbonate (0.591 g, 5.58 mmol), [1,1'-bis(diphenylphosphino)ferrocene] dichloropalladium (II) (0.272 g, 0.372 mmol), 1,4-dioxane (32.8 ml), and water (4.37 ml). The mixture was degassed, sealed, and heated to 90° C. whilst stirring for 4 h. The mixture was cooled, diluted with EtOAc, and the layers were separated. The aqueous layer was further extracted with EtOAc, and the combined organic layers were washed with brine, dried of magnesium sulfate, filtered, and concentrated in vacuo. The crude residue was then purified by silica gel chromatography (20% EtOAc/hexanes) to provide the desired compound as a yellow solid. LC-MS calculated for $C_{23}H_{20}ClN_4$ $(M+H)^+$: m/z=387.1; found 387.1.

Step 3: N-(2-chloro-2'-methyl-3'-((3-vinyl-1,7-naphthyridin-8-yl)amino)-[1,1'-biphenyl]-3-yl)-5-(dimethoxymethyl)picolinamide

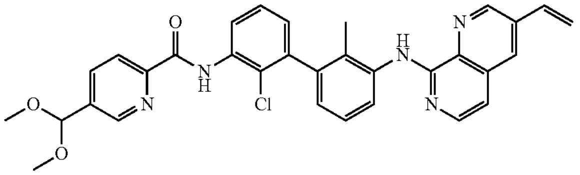 [SMILES: C=Cc1cnc2c(Nc3cccc(-c4cccc(NC(=O)c5ccc(C(OC)OC)cn5)c4Cl)c3C)nccc2c1]

To a solution of 2'-chloro-2-methyl-N3-(3-vinyl-1,7-naphthyridin-8-yl)-[1,1'-biphenyl]-3,3'-diamine (0.682 g, 1.763 mmol) and methyl 5-(dimethoxymethyl)picolinate (Combi-Blocks, cat #QY-1318: 0.372 g, 1.763 mmol) in THF (17.63 ml) was added 1.0 M Potassium tert-butoxide in THF (2.64 ml, 2.64 mmol) at rt. The mixture was stirred at rt for 2 h. Water was added to quench the reaction. The layers were separated and the water layer was further extracted with ethyl acetate. The combined organic layers were washed with brine, dried over magnesium sulfate, filtered and concentrated in vacuo. The crude orange foam was used directly in the next step without further purification. LC-MS calculated for $C_{32}H_{29}ClN_5O_3(M+H)^+$: m/z=566.2; found 566.3.

Step 4: N-(2-chloro-2'-methyl-3'-((3-vinyl-1,7-naphthyridin-8-yl)amino)-[1,1'-biphenyl]-3-yl)-5-formylpicolinamide

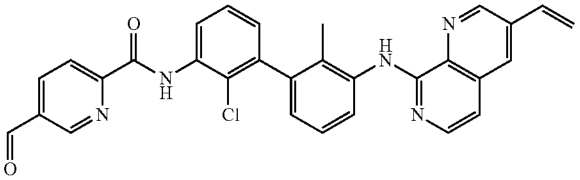 [SMILES: C=Cc1cnc2c(Nc3cccc(-c4cccc(NC(=O)c5ccc(C=O)cn5)c4Cl)c3C)nccc2c1]

This compound was prepared using a similar procedure as described for Example 2, Step 4 with N-(2-chloro-2'-methyl-3'-((3-vinyl-1,7-naphthyridin-8-yl)amino)-[1,1'-biphenyl]-3-yl)-5-(dimethoxymethyl)picolinamide replacing 5-(dimethoxymethyl)-N-(2-fluoro-3'-((3-(((2-hydroxyethyl)amino)methyl)-1,7-naphthyridin-8-yl)amino)-2'-methyl-[1,1'-biphenyl]-3-yl)picolinamide. LC-MS calculated for $C_{30}H_{23}ClN_5O_2(M+H)^+$: m/z=520.2; found 520.2.

Step 5: (R)-N-(2-chloro-2'-methyl-3'-((3-vinyl-1,7-naphthyridin-8-yl)amino)-[1,1'-biphenyl]-3-yl)-5-((3-hydroxypyrrolidin-1-yl)methyl)picolinamide

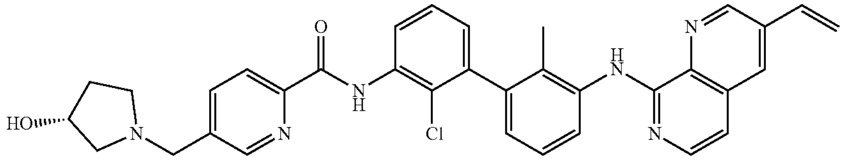 [SMILES: C=Cc1cnc2c(Nc3cccc(-c4cccc(NC(=O)c5ccc(CN6CC[C@@H](O)C6)cn5)c4Cl)c3C)nccc2c1]

A mixture of N-(2-chloro-2'-methyl-3'-((3-vinyl-1,7-naphthyridin-8-yl)amino)-[1,1'-biphenyl]-3-yl)-5-formylpicolinamide (0.180 g, 0.346 mmol) and (R)-3-hydroxypyrrolidine (Combi-Blocks, cat #AM-2005: 0.090 g, 1.038 mmol) in methylene chloride (1.731 ml) and N,N-diisopropylethylamine (0.301 ml, 1.731 mmol) was stirred at rt for 1 h. Sodium triacetoxyborohydride (0.220 g, 1.038 mmol) was carefully added in portions. The reaction was stirred at rt for 2 h. The reaction was quenched with a saturated aqueous solution of sodium bicarbonate. The mixture was then extracted with a 3:1 mixture of chloroform/IPA. The combined organic layers were washed with brine, dried over sodium sulfate, and then concentrated in vacuo. The crude residue was purified by column chromatography (0→20% methanol/DCM). LC-MS calculated for $C_{34}H_{32}ClN_6O_2$ $(M+H)^+$: m/z=591.2; found 591.4.

Step 6: (R)-N-(2-chloro-3'-((3-formyl-1,7-naphthyridin-8-yl)amino)-2'-methyl-[1,1'-biphenyl]-3-yl)-5-((3-hydroxypyrrolidin-1-yl)methyl)picolinamide

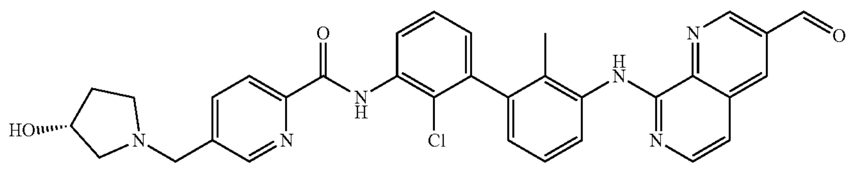 [SMILES: Cc1c(Nc2nccc3cc(C=O)cnc23)cccc1-c1cccc(NC(=O)c2ccc(CN3CC[C@@H](O)C3)cn2)c1Cl]

A flask was charged with (R)-N-(2-chloro-2'-methyl-3'-((3-vinyl-1,7-naphthyridin-8-yl)amino)-[1,1'-biphenyl]-3-yl)-5-((3-hydroxypyrrolidin-1-yl)methyl)picolinamide (0.241 g, 0.408 mmol), 1,4-dioxane (4.5 mL) and water (2.3 mL). A 4% osmium tetroxide solution in water (0.181 ml, 0.029 mmol) was added to the reaction mixture. After 5 min of stirring, sodium periodate (0.349 g, 1.631 mmol) was added and the mixture was stirred for 3 h. The mixture was diluted with water (2 mL) and EtOAc (5 mL), and the layers were separated. The aqueous layer was further extracted with EtOAc. The combined organic extracts were washed with brine, dried over sodium sulfate, filtered, and concentrated in vacuo. The crude aldehyde was purified by silica gel chromatography (20% MeOH/DCM). LC-MS calculated for $C_{33}H_{30}ClN_6O_3(M+H)^+$: m/z=593.2; found 593.1.

Step 7: N-(2-chloro-3'-((3-(((R)-3-hydroxypyrrolidin-1-yl)methyl)-1,7-naphthyridin-8-yl)amino)-2'-methyl-[1,1'-biphenyl]-3-yl)-5-(((R)-3-hydroxypyrrolidin-1-yl)methyl)picolinamide To a vial was added (R)-N-(2-chloro-3'-((3-formyl-1,7-naphthyridin-8-yl)amino)-2'-methyl-[1,1'-biphenyl]-3-yl)-5-((3-hydroxypyrrolidin-1-yl)methyl)picolinamide (0.030 g, 0.051 mmol), ethanolamine (Aldrich, cat #398136: 9.3 mg, 0.152 mmol), dichloromethane (0.829 ml) and N,N-diisopropylethylamine (0.053 ml, 0.303 mmol). The reaction was stirred at rt for 2 h, then sodium triacetoxyborohydride (0.054 g, 0.253 mmol) was added. The reaction was stirred for 2 h, then the mixture was diluted with methanol and purified by prep HPLC (pH=2, acetonitrile/water+TFA) to provide the desired compound as the TFA salt. LC-MS calculated for $C_{37}H_{39}ClN_7O_3$ $(M+H)^+$: m/z=664.3; found 664.2.

Example 7: (R)-1-((8-((2'-chloro-3'-(5-(((R)-3-hydroxypyrrolidin-1-yl)methyl)picolinamido)-2-methyl-[1,1'-biphenyl]-3-yl)amino)-1,7-naphthyridin-3-yl)methyl)pyrrolidine-3-carboxylic acid

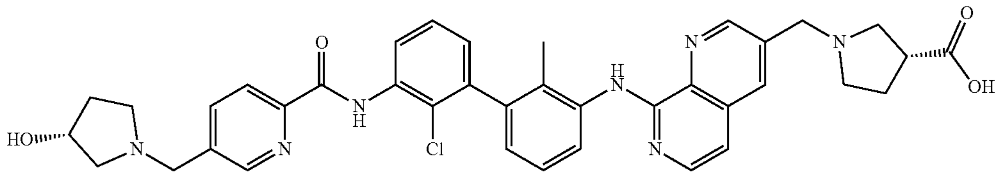 [SMILES: Cc1c(Nc2nccc3cc(CN4CC[C@@H](C(=O)O)C4)cnc23)cccc1-c1cccc(NC(=O)c2ccc(CN3CC[C@@H](O)C3)cn2)c1Cl]

To a vial was added (R)-N-(2-chloro-3'-((3-formyl-1,7-naphthyridin-8-yl)amino)-2'-methyl-[1,1'-biphenyl]-3-yl)-5-((3-hydroxypyrrolidin-1-yl)methyl)picolinamide (Example 6, Step 6: 0.030 g, 0.051 mmol), (R)-pyrrolidine-3-carboxylic acid (Combi-Blocks, cat #ST-7698: 0.017 g, 0.152 mmol), dichloromethane (0.829 ml) and triethylamine (0.016 ml, 0.115 mmol). The reaction was stirred at rt for 2 h, then sodium triacetoxyborohydride (0.054 g, 0.253 mmol) and acetic acid (8.69 μl, 0.152 mmol) were added. The reaction was stirred for 2 h, then the mixture was diluted with methanol and purified by prep HPLC (pH=2, acetonitrile/water+TFA) to provide the compound as the TFA salt. LC-MS calculated for $C_{38}H_{39}ClN_7O_4(M+H)^+$: m/z=692.3; found 692.2.

Example 8: (R)-1-((8-((2'-chloro-3'-(5-((3-hydroxypyrrolidin-1-yl)methyl)picolinamido)-2-methyl-[1,1'-biphenyl]-3-yl)amino)-1,7-naphthyridin-3-yl)methyl)azetidine-3-carboxylic acid

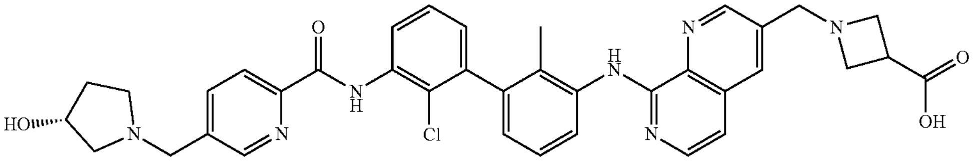 [SMILES: Cc1c(Nc2nccc3cc(CN4CC(C(=O)O)C4)cnc23)cccc1-c1cccc(NC(=O)c2ccc(CN3CC[C@@H](O)C3)cn2)c1Cl]

This compound was prepared using a similar procedure as described for Example 7 with azetidine-3-carboxylic acid (Aldrich, cat #391131) replacing (R)-pyrrolidine-3-carboxylic acid. LC-MS calculated for $C_{37}H_{37}ClN_7O_4$ $(M+H)^+$: m/z=678.3; found 678.3.

Example 9

(R)-1-((8-((3'-((3-(((R)-3-hydroxypyrrolidin-1-yl)methyl)-1,7-naphthyridin-8-yl)amino)-2,2'-dimethyl-[1,1'-biphenyl]-3-yl)amino)-1,7-naphthyridin-3-yl)methyl)pyrrolidine-3-carboxylic acid

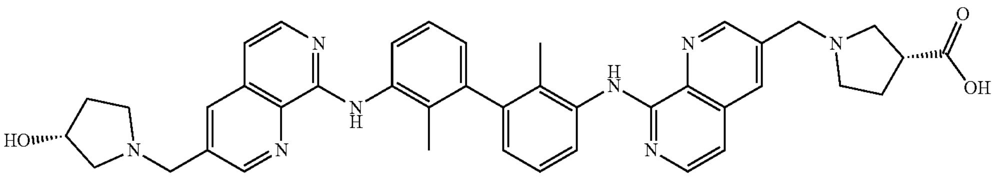 [SMILES: Cc1c(Nc2nccc3cc(CN4CC[C@@H](O)C4)cnc23)cccc1-c1cccc(Nc2nccc3cc(CN4CC[C@@H](C(=O)O)C4)cnc23)c1C]

Step 1: 8-((3-bromo-2-methylphenyl)amino)-1,7-naphthyridine-3-carbaldehyde

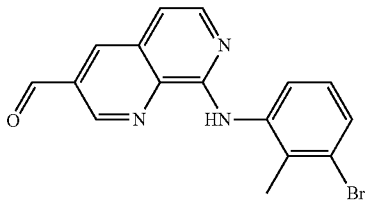 [SMILES: Cc1c(Br)cccc1Nc1nccc2cc(C=O)cnc12]

A suspension of (8-((3-bromo-2-methylphenyl)amino)-1,7-naphthyridin-3-yl)methanol (Affinity Research Chemicals, #ARI-0169: 300.0 mg, 0.872 mmol) and manganese dioxide (1515 mg, 17.43 mmol) in DCM (8716 µl) was stirred at 45° C. for 1 h. The reaction was filtered through Celite® and the filtrate was concentrated to yield a crude residue, which was used directly in the next step without further purification. LC-MS calculated for $C_{16}H_{13}BrN_3O$ $(M+H)^+$: m/z=342.0; found 342.0.

Step 2: (R)-1-((8-((3-bromo-2-methylphenyl)amino)-1,7-naphthyridin-3-yl)methyl)pyrrolidin-3-ol

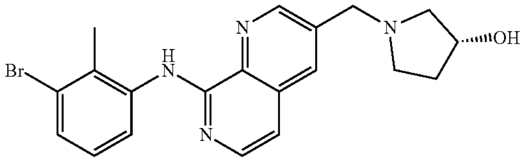 [SMILES: Cc1c(Br)cccc1Nc1nccc2cc(CN3CC[C@@H](O)C3)cnc12]

A mixture of 8-((3-bromo-2-methylphenyl)amino)-1,7-naphthyridine-3-carbaldehyde (0.100 g, 0.292 mmol) and (R)-3-hydroxypyrrolidine (Combi-Blocks, #AM-2005: 0.025 g, 0.292 mmol) in 1,2-dichloroethane (1.46 ml) and N,N-diisopropylethylamine (0.051 ml, 0.292 mmol) was stirred at rt for 1 h. Sodium triacetoxyborohydride (0.093 g, 0.438 mmol) was carefully added in portions. The reaction was stirred at rt for 2 h, then quenched with a saturated aqueous solution of sodium bicarbonate. The mixture was then extracted with a 3:1 mixture of chloroform/IPA. The combined organic layers were dried over sodium sulfate, then concentrated in vacuo. The crude residue was purified by silica gel chromatography (0→30% methanol/DCM) to give the desired product. LC-MS calculated for $C_{20}H_{22}BrN_4O$ $(M+H)^+$: m/z=413.1; found 413.1.

Step 3: (8-((2-methyl-3-(4,4,5,5-tetramethyl-1,3,2-dioxaborolan-2-yl)phenyl)amino)-1,7-naphthyridin-3-yl)methanol

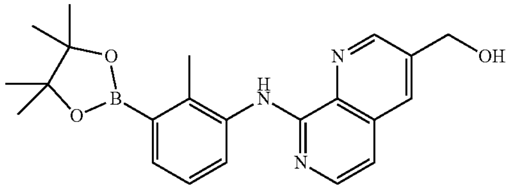 [SMILES: Cc1c(Nc2nccc3cc(CO)cnc23)cccc1B1OC(C)(C)C(C)(C)O1]

A mixture of (8-((3-bromo-2-methylphenyl)amino)-1,7-naphthyridin-3-yl)methanol (Affinity Research Chemicals, #ARI-0169: 0.300 g, 0.872 mmol), bis(pinacolato)diboron (Aldrich, #473294: 0.266 g, 1.046 mmol), dichloro[1,1'-bis(diphenylphosphino)ferrocene]palladium (II) dichloromethane adduct (0.071 g, 0.087 mmol) and potassium acetate (0.214 g, 2.179 mmol) was charged with nitrogen and stirred at 110° C. for 2 h. The crude was diluted with DCM, and then filtered through Celite®. The filtrate was concentrated, and the resulting residue was used directly in the next step without further purification. LC-MS calculated for $C_{22}H_{27}BN_3O_3(M+H)^+$: m/z=392.2; found 392.3.

Step 4: (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol

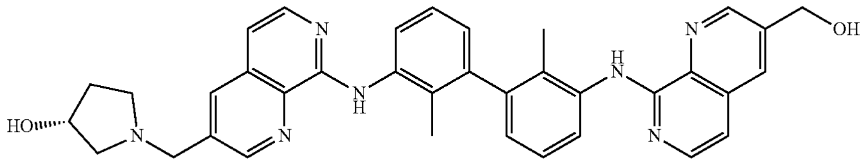 [SMILES: Cc1c(Nc2nccc3cc(CO)cnc23)cccc1-c1cccc(Nc2nccc3cc(CN4CC[C@@H](O)C4)cnc23)c1C]

To a vial was added (8-((2-methyl-3-(4,4,5,5-tetramethyl-1,3,2-dioxaborolan-2-yl)phenyl)amino)-1,7-naphthyridin-3-yl)methanol (0.162 g, 0.414 mmol), (R)-1-((8-((3-bromo-2-methylphenyl)amino)-1,7-naphthyridin-3-yl)methyl) pyrrolidin-3-ol (0.163 g, 0.394 mmol), 1 M aqueous sodium carbonate (0.789 mmol), [1,1'-bis(di-cyclohexylphosphino) ferrocene]-dichloropalladium (II) (0.029 g, 0.039 mmol), and 1,4-dioxane (3.48 ml). The mixture was purged with nitrogen, sealed, and heated to 90° C. whilst stirring for 2 h. The mixture was cooled, diluted with EtOAc and filtered through Celite®. The filtrate was concentrated and purified using silica gel chromatography (20% MeOH/DCM) to provide the desired compound as an orange solid. LC-MS calculated for $C_{36}H_{36}N_7O_2$ $(M+H)^+$: m/z=598.3; found 598.4.

Step 5: (R)-8-((3'-((3-((3-hydroxypyrrolidin-1-yl) methyl)-1,7-naphthyridin-8-yl)amino)-2,2'-dimethyl-[1,1'-biphenyl]-3-yl)amino)-1,7-naphthyridine-3-carbaldehyde

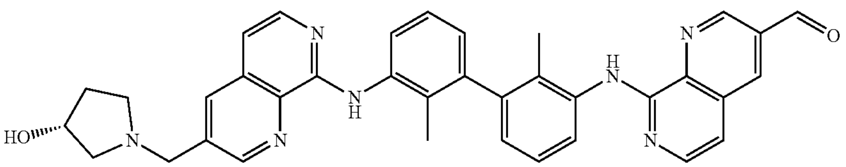 [SMILES: Cc1c(Nc2nccc3cc(C=O)cnc23)cccc1-c1cccc(Nc2nccc3cc(CN4CC[C@@H](O)C4)cnc23)c1C]

To a solution of (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol (0.0715 g, 0.12 mmol) in DCM (1.20 ml) was added manganese dioxide (0.208 g, 2.392 mmol). The resulting mixture was heated at 45° C. for 30 min. After cooling, the mixture was filtered through Celite® and the filtrate was concentrated. The crude orange solid was used directly in the next step. LC-MS calculated for $C_{36}H_{34}N_7O_2$ $(M+H)^+$: m/z=596.3; found 596.5.

Step 6: (R)-1-((8-((3'-((3-(((R)-3-hydroxypyrrolidin-1-yl)methyl)-1,7-naphthyridin-8-yl)amino)-2,2'-dimethyl-[1,1'-biphenyl]-3-yl)amino)-1,7-naphthyridin-3-yl)methyl)pyrrolidine-3-carboxylic acid To a vial was added (R)-8-((3'-((3-((3-hydroxypyrrolidin-1-yl)methyl)-1,7-naphthyridin-8-yl)amino)-2,2'-dimethyl-[1,1'-biphenyl]-3-yl)amino)-1,7-naphthyridine-3-carbaldehyde (0.013 g, 0.022 mmol), (R)-pyrrolidine-3-carboxylic acid (Combi-Blocks, #ST-7698: 7.5 mg, 0.065 mmol), 1,2-dichloroethane (0.336 ml) and triethylamine (9.13 μl, 0.065 mmol). The reaction was stirred at rt for 2 h, then sodium triacetoxyborohydride (0.023 g, 0.109 mmol) and acetic acid (3.75 μl, 0.065 mmol) were added. The reaction was stirred for 2 h, then the mixture was diluted with methanol and purified by prep HPLC (pH=2, acetonitrile/water+TFA) to give the desired product as the TFA salt. LC-MS calculated for $C_{41}H_{43}N_8O_3$ $(M+H)^+$: m/z=695.3; found 695.3. $^1H$ NMR (500 MHz, DMSO) δ 10.72 (br s, 2H), 9.11 (m, 2H), 8.54 (m, 2H), 8.02 (m, 4H), 7.42 (m, 2H), 7.26 (m, 2H), 7.11 (m, 2H), 4.70 (m, 4H), 4.47 (m, 1H), 3.82-3.08 (m, 10H), 2.38-2.18 (m, 2H), 2.10 (s, 6H), 2.05-1.82 (m, 2H).

Example 10

(S)-1-((8-((3'-((3-(((R)-3-hydroxypyrrolidin-1-yl) methyl)-1,7-naphthyridin-8-yl)amino)-2,2'-dimethyl-[1,1'-biphenyl]-3-yl)amino)-1,7-naphthyridin-3-yl) methyl)pyrrolidine-3-carboxylic acid

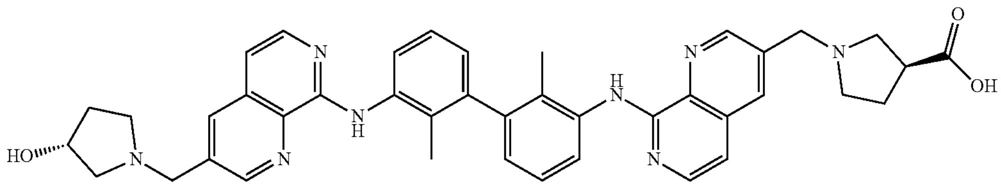 [SMILES: Cc1c(Nc2nccc3cc(CN4CC[C@@H](O)C4)cnc23)cccc1-c1cccc(Nc2nccc3cc(CN4CC[C@H](C(=O)O)C4)cnc23)c1C]

This compound was prepared using similar procedures as described for Example 9 with (S)-pyrrolidine-3-carboxylic acid (Combi-Blocks, #ST-1381) replacing (R)-pyrrolidine-3-carboxylic acid in Step 6. The reaction was diluted with MeOH and then purified by prep-HPLC (pH=2, acetonitrile/water+TFA) to give the desired product as the TFA salt. LC-MS calculated for $C_{41}H_{43}N_8O_3$ $(M+H)^+$: m/z=695.3; found 695.3.

Example 11

(R)-1-((8-((3'-((3-(((2-hydroxyethyl)amino)methyl)-1,7-naphthyridin-8-yl)amino)-2,2'-dimethyl-[1,1'-biphenyl]-3-yl)amino)-1,7-naphthyridin-3-yl)methyl)pyrrolidine-3-carboxylic acid

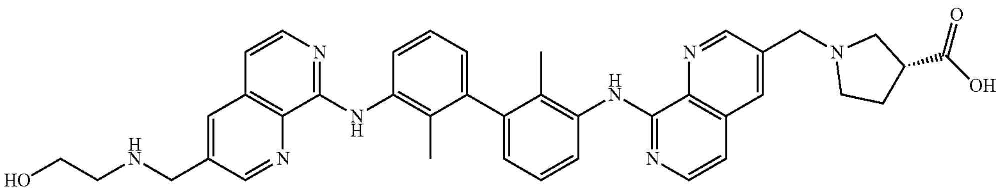 [SMILES: Cc1c(Nc2nccc3cc(CNCCO)cnc23)cccc1-c1cccc(Nc2nccc3cc(CN4CC[C@@H](C(=O)O)C4)cnc23)c1C]

This compound was prepared using similar procedures as described for Example 9 with ethanolamine (Aldrich, #411000) replacing (R)-3-hydroxypyrrolidine in Step 2. The reaction mixture was diluted with MeOH and then purified by prep-HPLC (pH=6.5, acetonitrile/water+$NH_4OAc$) to give the desired product. LC-MS calculated for $C_{39}H_{41}N_8O_3$ $(M+H)^+$: m/z=669.3; found 669.4.

Example 12

(R)-1-((8-((3'-((3-(((S)-3-hydroxypyrrolidin-1-yl)methyl)-1,7-naphthyridin-8-yl)amino)-2,2'-dimethyl-[1,1'-biphenyl]-3-yl)amino)-1,7-naphthyridin-3-yl)methyl)pyrrolidine-3-carboxylic acid

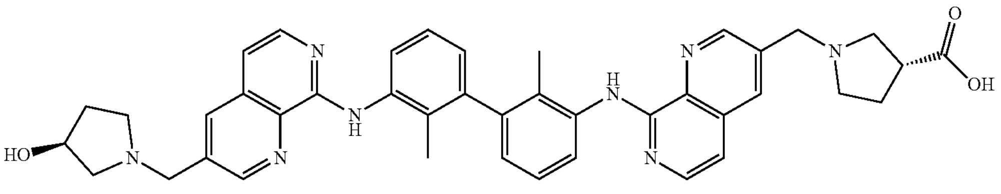 [SMILES: Cc1c(Nc2nccc3cc(CN4CC[C@H](O)C4)cnc23)cccc1-c1cccc(Nc2nccc3cc(CN4CC[C@@H](C(=O)O)C4)cnc23)c1C]

This compound was prepared using similar procedures as described for Example 9 with (S)-3-hydroxypyrrolidine (Combi-Blocks, #SS-7948) replacing (R)-3-hydroxypyrrolidine in Step 2. The reaction was diluted with MeOH and then purified by prep-HPLC (pH=2, acetonitrile/water+TFA) to give the desired product as the TFA salt. LC-MS calculated for $C_{41}H_{43}N_8O_3$ $(M+H)^+$: m/z=695.3; found 695.4.

Example 13

(S)-1-((8-((3'-((3-(((S)-3-hydroxypyrrolidin-1-yl)methyl)-1,7-naphthyridin-8-yl)amino)-2,2'-dimethyl-[1,1'-biphenyl]-3-yl)amino)-1,7-naphthyridin-3-yl)methyl)pyrrolidine-3-carboxylic acid

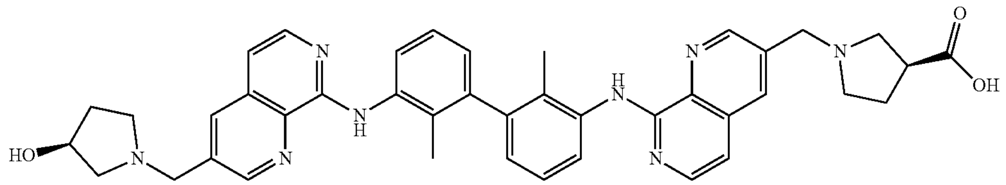 [SMILES: Cc1c(Nc2nccc3cc(CN4CC[C@H](O)C4)cnc23)cccc1-c1cccc(Nc2nccc3cc(CN4CC[C@H](C(=O)O)C4)cnc23)c1C]

This compound was prepared using similar procedures as described for Example 9 with (S)-3-hydroxypyrrolidine replacing (R)-3-hydroxypyrrolidine in Step 2 and (S)-pyrrolidine-3-carboxylic acid replacing (R)-pyrrolidine-3-carboxylic acid in Step 6. The reaction mixture was diluted with MeOH and then purified by prep-HPLC (pH=2, acetonitrile/water+TFA) to give the desired product as the TFA salt. LC-MS calculated for $C_{41}H_{43}N_8O_3$ $(M+H)^+$: m/z=695.3; found 695.3.

Example 14

1-((8-(2-chloro-3'-(1,5-dimethyl-4,5,6,7-tetrahydro-1H-imidazo[4,5-c]pyridine-2-carboxamido)-2'-methylbiphenyl-3-ylamino)-1,7-naphthyridin-3-yl)methyl)azetidine-3-carboxylic acid

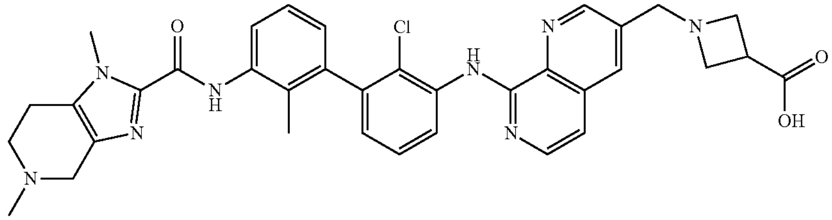 [SMILES: Cc1c(NC(=O)c2nc3c(n2C)CCN(C)C3)cccc1-c1cccc(Nc2nccc3cc(CN4CC(C(=O)O)C4)cnc23)c1Cl]

Step 1: tert-butyl 1-methyl-6,7-dihydro-1H-imidazo[4,5-c]pyridine-5(4H)-carboxylate

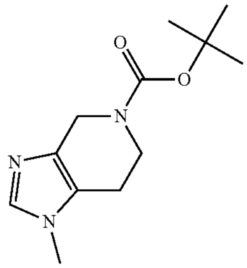 [SMILES: Cn1cnc2c1CCN(C(=O)OC(C)(C)C)C2]

A solution of 1-methyl-4,5,6,7-tetrahydro-1H-imidazo[4,5-c]pyridine (Accela, cat #SY032476: 2.0 g, 14.58 mmol) and $(Boc)_2O$ (3.38 mL, 14.58 mmol) in dichloromethane (60.0 mL) was stirred at room temperature for 1 h. The reaction was quenched with saturated aqueous $NaHCO_3$ solution, and extracted with ethyl acetate. The combined organic layers were washed with brine, dried over $Na_2SO_4$, filtered, and concentrated under reduced pressure. The crude product was used for next step without further purification. LC-MS calculated for $C_{12}H_{20}N_3O_2$ $(M+H)^+$: m/z=238.2; found 238.2.

Step 2: 5-tert-butyl 2-methyl 1-methyl-6,7-dihydro-1H-imidazo[4,5-c]pyridine-2,5(4H)-dicarboxylate

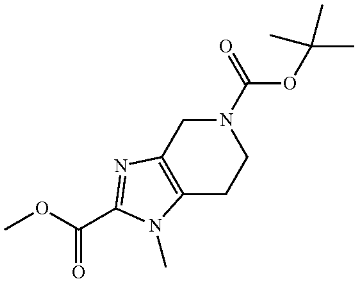 [SMILES: COC(=O)c1nc2c(n1C)CCN(C(=O)OC(C)(C)C)C2]

To a solution of tert-butyl 1-methyl-6,7-dihydro-1H-imidazo[4,5-c]pyridine-5(4H)-carboxylate (Crude product from Step 1) in tetrahydrofuran (60.0 mL) was added n-Butyllithium in hexanes (2.5 M, 7.00 mL, 17.49 mmol) at −78° C., dropwise. The reaction mixture was stirred at −78° C. for 10 min prior to the addition of methyl chloroformate (1.7 mL, 21.9 mmol). After being stirred at −78° C. for 15 min, the reaction was then quenched with saturated aqueous $NaHCO_3$ solution, and extracted with ethyl acetate, dried over $Na_2SO_4$, filtered, and concentrated under reduced pressure. The residue was purified by flash chromatography on a silica gel column eluting with 80% ethyl acetate in hexanes to afford the desired product ( ). LC-MS calculated for $C_{14}H_{22}N_3O_4$ $(M+H)^+$: m/z=296.2; found 296.3.

Step 3: tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate

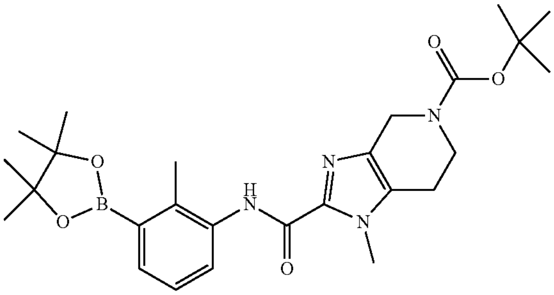 [SMILES: Cc1c(NC(=O)c2nc3c(n2C)CCN(C(=O)OC(C)(C)C)C3)cccc1B1OC(C)(C)C(C)(C)O1]

Potassium tert-butoxide (0.122 ml, 0.122 mmol) was added to a solution of 5-tert-butyl 2-methyl 1-methyl-1,4,6,7-tetrahydro-5H-imidazo[4,5-c]pyridine-2,5-dicarboxylate (30 mg, 0.102 mmol) and 2-methyl-3-(4,4,5,5-tetramethyl-1,3,2-dioxaborolan-2-yl)aniline (Combi-Blocks, cat #PN-9127: 23.68 mg, 0.102 mmol) in THF (0.2 ml). After being stirred at rt for 2 h, the reaction mixture was quenched with water, and extracted with ethyl acetate. The combined organic layers were washed with brine, dried over $Na_2SO_4$, filtered and concentrated under reduced pressure. The residue was purified by flash chromatography on a silica gel column with ethyl acetate in hexanes (0-40%) to afford the product. LC-MS calculated for $C_{26}H_{38}BN_4O_5(M+H)^+$: m/z=497.3; found 497.2.

Step 4: 8-chloro-3-vinyl-1,7-naphthyridine

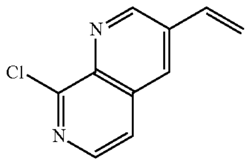

A mixture of 3-bromo-8-chloro-1,7-naphthyridine (PharmaBlock, cat #PBLJ2743: 0.200 g, 0.821 mmol), 4,4,5,5-tetramethyl-2-vinyl-1,3,2-dioxaborolane (Aldrich, cat #663348: 153 μL, 0.904 mmol), sodium carbonate (0.174 g, 1.64 mmol) and [1,1'-bis(di-cyclohexylphosphino)ferrocene]dichloropalladium(II) (Aldrich, cat #701998: 6.2 mg, 0.0082 mmol) in tert-butyl alcohol (5.91 mL, 61.8 mmol) and water (6 mL, 300 mmol) was degassed and sealed. It was stirred at 110° C. for 2 h. The reaction mixture was cooled then extracted with ethyl acetate (3×20 mL). The combined organic layers were washed with brine, dried over $MgSO_4$, filtered and concentrated under reduced pressure. The crude residue was used directly in the next step without further purification. LC-MS calculated for $C_{10}H_8ClN_2$ $(M+H)^+$: m/z=191.0; found 191.0.

Step 5: N-(3-bromo-2-chlorophenyl)-3-vinyl-1,7-naphthyridin-8-amine

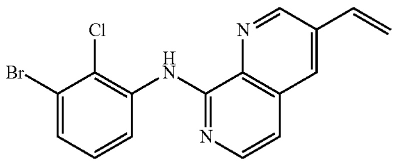 [SMILES: C=Cc1cnc2c(Nc3cccc(Br)c3Cl)nccc2c1]

In a vial, 3-bromo-2-chloroaniline (Enamine, cat #EN300-105778:0.476 g, 2.304 mmol) and 8-chloro-3-vinyl-1,7-naphthyridine (0.366 g, 1.920 mmol) were suspended in isopropanol (9.60 ml). Sulfuric acid (0.102 ml, 1.920 mmol) was added to the reaction mixture. The resulting mixture was heated to 100° C. for 1 h. The mixture was cooled to rt then quenched with aqueous saturated sodium bicarbonate, and diluted with DCM. The layers were separated and the water layer was further extracted with DCM. The combined organic layers were dried over magnesium sulfate, filtered and concentrated in vacuo. The crude solid was purified by column chromatography (0→2% methanol/DCM). LC-MS calculated for $C_{16}H_{12}BrClN_3$ $(M+H)^+$: m/z=360.0; found 360.0.

Step 6: 8-((3-bromo-2-chlorophenyl)amino)-1,7-naphthyridine-3-carbaldehyde

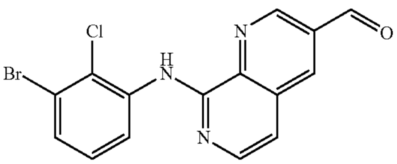 [SMILES: O=Cc1cnc2c(Nc3cccc(Br)c3Cl)nccc2c1]

A flask was charged with N-(3-bromo-2-chlorophenyl)-3-vinyl-1,7-naphthyridin-8-amine (0.586 g, 1.625 mmol), 1,4-dioxane (40 mL) and water (40 mL). A 4% osmium tetroxide solution in water (0.207 ml, 0.032 mmol) was added to the reaction mixture. After 5 min, sodium periodate (1.390 g, 6.50 mmol) was added. The mixture was stirred overnight at rt. The reaction was diluted with water and ethyl acetate. The layers were separated and the aqueous layer was further extracted with EtOAc. The combined organic extracts were washed with brine, dried over sodium sulfate, filtered, and concentrated in vacuo. The crude product was purified by silica gel chromatography (0→60% EtOAc/hexanes). LC-MS calculated for $C_{15}H_{10}BrClN_3O$ $(M+H)^+$: m/z=362.0; found 362.0.

Step 7: methyl 1-((8-((3-bromo-2-chlorophenyl)amino)-1,7-naphthyridin-3-yl)methyl)azetidine-3-carboxylate

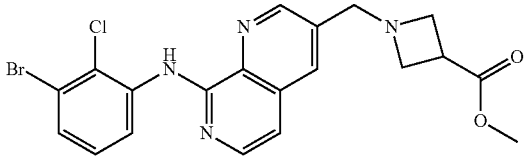 [SMILES: COC(=O)C1CN(Cc2cnc3c(Nc4cccc(Br)c4Cl)nccc3c2)C1]

A mixture of 8-((3-bromo-2-chlorophenyl)amino)-1,7-naphthyridine-3-carbaldehyde (0.272 g, 0.750 mmol) and methyl azetidine-3-carboxylate, HCl (Combi-Blocks, cat #SS-3302:125 mg, 0.825 mmol) in methylene chloride (3.75 ml) and N,N-diisopropylethylamine (0.392 ml, 2.250 mmol) was stirred at rt for 1 h. Sodium triacetoxyborohydride (0.477 g, 2.250 mmol) was added in portions. The reaction was stirred at rt for 2 h, then sodium tetrahydroborate (0.060 ml, 1.500 mmol) and methanol (6 mL) were added carefully. After stirring overnight, the reaction was quenched with a saturated solution of sodium bicarbonate. The mixture was then extracted with a 3:1 mixture of chloroform/isopropanol. The combined organic layers were washed with brine, dried over sodium sulfate, and concentrated under reduced pressure. The crude residue was purified by column chromatography (methanol/DCM). LC-MS calculated for $C_{20}H_{19}BrClN_4O_2(M+H)^+$: m/z=461.0; found 461.1.

Step 8: tert-butyl 2-((2'-chloro-3'-((3-((3-(methoxycarbonyl)azetidin-1-yl)methyl)-1,7-naphthyridin-8-yl)amino)-2-methyl-[1,1'-biphenyl]-3-yl)carbamoyl)-1-methyl-1,4,6,7-tetrahydro-5H-imidazo[4,5-c]pyridine-5-carboxylate

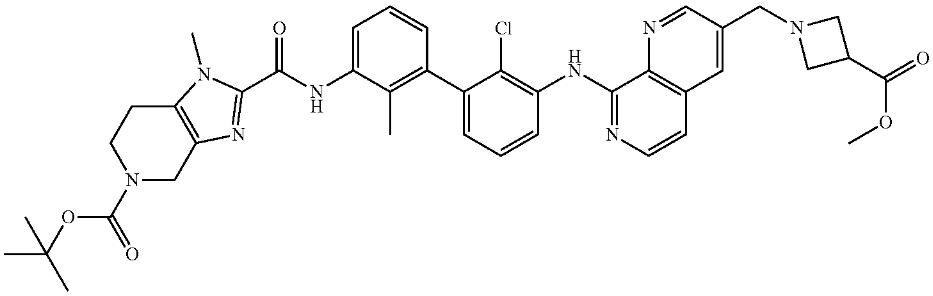 [SMILES: COC(=O)C1CN(Cc2cnc3c(Nc4cccc(-c5cccc(NC(=O)c6nc7c(n6C)CCN(C(=O)OC(C)(C)C)C7)c5C)c4Cl)nccc3c2)C1]

To a vial was added tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate (Step 3: 0.037 g, 0.074 mmol), methyl 1-((8-((3-bromo-2-chlorophenyl)amino)-1,7-naphthyridin-3-yl)methyl)azetidine-3-carboxylate (0.034 g, 0.074 mmol), sodium carbonate (8.58 mg, 0.081 mmol), (1,1'-bis(diphenylphosphino)ferrocene)-dichloropalladium(II) (5.39 mg, 7.36 μmol), 1,4-dioxane (0.650 ml), and water (0.087 ml). The mixture was degassed, sealed, and heated to 90° C. whilst stirring for 18 h. The mixture was cooled, diluted with water and methylene chloride, and the layers were separated. The aqueous layer was further extracted with methylene chloride and the combined organic layers were dried over $MgSO_4$, filtered, and concentrated in vacuo. The crude residue was purified by silica gel chromatography (15% MeOH/DCM) to provide the desired product. LC-MS calculated for $C_{40}H_{44}ClN_8O_5(M+H)^+$: m/z=751.3; found 751.3.

Step 9: methyl 1-((8-(2-chloro-2'-methyl-3'-(1-methyl-4,5,6,7-tetrahydro-JH-imidazo[4,5-c]pyridine-2-carboxamido)biphenyl-3-ylamino)-1,7-naphthyridin-3-yl)methyl)azetidine-3-carboxylate

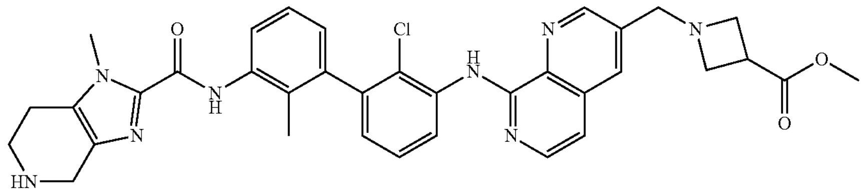 [SMILES: COC(=O)C1CN(Cc2cnc3c(Nc4cccc(-c5cccc(NC(=O)c6nc7c(n6C)CCNC7)c5C)c4Cl)nccc3c2)C1]

To a vial was added tert-butyl 2-((2'-chloro-3'-((3-((3-(methoxycarbonyl)azetidin-1-yl)methyl)-1,7-naphthyridin-8-yl)amino)-2-methyl-[1,1'-biphenyl]-3-yl)carbamoyl)-1-methyl-1,4,6,7-tetrahydro-5H-imidazo[4,5-c]pyridine-5-carboxylate (0.041 g, 0.055 mmol), DCM (0.6 mL), and TFA (0.084 mL, 1.091 mmol). The reaction was stirred at rt for 1 h. The mixture was concentrated under reduced pressure, and the resulting residue was redissolved in DCM and washed with a saturated aqueous solution of sodium bicarbonate. The layers were separated, and the organic layer was dried over $MgSO_4$, filtered, and concentrated under reduced pressure. The crude residue was then used directly in the next step without further purification. LC-MS calculated for $C_{35}H_{36}ClN_8O_3(M+H)^+$: m/z=651.3; found 651.4.

Step 10: methyl 1-((8-(2-chloro-3'-(1,5-dimethyl-4,5,6,7-tetrahydro-1H-imidazo[4,5-c]pyridine-2-carboxamido)-2'-methylbiphenyl-3-ylamino)-1,7-naphthyridin-3-yl)methyl)azetidine-3-carboxylate

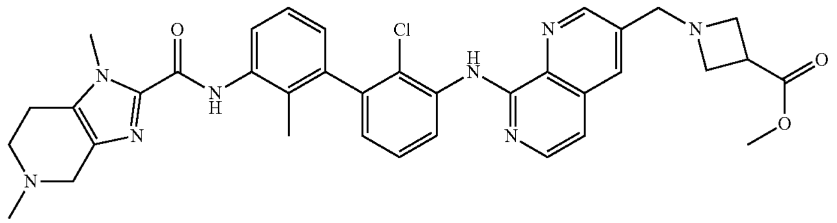 [SMILES: COC(=O)C1CN(Cc2cnc3c(Nc4cccc(-c5cccc(NC(=O)c6nc7c(n6C)CCN(C)C7)c5C)c4Cl)nccc3c2)C1]

A mixture of methyl 1-((8-((2-chloro-2'-methyl-3'-(1-methyl-4,5,6,7-tetrahydro-1H-imidazo[4,5-c]pyridine-2-carboxamido)-[1,1'-biphenyl]-3-yl)amino)-1,7-naphthyridin-3-yl)methyl)azetidine-3-carboxylate (0.032 g, 0.049 mmol) and 12.3 M formaldehyde in water (7.99 μl, 0.098 mmol) in methylene chloride (0.430 ml) and methanol (0.061 ml) was stirred at rt for 30 min after which time, acetic acid (0.017 ml, 0.295 mmol) and sodium triacetoxyborohydride (0.052 g, 0.246 mmol) were added. The mixture was stirred at rt for 45 min and the reaction was quenched with a saturated aqueous sodium bicarbonate solution. The mixture was extracted with a 3:1 mixture of chloroform/isopropanol, and the combined organic layers were dried over sodium sulfate, filtered, and concentrated under reduced pressure. The crude product was purified by column chromatography (0→30% methanol/DCM). LC-MS calculated for $C_{36}H_{38}ClN_8O_3(M+H)^+$: m/z=665.3; found 665.4.

Step 11: 1-((8-(2-chloro-3'-(1,5-dimethyl-4,5,6,7-tetrahydro-1H-imidazo[4,5-c]pyridine-2-carboxamido)-2'-methylbiphenyl-3-ylamino)-1,7-naphthyridin-3-yl)methyl)azetidine-3-carboxylic acid To a solution of methyl 1-((8-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)amino)-1,7-naphthyridin-3-yl)methyl)azetidine-3-carboxylate (27 mg, 0.041 mmol) in THF (203 μl) was added lithium hydroxide (3.89 mg, 0.162 mmol) in water (203 μl). The mixture was stirred at rt for 30 min. The mixture was diluted with methanol and purified by prep HPLC (pH=2, acetonitrile/water+TFA) to provide the compound as its TFA salt. LC-MS calculated for $C_{35}H_{36}ClN_8O_3(M+H)^+$: m/z=651.3; found 651.3.

Example 15

(R)-1-((5-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6-oxo-1,6-dihydropyridin-3-yl)methyl)pyrrolidine-3-carboxylicacid

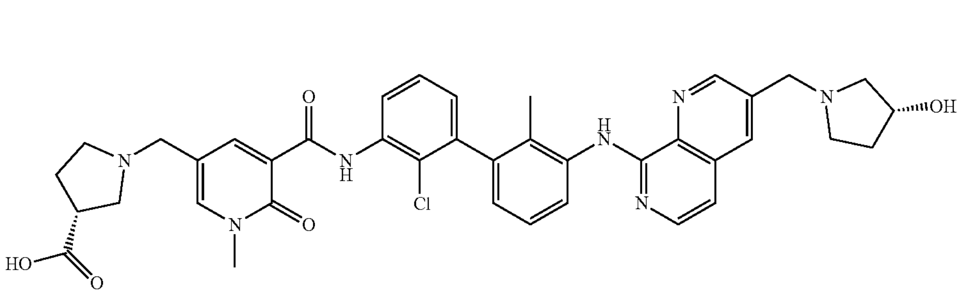 [SMILES: Cc1c(Nc2nccc3cc(CN4CC[C@@H](O)C4)cnc23)cccc1-c1cccc(NC(=O)c2cc(CN3CC[C@@H](C(=O)O)C3)cn(C)c2=O)c1Cl]

Step 1: 2-chloro-3-(4,4,5,5-tetramethyl-1,3,2-dioxaborolan-2-yl)aniline

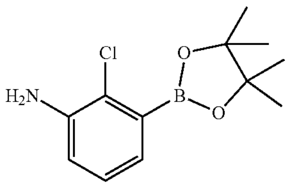 [SMILES: CC1(C)OB(c2cccc(N)c2Cl)OC1(C)C]

In a vial was combined: 4,4,5,5,4',4',5',5'-Octamethyl-[2,2']bi[[1,3,2]dioxaborolanyl](6.15 g, 24.22 mmol), potassium acetate (2.85 g, 29.1 mmol), 3-bromo-2-chloroaniline (Enamine, cat #EN300-105778: 2.00 g, 9.69 mmol), 1,4-dioxane (48.4 ml) and [1,1'-bis(diphenylphosphino)ferrocene] dichloropalladium (II) (0.354 g, 0.484 mmol). The vial was flushed with nitrogen and was stirred at 110° C. for 2 h. The mixture was cooled, and filtered through Celite®, and concentrated under reduced pressure. The crude residue was purified by silica gel chromatography (EtOAc/hexanes) to provide the desired compound as a white solid. LC-MS calculated for $C_{12}H_{18}BClNO_2$ $(M+H)^+$: m/z=254.1; found 254.1.

Step 2: 8-((3-bromo-2-methylphenyl)amino)-1,7-naphthyridine-3-carbaldehyde

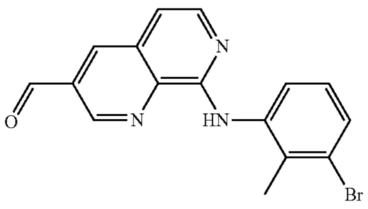 [SMILES: Cc1c(Br)cccc1Nc1nccc2cc(C=O)cnc12]

A suspension of (8-((3-bromo-2-methylphenyl)amino)-1,7-naphthyridin-3-yl)methanol (Affinity Research Chemicals, #ARI-0169: 300.0 mg, 0.872 mmol) and manganese dioxide (1515 mg, 17.43 mmol) in DCM (8716 μl) was stirred at 45° C. for 1 h. The reaction was filtered through Celite® and the filtrate was concentrated to yield a crude residue, which was used directly in the next step without further purification. LC-MS calculated for $C_{16}H_{13}BrN_3O$ $(M+H)^+$: m/z=342.0; found 342.0.

Step 3: (R)-1-((8-((3-bromo-2-methylphenyl)amino)-1,7-naphthyridin-3-yl)methyl)pyrrolidin-3-ol

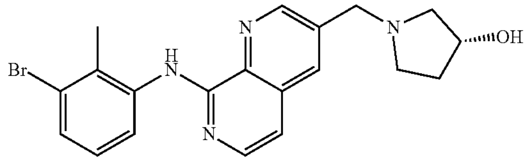 [SMILES: Cc1c(Br)cccc1Nc1nccc2cc(CN3CC[C@@H](O)C3)cnc12]

A mixture of 8-((3-bromo-2-methylphenyl)amino)-1,7-naphthyridine-3-carbaldehyde (0.100 g, 0.292 mmol) and (R)-3-hydroxypyrrolidine (Combi-Blocks, #AM-2005: 0.025 g, 0.292 mmol) in 1,2-dichloroethane (1.46 ml) and N,N-diisopropylethylamine (0.051 ml, 0.292 mmol) was stirred at rt for 1 h. Sodium triacetoxyborohydride (0.093 g, 0.438 mmol) was added in portions. The reaction was stirred at rt for 2 h, then quenched with a saturated aqueous solution of sodium bicarbonate. The mixture was then extracted with a 3:1 mixture of chloroform/isopropanol. The combined organic layers were dried over sodium sulfate, and concentrated in vacuo. The crude residue was purified by silica gel chromatography (0→30% methanol/DCM) to give the desired product. LC-MS calculated for $C_{20}H_{22}BrN_4O$ $(M+H)^+$: m/z=413.1; found 413.1.

Step 4: (R)-1-((8-(3'-amino-2'-chloro-2-methylbiphenyl-3-ylamino)-1,7-naphthyridin-3-yl)methyl)pyrrolidin-3-ol

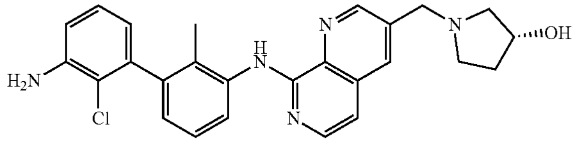 [SMILES: Cc1c(Nc2nccc3cc(CN4CC[C@@H](O)C4)cnc23)cccc1-c1cccc(N)c1Cl]

To a vial was added 2-chloro-3-(4,4,5,5-tetramethyl-1,3,2-dioxaborolan-2-yl)aniline (Step 1: 0.101 g, 0.399 mmol), (R)-1-((8-((3-bromo-2-methylphenyl)amino)-1,7-naphthyridin-3-yl)methyl)pyrrolidin-3-ol (0.165 g, 0.399 mmol), sodium carbonate (0.047 g, 0.439 mmol), (1,1'-bis(diphenylphosphino)ferrocene)-dichloropalladium(II) (0.029 g, 0.040 mmol), 1,4-dioxane (3.52 ml), and water (0.470 ml). The mixture was degassed, sealed, and heated to 90° C. whilst stirring for 18 h. The mixture was cooled, diluted with water and methylene chloride, and the layers were separated. The aqueous layer was further extracted with methylene chloride, and the combined organic layers were dried over $MgSO_4$, filtered, and concentrated in vacuo. The crude residue was purified by silica gel chromatography (15% MeOH/DCM) to provide the desired product. LC-MS calculated for $C_{26}H_{27}ClN_5O$ $(M+H)^+$: m/z=460.2; found 460.3.

Step 5: methyl 5-bromo-1-methyl-2-oxo-1,2-dihydropyridine-3-carboxylate

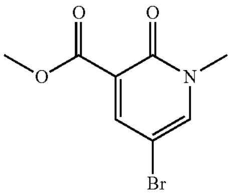

Methyl iodide (1.713 ml, 27.5 mmol) was added to a mixture of 5-bromo-2-hydroxynicotinic acid (Combi-Blocks, cat #CA-4087: 2.0 g, 9.17 mmol), and potassium carbonate (1.811 ml, 20.18 mmol) in methanol (45.9 mL), which was stirred at 70° C. overnight. The solvent was removed, and the crude mixture was extracted with DCM/water. The organic extracts were dried over $MgSO_4$, filtered, and concentrated under reduced pressure. The crude product was used directly in the next step without further purification. LC-MS calculated for $C_8H_9BrNO_3$ $(M+H)^+$: m/z=246.0; found 246.0.

Step 6: 1-methyl-2-oxo-5-vinyl-1,2-dihydropyridine-3-carboxylic acid

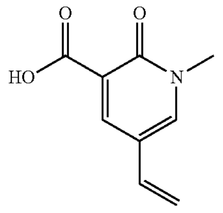

A mixture of methyl 5-bromo-1-methyl-2-oxo-1,2-dihydropyridine-3-carboxylate (745 mg, 3.03 mmol), 4,4,5,5-tetramethyl-2-vinyl-1,3,2-dioxaborolane (565 µl, 3.33 mmol), tetrakis(triphenylphosphine)palladium(0) (175.0 mg, 0.151 mmol), 2.0 M sodium carbonate in water (4543 µl, 9.09 mmol) and 1,4-dioxane (6058 µl) was sparged with nitrogen and then heated at 100° C. for 30 min. The mixture was partitioned between EtOAc and water and the layers separated. The organic layer was washed with brine, dried over $MgSO_4$, filtered and concentrated under reduced pressure. The crude residue was used directly in the next step without further purification. LC-MS calculated for $C_9H_{10}NO_3$ $(M+H)^+$: m/z=180.1; found 180.1.

Step 7: (R)-N-(2-chloro-3'-(3-((3-hydroxypyrrolidin-1-yl)methyl)-1,7-naphthyridin-8-ylamino)-2'-methylbiphenyl-3-yl)-1-methyl-2-oxo-5-vinyl-1,2-dihydropyridine-3-carboxamide

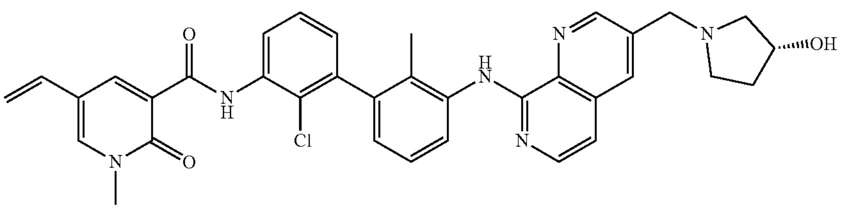 [SMILES: C=Cc1cc(C(=O)Nc2cccc(-c3cccc(Nc4nccc5cc(CN6CC[C@@H](O)C6)cnc45)c3C)c2Cl)c(=O)n(C)c1]

A mixture of 1-methyl-2-oxo-5-vinyl-1,2-dihydropyridine-3-carboxylic acid (0.0550 g, 0.307 mmol), (R)-1-((8-((3'-amino-2'-chloro-2-methyl-[1,1'-biphenyl]-3-yl)amino)-1,7-naphthyridin-3-yl)methyl)pyrrolidin-3-ol (Step 4: 0.141 g, 0.307 mmol), N-[(dimethylamino)-1H-1,2,3-triazolo-[4,5-b]pyridin-1-ylmethylene]-N-methylmethanaminium hexafluorophosphate N-oxide (0.140 g, 0.368 mmol), and N,N-diisopropylethylamine (0.107 ml, 0.614 mmol) in 1,2-dichloroethane (4.39 ml) was stirred at rt for 2 h. The mixture was concentrated under reduced pressure. The residue was diluted with ethyl acetate, and washed with water followed by brine. The organic layer was dried over $MgSO_4$, filtered and concentrated under reduced pressure. The crude residue was purified by silica gel chromatography (MeOH/DCM) to provide the desired compound. LC-MS calculated for $C_{35}H_{34}ClN_6O_3$ $(M+H)^+$: m/z=621.2; found 621.4.

Step 8: (R)-N-(2-chloro-3'-(3-((3-hydroxypyrrolidin-1-yl)methyl)-1,7-naphthyridin-8-ylamino)-2'-methylbiphenyl-3-yl)-5-formyl-1-methyl-2-oxo-1,2-dihydropyridine-3-carboxamide

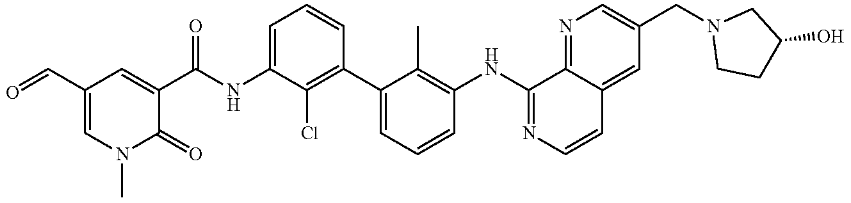 [SMILES: Cc1c(Nc2nccc3cc(CN4CC[C@@H](O)C4)cnc23)cccc1-c1cccc(NC(=O)c2cc(C=O)cn(C)c2=O)c1Cl]

A flask was charged with (R)-N-(2-chloro-3'-((3-((3-hydroxypyrrolidin-1-yl)methyl)-1,7-naphthyridin-8-yl)amino)-2'-methyl-[1,1'-biphenyl]-3-yl)-1-methyl-2-oxo-5-vinyl-1,2-dihydropyridine-3-carboxamide (0.131 g, 0.211 mmol), 1,4-dioxane (40 mL) and water (40 mL). A 4% osmium tetroxide solution in water (0.094 ml, 0.015 mmol) was added to the reaction mixture. After 5 min, sodium periodate (0.361 g, 1.687 mmol) was added. The mixture was stirred overnight at rt. The mixture was diluted with water (2 mL) and 3:1 chloroform/isopropanol (5 mL), and the layers were separated. The organic extract was dried over sodium sulfate, filtered, and concentrated in vacuo. The crude aldehyde was purified by silica gel chromatography (20% MeOH/DCM). LC-MS calculated for $C_{34}H_{32}ClN_6O_4$ $(M+H)^+$: m/z=623.2; found 623.4.

Step 9: (R)-1-((5-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6-oxo-1,6-dihydropyridin-3-yl)methyl)pyrrolidine-3-carboxylic acid To a vial was added (R)-N-(2-chloro-3'-((3-((3-hydroxypyrrolidin-1-yl)methyl)-1,7-naphthyridin-8-yl)amino)-2'-methyl-[1,1'-biphenyl]-3-yl)-5-formyl-1-methyl-2-oxo-1,2-dihydropyridine-3-carboxamide (0.022 g, 0.035 mmol), (R)-pyrrolidine-3-carboxylic acid (Combi-Blocks, cat #ST-7698: 0.012 g, 0.106 mmol), dichloromethane (0.579 ml) and triethylamine (0.016 ml, 0.115 mmol). The reaction was stirred at rt for 2 h, then sodium triacetoxyborohydride (0.037 g, 0.177 mmol) and acetic acid (6.06 µl, 0.106 mmol) were added. The reaction was stirred for 2 h, then the mixture was diluted with methanol and purified by prep HPLC (pH=2, acetonitrile/water+TFA) to provide the desired compound as its TFA salt. LC-MS calculated for $C_{39}H_{41}ClN_7O_5(M+H)^+$: m/z=722.3; found 722.2.

Example 16

(R)-1-((8-(2,2'-dichloro-3'-(5-((3-hydroxypyrrolidin-1-yl)methyl)-1-methyl-2-oxo-1,2-dihydropyridine-3-carboxamido)biphenyl-3-ylamino)-1,7-naphthyridin-3-yl)methyl)azetidine-3-carboxylic acid

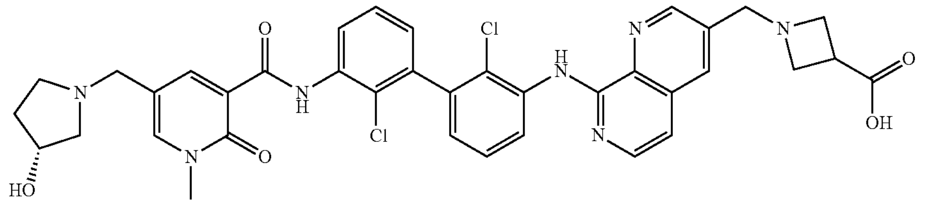 [SMILES: Cn1cc(CN2CC[C@@H](O)C2)cc(C(=O)Nc2cccc(-c3cccc(Nc4nccc5cc(CN6CC(C(=O)O)C6)cnc45)c3Cl)c2Cl)c1=O]

Step 1: methyl 1-((8-(3'-amino-2,2'-dichlorobiphenyl-3-ylamino)-1,7-naphthyridin-3-yl)methyl)azetidine-3-carboxylate

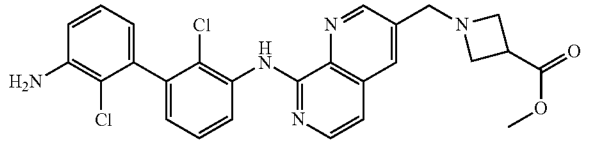 [SMILES: COC(=O)C1CN(Cc2cnc3c(Nc4cccc(-c5cccc(N)c5Cl)c4Cl)nccc3c2)C1]

To a vial was added 2-chloro-3-(4,4,5,5-tetramethyl-1,3,2-dioxaborolan-2-yl)aniline (Example 15, Step 1: 0.137 g, 0.539 mmol), methyl 1-((8-((3-bromo-2-chlorophenyl)amino)-1,7-naphthyridin-3-yl)methyl)azetidine-3-carboxylate (Example 14, Step 7: 0.166 g, 0.360 mmol), sodium carbonate (0.057 g, 0.539 mmol), (1,1'-bis(diphenylphosphino)ferrocene)-dichloropalladium(II) (0.026 g, 0.036 mmol), 1,4-dioxane (3.17 ml), and water (0.423 ml). The mixture was degassed, sealed, and heated to 90° C. whilst stirring for 1 h. The mixture was cooled, diluted with water and 3:1 chloroform/isopropanol, and the layers were separated. The aqueous layer was further extracted with 3:1 chloroform/isopropanol, and the combined organic extracts were dried over $MgSO_4$, filtered, and concentrated in vacuo. The desired compound was purified by silica gel chromatography (20% MeOH/DCM). LC-MS calculated for $C_{26}H_{24}Cl_2N_5O_2$ $(M+H)^+$: m/z=508.1; found 508.2.

Step 2: methyl 1-((8-(2,2'-dichloro-3'-(1-methyl-2-oxo-5-vinyl-1,2-dihydropyridine-3-carboxamido)biphenyl-3-ylamino)-1,7-naphthyridin-3-yl)methyl)azetidine-3-carboxylate

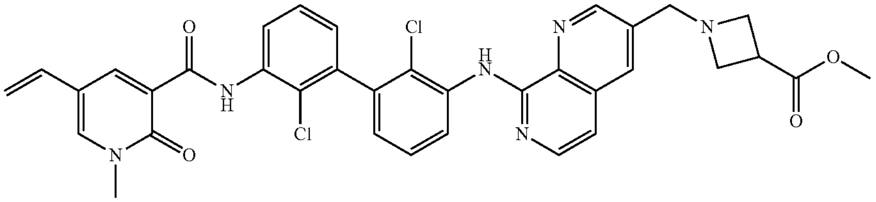 [SMILES: C=Cc1cc(C(=O)Nc2cccc(-c3cccc(Nc4nccc5cc(CN6CC(C(=O)OC)C6)cnc45)c3Cl)c2Cl)c(=O)n(C)c1]

In a vial, 1-methyl-2-oxo-5-vinyl-1,2-dihydropyridine-3-carboxylic acid (Example 15, Step 6: 0.051 g, 0.285 mmol) HATU (0.130 g, 0.342 mmol) and N,N-diisopropylethylamine (0.099 ml, 0.569 mmol) were dissolved in DMF (2.85 ml). After stirring for 5 min, methyl 1-((8-(3'-amino-2,2'-dichlorobiphenyl-3-ylamino)-1,7-naphthyridin-3-yl)methyl)azetidine-3-carboxylate (0.285 mmol) was added, and the resulting mixture was stirred at 40° C. for 24 h. Excess DMF was concentrated, and the resulting oil was diluted with EtOAc and water. The layers were separated and the water layer was further extracted with ethyl acetate. The combined organic layers were washed with brine, dried over magnesium sulfate, filtered and concentrated in vacuo. After concentrating, the crude residue was triturated with DCM and filtered to provide the desired product. The filtrate was purified by silica gel chromatography (20% MeOH/DCM) to provide additional desired product. LC-MS calculated for $C_{35}H_{31}C_{12}N_6O_4$ $(M+H)^+$: m/z=669.2; found 669.1.

Step 3: methyl 1-((8-(2,2'-dichloro-3'-(5-formyl-1-methyl-2-oxo-1,2-dihydropyridine-3-carboxamido)biphenyl-3-ylamino)-1,7-naphthyridin-3-yl)methyl)azetidine-3-carboxylate

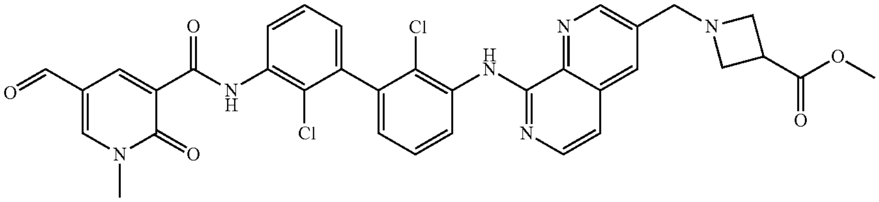 [SMILES: COC(=O)C1CN(Cc2cnc3c(Nc4cccc(-c5cccc(NC(=O)c6cc(C=O)cn(C)c6=O)c5Cl)c4Cl)nccc3c2)C1]

This compound was prepared using similar procedures as described for Example 14 with methyl 1-((8-(2,2'-dichloro-3'-(1-methyl-2-oxo-5-vinyl-1,2-dihydropyridine-3-carboxamido)biphenyl-3-ylamino)-1,7-naphthyridin-3-yl)methyl) azetidine-3-carboxylate replacing N-(3-bromo-2-chlorophenyl)-3-vinyl-1,7-naphthyridin-8-amine in Step 6. The crude product was purified by silica gel chromatography (20% MeOH/DCM) to provide the desired product. LC-MS calculated for $C_{34}H_{29}Cl_2N_6O_5$ $(M+H)^+$: m/z=671.2; found 671.4.

Step 4: (R)-methyl 1-((8-(2,2'-dichloro-3'-(5-((3-hydroxypyrrolidin-1-yl)methyl)-1-methyl-2-oxo-1,2-dihydropyridine-3-carboxamido)biphenyl-3-ylamino)-1,7-naphthyridin-3-yl)methyl)azetidine-3-carboxylate

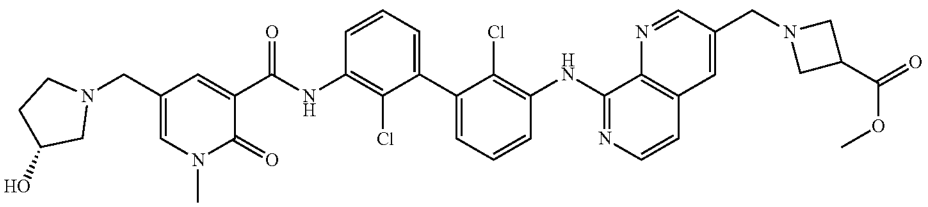 [SMILES: COC(=O)C1CN(Cc2cnc3c(Nc4cccc(-c5cccc(NC(=O)c6cc(CN7CC[C@@H](O)C7)cn(C)c6=O)c5Cl)c4Cl)nccc3c2)C1]

This compound was prepared using similar procedures as described for Example 15 with methyl 1-((8-(2,2'-dichloro-3'-(5-formyl-1-methyl-2-oxo-1,2-dihydropyridine-3-carboxamido)biphenyl-3-ylamino)-1,7-naphthyridin-3-yl) methyl)azetidine-3-carboxylate replacing 8-((3-bromo-2-methylphenyl)amino)-1,7-naphthyridine-3-carbaldehyde in Step 3. The crude product was purified by silica gel chromatography (MeOH/DCM) to provide the desired product. LC-MS calculated for $C_{38}H_{38}Cl_2N_7O_5$ $(M+H)^+$: m/z=742.2; found 742.4.

Step 5: (R)-1-((8-(2,2'-dichloro-3'-(5-((3-hydroxypyrrolidin-1-yl)methyl)-1-methyl-2-oxo-1,2-dihydropyridine-3-carboxamido)biphenyl-3-ylamino)-1,7-naphthyridin-3-yl)methyl)azetidine-3-carboxylic acid This compound was prepared using similar procedures as described for Example 14 with (R)-methyl 1-((8-(2,2'-dichloro-3'-(5-((3-hydroxypyrrolidin-1-yl)methyl)-1-methyl-2-oxo-1,2-dihydropyridine-3-carboxamido)biphenyl-3-ylamino)-1,7-naphthyridin-3-yl)methyl)azetidine-3-carboxylate replacing methyl 1-((8-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)amino)-1,7-naphthyridin-3-yl)methyl)azetidine-3-carboxylate in Step 11. The reaction mixture was diluted with methanol and purified by prep HPLC (pH=2, acetonitrile/water+TFA) to provide the desired compound as its TFA salt. LC-MS calculated for $C_{37}H_{36}C_{12}N_7O_5$ $(M+H)^+$: m/z=728.2; found 728.1.

Example 17

1-((8-(2,2'-dichloro-3'-(5-((2-hydroxyethylamino) methyl)-1-methyl-2-oxo-1,2-dihydropyridine-3-carboxamido)biphenyl-3-ylamino)-1,7-naphthyridin-3-yl)methyl)azetidine-3-carboxylic acid

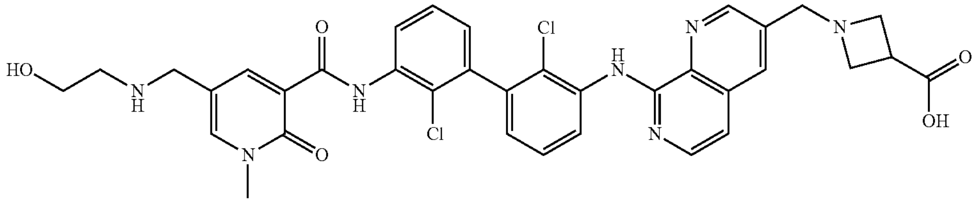 [SMILES: Cn1cc(CNCCO)cc(C(=O)Nc2cccc(-c3cccc(Nc4nccc5cc(CN6CC(C(=O)O)C6)cnc45)c3Cl)c2Cl)c1=O]

Step 1: methyl 1-((8-(2,2'-dichloro-3'-(5-((2-hydroxyethylamino)methyl)-1-methyl-2-oxo-1,2-dihydropyridine-3-carboxamido)biphenyl-3-ylamino)-1,7-naphthyridin-3-yl)methyl)azetidine-3-carboxylate

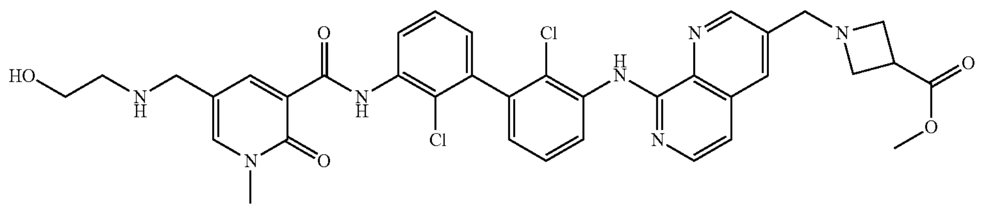 [SMILES: COC(=O)C1CN(Cc2cnc3c(Nc4cccc(-c5cccc(NC(=O)c6cc(CNCCO)cn(C)c6=O)c5Cl)c4Cl)nccc3c2)C1]

A mixture of methyl 1-((8-((2,2'-dichloro-3'-(5-formyl-1-methyl-2-oxo-1,2-dihydropyridine-3-carboxamido)-[1,1'-biphenyl]-3-yl)amino)-1,7-naphthyridin-3-yl)methyl)azetidine-3-carboxylate (Example 16, Step 3: 0.020 g, 0.030 mmol) and ethanolamine (Aldrich, cat #411000: 0.089 mmol) in methylene chloride (0.596 ml) and N,N-diisopropylethylamine (0.026 ml, 0.149 mmol) was stirred at rt for 1 h. Sodium triacetoxyborohydride (0.019 g, 0.089 mmol) was carefully added. The reaction was stirred at rt for 2 h and sodium tetrahydroborate (2.384 μl, 0.060 mmol) and methanol (6 mL) were carefully added. The mixture was stirred overnight, and the reaction was quenched with a saturated solution of sodium bicarbonate. The mixture was then extracted with a 3:1 mixture of chloroform/isopropanol. The combined organic layers were washed with brine, dried over sodium sulfate, and then concentrated in vacuo. The crude residue was purified by column chromatography (0→50% methanol/DCM). LC-MS calculated for $C_{36}H_{36}Cl_2N_7O_5$ $(M+H)^+$: m/z=716.2; found 716.3.

Step 2: 1-((8-(2,2'-dichloro-3'-(5-((2-hydroxyethylamino)methyl)-1-methyl-2-oxo-1,2-dihydropyridine-3-carboxamido)biphenyl-3-ylamino)-1,7-naphthyridin-3-yl)methyl)azetidine-3-carboxylic acid This compound was prepared using similar procedures as described for Example 14 with methyl 1-((8-(2,2'-dichloro-3'-(5-((2-hydroxyethylamino)methyl)-1-methyl-2-oxo-1,2-dihydropyridine-3-carboxamido)biphenyl-3-ylamino)-1,7-naphthyridin-3-yl)methyl)azetidine-3-carboxylate replacing methyl 1-((8-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)amino)-1,7-naphthyridin-3-yl)methyl)azetidine-3-carboxylate in Step 11. The reaction mixture was diluted with methanol and purified by prep HPLC (pH=2, acetonitrile/water+TFA) to provide the desired compound as its TFA salt. LC-MS calculated for $C_{35}H_{34}Cl_2N_7O_5$ $(M+H)^+$: m/z=702.2; found 702.2.

Example 18

1-((8-(2,2'-dichloro-3'-(5-((2-hydroxy-2-methylpropylamino)methyl)-1-methyl-2-oxo-1,2-dihydropyridine-3-carboxamido)biphenyl-3-ylamino)-1,7-naphthyridin-3-yl)methyl)azetidine-3-carboxylicacid

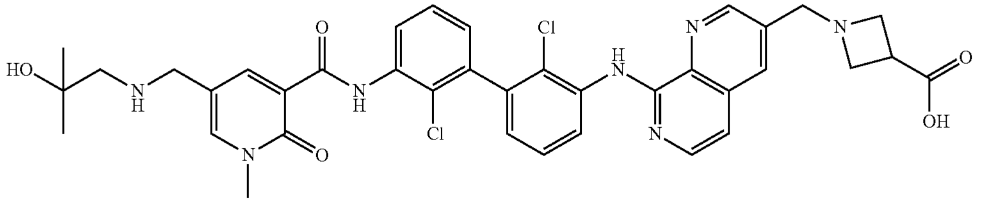 [SMILES: Cn1cc(CNCC(C)(C)O)cc(C(=O)Nc2cccc(-c3cccc(Nc4nccc5cc(CN6CC(C(=O)O)C6)cnc45)c3Cl)c2Cl)c1=O]

Step 1: methyl 1-((8-(2,2'-dichloro-3'-(5-((2-hydroxy-2-methylpropylamino)methyl)-1-methyl-2-oxo-1,2-dihydropyridine-3-carboxamido)biphenyl-3-ylamino)-1,7-naphthyridin-3-yl)methyl)azetidine-3-carboxylate

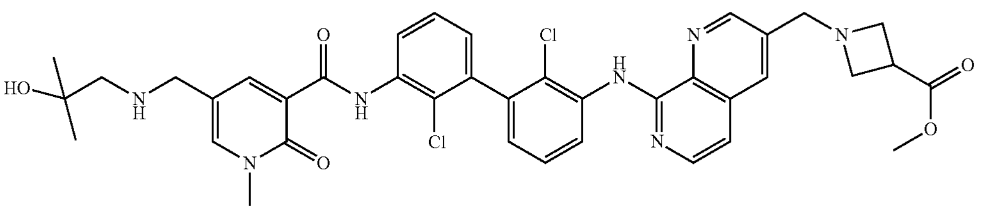 [SMILES: COC(=O)C1CN(Cc2cnc3c(Nc4cccc(-c5cccc(NC(=O)c6cc(CNCC(C)(C)O)cn(C)c6=O)c5Cl)c4Cl)nccc3c2)C1]

This compound was prepared using similar procedures as described for Example 17 with 1-amino-2-methyl-2-propanol (Aldrich, cat #777625) replacing ethanolamine in Step 1. The crude residue was purified by column chromatography (0→50% methanol/DCM). LC-MS calculated for $C_{38}H_{40}Cl_2N_7O_5$ $(M+H)^+$: m/z=744.2; found 744.4.

Step 2: 1-((8-(2,2'-dichloro-3'-(5-((2-hydroxy-2-methylpropylamino)methyl)-1-methyl-2-oxo-1,2-dihydropyridine-3-carboxamido)biphenyl-3-ylamino)-1,7-naphthyridin-3-yl)methyl)azetidine-3-carboxylic acid This compound was prepared using similar procedures as described for Example 14 with methyl 1-((8-(2,2'-dichloro-3'-(5-((2-hydroxy-2-methylpropylamino)methyl)-1-methyl-2-oxo-1,2-dihydropyridine-3-carboxamido)biphenyl-3-ylamino)-1,7-naphthyridin-3-yl)methyl)azetidine-3-carboxylate replacing methyl 1-((8-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)amino)-1,7-naphthyridin-3-yl)methyl)azetidine-3-carboxylate in Step 11. The reaction mixture was diluted with methanol and purified by prep HPLC (pH=2, acetonitrile/water+TFA) to provide the desired compound as its TFA salt. LC-MS calculated for $C_{37}H_{38}Cl_2N_7O_5$ $(M+H)^+$: m/z=730.2; found 730.2.

Example 19

2,2'-(((((2,2'-dimethyl-[1,1'-biphenyl]-3,3'-diyl)bis(azanediyl))bis(1,7-naphthyridine-8,3-diyl))bis(methylene))bis(azanediyl))bis(ethan-1-ol)

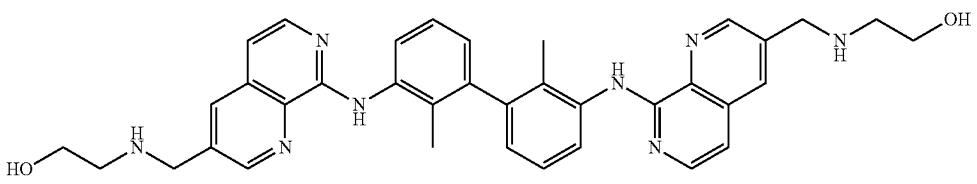 [SMILES: Cc1c(Nc2nccc3cc(CNCCO)cnc23)cccc1-c1cccc(Nc2nccc3cc(CNCCO)cnc23)c1C]

Step 1: 2-((8-(3-bromo-2-methylphenylamino)-1,7-naphthyridin-3-yl)amino)ethanol

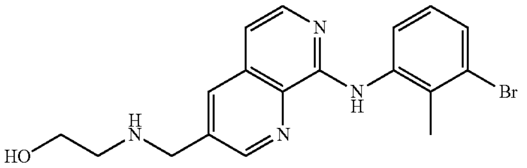 [SMILES: Cc1c(Br)cccc1Nc1nccc2cc(CNCCO)cnc12]

A mixture of 8-((3-bromo-2-methylphenyl)amino)-1,7-naphthyridine-3-carbaldehyde (Example 15, Step 2: 0.100 g, 0.292 mmol) and ethanolamine (Aldrich, cat #411000: 0.292 mmol) in 1,2-dichloroethane (1.46 ml) and N,N-diisopropylethylamine (0.051 ml, 0.292 mmol) was stirred at rt for 1 h. Sodium triacetoxyborohydride (0.093 g, 0.438 mmol) was carefully added in portions. The reaction was stirred at rt for 2 h, then methanol (1 mL) and sodium borohydride (0.584 mmol) were added. The reaction was quenched with a saturated aqueous solution of sodium bicarbonate. The mixture was then extracted with a 3:1 mixture of chloroform/isopropanol. The combined organic layers were dried over sodium sulfate, then concentrated in vacuo. The crude residue was purified by silica gel chromatography (0→50% methanol/DCM) to give the desired product. LC-MS calculated for $C_{18}H_{20}BrN_4O$ $(M+H)^+$: m/z=387.1; found 387.2.

Step 2: (8-((2-methyl-3-(4,4,5,5-tetramethyl-1,3,2-dioxaborolan-2-yl)phenyl)amino)-1,7-naphthyridin-3-yl)methanol

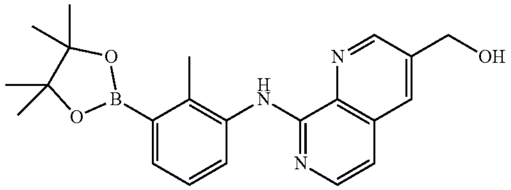 [SMILES: Cc1c(Nc2nccc3cc(CO)cnc23)cccc1B1OC(C)(C)C(C)(C)O1]

A mixture of (8-((3-bromo-2-methylphenyl)amino)-1,7-naphthyridin-3-yl)methanol (Affinity Research Chemicals, cat #ARI-0169: 0.300 g, 0.872 mmol), bis(pinacolato)diboron (Aldrich, #473294: 0.266 g, 1.046 mmol), dichloro[1,1'-bis(diphenylphosphino)ferrocene]palladium (II) dichloromethane adduct (0.071 g, 0.087 mmol) and potassium acetate (0.214 g, 2.179 mmol) was charged with nitrogen and stirred at 110° C. for 2 h. The crude was diluted with DCM, and then filtered through Celite®. The filtrate was concentrated, and the resulting residue was used directly in the next step without further purification. LC-MS calculated for $C_{22}H_{27}BN_3O_3(M+H)^+$: m/z=392.2; found 392.3.

Step 3: 2-((8-(3'-(3-(hydroxymethyl)-1,7-naphthyridin-8-ylamino)-2,2'-dimethylbiphenyl-3-ylamino)-1,7-naphthyridin-3-yl)amino)ethanol

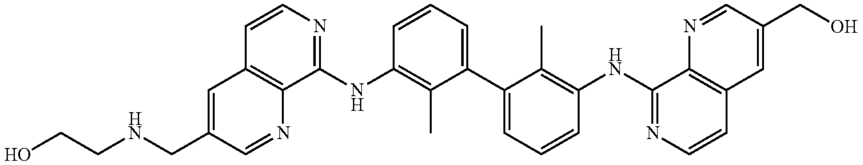 [SMILES: Cc1c(Nc2nccc3cc(CO)cnc23)cccc1-c1cccc(Nc2nccc3cc(CNCCO)cnc23)c1C]

To a vial was added (8-((2-methyl-3-(4,4,5,5-tetramethyl-1,3,2-dioxaborolan-2-yl)phenyl)amino)-1,7-naphthyridin-3-yl)methanol (0.064 g, 0.165 mmol), 2-((8-(3-bromo-2-methylphenylamino)-1,7-naphthyridin-3-yl)methylamino)ethanol (Step 1: 0.058 g, 0.150 mmol), 1 M aqueous sodium carbonate (0.300 mmol), (1,1'-bis(di-cyclohexylphosphino)ferrocene)-dichloropalladium(II) (10.96 mg, 0.015 mmol), and 1,4-dioxane (1.321 ml). The mixture was degassed, sealed, and heated to 90° C. whilst stirring for 4 h. The mixture was cooled, diluted with EtOAc and filtered through Celite®. The filtrate was concentrated and the crude residue was purified using silica gel chromatography (MeOH/DCM). LC-MS calculated for $C_{34}H_{34}N_7O_2$ $(M+H)^+$: m/z=572.3; found 572.4.

Step 4: 8-(3'-(3-((2-hydroxyethylamino)methyl)-1,7-naphthyridin-8-ylamino)-2,2'-dimethylbiphenyl-3-ylamino)-1,7-naphthyridine-3-carbaldehyde

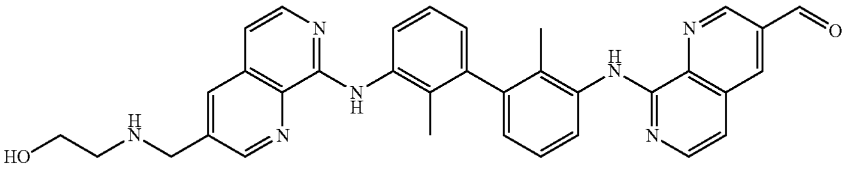 [SMILES: Cc1c(Nc2nccc3cc(C=O)cnc23)cccc1-c1cccc(Nc2nccc3cc(CNCCO)cnc23)c1C]

This compound was prepared using similar procedures as described for Example 9 with 2-((8-(3'-(3-(hydroxymethyl)-1,7-naphthyridin-8-ylamino)-2,2'-dimethylbiphenyl-3-ylamino)-1,7-naphthyridin-3-yl)amino)ethanol replacing (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol in Step 5. LC-MS calculated for $C_{34}H_{32}N_7O_2$ $(M+H)^+$: m/z=570.3; found 570.4.

Step 5: 2,2'-(((((2,2'-dimethyl-[1,1'-biphenyl]-3,3'-diyl)bis(azanediyl))bis(1,7-naphthyridine-8,3-diyl))bis(methylene))bis(azanediyl))bis(ethan-1-ol)

To a vial was added 8-(3'-(3-((2-hydroxyethylamino)methyl)-1,7-naphthyridin-8-ylamino)-2,2'-dimethylbiphenyl-3-ylamino)-1,7-naphthyridine-3-carbaldehyde (0.034 g, 0.065 mmol), ethanolamine (Aldrich, cat #411000: 0.024 mL, 0.194 mmol), dichloromethane (0.997 ml) and N,N-diisopropylethylamine (0.027 ml, 0.194 mmol). The reaction was stirred at rt for 2 h, then sodium triacetoxyborohydride (0.041 g, 0.194 mmol) and acetic acid (0.011 ml, 0.194 mmol) were added. After 2 h, sodium borohydride (0.130 mmol) and methanol (0.350 mL) were carefully added. The mixture was stirred overnight, then the mixture was diluted with methanol and purified by prep HPLC (pH=2, acetonitrile/water+TFA) to provide the desired compound as its TFA salt. LC-MS calculated for $C_{36}H_{39}N_8O_2$ $(M+H)^+$: m/z=615.3; found 615.3.

Example 20

(3R,3'R)-1,1'-((((2,2'-dimethyl-[1,1'-biphenyl]-3,3'-diyl)bis(azanediyl))bis(1,7-naphthyridine-8,3-diyl))bis(methylene))bis(pyrrolidin-3-ol)

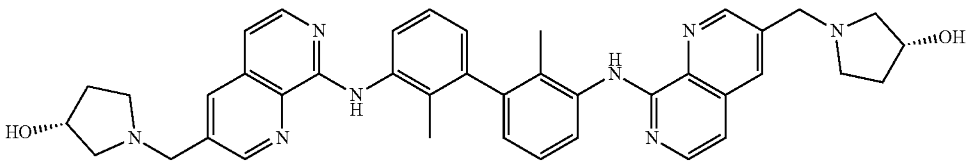 [SMILES: Cc1c(Nc2nccc3cc(CN4CC[C@@H](O)C4)cnc23)cccc1-c1cccc(Nc2nccc3cc(CN4CC[C@@H](O)C4)cnc23)c1C]

Step 1: 8-((3-bromo-2-methylphenyl)amino)-1,7-naphthyridine-3-carbaldehyde

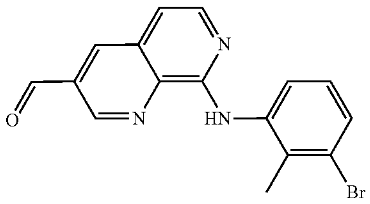 [SMILES: Cc1c(Br)cccc1Nc1nccc2cc(C=O)cnc12]

A suspension of (8-((3-bromo-2-methylphenyl)amino)-1,7-naphthyridin-3-yl)methanol (Affinity Research Chemicals, cat #ARI-0169: 300.0 mg, 0.872 mmol) and manganese dioxide (1515 mg, 17.43 mmol) in DCM (8716 μl) was stirred at 45° C. for 1 h. The reaction was filtered through Celite® and the filtrate was concentrated to yield a crude residue, which was used directly in the next step without further purification. LC-MS calculated for $C_{16}H_{13}BrN_3O$ $(M+H)^+$: m/z=342.0; found 342.0.

Step 2: (R)-1-((8-((3-bromo-2-methylphenyl)amino)-1,7-naphthyridin-3-yl)methyl)pyrrolidin-3-ol

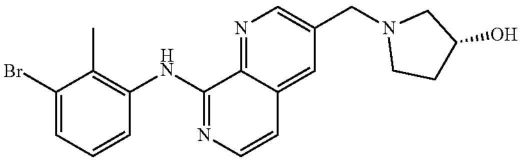 [SMILES: Cc1c(Br)cccc1Nc1nccc2cc(CN3CC[C@@H](O)C3)cnc12]

A mixture of 8-((3-bromo-2-methylphenyl)amino)-1,7-naphthyridine-3-carbaldehyde (0.100 g, 0.292 mmol) and (R)-3-hydroxypyrrolidine (Combi-Blocks, cat #AM-2005: 0.025 g, 0.292 mmol) in 1,2-dichloroethane (1.46 ml) and N,N-diisopropylethylamine (0.051 ml, 0.292 mmol) was stirred at rt for 1 h. Sodium triacetoxyborohydride (0.093 g, 0.438 mmol) was carefully added in portions. The reaction was stirred at rt for 2 h, then quenched with a saturated aqueous solution of sodium bicarbonate. The mixture was then extracted with a 3:1 mixture of chloroform/isopropanol. The combined organic layers were dried over sodium sulfate, then concentrated in vacuo. The crude residue was purified by silica gel chromatography (0→30% methanol/DCM) to give the desired product. LC-MS calculated for $C_{20}H_{22}BrN_4O$ $(M+H)^+$: m/z=413.1; found 413.1.

Step 3: (8-((2-methyl-3-(4,4,5,5-tetramethyl-1,3,2-dioxaborolan-2-yl)phenyl)amino)-1,7-naphthyridin-3-yl)methanol

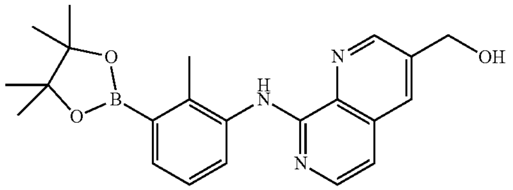 [SMILES: Cc1c(Nc2nccc3cc(CO)cnc23)cccc1B1OC(C)(C)C(C)(C)O1]

A mixture of (8-((3-bromo-2-methylphenyl)amino)-1,7-naphthyridin-3-yl)methanol (Affinity Research Chemicals, cat #ARI-0169: 0.300 g, 0.872 mmol), bis(pinacolato)diboron (Aldrich, cat #473294: 0.266 g, 1.046 mmol), dichloro[1,1'-bis(diphenylphosphino)ferrocene]palladium (II) dichloromethane adduct (0.071 g, 0.087 mmol) and potassium acetate (0.214 g, 2.179 mmol) was charged with nitrogen and stirred at 110° C. for 2 h. The crude was diluted with DCM, and then filtered through Celite®. The filtrate was concentrated, and the resulting residue was used directly in the next step without further purification. LC-MS calculated for $C_{22}H_{27}BN_3O_3(M+H)^+$: m/z=392.2; found 392.3.

Step 4: (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol

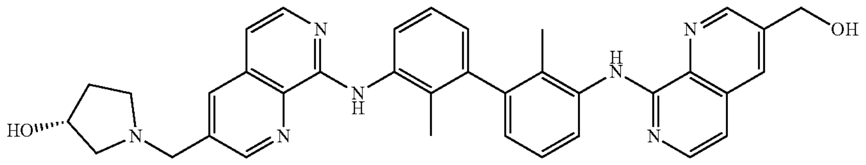 [SMILES: Cc1c(Nc2nccc3cc(CO)cnc23)cccc1-c1cccc(Nc2nccc3cc(CN4CC[C@@H](O)C4)cnc23)c1C]

To a vial was added (8-((2-methyl-3-(4,4,5,5-tetramethyl-1,3,2-dioxaborolan-2-yl)phenyl)amino)-1,7-naphthyridin-3-yl)methanol (0.162 g, 0.414 mmol), (R)-1-((8-((3-bromo-2-methylphenyl)amino)-1,7-naphthyridin-3-yl)methyl) pyrrolidin-3-ol (0.163 g, 0.394 mmol), 1 M aqueous sodium carbonate (0.789 mmol), [1,1'-bis(di-cyclohexylphosphino) ferrocene]-dichloropalladium (II) (0.029 g, 0.039 mmol), and 1,4-dioxane (3.48 ml). The mixture was purged with nitrogen, sealed, and heated to 90° C. whilst stirring for 2 h. The mixture was cooled, diluted with EtOAc and filtered through Celite®. The filtrate was concentrated and purified using silica gel chromatography (20% MeOH/DCM) to provide the desired compound as an orange solid. LC-MS calculated for $C_{36}H_{36}N_7O_2$ $(M+H)^+$: m/z=598.3; found 598.4.

Step 5: (R)-8-((3'-((3-((3-hydroxypyrrolidin-1-yl) methyl)-1,7-naphthyridin-8-yl)amino)-2,2'-dimethyl-[1,1'-biphenyl]-3-yl)amino)-1,7-naphthyridine-3-carbaldehyde

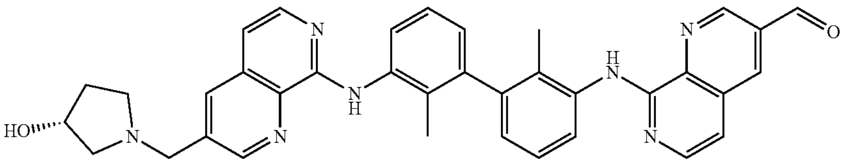 [SMILES: Cc1c(Nc2nccc3cc(C=O)cnc23)cccc1-c1cccc(Nc2nccc3cc(CN4CC[C@@H](O)C4)cnc23)c1C]

To a solution of (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol (0.0715 g, 0.12 mmol) in DCM (1.20 ml) was added manganese dioxide (0.208 g, 2.392 mmol). The resulting mixture was heated at 45° C. for 30 min. After cooling, the mixture was filtered through Celite® and the filtrate was concentrated. The crude orange solid was used directly in the next step. LC-MS calculated for $C_{36}H_{34}N_7O_2$ $(M+H)^+$: m/z=596.3; found 596.5.

Step 6: (3R,3'R)-1,1'-((((2,2'-dimethyl-[1,1'-biphenyl]-3,3'-diyl)bis(azanediyl))bis(1,7-naphthyridine-8,3-diyl))bis(methylene))bis(pyrrolidin-3-ol)

To a vial was added (R)-8-((3'-((3-((3-hydroxypyrrolidin-1-yl)methyl)-1,7-naphthyridin-8-yl)amino)-2,2'-dimethyl-[1,1'-biphenyl]-3-yl)amino)-1,7-naphthyridine-3-carbaldehyde (0.0085 g, 0.014 mmol), (R)-pyrrolidin-3-ol (Combi-Blocks, cat #AM-2005: 4 mg, 0.043 mmol), dichloromethane (0.357 ml) and triethylamine (5.97 μl, 0.043 mmol). The reaction was stirred at rt for 2 h, then sodium triacetoxyborohydride (0.015 g, 0.071 mmol) and acetic acid (2.451 μl, 0.043 mmol) were added. The reaction was stirred for 2 h, then the mixture was diluted with methanol and purified by prep HPLC (pH=2, acetonitrile/water+TFA) to provide the desired compound as its TFA salt. LC-MS calculated for $C_{40}H_{43}N_8O_2$ $(M+H)^+$: m/z=667.3; found 667.3. $^1H$ NMR (600 MHz, DMSO) δ 10.68 (s, 2H), 9.09 (s, 2H), 8.53 (s, 2H), 7.96 (m, 4H), 7.41 (s, 2H), 7.24 (s, 2H), 7.10 (s, 2H), 5.62 (br s, 2H), 4.70 (m, 4H), 4.46 (m, 2H), 3.70-3.10 (ovrlp m, 8H), 2.31 (s, 2H), 2.07 (s, 6H), 1.93 (m, 2H).

Example 21

(R)-1-((8-(3'-(3-((2-hydroxyethylamino)methyl)-1,7-naphthyridin-8-ylamino)-2,2'-dimethylbiphenyl-3-ylamino)-1,7-naphthyridin-3-yl)methyl)pyrrolidin-3-ol

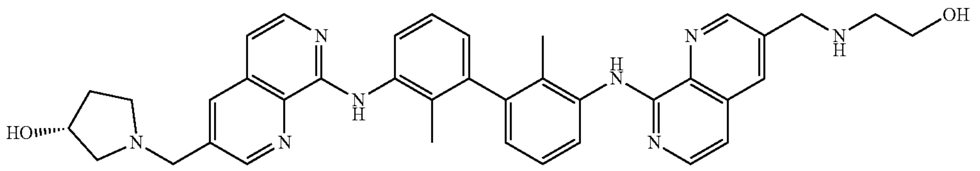

This compound was prepared using similar procedures as described for Example 20 with ethanolamine (Aldrich, cat #411000) replacing (R)-pyrrolidin-3-ol in Step 6. The reaction mixture was diluted with methanol and purified by prep HPLC (pH=2, acetonitrile/water+TFA) to provide the desired compound as its TFA salt. LC-MS calculated for $C_{38}H_{41}N_8O_2$ $(M+H)^+$: m/z=641.3; found 641.3.

Example 22

(3R,3'R)-1,1'-((((2,2'-dichloro-[1,1'-biphenyl]-3,3'-diyl)bis(azanediyl))bis(1,7-naphthyridine-8,3-diyl))bis(methylene))bis(pyrrolidin-3-ol)

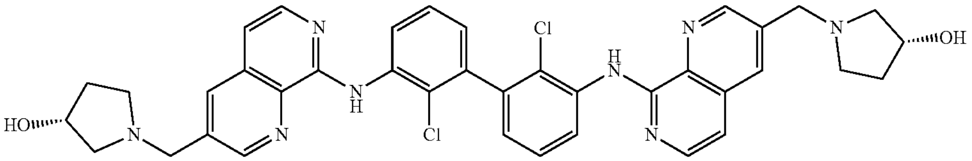 [SMILES: O[C@@H]1CCN(Cc2cnc3c(Nc4cccc(-c5cccc(Nc6nccc7cc(CN8CC[C@@H](O)C8)cnc67)c5Cl)c4Cl)nccc3c2)C1]

Step 1: 8-chloro-3-vinyl-1,7-naphthyridine

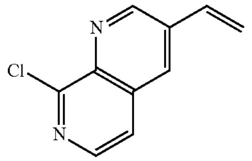

A mixture of 3-bromo-8-chloro-1,7-naphthyridine (PharmaBlock, cat #PBLJ2743: 0.200 g, 0.821 mmol), 4,4,5,5-tetramethyl-2-vinyl-1,3,2-dioxaborolane (Aldrich, cat #663348: 153 μL, 0.904 mmol), sodium carbonate (0.174 g, 1.64 mmol) and [1,1'-bis(di-cyclohexylphosphino)ferrocene]dichloropalladium(II) (Aldrich, cat #701998: 6.2 mg, 0.0082 mmol) in tert-butyl alcohol (5.91 mL, 61.8 mmol) and water (6 mL, 300 mmol) was degassed and sealed. It was stirred at 110° C. for 2 h. The reaction mixture was cooled then extracted with ethyl acetate (3×20 mL). The combined organic layers were washed with brine, dried over $MgSO_4$, filtered and concentrated under reduced pressure. The crude residue was used directly in the next step without further purification. LC-MS calculated for $C_{10}H_8ClN_2$ $(M+H)^+$: m/z=191.0; found 191.0.

Step 2: 8-chloro-1,7-naphthyridine-3-carbaldehyde

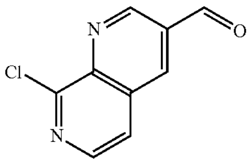 [SMILES: O=Cc1cnc2c(Cl)nccc2c1]

A flask was charged with 8-chloro-3-vinyl-1,7-naphthyridine (391. mg, 2.05 mmol), 1,4-dioxane (40. mL), a stir bar and water (40. mL). To this suspension was added a 4% w/w mixture of osmium tetraoxide in water (0.84 mL, 0.132 mmol). The reaction was stirred for 5 min then sodium periodate (3.23 g, 15.11 mmol) was added and stirred for 3 h. The mixture was diluted with water (20 mL) and EtOAc (20 mL). The layers were separated and the aqueous layer was further extracted with EtOAc (2×20 mL). The combined organic extracts were washed with brine, dried over sodium sulfate, filtered, and concentrated in vacuo. The crude aldehyde was purified by silica gel chromatography (0→60% EtOAc/hexanes). LC-MS calculated for $C_9H_6ClN_2O$ $(M+H)^+$: m/z=193.0; found 192.9.

Step 3: (R)-1-((8-chloro-1,7-naphthyridin-3-yl)methyl)pyrrolidin-3-ol

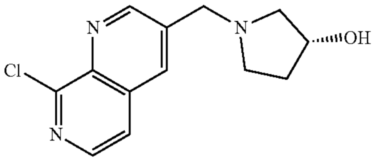 [SMILES: O[C@@H]1CCN(Cc2cnc3c(Cl)nccc3c2)C1]

This compound was prepared using similar procedures as described for Example 20 with 8-chloro-1,7-naphthyridine-3-carbaldehyde replacing 8-((3-bromo-2-methylphenyl)amino)-1,7-naphthyridine-3-carbaldehyde in Step 2. The crude amine was purified by silica gel chromatography (0→25% MeOH/DCM). LC-MS calculated for $C_{13}H_{15}ClN_3O$ $(M+H)^+$: m/z=264.1; found 264.1.

Step 4: (R)-1-((8-(3-bromo-2-chlorophenylamino)-1,7-naphthyridin-3-yl)methyl)pyrrolidin-3-ol

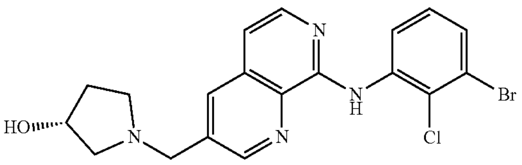 [SMILES: O[C@@H]1CCN(Cc2cnc3c(Nc4cccc(Br)c4Cl)nccc3c2)C1]

In a vial, 3-bromo-2-chloroaniline (Enamine, cat #EN300-105778: 0.063 g, 0.303 mmol) and (R)-1-((8-chloro-1,7-naphthyridin-3-yl)methyl)pyrrolidin-3-ol (0.080 g, 0.303 mmol) were suspended in isopropanol (1.517 ml). Sulfuric acid (0.016 ml, 0.303 mmol) was added to the reaction mixture. The resulting mixture was heated to 100° C. for 1 h. The mixture was cooled, quenched with aqueous saturated sodium bicarbonate, and diluted with 3:1 chloroform/isopropanol. The layers were separated and the water layer was further extracted with 3:1 chloroform/isopropanol. The combined organic layers were dried over magnesium sulfate, filtered and concentrated in vacuo. The crude solid was purified by column chromatography (0→25% Methanol/DCM). LC-MS calculated for $C_{19}H_{19}BrClN_4O$ $(M+H)^+$: m/z=433.0; found 433.0.

Step 5: (R)-1-((8-(2-chloro-3-(4,4,5,5-tetramethyl-1,3,2-dioxaborolan-2-yl)phenylamino)-1,7-naphthyridin-3-yl)methyl)pyrrolidin-3-ol

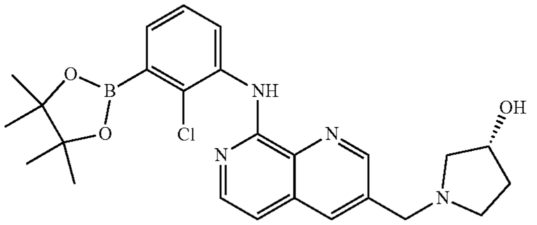 [SMILES: CC1(C)OB(c2cccc(Nc3nccc4cc(CN5CC[C@@H](O)C5)cnc34)c2Cl)OC1(C)C]

This compound was prepared using similar procedures as described for Example 20 with (R)-1-((8-(3-bromo-2-chlorophenylamino)-1,7-naphthyridin-3-yl)methyl)pyrrolidin-3-ol replacing (8-((3-bromo-2-methylphenyl)amino)-1,7-naphthyridin-3-yl)methanol in Step 3. The crude boronic ester was used directly in the next step without further purification. LC-MS calculated for $C_{25}H_{31}BClN_4O_3$$(M+H)^+$: m/z=481.2; found 481.2.

Step 6: (3R,3'R)-1,1'-((((2,2'-dichloro-[1,1'-biphenyl]-3,3'-diyl)bis(azanediyl))bis(1,7-naphthyridine-8,3-diyl))bis(methylene))bis(pyrrolidin-3-ol)

To a vial was added (R)-1-((8-((3-bromo-2-chlorophenyl)amino)-1,7-naphthyridin-3-yl)methyl)pyrrolidin-3-ol (0.010 g, 0.023 mmol), (R)-1-((8-((2-chloro-3-(4,4,5,5-tetramethyl-1,3,2-dioxaborolan-2-yl)phenyl)amino)-1,7-naphthyridin-3-yl)methyl)pyrrolidin-3-ol (0.011 g, 0.023 mmol), 1 M aqueous sodium carbonate (0.046 mmol), dioxane (0.231 ml), (1,1'-bis(di-cyclohexylphosphino)ferrocene)-dichloropalladium(II) (1.687 mg, 2.306 μmol), and a stir bar. The mixture was sparged with nitrogen and heated at 90° C. for 2 h. The mixture was diluted with methanol and purified by prep HPLC (pH=2, acetonitrile/water+TFA) to provide the desired compound as its TFA salt. LC-MS calculated for $C_{38}H_{37}C_{12}N_8O_2$ $(M+H)^+$: m/z=707.2; found 707.3.

Example 23

(R)-1-((4-(3'-(3-(((R)-3-hydroxypyrrolidin-1-yl)methyl)-1,7-naphthyridin-8-ylamino)-2,2'-dimethylbiphenyl-3-ylamino)pyrido[3,2-d]pyrimidin-7-yl)methyl)pyrrolidin-3-ol

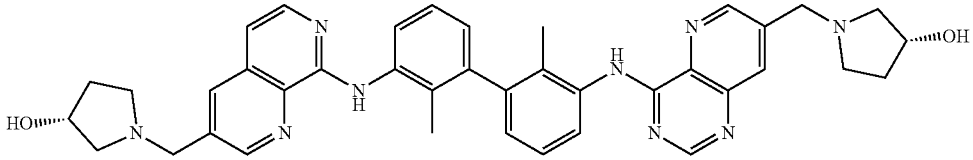 [SMILES: Cc1c(Nc2nccc3cc(CN4CC[C@@H](O)C4)cnc23)cccc1-c1cccc(Nc2ncnc3cc(CN4CC[C@@H](O)C4)cnc23)c1C]

Step 1: (R)-1-((8-(3'-amino-2,2'-dimethylbiphenyl-3-ylamino)-1,7-naphthyridin-3-yl)methyl)pyrrolidin-3-ol

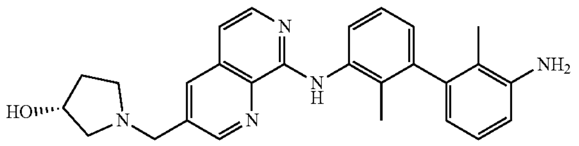 [SMILES: Cc1c(N)cccc1-c1cccc(Nc2nccc3cc(CN4CC[C@@H](O)C4)cnc23)c1C]

To a vial was added 2-methyl-3-(4,4,5,5-tetramethyl-1,3,2-dioxaborolan-2-yl)aniline (Combi-Blocks, cat #PN-9127: 0.108 g, 0.465 mmol), (R)-1-((8-((3-bromo-2-methylphenyl)amino)-1,7-naphthyridin-3-yl)methyl)pyrrolidin-3-ol (Example 15, Step 3: 0.192 g, 0.465 mmol), 1 M aqueous sodium carbonate (0.929 mmol), (1,1'-bis(di-cyclohexylphosphino)ferrocene)-dichloropalladium(II) (0.034 g, 0.046 mmol), and 1,4-dioxane (3.10 mL). The mixture was degassed, sealed, and heated to 90° C. whilst stirring for 4 h. The mixture was cooled, diluted with EtOAc and filtered through celite. The filtrate was concentrated and the crude solid was purified by column chromatography (0→25% Methanol/DCM). LC-MS calculated for $C_{27}H_{30}N_5O$ $(M+H)^+$: m/z=440.2; found 440.3.

Step 2: (R)-1-((8-(3'-(7-bromopyrido[3,2-d]pyrimidin-4-ylamino)-2,2'-dimethylbiphenyl-3-ylamino)-1,7-naphthyridin-3-yl)methyl)pyrrolidin-3-ol

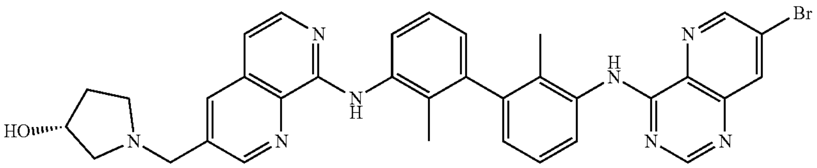 [SMILES: Cc1c(Nc2nccc3cc(CN4CC[C@@H](O)C4)cnc23)cccc1-c1cccc(Nc2ncnc3cc(Br)cnc23)c1C]

To a vial was added 7-bromo-4-chloropyrido[3,2-d]pyrimidine (Synthonix, cat #B0473: 0.187 g, 0.765 mmol), (R)-1-((8-((3'-amino-2,2'-dimethyl-[1,1'-biphenyl]-3-yl)amino)-1,7-naphthyridin-3-yl)methyl)pyrrolidin-3-ol (0.336 g, 0.765 mmol), 2-propanol (3.82 ml), a stir bar and sulfuric acid (0.041 ml, 0.765 mmol). The mixture was heated to 100° C. for 2 h. After cooling to rt, the mixture was diluted with 3:1 $CHCl_3$/isopropanol and aqueous saturated sodium bicarbonate. The layers were separated, and the aqueous phase was further extracted. The combined organic layers were dried over $MgSO_4$, filtered, and concentrated in vacuo. The crude solid was washed with ether to provide the desired product as a yellow solid. LC-MS calculated for $C_{34}H_{32}BrN_8O$ $(M+H)^+$: m/z=647.2; found 647.3.

Step 3: (R)-1-((8-(2,2'-dimethyl-3'-(7-vinylpyrido[3,2-d]pyrimidin-4-ylamino)biphenyl-3-ylamino)-1,7-naphthyridin-3-yl)methyl)pyrrolidin-3-ol

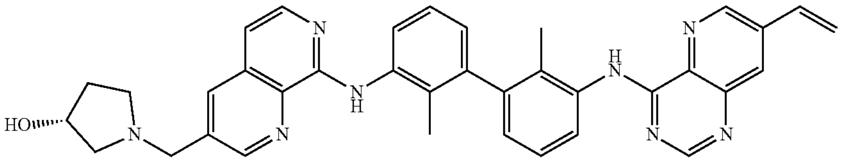 [SMILES: C=Cc1cnc2c(Nc3cccc(-c4cccc(Nc5nccc6cc(CN7CC[C@@H](O)C7)cnc56)c4C)c3C)ncnc2c1]

A mixture of (R)-1-((8-((3'-((7-bromopyrido[3,2-d]pyrimidin-4-yl)amino)-2,2'-dimethyl-[1,1'-biphenyl]-3-yl)amino)-1,7-naphthyridin-3-yl)methyl)pyrrolidin-3-ol (0.248 g, 0.383 mmol), 4,4,5,5-tetramethyl-2-vinyl-1,3,2-dioxaborolane (0.130 ml, 0.766 mmol), sodium carbonate (0.074 ml, 0.766 mmol) and (1,1'-bis(di-cyclohexylphosphino)ferrocene)-dichloropalladium(II) (0.015 g, 0.019 mmol) in 1,4-dioxane (1.915 mL) and water (0.479 mL) was degassed and sealed. It was stirred at 90° C. for 1.5 h. The mixture was cooled to rt, and water and 3:1 chloroform/isopropanol were added. The layers were separated and the aqueous layer was further extracted with 3:1 chloroform/isopropanol. The combined organic layers were dried over $Na_2SO_4$, filtered, and concentrated in vacuo. The crude solid was then washed with ether to provide the desired compound as a yellow solid. LC-MS calculated for $C_{36}H_{35}N_8O$ $(M+H)^+$: m/z=595.3; found 595.3.

Step 4: (R)-4-(3'-(3-((3-hydroxypyrrolidin-1-yl)methyl)-1,7-naphthyridin-8-ylamino)-2,2'-dimethylbiphenyl-3-ylamino)pyrido[3,2-d]pyrimidine-7-carbaldehyde

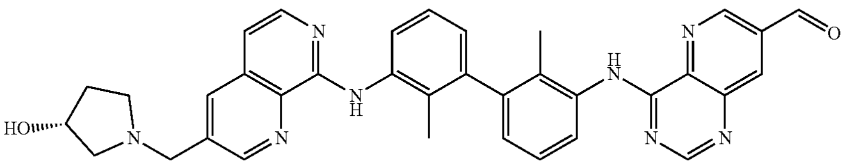 [SMILES: Cc1c(Nc2nccc3cc(CN4CC[C@@H](O)C4)cnc23)cccc1-c1cccc(Nc2ncnc3cc(C=O)cnc23)c1C]

To a flask was added (R)-1-((8-((2,2'-dimethyl-3'-((7-vinylpyrido[3,2-d]pyrimidin-4-yl)amino)-[1,1'-biphenyl]-3-yl)amino)-1,7-naphthyridin-3-yl)methyl)pyrrolidin-3-ol (0.128 g, 0.215 mmol), THF (3.8 mL), water (1 mL), sodium periodate (0.655 g, 3.06 mmol), and 4% osmium tetroxide solution in water (0.170 ml, 0.027 mmol). The resulting mixture was stirred for 1 h at rt. The mixture was diluted with water and 3:1 $CHCl_3$/isopropanol and the layers were separated. The aqueous layer was further extracted with $CHCl_3$/isopropanol (3:1). The combined organic layers were washed dried over $MgSO_4$, filtered, and concentrated in vacuo. The resulting solid was washed with ether to provide the desired product as a brown solid. LC-MS calculated for $C_{35}H_{33}N_8O_2$ $(M+H)^+$: m/z=597.3; found 597.5.

Step 5: (R)-1-((4-(3'-(3-(((R)-3-hydroxypyrrolidin-1-yl)methyl)-1,7-naphthyridin-8-ylamino)-2,2'-dimethylbiphenyl-3-ylamino)pyrido[3,2-d]pyrimidin-7-yl)methyl)pyrrolidin-3-ol To a vial was added (R)-4-((3'-((3-((3-hydroxypyrrolidin-1-yl)methyl)-1,7-naphthyridin-8-yl)amino)-2,2'-dimethyl-[1,1'-biphenyl]-3-yl)amino)pyrido[3,2-d]pyrimidine-7-carbaldehyde (0.064 g, 0.107 mmol), (R)-pyrrolidin-3-ol (Combi-Blocks, cat #AM-2005: 0.037 g, 0.322 mmol), 1,2-dichloroethane (1.073 ml) and triethylamine (0.045 ml, 0.322 mmol). The reaction was stirred at rt for 2 h, then sodium triacetoxyborohydride (0.114 g, 0.536 mmol) and acetic acid (0.018 ml, 0.322 mmol) were added. The reaction was stirred for 2 h, then the mixture was diluted with methanol and purified by prep HPLC (pH=2, acetonitrile/water+TFA) to provide the desired compound as its TFA salt. LC-MS calculated for $C_{39}H_{42}N_9O_2$ $(M+H)^+$: m/z=668.3; found 668.3.

Example 24

(R)-1-((8-(3'-(7-((2-hydroxyethylamino)methyl)pyrido[3,2-d]pyrimidin-4-ylamino)-2,2'-dimethylbiphenyl-3-ylamino)-1,7-naphthyridin-3-yl)methyl)pyrrolidin-3-ol

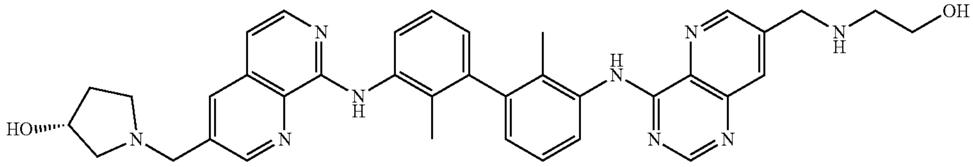

This compound was prepared using similar procedures as described for Example 23 with ethanolamine (Aldrich, cat #411000) replacing (R)-pyrrolidin-3-ol in Step 5. The reaction mixture was diluted with methanol and purified by prep HPLC (pH=2, acetonitrile/water+TFA) to provide the desired compound as its TFA salt. LC-MS calculated for $C_{37}H_{40}N_9O_2$ $(M+H)^+$: m/z=642.3; found 642.3.

Example 25

(R)-1-((8-(3'-(7-(((2-hydroxyethyl)(methyl)amino)methyl)pyrido[3,2-d]pyrimidin-4-ylamino)-2,2'-dimethylbiphenyl-3-ylamino)-1,7-naphthyridin-3-yl)methyl)pyrrolidin-3-ol

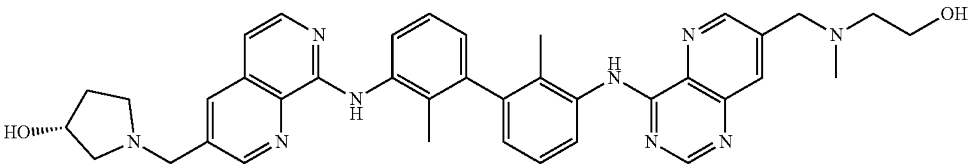

This compound was prepared using similar procedures as described for Example 23 with 2-(methylamino)ethanol (Aldrich, cat #471445) replacing (R)-pyrrolidin-3-ol in Step 5. The reaction mixture was diluted with methanol and purified by prep HPLC (pH=2, acetonitrile/water+TFA) to provide the desired compound as its TFA salt. LC-MS calculated for $C_{38}H_{42}N_9O_2$ $(M+H)^+$: m/z=656.3; found 656.4.

Example 26

(R)-1-((8-(3'-(3-(((R)-3-hydroxypyrrolidin-1-yl)methyl)-1,7-naphthyridin-8-ylamino)-2,2'-dimethylbiphenyl-3-ylamino)-1,7-naphthyridin-3-yl)methyl)-N,N-dimethylpyrrolidine-3-carboxamide

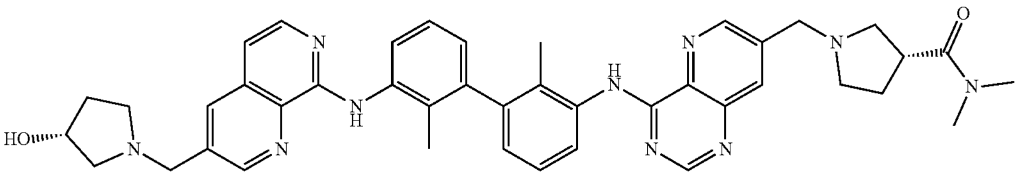 [SMILES: Cc1c(Nc2nccc3cc(CN4CC[C@@H](O)C4)cnc23)cccc1-c1cccc(Nc2ncnc3cc(CN4CC[C@@H](C(=O)N(C)C)C4)cnc23)c1C]

A mixture of (R)-1-((8-((3'-((3-(((R)-3-hydroxypyrrolidin-1-yl)methyl)-1,7-naphthyridin-8-yl)amino)-2,2'-dimethyl-[1,1'-biphenyl]-3-yl)amino)-1,7-naphthyridin-3-yl)methyl)pyrrolidine-3-carboxylic acid (Example 9, Step 6: 0.007 g, 5.08 μmol), 2.0 M dimethylamine in THF (0.102 mmol), HATU (2.316 mg, 6.09 μmol), and N,N-diisopropylethylamine (8.84 μl, 0.051 mmol) in DMF (0.051 ml) was stirred at r.t. for 2 h. The reaction mixture was diluted with methanol and purified by prep HPLC (pH=2, acetonitrile/water+TFA) to provide the desired compound as its TFA salt. LC-MS calculated for $C_{43}H_{48}N_9O_2$ $(M+H)^+$: m/z=722.4; found 722.4.

Example 27

(R)-1-((8-(3'-(7-(((S)-2-hydroxypropylamino)methyl)pyrido[3,2-d]pyrimidin-4-ylamino)-2,2'-dimethylbiphenyl-3-ylamino)-1,7-naphthyridin-3-yl)methyl)pyrrolidin-3-ol

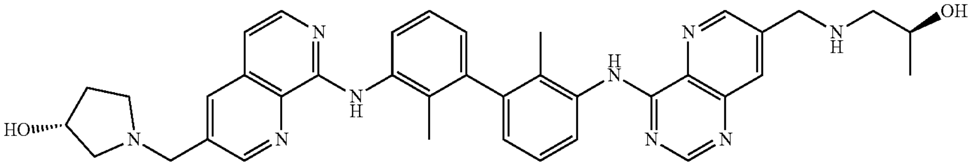 [SMILES: Cc1c(Nc2nccc3cc(CN4CC[C@@H](O)C4)cnc23)cccc1-c1cccc(Nc2ncnc3cc(CNC[C@H](C)O)cnc23)c1C]

This compound was prepared using similar procedures as described for Example 23 with (S)-(+)-1-amino-2-propanol (Aldrich, cat #238864) replacing (R)-pyrrolidin-3-ol in Step 5. The reaction mixture was diluted with methanol and purified by prep HPLC (pH=2, acetonitrile/water+TFA) to provide the desired compound as its TFA salt. LC-MS calculated for $C_{38}H_{42}N_9O_2$ $(M+H)^+$: m/z=656.3; found 656.3.

Example 28

(R)-1-((8-(3'-(5-(((R)-3-hydroxypyrrolidin-1-yl)methyl)-1-methyl-2-oxo-1,2-dihydropyridine-3-carboxamido)-2,2'-dimethylbiphenyl-3-ylamino)-1,7-naphthyridin-3-yl)methyl)pyrrolidine-3-carboxylic acid

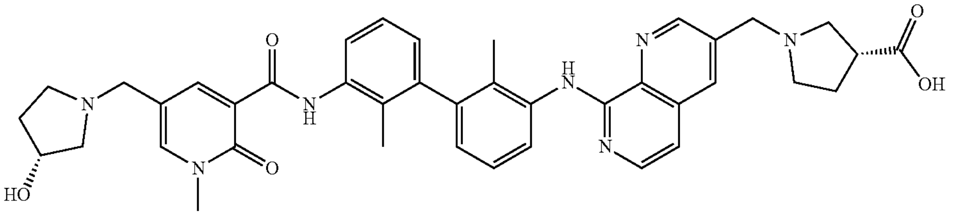 [SMILES: Cc1c(NC(=O)c2cc(CN3CC[C@@H](O)C3)cn(C)c2=O)cccc1-c1cccc(Nc2nccc3cc(CN4CC[C@@H](C(=O)O)C4)cnc23)c1C]

Step 1: N-(3-bromo-2-methylphenyl)-1-methyl-2-oxo-5-vinyl-1,2-dihydropyridine-3-carboxamide

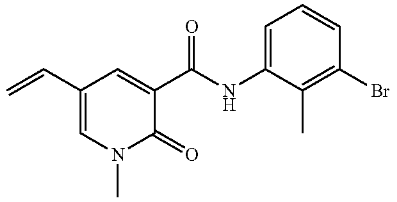 [SMILES: C=Cc1cc(C(=O)Nc2cccc(Br)c2C)c(=O)n(C)c1]

A mixture of 1-methyl-2-oxo-5-vinyl-1,2-dihydropyridine-3-carboxylic acid (Example 15, Step 6: 1.3 g, 7.26 mmol), 3-bromo-2-methylaniline (Aldrich, cat #530018: 0.894 ml, 7.26 mmol), HATU (3.31 g, 8.71 mmol), and N,N-diisopropylethylamine (2.53 ml, 14.51 mmol) in 1,2-dichloroethane (36.3 ml) was stirred at rt for 2 h. The mixture was concentrated under reduced pressure. The residue was diluted with ethyl acetate, and the resulting mixture was washed with water and brine. The organic layer was dried over $MgSO_4$, filtered and concentrated under reduced pressure. The crude residue was used directly in the next step without further purification. LC-MS calculated for $C_{16}H_{16}BrN_2O_2(M+H)^+$: m/z=347.0; found 347.0.

Step 2: N-(3-bromo-2-methylphenyl)-5-formyl-1-methyl-2-oxo-1,2-dihydropyridine-3-carboxamide

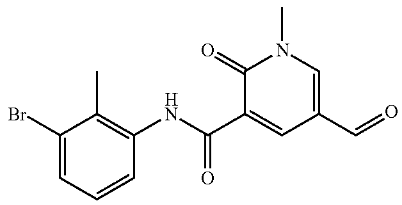 [SMILES: Cc1c(Br)cccc1NC(=O)c1cc(C=O)cn(C)c1=O]

This compound was prepared using similar procedures as described for Example 23, Step 4 with N-(3-bromo-2-methylphenyl)-1-methyl-2-oxo-5-vinyl-1,2-dihydropyridine-3-carboxamide replacing (R)-1-((8-((2,2'-dimethyl-3'-((7-vinylpyrido[3,2-d]pyrimidin-4-yl)amino)-[1,1'-biphenyl]-3-yl)amino)-1,7-naphthyridin-3-yl)methyl)pyrrolidin-3-ol. The crude aldehyde was purified by silica gel chromatography (5% MeOH/DCM). LC-MS calculated for $C_{15}H_{14}BrN_2O_3(M+H)^+$: m/z=349.0; found 349.1.

Step 3: (R)-N-(3-bromo-2-methylphenyl)-5-((3-hydroxypyrrolidin-1-yl)methyl)-1-methyl-2-oxo-1,2-dihydropyridine-3-carboxamide

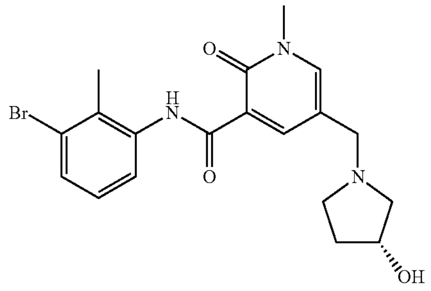 [SMILES: Cc1c(Br)cccc1NC(=O)c1cc(CN2CC[C@@H](O)C2)cn(C)c1=O]

This compound was prepared using similar procedures as described for Example 20, Step 2 with N-(3-bromo-2-methylphenyl)-5-formyl-1-methyl-2-oxo-1,2-dihydropyridine-3-carboxamide replacing 8-((3-bromo-2-methylphenyl)amino)-1,7-naphthyridine-3-carbaldehyde. The crude amine was purified by silica gel chromatography (20% MeOH/DCM). LC-MS calculated for $C_{19}H_{23}BrN_3O_3(M+H)^+$: m/z=420.1; found 420.1.

Step 4: (R)-N-(3'-(3-(hydroxymethyl)-1,7-naphthyridin-8-ylamino)-2,2'-dimethylbiphenyl-3-yl)-5-((3-hydroxypyrrolidin-1-yl)methyl)-1-methyl-2-oxo-1,2-dihydropyridine-3-carboxamide

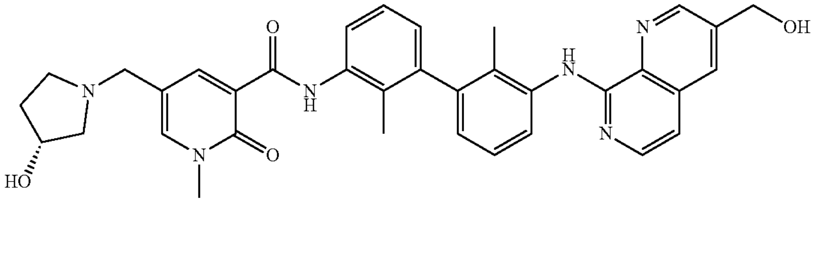 [SMILES: Cc1c(NC(=O)c2cc(CN3CC[C@@H](O)C3)cn(C)c2=O)cccc1-c1cccc(Nc2nccc3cc(CO)cnc23)c1C]

This compound was prepared using similar procedures as described for Example 20, Step 4 with (R)-N-(3-bromo-2-methylphenyl)-5-((3-hydroxypyrrolidin-1-yl)methyl)-1-methyl-2-oxo-1,2-dihydropyridine-3-carboxamide replacing (R)-1-((8-((3-bromo-2-methylphenyl)amino)-1,7-naphthyridin-3-yl)methyl)pyrrolidin-3-ol. The crude amine was purified by silica gel chromatography (20% MeOH/DCM). LC-MS calculated for $C_{35}H_{37}N_6O_4$ $(M+H)^+$: m/z=605.3; found 605.3.

Step 5: (R)-N-(3'-(3-formyl-1,7-naphthyridin-8-ylamino)-2,2'-dimethylbiphenyl-3-yl)-5-((3-hydroxypyrrolidin-1-yl)methyl)-1-methyl-2-oxo-1,2-dihydropyridine-3-carboxamide

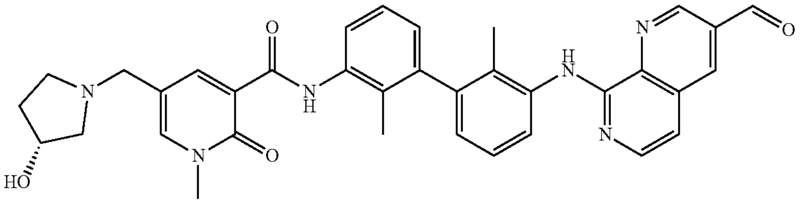 [SMILES: Cc1c(NC(=O)c2cc(CN3CC[C@@H](O)C3)cn(C)c2=O)cccc1-c1cccc(Nc2nccc3cc(C=O)cnc23)c1C]

This compound was prepared using similar procedures as described for Example 20, Step 5 with (R)-N-(3'-(3-(hydroxymethyl)-1,7-naphthyridin-8-ylamino)-2,2'-dimethylbiphenyl-3-yl)-5-((3-hydroxypyrrolidin-1-yl)methyl)-1-methyl-2-oxo-1,2-dihydropyridine-3-carboxamide replacing (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol. LC-MS calculated for $C_{35}H_{35}N_6O_4$ $(M+H)^+$: m/z=603.3; found 603.3.

Step 6: (R)-1-((8-(3'-(5-(((R)-3-hydroxypyrrolidin-1-yl)methyl)-1-methyl-2-oxo-1,2-dihydropyridine-3-carboxamido)-2,2'-dimethylbiphenyl-3-ylamino)-1,7-naphthyridin-3-yl)methyl)pyrrolidine-3-carboxylic acid To a vial was added (R)-N-(3'-(3-formyl-1,7-naphthyridin-8-ylamino)-2,2'-dimethylbiphenyl-3-yl)-5-((3-hydroxypyrrolidin-1-yl)methyl)-1-methyl-2-oxo-1,2-dihydropyridine-3-carboxamide (0.010 g, 0.017 mmol), (R)-pyrrolidine-3-carboxylic acid (Combi-Blocks, cat #ST-7698: 6 mg, 0.050 mmol), 1,2-dichloroethane (0.4 ml) and triethylamine (6.94 μl, 0.050 mmol). The reaction was stirred at rt for 2 h, then sodium triacetoxyborohydride (0.018 g, 0.083 mmol) and acetic acid (2.85 μl, 0.050 mmol) were added. The reaction was stirred for 2 h, then the mixture was diluted with methanol and purified by prep HPLC (pH=2, acetonitrile/water+TFA) to give the desired product as the TFA salt. LC-MS calculated for $C_{40}H_{44}N_7O_5$ $(M+H)^+$: m/z=702.3; found 702.3.

Example 29

(R)-1-((8-(3'-(7-(((R)-2-hydroxypropylamino)methyl)pyrido[3,2-d]pyrimidin-4-ylamino)-2,2'-dimethylbiphenyl-3-ylamino)-1,7-naphthyridin-3-yl)methyl)pyrrolidin-3-ol

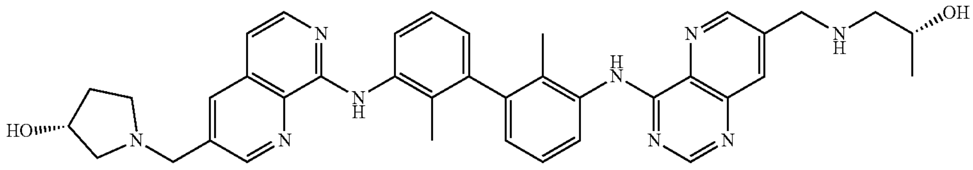 [SMILES: Cc1c(Nc2nccc3cc(CN4CC[C@@H](O)C4)cnc23)cccc1-c1cccc(Nc2ncnc3cc(CNC[C@@H](C)O)cnc23)c1C]

This compound was prepared using similar procedures as described for Example 23 with (R)-(+)-1-amino-2-propanol (Aldrich, cat #238856) replacing (R)-pyrrolidin-3-ol in Step 5. The reaction mixture was diluted with methanol and purified by prep HPLC (pH=2, acetonitrile/water+TFA) to provide the desired compound as its TFA salt. LC-MS calculated for $C_{38}H_{42}N_9O_2$ $(M+H)^+$: m/z=656.3; found 656.4.

Example 30

(R)-1-((8-(3'-(7-((2-hydroxy-2-methylpropylamino)methyl)pyrido[3,2-d]pyrimidin-4-ylamino)-2,2'-dimethylbiphenyl-3-ylamino)-1,7-naphthyridin-3-yl)methyl)pyrrolidin-3-ol

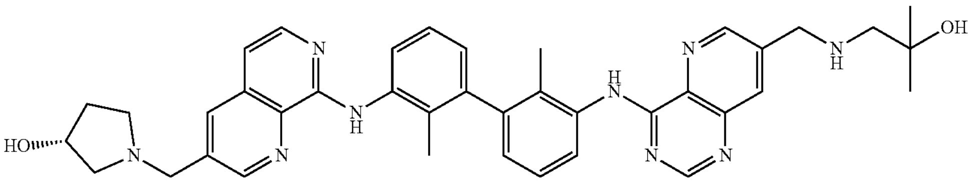 [SMILES: Cc1c(Nc2nccc3cc(CN4CC[C@@H](O)C4)cnc23)cccc1-c1cccc(Nc2ncnc3cc(CNCC(C)(C)O)cnc23)c1C]

This compound was prepared using similar procedures as described for Example 23 with 1-amino-2-methyl-2-propanol (Aldrich, cat #777625) replacing (R)-pyrrolidin-3-ol in Step 5. The reaction mixture was diluted with methanol and purified by prep HPLC (pH=2, acetonitrile/water+TFA) to provide the desired compound as its TFA salt. LC-MS calculated for $C_{39}H_{44}N_9O_2$ $(M+H)^+$: m/z=670.3; found 670.4.

Example 31

(R)-1-((8-(2'-chloro-3'-(1,5-dimethyl-4,5,6,7-tetrahydro-1H-imidazo[4,5-c]pyridine-2-carboxamido)-2-methylbiphenyl-3-ylamino)-1,7-naphthyridin-3-yl)methyl)pyrrolidine-3-carboxylic acid

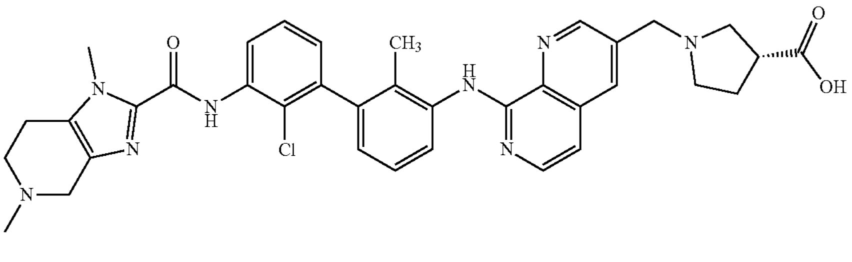

Step 1: tert-butyl 1-methyl-1,4,6,7-tetrahydro-5H-imidazo[4,5-c]pyridine-5-carboxylate

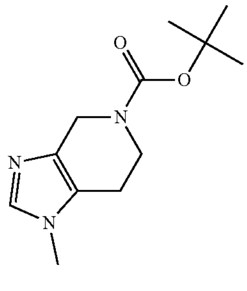 [SMILES: Cn1cnc2c1CCN(C(=O)OC(C)(C)C)C2]

A solution of 1-methyl-4,5,6,7-tetrahydro-1H-imidazo[4,5-c]pyridine (Accela, cat #SY032476: 2.0 g, 14.58 mmol) and $(Boc)_2O$ (3.38 mL, 14.58 mmol) in dichloromethane (60.0 mL) was stirred at room temperature for 1 h. The reaction was quenched with saturated aqueous $NaHCO_3$ solution, and extracted with ethyl acetate. The combined organic layers were washed with brine, dried over $Na_2SO_4$, filtered, and concentrated under reduced pressure. The crude product was used for next step without further purification. LC-MS calculated for $C_{12}H_{20}N_3O_2$ $(M+H)^+$: m/z=238.2; found 238.2.

Step 2: 5-tert-butyl 2-methyl 1-methyl-6,7-dihydro-1H-imidazo[4,5-c]pyridine-2,5(4H)-dicarboxylate

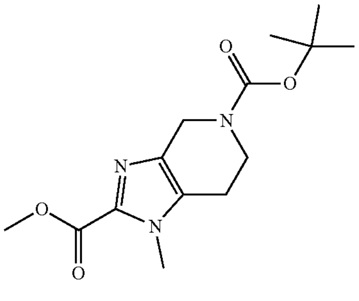 [SMILES: COC(=O)c1nc2c(n1C)CCN(C(=O)OC(C)(C)C)C2]

n-Butyllithium in hexanes (2.5 M, 7.00 mL, 17.49 mmol) was added to a cold (−78° C.) solution of the crude product from Step 1 in tetrahydrofuran (60.0 mL). The reaction mixture was stirred at −78° C. for 10 min prior to the addition of methyl chloroformate (1.7 mL, 21.9 mmol). After being stirred at −78° C. for 15 min, the reaction was then quenched with saturated aqueous $NaHCO_3$ solution, and extracted with ethyl acetate, dried over $Na_2SO_4$, filtered, and concentrated under reduced pressure. The residue was purified by flash chromatography on a silica gel column eluting with 80% ethyl acetate in hexanes to afford the desired product ( ). LC-MS calculated for $C_{14}H_{22}N_3O_4$ $(M+H)^+$: m/z=296.2; found 296.3.

Step 3: tert-butyl 2-((3-bromo-2-chlorophenyl)carbamoyl)-1-methyl-1,4,6,7-tetrahydro-5H-imidazo[4,5-c]pyridine-5-carboxylate

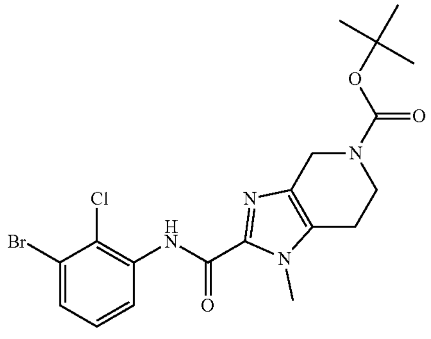 [SMILES: Cn1c(C(=O)Nc2cccc(Br)c2Cl)nc2c1CCN(C(=O)OC(C)(C)C)C2]

Potassium tert-butoxide in tetrahydrofuran (1.0 M, 3.39 mL, 3.39 mmol) was added to a solution of 5-tert-butyl 2-methyl 1-methyl-6,7-dihydro-1H-imidazo[4,5-c]pyridine-2,5(4H)-dicarboxylate (Step 2: 500 mg, 1.69 mmol) and 3-bromo-2-chloroaniline (348 mg, 1.69 mmol) in tetrahydrofuran (12.0 mL). After being stirred at room temperature for 1 h, the reaction mixture was quenched with water, and extracted with ethyl acetate. The combined organic layers were washed with brine, dried over $Na_2SO_4$, filtered, and concentrated under reduced pressure. The residue was purified by flash chromatography on a silica gel column eluting with 50% ethyl acetate in hexanes to afford the desired product. LC-MS calculated for $C_{19}H_{23}BrClN_4O_3(M+H)^+$: m/z=469.1/471.1; found 469.1/471.1.

Step 4: N-(3-bromo-2-chlorophenyl)-1,5-dimethyl-4,5,6,7-tetrahydro-1H-imidazo[4,5-c]pyridine-2-carboxamide

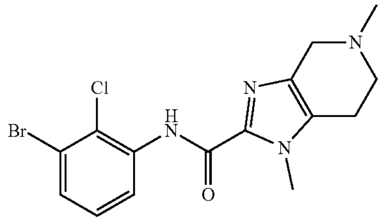 [SMILES: CN1CCc2c(nc(C(=O)Nc3cccc(Br)c3Cl)n2C)C1]

A solution of tert-butyl 2-((3-bromo-2-chlorophenyl)carbamoyl)-1-methyl-1,4,6,7-tetrahydro-5H-imidazo[4,5-c]pyridine-5-carboxylate (Step 3: 300 mg, 0.64 mmol) in trifluoroacetic acid (0.2 mL) and dichloromethane (0.4 mL) was stirred at room temperature for 1 h. The solvent was evaporated, and the residue was dissolved in tetrahydrofuran (1.0 mL). 37% formaldehyde in water (0.48 mL, 6.39 mmol) and sodium triacetoxyborohydride (406 mg, 1.92 mmol) were successively added. After being stirred at room temperature for 1 h, the mixture was quenched with sat. aq. $NaHCO_3$ solution and was extracted with ethyl acetate. The combined organic layers were washed with brine, dried over $Na_2SO_4$, filtered and concentrated under reduced pressure. The residue was purified by flash chromatography on a silica gel column eluting with 10% methanol in dichloromethane to afford the desired product. LC-MS calculated for $C_{15}H_{17}BrClN_4O$ $(M+H)^+$: m/z=383.0/385.0; found 383.0/385.0.

Step 5: N-(2-chloro-3'-((3-(hydroxymethyl)-1,7-naphthyridin-8-yl)amino)-2'-methyl-[1,1'-biphenyl]-3-yl)-1,5-dimethyl-4,5,6,7-tetrahydro-1H-imidazo[4,5-c]pyridine-2-carboxamide

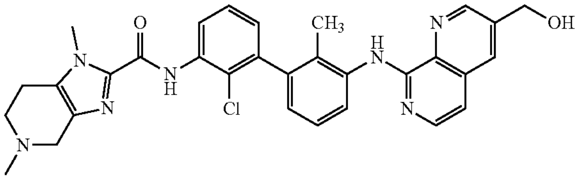 [SMILES: Cc1c(Nc2nccc3cc(CO)cnc23)cccc1-c1cccc(NC(=O)c2nc3c(n2C)CCN(C)C3)c1Cl]

A mixture of N-(3-bromo-2-chlorophenyl)-1,5-dimethyl-4,5,6,7-tetrahydro-1H-imidazo[4,5-c]pyridine-2-carboxamide (Step 4: 60 mg, 0.156 mmol), (8-((2-methyl-3-(4,4,5,5-tetramethyl-1,3,2-dioxaborolan-2-yl)phenyl)amino)-1,7-naphthyridin-3-yl)methanol (Example 9, Step 3: 73.4 mg, 0.188 mmol), sodium carbonate (66.3 mg, 0.626 mmol) and [1,1'-bis(di-cyclohexylphosphino)ferrocene]dichloropalladium(II) (11.8 mg, 0.016 mmol) in 1,4-dioxane (0.8 mL) and water (0.8 mL) was charged with nitrogen and stirred at 100° C. for 2 h. The reaction mixture was diluted with water and extracted with ethyl acetate. The combined organic layers were washed with brine, dried over $Na_2SO_4$, filtered, and concentrated under reduced pressure. The residue was purified by flash chromatography on a silica gel column eluting with 10% methanol in dichloromethane to afford the desired product. LC-MS calculated for $C_{31}H_{31}ClN_7O_2(M+H)^+$: m/z=568.2; found 568.3.

Step 6: N-(2-chloro-3'-((3-formyl-1,7-naphthyridin-8-yl)amino)-2'-methyl-[1,1'-biphenyl]-3-yl)-1,5-dimethyl-4,5,6,7-tetrahydro-1H-imidazo[4,5-c]pyridine-2-carboxamide

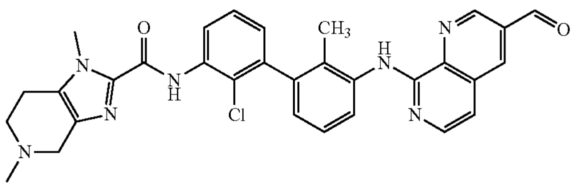 [SMILES: Cc1c(Nc2nccc3cc(C=O)cnc23)cccc1-c1cccc(NC(=O)c2nc3c(n2C)CCN(C)C3)c1Cl]

A suspension of N-(2-chloro-3'-((3-(hydroxymethyl)-1,7-naphthyridin-8-yl)amino)-2'-methyl-[1,1'-biphenyl]-3-yl)-1,5-dimethyl-4,5,6,7-tetrahydro-1H-imidazo[4,5-c]pyridine-2-carboxamide (Step 5: 40 mg, 0.070 mmol) and manganese dioxide (92 mg, 1.056 mmol) in dichloromethane (0.5 mL) was stirred at 45° C. for 30 min. The reaction was filtered through a short pad of Celite® and then concentrated to yield a crude residue, which was used directly without further purification. LC-MS calculated for $C_{31}H_{29}ClN_7O_2$ $(M+H)^+$: m/z=566.2; found 566.2.

Step 7: (R)-1-((8-(2'-chloro-3'-(1,5-dimethyl-4,5,6,7-tetrahydro-1H-imidazo[4,5-c]pyridine-2-carboxamido)-2-methylbiphenyl-3-ylamino)-1,7-naphthyridin-3-yl)methyl)pyrrolidine-3-carboxylic acid A mixture of N-(2-chloro-3'-((3-formyl-1,7-naphthyridin-8-yl)amino)-2'-methyl-[1,1'-biphenyl]-3-yl)-1,5-dimethyl-4,5,6,7-tetrahydro-1H-imidazo[4,5-c]pyridine-2-carboxamide (Step 6: 39.9 mg, 0.070 mmol) and (R)-pyrrolidine-3-carboxylic acid (24.3 mg, 0.211 mmol) in dichloromethane (0.5 mL) was stirred at room temperature for 1 h. Then sodium triacetoxyborohydride (14.92 mg, 0.070 mmol) and acetic acid (4.03 µl, 0.070 mmol) was added. After being stirred at room temperature for 1 h, the reaction was diluted with MeOH and then purified by prep-HPLC (pH=10, acetonitrile/water+$NH_4OH$) to give the desired product. LC-MS calculated for $C_{36}H_{38}ClN_8O_3(M+H)^+$: m/z=665.3; found 665.4.

Example 32

(S)—N-(2-chloro-3'-(3-((3-hydroxypyrrolidin-1-yl)methyl)-1,7-naphthyridin-8-ylamino)-2'-methylbiphenyl-3-yl)-1,5-dimethyl-4,5,6,7-tetrahydro-1H-imidazo[4,5-c]pyridine-2-carboxamide

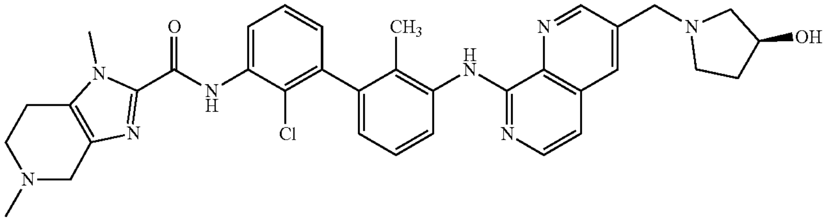 [SMILES: Cc1c(Nc2nccc3cc(CN4CC[C@H](O)C4)cnc23)cccc1-c1cccc(NC(=O)c2nc3c(n2C)CCN(C)C3)c1Cl]

This compound was prepared using similar procedures as described for Example 31, Step 7 with (S)-pyrrolidin-3-ol (Combi-Blocks, cat #SS-7948) replacing (R)-pyrrolidine-3-carboxylic acid. The reaction mixture was purified by prep-HPLC (pH=10, acetonitrile/water+$NH_4OH$) to give the desired product. LC-MS calculated for $C_{35}H_{38}ClN_8O_2$ $(M+H)^+$: m/z=637.3; found 637.4.

Example 33

(R)-1-((8-(2'-chloro-3'-(1,5-dimethyl-4,5,6,7-tetrahydro-1H-imidazo[4,5-c]pyridine-2-carboxamido)-2-methylbiphenyl-3-ylamino)-1,7-naphthyridin-3-yl)methyl)-3-methylpyrrolidine-3-carboxylic acid

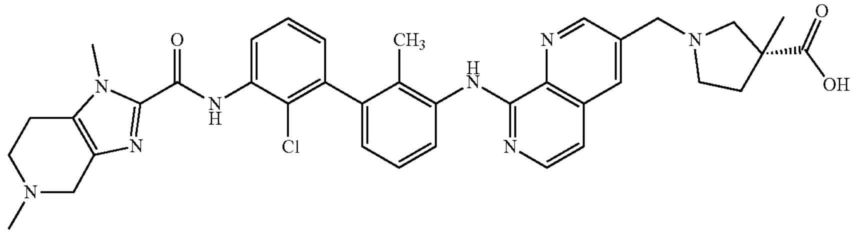 [SMILES: Cc1c(Nc2nccc3cc(CN4CC[C@@](C)(C(=O)O)C4)cnc23)cccc1-c1cccc(NC(=O)c2nc3c(n2C)CCN(C)C3)c1Cl]

This compound was prepared using similar procedures as described for Example 31, Step 7 with (R)-3-methylpyrrolidine-3-carboxylic acid (Ark Pharm, cat #AK601708) replacing (R)-pyrrolidine-3-carboxylic acid. The reaction mixture was purified by prep-HPLC (pH=2, acetonitrile/water+TFA) to give the desired product. LC-MS calculated for $C_{37}H_{40}ClN_8O_3(M+H)^+$: m/z=679.3; found 679.2.

Example 34

(R)-1-((8-((2,2'-dimethyl-3'-(4,5,6,7-tetrahydrothiazolo[5,4-c]pyridin-2-yl)-[1,1'-biphenyl]-3-yl)amino)-1,7-naphthyridin-3-yl)methyl)pyrrolidine-3-carboxylic acid

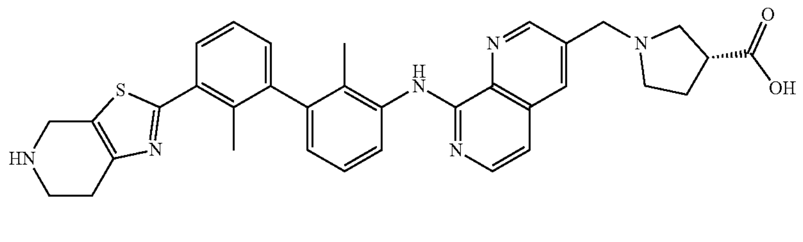 [SMILES: Cc1c(Nc2nccc3cc(CN4CC[C@@H](C(=O)O)C4)cnc23)cccc1-c1cccc(-c2nc3c(s2)CNCC3)c1C]

Step 1: tert-butyl 2-(3'-((3-(hydroxymethyl)-1,7-naphthyridin-8-yl)amino)-2,2'-dimethyl-[1,1'-biphenyl]-3-yl)-6,7-dihydrothiazolo[5,4-c]pyridine-5(4H)-carboxylate

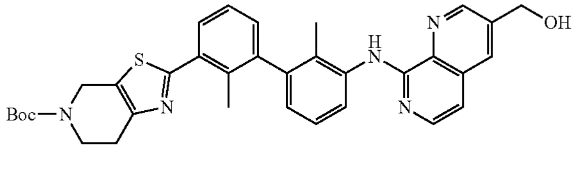 [SMILES: Cc1c(Nc2nccc3cc(CO)cnc23)cccc1-c1cccc(-c2nc3c(s2)CN(C(=O)OC(C)(C)C)CC3)c1C]

This compound was prepared using similar procedures as described for Example 1, Step 7 with (8-((3-bromo-2-methylphenyl)amino)-1,7-naphthyridin-3-yl)methanol (Affinity Research Chemicals, #ARI-0169) replacing 2-(((8-((3-bromo-2-chlorophenyl)amino)-1,7-naphthyridin-3-yl)methyl)amino)ethan-1-ol. After 5 h, saturated aqueous $NaHCO_3$ (5 mL) solution was added to the reaction mixture followed by extraction with dichloromethane (5 mL×3). The combined organic layers were dried over $Na_2SO_4$, filtered and concentrated. The crude product was used for next step without further purification. LC-MS calculated for $C_{34}H_{36}N_5O_3S$ $(M+H)^+$: m/z=594.2; found 594.3.

Step 2: tert-butyl 2-(3'-((3-formyl-1,7-naphthyridin-8-yl)amino)-2,2'-dimethyl-[1,1'-biphenyl]-3-yl)-6,7-dihydrothiazolo[5,4-c]pyridine-5(4H)-carboxylate

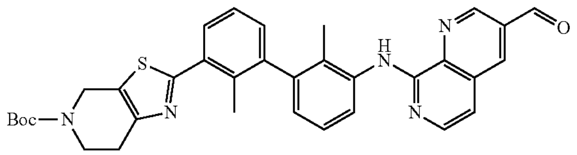 [SMILES: Cc1c(Nc2nccc3cc(C=O)cnc23)cccc1-c1cccc(-c2nc3c(s2)CN(C(=O)OC(C)(C)C)CC3)c1C]

To a solution of tert-butyl 2-(3'-((3-(hydroxymethyl)-1,7-naphthyridin-8-yl)amino)-2,2'-dimethyl-[1,1'-biphenyl]-3-yl)-6,7-dihydrothiazolo[5,4-c]pyridine-5(4H)-carboxylate (130 mg, 0.22 mmol) in DCM (2 mL) was added Dess-Martin periodinane (186 mg, 0.44 mmol). After 1 h, saturated $NaHCO_3$ (5 mL) was added to the reaction mixture followed by extraction with dichloromethane (5 mL×3). The combined organic layers were dried $Na_2SO_4$, filtered and concentrated. The crude product was used for next step without further purification. LC-MS calculated for $C_{34}H_{34}N_5O_3S$ $(M+H)^+$: m/z=592.2; found 592.3.

Step 3: (R)-1-((8-((2,2'-dimethyl-3'-(4,5,6,7-tetrahydrothiazolo[5,4-c]pyridin-2-yl)-[1,1'-biphenyl]-3-yl)amino)-1,7-naphthyridin-3-yl)methyl)pyrrolidine-3-carboxylic acid To a solution of tert-butyl 2-(3'-((3-formyl-1,7-naphthyridin-8-yl)amino)-2,2'-dimethyl-[1,1'-biphenyl]-3-yl)-6,7-dihydrothiazolo[5,4-c]pyridine-5(4H)-carboxylate (10 mg, 0.017 mmol) and DIPEA (5 uL) in DCM (0.5 mL) was added (R)-pyrrolidine-3-carboxylic acid (5.8 mg, 0.05 mmol). After 1 h, sodium triacetoxyborohydride (6.6 mg, 0.033 mmol) was added to the reaction mixture. After 2 h, TFA (0.5 mL) was added to the reaction mixture. After another 1 h, the reaction mixture was concentrated, then dissolved in MeOH and purified by prep HPLC (pH=2, acetonitrile/water+TFA) to provide the compound as the TFA salt. LC-MS calculated for $C_{34}H_{35}N_6O_2S$ $(M+H)^+$: m/z=591.2; found 591.3.

Example 35

(R)-1-((8-((2,2'-dimethyl-3'-(4,5,6,7-tetrahydrothiazolo[5,4-c]pyridin-2-yl)-[1,1'-biphenyl]-3-yl)amino)-1,7-naphthyridin-3-yl)methyl)pyrrolidin-3-ol

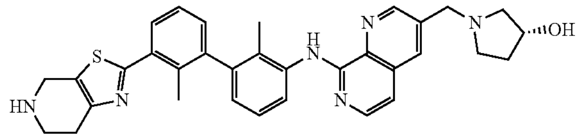 [SMILES: Cc1c(Nc2nccc3cc(CN4CC[C@@H](O)C4)cnc23)cccc1-c1cccc(-c2nc3c(s2)CNCC3)c1C]

This compound was prepared using similar procedures as described for Example 34 with (R)-3-hydroxypyrrolidine replacing (R)-pyrrolidine-3-carboxylic acid in Step 3. The reaction mixture was diluted with MeOH then purified by prep-HPLC (pH=2, acetonitrile/water+TFA) to give the desired product as the TFA salt. LC-MS calculated for $C_{33}H_{35}N_{60}S$ $(M+H)^+$: m/z=563.3; found 563.3.

Example 36

(S)-1-((8-((2,2'-dimethyl-3'-(4,5,6,7-tetrahydrothiazolo[5,4-c]pyridin-2-yl)-[1,1'-biphenyl]-3-yl)amino)-1,7-naphthyridin-3-yl)methyl)pyrrolidin-3-ol

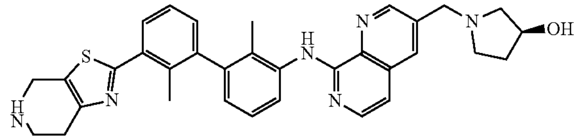 [SMILES: Cc1c(Nc2nccc3cc(CN4CC[C@H](O)C4)cnc23)cccc1-c1cccc(-c2nc3c(s2)CNCC3)c1C]

This compound was prepared using similar procedures as described for Example 34 with (S)-3-hydroxypyrrolidine replacing (R)-pyrrolidine-3-carboxylic acid in Step 3. The reaction mixture was diluted with MeOH then purified by prep-HPLC (pH=2, acetonitrile/water+TFA) to give the desired product as the TFA salt. LC-MS calculated for $C_{33}H_{35}N_6OS$ $(M+H)^+$: m/z=563.3; found 563.3.

Example 37

(R)-2-(dimethylamino)-1-(2-(3'-((3-((3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]oxazol-5-yl)ethan-1-one

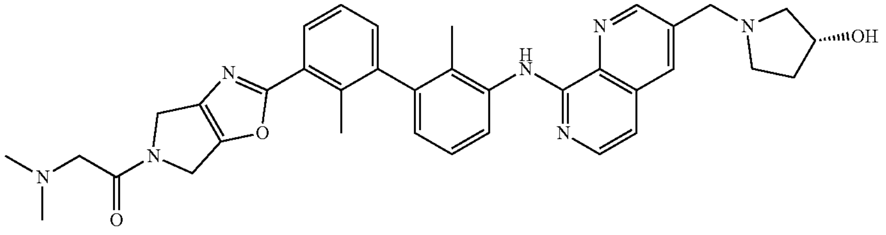 [SMILES: Cc1c(Nc2nccc3cc(CN4CC[C@@H](O)C4)cnc23)cccc1-c1cccc(-c2nc3c(o2)CN(C(=O)CN(C)C)C3)c1C]

Step 1: Benzyl 6-oxa-3-azabicyclo[3.1.0]hexane-3-carboxylate

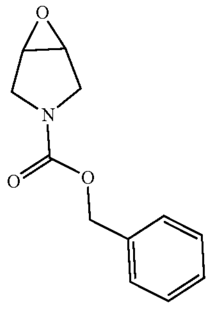 [SMILES: O=C(OCc1ccccc1)N1CC2OC2C1]

To a solution of benzyl 2,5-dihydro-1H-pyrrole-1-carboxylate (12.4 g, 61.0 mmol) in DCM (200 ml) was added m-CPBA (16.20 g, 61.0 mmol). The resulting mixture was stirred at room temperature for 3 h. The reaction was quenched with saturated aqueous $NaHCO_3$ solution, the organic layer was separated, and the aqueous layer was extracted with DCM. The combined organic layers were dried over $Na_2SO_4$, filtered and concentrated. The crude product was purified using flash chromatography (eluting with 0-50% ethyl acetate in hexanes) to give the desired product as clear oil (13 g, 97%). LC-MS calculated for $C_{12}H_{14}NO_3$ $(M+H)^+$: m/z=220.1; found 220.1.

Step 2: Benzyl 3-amino-4-hydroxypyrrolidine-1-carboxylate

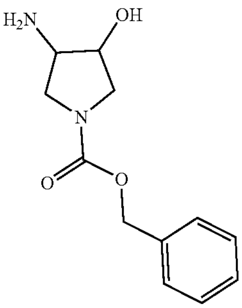 [SMILES: NC1CN(C(=O)OCc2ccccc2)CC1O]

To a flask was charged with benzyl 6-oxa-3-azabicyclo[3.1.0]hexane-3-carboxylate (13.0 g, 59.3 mmol) and ammonium hydroxide (115 ml, 2.96 mol). The reaction mixture was heated at 90° C. overnight. The solvent was removed. The residue was used in the next step without further purification. LC-MS calculated for $C_{12}H_{17}N_2O_3$ $(M+H)^+$: m/z=237.1; found 237.1.

Step 3: Benzyl 3-(3-bromo-2-methylbenzamido)-4-hydroxypyrrolidine-1-carboxylate

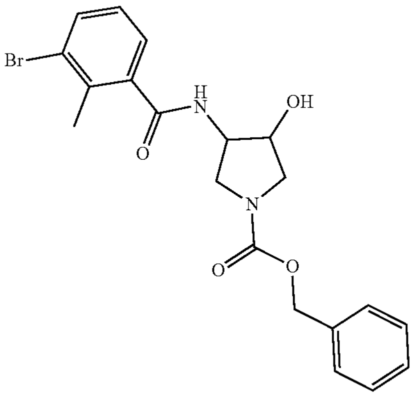 [SMILES: Cc1c(Br)cccc1C(=O)NC1CN(C(=O)OCc2ccccc2)CC1O]

A solution of 3-bromo-2-methylbenzoic acid (9.70 g, 45.1 mmol) in N,N-dimethylformamide (226 ml) was added N,N,N',N'-tetramethyl-O-(7-azabenzotriazol-1-yl)uronium hexafluorophosphate (18.87 g, 49.6 mmol). After stirring for 5 min, benzyl 3-amino-4-hydroxypyrrolidine-1-carboxylate (10.66 g, 45.1 mmol) and N,N-diisopropylethylamine (23.57 ml, 135 mmol) were added. The reaction mixture was stirred at room temperature for 2 h. The reaction was diluted with water, and the aqueous layer was extracted with DCM. The combined organic layers were dried over $Na_2SO_4$, filtered and concentrated. The residue was purified with flash chromatography (eluting with 0-60% ethyl acetate in hexanes) to give the desired product (11.5 g, 59%). LC-MS calculated for $C_{20}H_{22}BrN_2O_4$$(M+H)^+$: m/z=433.1, 435.1; found 433.1, 435.1.

Step 4: benzyl 3-(3-bromo-2-methylbenzamido)-4-oxopyrrolidine-1-carboxylate

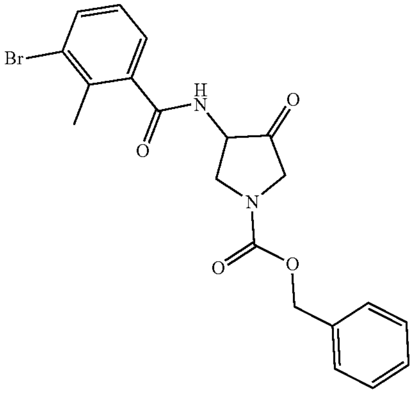 [SMILES: Cc1c(Br)cccc1C(=O)NC1CN(C(=O)OCc2ccccc2)CC1=O]

To a solution of benzyl 3-(3-bromo-2-methylbenzamido)-4-hydroxypyrrolidine-1-carboxylate (16.50 g, 38.1 mmol) in DCM (200 ml) was added Dess-Martin periodinane (19.38 g, 45.7 mmol). The resulting mixture was stirred at room temperature for 2 h. The reaction mixture was diluted with $Et_2O$ and 1 M NaOH solution. After stirring for 1 h, the organic layer was separated and dried over $Na_2SO_4$, filtered and concentrated. The residue was purified with flash chromatography (eluting with 0-50% ethyl acetate in hexanes) to give the desired product (9.2 g, 56%). LC-MS calculated for $C_{20}H_{20}BrN_2O_4(M+H)^+$: m/z=431.1, 433.1; found 431.1, 433.1.

Step 5: benzyl 2-(3-bromo-2-methylphenyl)-4,6-dihydro-5H-pyrrolo[3,4-d]oxazole-5-carboxylate

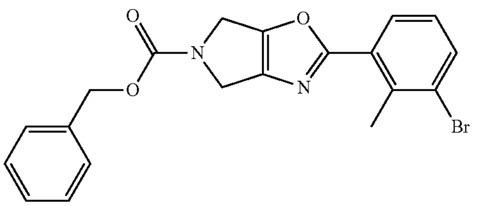 [SMILES: Cc1c(Br)cccc1-c1nc2c(o1)CN(C(=O)OCc1ccccc1)C2]

To a solution of benzyl 3-(3-bromo-2-methylbenzamido)-4-oxopyrrolidine-1-carboxylate (9.23 g, 21.40 mmol) in 1,4-dioxane (100 ml) was added $POCl_3$ (1.995 ml, 21.40 mmol). The resulting mixture was stirred at 110° C. for 3 h. After cooling to room temperature, the reaction mixture was diluted with saturated $NaHCO_3$ solution and ethyl acetate. The aqueous layer was extracted with ethyl acetate. The combined organic layers were washed with brine, dried over $Na_2SO_4$, filtered and concentrated. The precipitate was collected via filtration and washed with ethyl acetate and hexanes to give the desired product as an off white solid (4.85 g, 55%). LC-MS calculated for $C_{20}H_{18}BrN_2O_3(M+H)^+$: m/z=413.0, 415.0; found 413.0, 415.0.

Step 6. 2-(3-Bromo-2-methylphenyl)-5,6-dihydro-4H-pyrrolo[3,4-d]oxazole

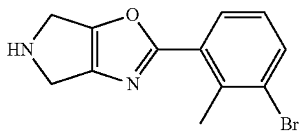 [SMILES: Cc1c(Br)cccc1-c1nc2c(o1)CNC2]

To solution of benzyl 2-(3-bromo-2-methylphenyl)-4,6-dihydro-5H-pyrrolo[3,4-d]oxazole-5-carboxylate (3.70 g, 8.95 mmol) in DCM (60 ml) was added 1 M $BBr_3$ in DCM solution (17.91 ml, 17.91 mmol) at 0° C. After stirring at same temperature for 1 h, the reaction mixture was diluted DCM and saturated $NaHCO_3$ solution. The resultant precipitate was collected vial filtration and dried under vacuum to give the desired product as white solid (2.0 g, 80%). LC-MS calculated for $C_{12}H_{12}BrN_2O$ $(M+H)^+$: m/z=279.0, 281.0; found 279.0, 281.0.

Step 7. 1-(2-(3-Bromo-2-methylphenyl)-4,6-dihydro-5H-pyrrolo[3,4-d]oxazol-5-yl)-2-(dimethylamino)ethan-1-one

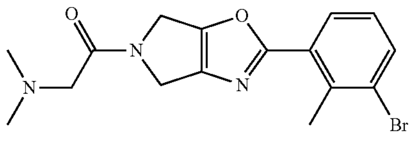 [SMILES: Cc1c(Br)cccc1-c1nc2c(o1)CN(C(=O)CN(C)C)C2]

A solution of dimethylglycine (20.5 mg, 0.199 mmol) in N,N-dimethylformamide (1 ml) was added N,N,N'N'-tetramethyl-O-(7-azabenzotriazol-1-yl)uronium hexafluorophosphate (104 mg, 0.274 mmol). After stirring for 5 min, 2-(3-bromo-2-methylphenyl)-5,6-dihydro-4H-pyrrolo[3,4-d]oxazole (55.5 mg, 0.199 mmol) and N,N-diisopropylethylamine (104 μl, 0.596 mmol) were added. The reaction mixture was stirred at room temperature for 2 h. The reaction mixture was diluted with water, and the aqueous layer was extracted with DCM. The combined organic layers were dried over $Na_2SO_4$, filtered and concentrated. The residue was purified with silica gel column (eluting with 0-30% MeOH in DCM) to give the desired product (35 mg, 49%). LC-MS calculated for $C_{16}H_{19}BrN_3O_2$ $(M+H)^+$: m/z=364.1, 366.1; found 364.1, 366.1.

Step 8. (R)-1-((8-((3-bromo-2-methylphenyl)amino)-1,7-naphthyridin-3-yl)methyl)pyrrolidin-3-ol

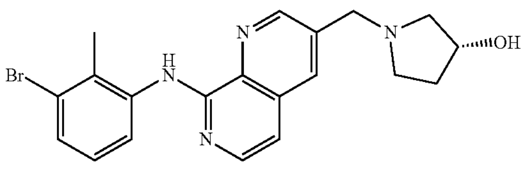 [SMILES: Cc1c(Br)cccc1Nc1nccc2cc(CN3CC[C@@H](O)C3)cnc12]

To a mixture of 8-((3-bromo-2-methylphenyl)amino)-1,7-naphthyridine-3-carbaldehyde (Example 9, Step 1: 340 mg, 0.994 mmol), (R)-pyrrolidin-3-ol (104 mg, 1.192 mmol) in DCM (1.0 ml) was added sodium triacetoxyborohydride (316 mg, 1.490 mmol). After stirring for 2 h at room temperature, the mixture was purified with flash chromatography (0-100% ethyl acetate in hexanes, then 0-35% methanol in DCM). LC-MS calculated for $C_{20}H_{22}BrN_4O$ $(M+H)^+$: m/z=413.1, 415.1; found 413.1, 415.1.

Step 9: (R)-1-((8-((2-methyl-3-(4,4,5,5-tetramethyl-1,3,2-dioxaborolan-2-yl)phenyl)amino)-1,7-naphthyridin-3-yl)methyl)pyrrolidin-3-ol

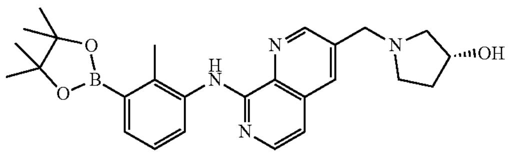 [SMILES: Cc1c(Nc2nccc3cc(CN4CC[C@@H](O)C4)cnc23)cccc1B1OC(C)(C)C(C)(C)O1]

A mixture of (R)-1-((8-((3-bromo-2-methylphenyl)amino)-1,7-naphthyridin-3-yl)methyl)pyrrolidin-3-ol (281 mg, 0.680 mmol), bis(pinacolato)diboron (207 mg, 0.816 mmol), dichloro[1,1'-bis(diphenylphosphino)ferrocene]palladium (II) dichloromethane adduct (55.5 mg, 0.068 mmol), 1,4-dioxane (3.4 mL) and potassium acetate (167 mg, 1.700 mmol) was stirred at 90° C. under $N_2$ atmosphere for 3 h. The crude was diluted with DCM, and then filtered through a pad of Celite®. The filtrate was concentrated and purified with flash chromatography (eluting with ethyl acetate in hexane 0-100%, then methanol/DCM 0-25%) (210 mg, 67%). LC-MS calculated for $C_{26}H_{34}BN_4O_3(M+H)^+$: m/z=461.3; found 461.2.

Step 10: (R)-2-(dimethylamino)-1-(2-(3'-((3-((3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]oxazol-5-yl)ethan-1-one A microwave vial charged with 1-(2-(3-bromo-2-methylphenyl)-4,6-dihydro-5H-pyrrolo[3,4-d]oxazol-5-yl)-2-(dimethylamino)ethan-1-one (9.49 mg, 0.026 mmol), (R)-1-((8-((2-methyl-3-(4,4,5,5-tetramethyl-1,3,2-dioxaborolan-2-yl)phenyl)amino)-1,7-naphthyridin-3-yl)methyl)pyrrolidin-3-ol (12 mg, 0.026 mmol), dicyclohexyl(2',4',6'-triisopropylbiphenyl-2-yl)phosphine-(2'-aminobiphenyl-2-yl)(chloro)palladium (1:1) (2.051 mg, 2.61 μmol) and tripotassium phosphate hydrate (13.21 mg, 0.057 mmol) was evacuated under high vacuum and refilled with nitrogen (repeated three times). 1,4-Dioxane (0.6 mL) and water (0.2 mL) was added and resulting mixture was stirred at 80° C. for 1 h. The reaction mixture was diluted with methanol and 1 N HCl solution and purified with prep-LC-MS (pH=2, acetonitrile/water+TFA) to give the desired product as white solid. LC-MS calculated for $C_{36}H_{40}N_7O_3$ $(M+H)^+$: m/z=618.3; found 618.3.

Example 38

(S)-2-(dimethylamino)-1-(2-(3'-((3-((3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]oxazol-5-yl)ethan-1-one

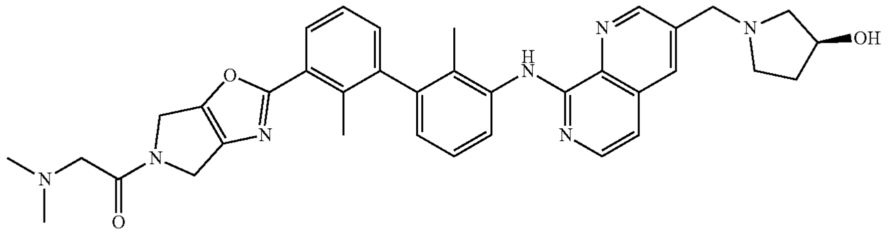 [SMILES: Cc1c(Nc2nccc3cc(CN4CC[C@H](O)C4)cnc23)cccc1-c1cccc(-c2nc3c(o2)CN(C(=O)CN(C)C)C3)c1C]

This compound was prepared using similar procedures as described for Example 37 with (S)-pyrrolidin-3-ol (Combi-Blocks, cat #SS-7948) replacing (R)-pyrrolidin-3-ol in Step 8. LC-MS calculated for $C_{36}H_{40}N_7O_3$ $(M+H)^+$: m/z=618.3; found 618.3.

Example 39

(R)-1-(2-(2-(3'-((3-((3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]oxazol-5-yl)-2-oxoethyl)azetidine-3-carboxylic acid

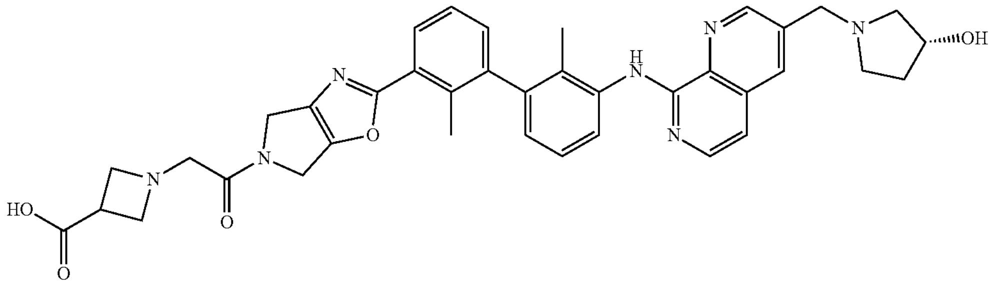 [SMILES: Cc1c(Nc2nccc3cc(CN4CC[C@@H](O)C4)cnc23)cccc1-c1cccc(-c2nc3c(o2)CN(C(=O)CN2CC(C(=O)O)C2)C3)c1C]

Step 1: 1-(2-(3-bromo-2-methylphenyl)-4,6-dihydro-5H-pyrrolo[3,4-d]oxazol-5-yl)-2-chloroethan-1-one

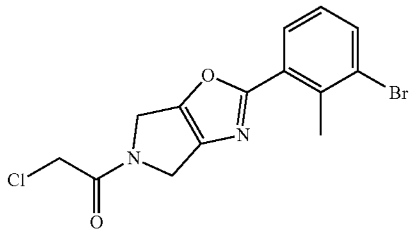 [SMILES: Cc1c(Br)cccc1-c1nc2c(o1)CN(C(=O)CCl)C2]

A solution of 2-(3-bromo-2-methylphenyl)-5,6-dihydro-4H-pyrrolo[3,4-d]oxazole (Example 37, Step 6: 1.04 g, 3.73 mmol) in $CH_2Cl_2$ (18 ml) was added 2-chloroacetyl chloride (0.421 g, 3.73 mmol) and N,N-diisopropylethylamine (1.947 ml, 11.18 mmol) at 0° C. The reaction mixture was stirred at room temperature for 2 h. The reaction was diluted with water, and the aqueous layer was extracted with DCM. The combined organic layers were dried over $Na_2SO_4$, filtered and concentrated. The residue was purified with flash chromatography (eluting with 0-60% ethyl acetate in hexanes) to give the desired product as white solid (0.65 g, 49%). LC-MS calculated for $C_{14}H_{13}BrClN_2O_2(M+H)^+$: m/z=355.0, 357.0; found 355.0, 357.0.

Step 2: 1-(2-(2-(3-bromo-2-methylphenyl)-4,6-dihydro-5H-pyrrolo[3,4-d]oxazol-5-yl)-2-oxoethyl) azetidine-3-carboxylic acid

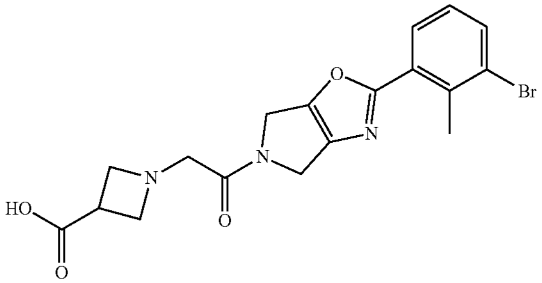 [SMILES: Cc1c(Br)cccc1-c1nc2c(o1)CN(C(=O)CN1CC(C(=O)O)C1)C2]

The mixture of 1-(2-(3-bromo-2-methylphenyl)-4,6-dihydro-5H-pyrrolo[3,4-d]oxazol-5-yl)-2-chloroethan-1-one (15 mg, 0.042 mmol), azetidine-3-carboxylic acid (Aldrich, cat #391131: 4.26 mg, 0.042 mmol), TEA (0.018 ml, 0.127 mmol) and N,N-dimethylformamide (1.0 ml) was heated at 60° C. for 2 h. The reaction mixture was diluted with methanol and 1 N HCl, then purified with prep-LC-MS (pH 2) to give the desired product C (12 mg, 67%). LC-MS calculated for $C_{18}H_{19}BrN_3O_4(M+H)^+$: m/z=420.1; found 420.1.

Step 3: (R)-1-(2-(2-(3'-((3-((3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo [3,4-d]oxazol-5-yl)-2-oxoethyl)azetidine-3-carboxylic acid This compound was prepared using similar procedures as described for Example 37, Step 10 with 1-(2-(2-(3-bromo-2-methylphenyl)-4,6-dihydro-5H-pyrrolo[3,4-d]oxazol-5-yl)-2-oxoethyl)azetidine-3-carboxylic acid replacing 1-(2-(3-bromo-2-methylphenyl)-4,6-dihydro-5H-pyrrolo[3,4-d] oxazol-5-yl)-2-(dimethylamino)ethan-1-one. LC-MS calculated for $C_{38}H_{40}N_7O_5$ $(M+H)^+$: m/z=674.3; found 674.3.

Example 40

(S)-1-(2-(2-(3'-((3-(((R)-3-hydroxypyrrolidin-1-yl) methyl)-1,7-naphthyridin-8-yl)amino)-2,2'-dimethyl-[1,1'-biphenyl]-3-yl)-4,6-dihydro-5H-pyrrolo[3,4-d] oxazol-5-yl)-2-oxoethyl)pyrrolidine-3-carboxylic acid

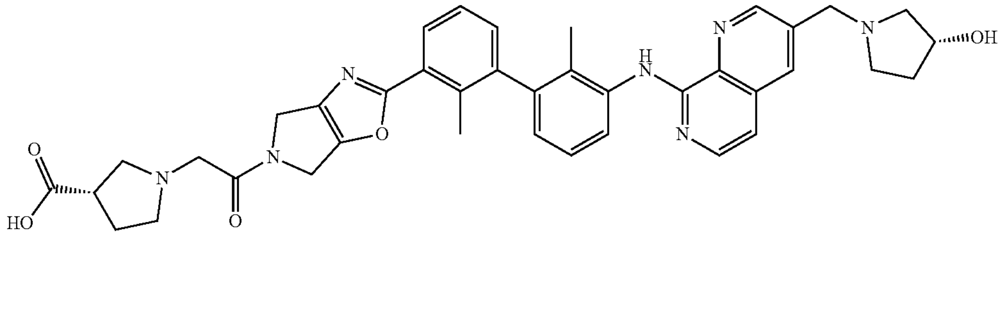 [SMILES: Cc1c(Nc2nccc3cc(CN4CC[C@@H](O)C4)cnc23)cccc1-c1cccc(-c2nc3c(o2)CN(C(=O)CN2CC[C@H](C(=O)O)C2)C3)c1C]

Step 1: (S)-1-(2-(2-(3-bromo-2-methylphenyl)-4,6-dihydro-5H-pyrrolo[3,4-d]oxazol-5-yl)-2-oxoethyl)pyrrolidine-3-carboxylic acid

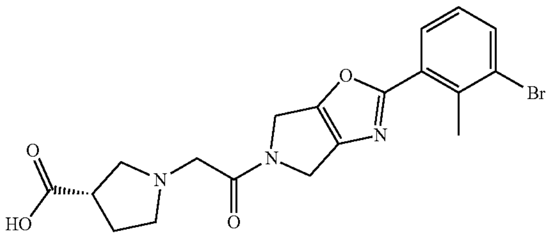 [SMILES: Cc1c(Br)cccc1-c1nc2c(o1)CN(C(=O)CN1CC[C@H](C(=O)O)C1)C2]

This compound was prepared using similar procedures as described for Example 39, Step 2 with (S)-pyrrolidine-3-carboxylic acid (Combi-Blocks, #ST-1381) replacing azetidine-3-carboxylic acid. LC-MS calculated for $C_{19}H_{21}BrN_3O_4$ $(M+H)^+$: m/z=434.1, 436.1; found 434.1, 436.1.

Step 2: (S)-1-(2-(2-(3'-((3-(((R)-3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]oxazol-5-yl)-2-oxoethyl)pyrrolidine-3-carboxylic acid This compound was prepared using similar procedures as described for Example 37, Step 10 with (S)-1-(2-(2-(3-bromo-2-methylphenyl)-4,6-dihydro-5H-pyrrolo[3,4-d]oxazol-5-yl)-2-oxoethyl)pyrrolidine-3-carboxylic acid replacing 1-(2-(3-bromo-2-methylphenyl)-4,6-dihydro-5H-pyrrolo[3,4-d]oxazol-5-yl)-2-(dimethylamino)ethan-1-one. LC-MS calculated for $C_{39}H_{42}N_7O_5$ $(M+H)^+$: m/z=688.3; found 688.3.

Example 41

(R)-1-(2-(2-(3'-((3-(((R)-3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]oxazol-5-yl)-2-oxoethyl)pyrrolidine-3-carboxylic acid

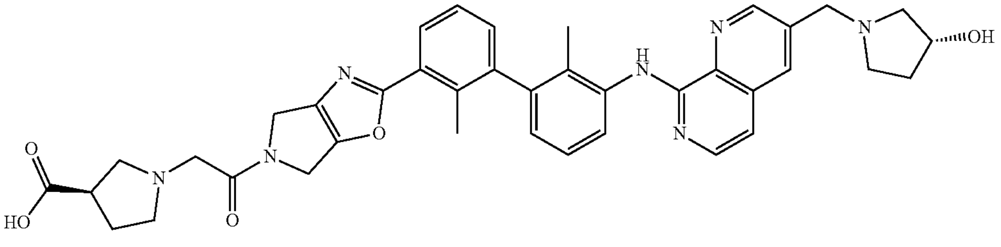 [SMILES: Cc1c(Nc2nccc3cc(CN4CC[C@@H](O)C4)cnc23)cccc1-c1cccc(-c2nc3c(o2)CN(C(=O)CN2CC[C@@H](C(=O)O)C2)C3)c1C]

Step 1: (R)-1-(2-(2-(3-bromo-2-methylphenyl)-4,6-dihydro-5H-pyrrolo[3,4-d]oxazol-5-yl)-2-oxoethyl)pyrrolidine-3-carboxylic acid

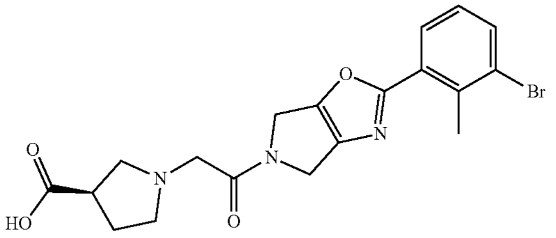 [SMILES: Cc1c(Br)cccc1-c1nc2c(o1)CN(C(=O)CN1CC[C@@H](C(=O)O)C1)C2]

This compound was prepared using similar procedures as described for Example 39, Step 2 with (R)-pyrrolidine-3-carboxylic acid (Combi-Blocks, cat #ST-7698) replacing azetidine-3-carboxylic acid. LC-MS calculated for $C_{19}H_{21}BrN_3O_4(M+H)^+$: m/z=434.1, 436.1; found 434.1, 436.1.

Step 2: (R)-1-(2-(2-(3'-((3-(((R)-3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]oxazol-5-yl)-2-oxoethyl)pyrrolidine-3-carboxylic acid This compound was prepared using similar procedures as described for Example 37, Step 10 with (R)-1-(2-(2-(3-bromo-2-methylphenyl)-4,6-dihydro-5H-pyrrolo[3,4-d]oxazol-5-yl)-2-oxoethyl)pyrrolidine-3-carboxylic acid replacing 1-(2-(3-bromo-2-methylphenyl)-4,6-dihydro-5H-pyrrolo[3,4-d]oxazol-5-yl)-2-(dimethylamino)ethan-1-one. LC-MS calculated for $C_{39}H_{42}N_7O_5$ $(M+H)^+$: m/z=688.3; found 688.3.

Example 42

(S)-1-(2-(2-(3'-((3-(((R)-3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]oxazol-5-yl)-2-oxoethyl)piperidine-2-carboxylic acid

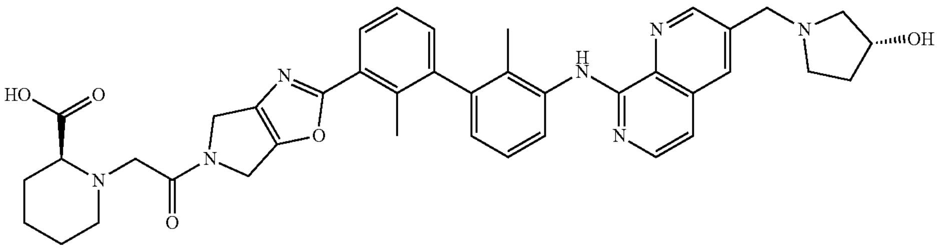 [SMILES: Cc1c(Nc2nccc3cc(CN4CC[C@@H](O)C4)cnc23)cccc1-c1cccc(-c2nc3c(o2)CN(C(=O)CN2CCCC[C@H]2C(=O)O)C3)c1C]

Step 1: (S)-1-(2-(2-(3-bromo-2-methylphenyl)-4,6-dihydro-5H-pyrrolo[3,4-d]oxazol-5-yl)-2-oxoethyl)piperidine-2-carboxylic acid

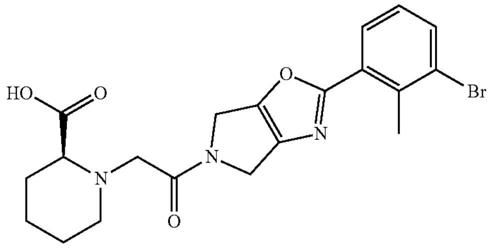 [SMILES: Cc1c(Br)cccc1-c1nc2c(o1)CN(C(=O)CN1CCCC[C@H]1C(=O)O)C2]

This compound was prepared using similar procedures as described for Example 39, Step 2 with (S)-piperidine-2-carboxylic acid (Alfa Aesar, cat #L15373) replacing azetidine-3-carboxylic acid. LC-MS calculated for $C_{20}H_{23}BrN_3O_4(M+H)^+$: m/z=448.1, 450.1; found 448.1, 450.1.

Step 2: (S)-1-(2-(2-(3'-((3-(((R)-3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]oxazol-5-yl)-2-oxoethyl)piperidine-2-carboxylic acid This compound was prepared using similar procedures as described for Example 37, Step 10 with (S)-1-(2-(2-(3-bromo-2-methylphenyl)-4,6-dihydro-5H-pyrrolo[3,4-d]oxazol-5-yl)-2-oxoethyl)piperidine-2-carboxylic acid replacing 1-(2-(3-bromo-2-methylphenyl)-4,6-dihydro-5H-pyrrolo[3,4-d]oxazol-5-yl)-2-(dimethylamino)ethan-1-one. LC-MS calculated for $C_{40}H_{44}N_7O_5$ $(M+H)^+$: m/z=702.3; found 702.3.

Example 43

(S)-1-(5-chloro-2-((5-cyanopyridin-3-yl)methoxy)-4-((3'-((3-(((R)-3-hydroxypyrrolidin-1-yl)methyl)-1,7-naphthyridin-8-yl)amino)-2,2'-dimethyl-[1,1'-biphenyl]-3-yl)methoxy)benzyl)piperidine-2-carboxylic acid

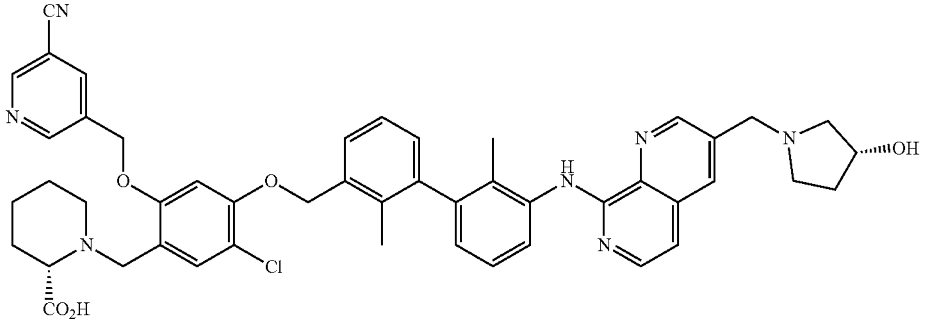 [SMILES: Cc1c(COc2cc(OCc3cncc(C#N)c3)c(CN3CCCC[C@H]3C(=O)O)cc2Cl)cccc1-c1cccc(Nc2nccc3cc(CN4CC[C@@H](O)C4)cnc23)c1C]

Step 1: 4-((3-bromo-2-methylbenzyl)oxy)-5-chloro-2-hydroxybenzaldehyde

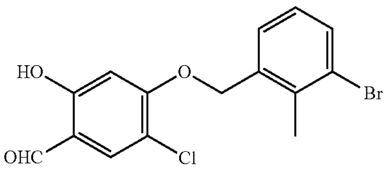 [SMILES: Cc1c(Br)cccc1COc1cc(O)c(C=O)cc1Cl]

To a mixture of (3-bromo-2-methylphenyl)methanol (Ark Pharm, cat #AK162869: 2.330 g, 11.59 mmol), 5-chloro-2,4-dihydroxybenzaldehyde (Ark Pharm, cat #AK199510: 2.0 g, 11.59 mmol) and triphenylphosphine (3.65 g, 13.91 mmol) in THF (10 ml) at 0° C. was added DIAD (2.93 ml, 15.07 mmol). The mixture was stirred at room temperature overnight. The mixture was concentrated and diluted with EtOAc. The solid was collected by filtration to give 4-((3-bromo-2-methylbenzyl)oxy)-5-chloro-2-hydroxybenzaldehyde (2.0 g, 5.62 mmol, 48.5% yield). LC-MS calculated for $C_{15}H_{13}BrClO_3$ $(M+H)^+$: m/z=355.0; found 355.2.

Step 2: 5-((5-((3-bromo-2-methylbenzyl)oxy)-4-chloro-2-formylphenoxy)methyl)nicotinonitrile

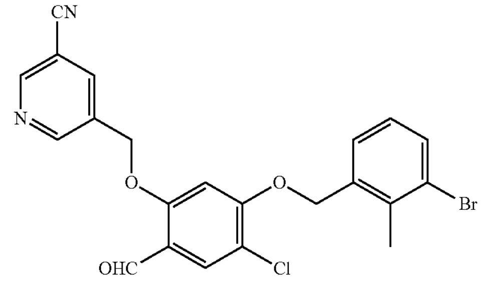 [SMILES: Cc1c(Br)cccc1COc1cc(OCc2cncc(C#N)c2)c(C=O)cc1Cl]

A mixture of 4-((3-bromo-2-methylbenzyl)oxy)-5-chloro-2-hydroxybenzaldehyde (2.0 g, 5.62 mmol), 5-(chloromethyl)nicotinonitrile (0.927 g, 6.07 mmol) and cesium carbonate (2.75 g, 8.44 mmol) in DMF (12 ml) was stirred at 70° C. for 3 hours. The mixture was poured into water. The solid was collected by filtration and air dried to give 5-((5-((3-bromo-2-methylbenzyl)oxy)-4-chloro-2-formylphenoxy)methyl)nicotinonitrile (2.2 g, 4.66 mmol, 83% yield). LC-MS calculated for $C_{22}H_{17}BrClN_2O_3(M+H)^+$: m/z=471.0; found 471.2.

Step 3: (R)-5-((4-chloro-2-formyl-5-((3'-((3-((3-hydroxypyrrolidin-1-yl)methyl)-1,7-naphthyridin-8-yl)amino)-2,2'-dimethyl-[1,1'-biphenyl]-3-yl)methoxy)phenoxy)methyl)nicotinonitrile

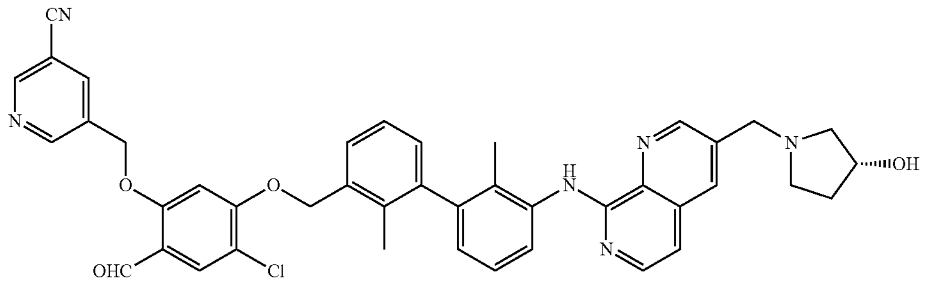 [SMILES: Cc1c(COc2cc(OCc3cncc(C#N)c3)c(C=O)cc2Cl)cccc1-c1cccc(Nc2nccc3cc(CN4CC[C@@H](O)C4)cnc23)c1C]

A mixture of 5-((5-((3-bromo-2-methylbenzyl)oxy)-4-chloro-2-formylphenoxy)methyl)nicotinonitrile (78 mg, 0.165 mmol), (R)-1-((8-((2-methyl-3-(4,4,5,5-tetramethyl-1,3,2-dioxaborolan-2-yl)phenyl)amino)-1,7-naphthyridin-3-yl)methyl)pyrrolidin-3-ol (Example 37, Step 9: 91 mg, 0.198 mmol), potassium carbonate (45.7 mg, 0.331 mmol) and (1,1'-bis(diphenylphosphino)ferrocene)-dichloropalladium(II) (12.1 mg, 0.017 mmol) in 1,4-dioxane (3 mL) and water (0.600 mL) was purged with nitrogen, and heated at 95° C. for 2 hours. The mixture was purified on prep-HPLC (pH=2, acetonitrile/water+TFA) to give (R)-5-((4-chloro-2-formyl-5-((3'-((3-((3-hydroxypyrrolidin-1-yl)methyl)-1,7-naphthyridin-8-yl)amino)-2,2'-dimethyl-[1,1'-biphenyl]-3-yl)methoxy)phenoxy)methyl)nicotinonitrile (60 mg, 0.083 mmol, 50.0% yield). LC-MS calculated for $C_{42}H_{38}ClN_6O_4$ $(M+H)^+$: m/z=725.3; found 725.2.

Step 4: (S)-1-(5-chloro-2-((5-cyanopyridin-3-yl)methoxy)-4-((3'-((3-(((R)-3-hydroxypyrrolidin-1-yl)methyl)-1,7-naphthyridin-8-yl)amino)-2,2'-dimethyl-[1,1'-biphenyl]-3-yl)methoxy)benzyl)piperidine-2-carboxylic acid Sodium triacetoxyborohydride (2.192 mg, 10.34 μmol) was added to a mixture of (R)-5-((4-chloro-2-formyl-5-((3'-((3-((3-hydroxypyrrolidin-1-yl)methyl)-1,7-naphthyridin-8-yl)amino)-2,2'-dimethyl-[1,1'-biphenyl]-3-yl)methoxy)phenoxy)methyl)nicotinonitrile (5 mg, 6.89 μmol), (S)-piperidine-2-carboxylic acid (1.4 mg, 10.34 μmol) and triethylamine (1.922 μL, 0.014 mmol) in DCM (1.0 mL) after stirring for 2 hours at room temperature. After stirring at room temperature overnight, the mixture was purified using prep-HPLC (pH=2, acetonitrile/water+TFA) to give the desired product as its TFA salt. LC-MS calculated for $C_{48}H_{49}ClN_7O_5(M+H)^+$: m/z=838.3; found 838.2.

Example 44

(R)-1-(5-chloro-2-((5-cyanopyridin-3-yl)methoxy)-4-((3'-((3-(((R)-3-hydroxypyrrolidin-1-yl)methyl)-1,7-naphthyridin-8-yl)amino)-2,2'-dimethyl-[1,1'-biphenyl]-3-yl)methoxy)benzyl)pyrrolidine-3-carboxylic acid

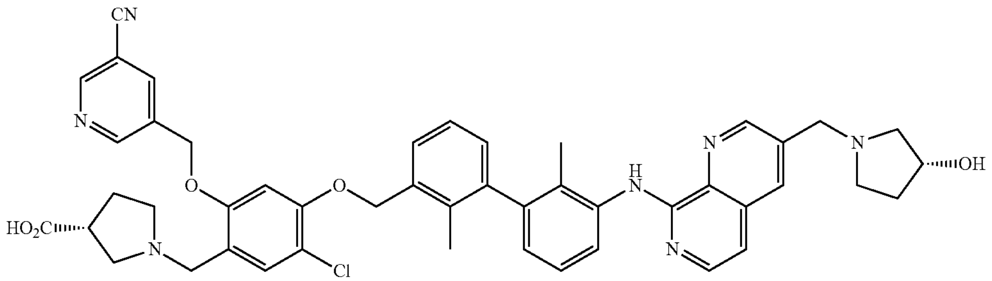 [SMILES: Cc1c(COc2cc(OCc3cncc(C#N)c3)c(CN3CC[C@@H](C(=O)O)C3)cc2Cl)cccc1-c1cccc(Nc2nccc3cc(CN4CC[C@@H](O)C4)cnc23)c1C]

Sodium triacetoxyborohydride (2.192 mg, 10.34 μmol) was added to a mixture of (R)-5-((4-chloro-2-formyl-5-((3'-((3-((3-hydroxypyrrolidin-1-yl)methyl)-1,7-naphthyridin-8-yl)amino)-2,2'-dimethyl-[1,1'-biphenyl]-3-yl)methoxy)phenoxy)methyl)nicotinonitrile (Example 43, Step 3: 5 mg, 6.9 μmol), (R)-pyrrolidine-3-carboxylic acid (Combi-Blocks, cat #ST-7698: 1.2 mg, 10.34 μmol) and triethylamine (1.9 μl, 0.014 mmol) in DCM (1.0 mL) after stirring for 2 h at room temperature. After stirring at room temperature for 2 h, the mixture was purified using prep-HPLC (pH=2, acetonitrile/water+TFA) to give the desired product as its TFA salt. LC-MS calculated for $C_{47}H_{47}ClN_7O_5(M+H)^+$: m/z=824.3; found 824.2.

Example 45

(R)-1-((8-(2'-Chloro-2-methyl-3'-(1-methyl-4,5,6,7-tetrahydro-1H-imidazo[4,5-c]pyridine-2-carboxamido)biphenyl-3-ylamino)-1,7-naphthyridin-3-yl)methyl)-3-methylpyrrolidine-3-carboxylic acid

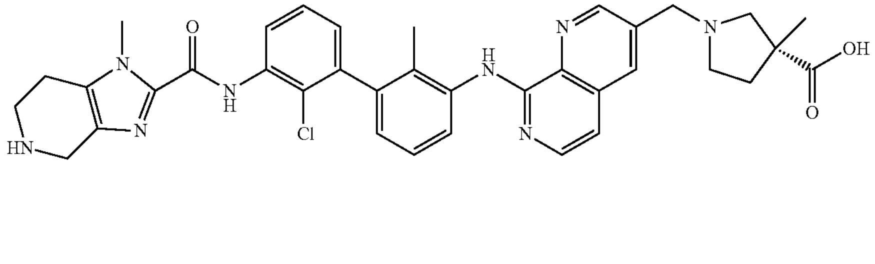 [SMILES: Cc1c(Nc2nccc3cc(CN4CC[C@@](C)(C(=O)O)C4)cnc23)cccc1-c1cccc(NC(=O)c2nc3c(n2C)CCNC3)c1Cl]

Step 1: 8-(2-methyl-3-(4,4,5,5-tetramethyl-1,3,2-dioxaborolan-2-yl)phenylamino)-1,7-naphthyridine-3-carbaldehyde

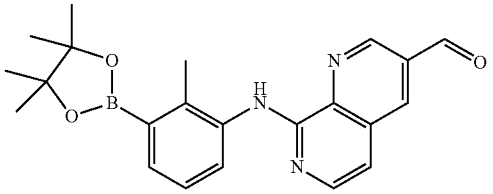 [SMILES: Cc1c(Nc2nccc3cc(C=O)cnc23)cccc1B1OC(C)(C)C(C)(C)O1]

A mixture of 8-((3-bromo-2-methylphenyl)amino)-1,7-naphthyridine-3-carbaldehyde (Example 9, Step 1: 0.684 g, 2.0 mmol), 4,4,4',4',5,5,5',5'-octamethyl-2,2'-bi(1,3,2-dioxaborolane) (0.660 g, 2.60 mmol), potassium acetate (0.393 g, 4.00 mmol), and $PdCl_2$(dppf) (0.146 g, 0.200 mmol) in dioxane (10.0 mL) was vacuumed and refilled with nitrogen 3 times and then the reaction mixture was stirred at 110° C. for 7 h. The mixture was diluted with EtOAc, filtered through Celite® and concentrated under reduced pressure. The residue was purified by column chromatography eluting with $CH_2Cl_2$ to give the desired product. LC-MS calculated for $C_{22}H_{25}BN_3O_3(M+H)^+$: m/z=390.2; found 390.3.

Step 2: tert-butyl 2-(2-chloro-3'-(3-formyl-1,7-naphthyridin-8-ylamino)-2'-methylbiphenyl-3-ylcarbamoyl)-1-methyl-6,7-dihydro-1H-imidazo[4,5-c]pyridine-5(4H)-carboxylate

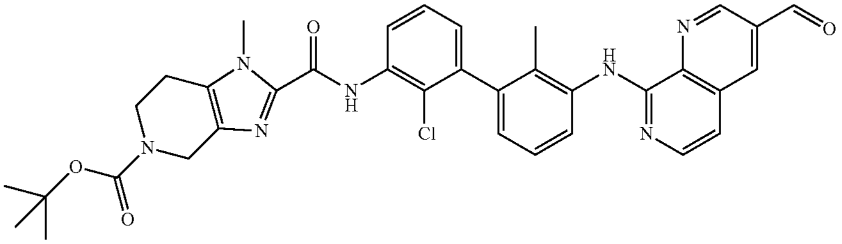 [SMILES: Cc1c(Nc2nccc3cc(C=O)cnc23)cccc1-c1cccc(NC(=O)c2nc3c(n2C)CCN(C(=O)OC(C)(C)C)C3)c1Cl]

A mixture of tert-butyl 2-((3-bromo-2-chlorophenyl)carbamoyl)-1-methyl-1,4,6,7-tetrahydro-5H-imidazo[4,5-c]pyridine-5-carboxylate (Example 31, Step 3: 0.12 g, 0.255 mmol), 8-(2-methyl-3-(4,4,5,5-tetramethyl-1,3,2-dioxaborolan-2-yl)phenylamino)-1,7-naphthyridine-3-carbaldehyde (0.10 g, 0.26 mmol), dichloro[1,1'-bis(diphenylphosphino)ferrocene]palladium (II) dichloromethane adduct (0.019 g, 0.023 mmol) and sodium carbonate (0.049 g, 0.464 mmol) in dioxane (2.4 mL)/water (0.6 mL) was evacuated and backfilled with $N_2$ 3 times. The reaction mixture was stirred at 110° C. for 24 h. The mixture was diluted with ethyl acetate and washed with water, dried over $Na_2SO_4$, filtered and concentrated in vacuo. The product was purified by column chromatography eluting with $CH_2Cl_2$/EtOAc (7:3). LC-MS calculated for $C_{35}H_{35}ClN_7O_4(M+H)^+$: m/z=652.2; found 652.2.

Step 3: (R)-1-((8-(3'-(5-(tert-butoxycarbonyl)-1-methyl-4,5,6,7-tetrahydro-1H-imidazo[4,5-c]pyridine-2-carboxamido)-2'-chloro-2-methylbiphenyl-3-ylamino)-1,7-naphthyridin-3-yl)methyl)-3-methylpyrrolidine-3-carboxylic acid

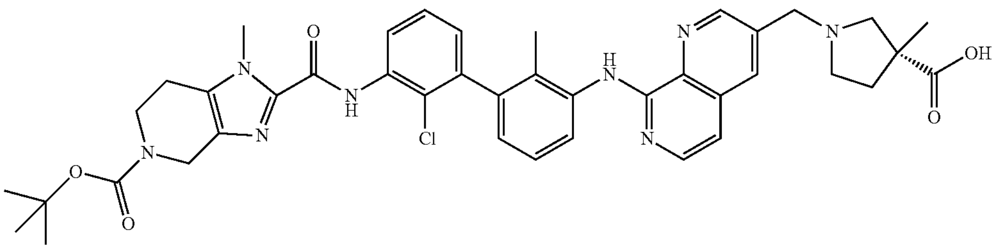 [SMILES: Cc1c(Nc2nccc3cc(CN4CC[C@@](C)(C(=O)O)C4)cnc23)cccc1-c1cccc(NC(=O)c2nc3c(n2C)CCN(C(=O)OC(C)(C)C)C3)c1Cl]

(R)-3-methylpyrrolidine-3-carboxylic acid (J&W Pharm-Lab, cat #75R0495: 0.071 g, 0.552 mmol) was added to a suspension of tert-butyl 2-((2-chloro-3'-((3-formyl-1,7-naphthyridin-8-yl)amino)-2'-methyl-[1,1'-biphenyl]-3-yl) carbamoyl)-1-methyl-1,4,6,7-tetrahydro-5H-imidazo[4,5-c] pyridine-5-carboxylate (0.12 g, 0.184 mmol) in $CH_2Cl_2$ (1.0 mL) followed by triethylamine (0.205 mL, 1.472 mmol). The mixture was stirred at rt for 1 h. At this time sodium triacetoxyborohydride (0.117 g, 0.552 mmol) was added and then stirred at rt for 2 h. The reaction was quenched with water, extracted with $CH_2Cl_2$/iPrOH, and the organic phase was dried over $MgSO_4$, filtered, and concentrated under reduced pressure. The crude product was used directly in the next step without further purification. LC-MS calculated for $C_{41}H_{46}ClN_8O_5(M+H)^+$: m/z=765.3; found 765.2.

Step 4: (R)-1-((8-(2'-chloro-2-methyl-3'-(1-methyl-4,5,6,7-tetrahydro-1H-imidazo[4,5-c]pyridine-2-carboxamido)biphenyl-3-ylamino)-1,7-naphthyridin-3-yl)methyl)-3-methylpyrrolidine-3-carboxylic acid TFA (2.0 mL) was added to a mixture of (R)-1-((8-((3'-(5-(tert-butoxycarbonyl)-1-methyl-4,5,6,7-tetrahydro-1H-imidazo[4,5-c]pyridine-2-carboxamido)-2'-chloro-2-methyl-[1,1'-biphenyl]-3-yl)amino)-1,7-naphthyridin-3-yl) methyl)-3-methylpyrrolidine-3-carboxylic acid (0.15 g) in $CH_2Cl_2$ (2.0 mL) and then stirred at rt for 30 min. The solvent was concentrated and the mixture was diluted with acetonitrile/water and purified by prep HPLC (pH=2, acetonitrile/water+TFA) to provide the desired compound as its TFA salt. LC-MS calculated for $C_{36}H_{38}ClN_8O_3(M+H)^+$: m/z=665.3; found 665.2.

Example 46

(R)-1-((8-(3'-(1,5-dimethyl-4,5,6,7-tetrahydro-1H-imidazo[4,5-c]pyridine-2-carboxamido)-2,2'-dimethylbiphenyl-3-ylamino)-1,7-naphthyridin-3-yl) methyl)pyrrolidine-3-carboxylic acid

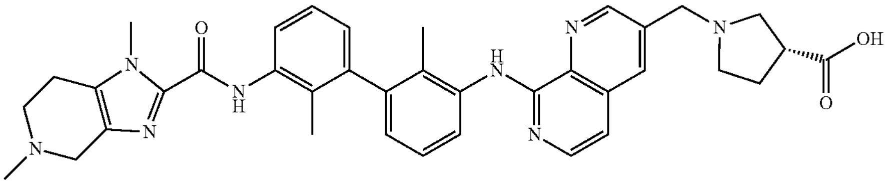 [SMILES: Cc1c(NC(=O)c2nc3c(n2C)CCN(C)C3)cccc1-c1cccc(Nc2nccc3cc(CN4CC[C@@H](C(=O)O)C4)cnc23)c1C]

Step 1: tert-butyl 2-(3-bromo-2-methylphenylcarbamoyl)-1-methyl-6,7-dihydro-1H-imidazo[4,5-c] pyridine-5(4H)-carboxylate

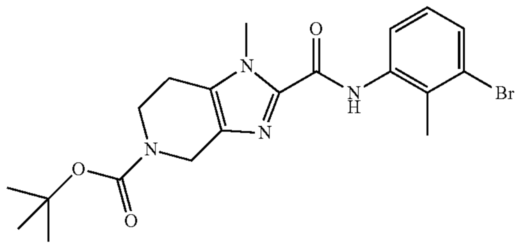 [SMILES: Cc1c(Br)cccc1NC(=O)c1nc2c(n1C)CCN(C(=O)OC(C)(C)C)C2]

Potassium tert-butoxide (1.0 M THF solution, 17.61 mL, 17.61 mmol) was added to a solution of 5-tert-butyl 2-methyl 1-methyl-6,7-dihydro-1H-imidazo[4,5-c]pyridine-2,5(4H)-dicarboxylate (Example 14, Step 2: 2.6 g, 8.80 mmol) and 3-bromo-2-methylaniline (Aldrich, cat #530018: 1.802 g, 9.68 mmol) in THF (45 mL) at 0° C. After being stirred at rt for 2 h, the reaction mixture was quenched with water, and extracted with ethyl acetate. The combined organic layers were washed with brine, dried over $Na_2SO_4$, filtered and concentrated under reduced pressure. The crude was stirred with 3:1 hexanes/EtOAc (40 mL) for 30 min and then filtered and dried to provide the desired product. LC-MS calculated for $C_{20}H_{26}BrN_4O_3(M+H)^+$: m/z=449.1; found 449.1.

Step 2: tert-butyl 2-(3'-(3-(hydroxymethyl)-1,7-naphthyridin-8-ylamino)-2,2'-dimethylbiphenyl-3-ylcarbamoyl)-1-methyl-6,7-dihydro-1H-imidazo[4,5-c]pyridine-5(4H)-carboxylate

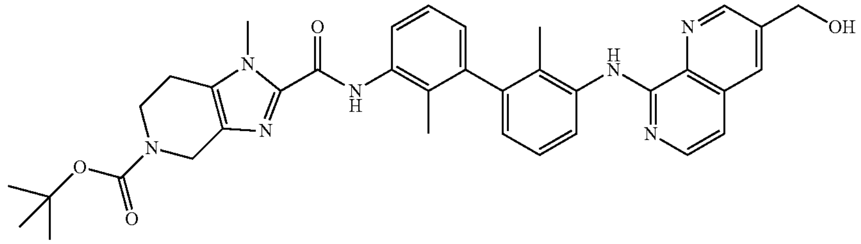 [SMILES: Cc1c(NC(=O)c2nc3c(n2C)CCN(C(=O)OC(C)(C)C)C3)cccc1-c1cccc(Nc2nccc3cc(CO)cnc23)c1C]

A mixture of tert-butyl 2-((3-bromo-2-methylphenyl)carbamoyl)-1-methyl-1,4,6,7-tetrahydro-5H-imidazo[4,5-c] pyridine-5-carboxylate (0.12 g, 0.267 mmol), (8-((2-methyl-3-(4,4,5,5-tetramethyl-1,3,2-dioxaborolan-2-yl)phenyl) amino)-1,7-naphthyridin-3-yl)methanol (Example 9, Step 3: 0.095 g, 0.243 mmol), dichloro[1,1'-bis(diphenylphosphino) ferrocene]palladium (II) dichloromethane adduct (0.020 g, 0.024 mmol) and sodium carbonate (0.051 g, 0.486 mmol) in dioxane (2.4 mL)/water (0.6 mL) was evacuated and backfilled with $N_2$. The evacuation/backfill sequence was repeated two additional times, and the reaction was stirred at 110° C. for 24 h. The mixture was diluted with ethyl acetate and washed with water, dried over $Na_2SO_4$, and concentrated under reduced pressure. The crude product was purified by column chromatography eluting with $CH_2Cl_2$/EtOAc (1:1). LC-MS calculated for $C_{36}H_{40}N_7O_4$ $(M+H)^+$: m/z=634.3; found 634.5.

Step 3: N-(3'-(3-(hydroxymethyl)-1,7-naphthyridin-8-ylamino)-2,2'-dimethylbiphenyl-3-yl)-1-methyl-4,5,6,7-tetrahydro-1H-imidazo[4,5-c]pyridine-2-carboxamide

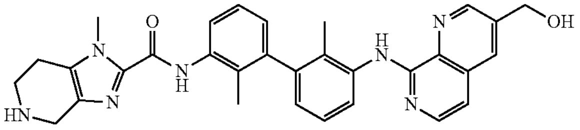 [SMILES: Cc1c(NC(=O)c2nc3c(n2C)CCNC3)cccc1-c1cccc(Nc2nccc3cc(CO)cnc23)c1C]

4 N HCl in dioxane (1.0 mL) was added to a mixture of tert-butyl 2-((3'-((3-(hydroxymethyl)-1,7-naphthyridin-8-yl)amino)-2,2'-dimethyl-[1,1'-biphenyl]-3-yl)carbamoyl)-1-methyl-1,4,6,7-tetrahydro-5H-imidazo[4,5-c]pyridine-5-carboxylate (0.10 g, 0.158 mmol) in $CH_2Cl_2$ (1.0 mL), and the reaction was stirred at rt for 2 h. The solvent was removed and the crude residue was used directly in the next step without further purification. LC-MS calculated for $C_{31}H_{32}N_7O_2$ (M+H)$^+$: m/z=534.3; found 534.3.

Step 4: N-(3'-(3-(hydroxymethyl)-1,7-naphthyridin-8-ylamino)-2,2'-dimethylbiphenyl-3-yl)-1,5-dimethyl-4,5,6,7-tetrahydro-1H-imidazo[4,5-c]pyridine-2-carboxamide

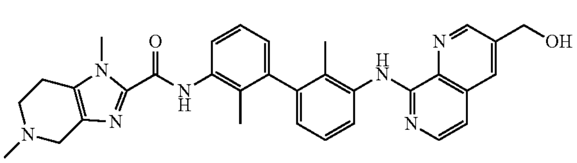 [SMILES: Cc1c(NC(=O)c2nc3c(n2C)CCN(C)C3)cccc1-c1cccc(Nc2nccc3cc(CO)cnc23)c1C]

Formaldehyde (36% $H_2O$ solution, 6.3 μL, 0.075 mmol) was added to a mixture of N-(3'-((3-(hydroxymethyl)-1,7-naphthyridin-8-yl)amino)-2,2'-dimethyl-[1,1'-biphenyl]-3-yl)-1-methyl-4,5,6,7-tetrahydro-1H-imidazo[4,5-c]pyridine-2-carboxamide (20.0 mg, 0.037 mmol) in $CH_2Cl_2$ (1.0 mL) followed by the addition of triethylamine (0.026 mL, 0.187 mmol). The mixture was stirred at rt for 10 min. At this time sodium triacetoxyborohydride (23.8 mg, 0.11 mmol) was added and then the mixture was stirred at rt for 30 min. The reaction mixture was quenched with water and then extracted with $CH_2Cl_2$. The combined organic phase was concentrated under reduced pressure and the crude product was used directly in the next step without further purification. LC-MS calculated for $C_{32}H_{34}N_7O_2$ (M+H)$^+$: m/z=548.3; found 548.4.

Step 5: N-(3'-(3-formyl-1,7-naphthyridin-8-ylamino)-2,2'-dimethylbiphenyl-3-yl)-1,5-dimethyl-4,5,6,7-tetrahydro-1H-imidazo[4,5-c]pyridine-2-carboxamide

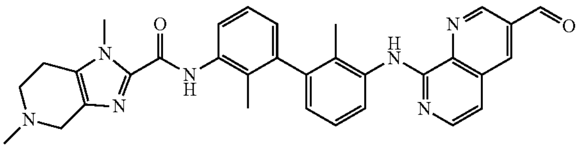 [SMILES: Cc1c(NC(=O)c2nc3c(n2C)CCN(C)C3)cccc1-c1cccc(Nc2nccc3cc(C=O)cnc23)c1C]

Manganese dioxide (0.143 g, 1.643 mmol) was added to a solution of N-(3'-((3-(hydroxymethyl)-1,7-naphthyridin-8-yl)amino)-2,2'-dimethyl-[1,1'-biphenyl]-3-yl)-1,5-dimethyl-4,5,6,7-tetrahydro-TH-imidazo[4,5-c]pyridine-2-carboxamide (0.060 g, 0.110 mmol) in $CH_2Cl_2$ (2.0 mL) and then the mixture was stirred at 40° C. overnight. The mixture was diluted with $CH_2Cl_2$, filtered through Celite® and then concentrated under reduced pressure to provide the desired product which was used directly in the next step. LC-MS calculated for $C_{32}H_{32}N_7O_2$ (M+H)$^+$: m/z=546.3; found 546.2.

Step 6: (R)-1-((8-(3'-(1,5-dimethyl-4,5,6,7-tetrahydro-1H-imidazo[4,5-c]pyridine-2-carboxamido)-2,2'-dimethylbiphenyl-3-ylamino)-1,7-naphthyridin-3-yl)methyl)pyrrolidine-3-carboxylic acid To a mixture of N-(3'-((3-formyl-1,7-naphthyridin-8-yl)amino)-2,2'-dimethyl-[1,1'-biphenyl]-3-yl)-1,5-dimethyl-4,5,6,7-tetrahydro-TH-imidazo[4,5-c]pyridine-2-carboxamide (0.010 g, 0.018 mmol) and (R)-pyrrolidine-3-carboxylic acid (Combi-Blocks, cat #ST-7698: 6.3 mg, 0.055 mmol) in $CH_2Cl_2$ (1.0 mL) was added triethylamine (6.3 μL, 0.11 mmol). After stirring for 10 min sodium triacetoxyborohydride (0.012 g, 0.055 mmol) was added, and the reaction was further stirred at rt for 2 h. The reaction was concentrated and the mixture was diluted with acetonitrile/water and purified by prep HPLC (pH=2, acetonitrile/water+TFA) to provide the desired compound as its TFA salt. LC-MS calculated for $C_{37}H_{41}N_8O_3$ (M+H)$^+$: m/z=645.3; found 645.4.

Example 47 trans-4-((2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid

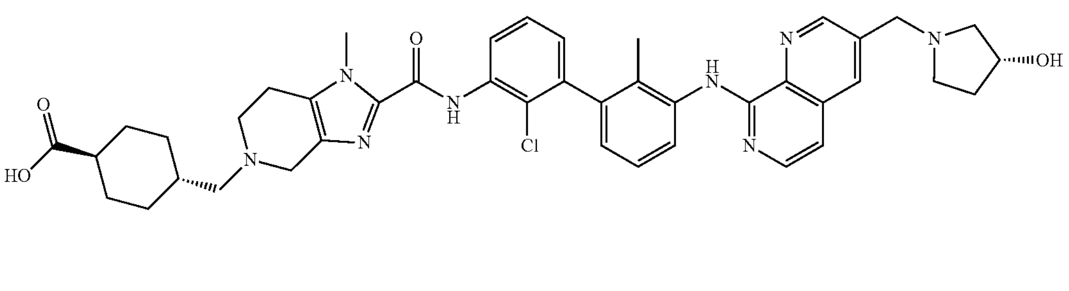 [SMILES: Cc1c(Nc2nccc3cc(CN4CC[C@@H](O)C4)cnc23)cccc1-c1cccc(NC(=O)c2nc3c(n2C)CCN(C[C@H]2CC[C@H](C(=O)O)CC2)C3)c1Cl]

Step 1: tert-butyl 2-(2-chloro-3-(4,4,5,5-tetramethyl-1,3,2-dioxaborolan-2-yl)phenylcarbamoyl)-1-methyl-6,7-dihydro-1H-imidazo[4,5-c]pyridine-5(4H)-carboxylate

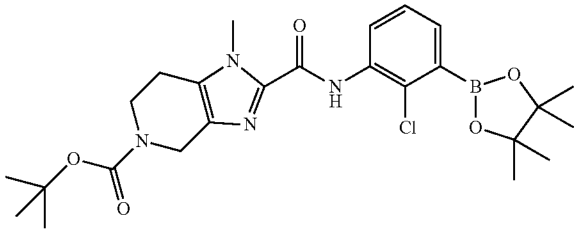 [SMILES: Cn1c(C(=O)Nc2cccc(B3OC(C)(C)C(C)(C)O3)c2Cl)nc2c1CCN(C(=O)OC(C)(C)C)C2]

Potassium tert-butoxide (1.0 M in THF, 2.20 mL, 2.20 mmol) was added to a solution of 5-tert-butyl 2-methyl 1-methyl-6,7-dihydro-1H-imidazo[4,5-c]pyridine-2,5(4H)-dicarboxylate (Example 14, Step 2: 0.295 g, 1.0 mmol) and 2-chloro-3-(4,4,5,5-tetramethyl-1,3,2-dioxaborolan-2-yl)aniline (Example 5, Step 1: 0.304 g, 1.200 mmol) in THF (4.0 mL). After being stirred at rt for 2 h, the reaction mixture was quenched with water, and extracted with ethyl acetate. The combined organic layers were washed with brine, dried over $Na_2SO_4$, filtered and concentrated under reduced pressure. The residue was purified by flash chromatography on a silica gel column eluting with ethyl acetate in hexanes (0-50%) to afford the desired product. LC-MS calculated for $C_{25}H_{35}BClN_4O_5(M+H)^+$: m/z=517.2; found 517.3.

Step 2: tert-butyl 2-(2-chloro-3'-(3-formyl-1,7-naphthyridin-8-ylamino)-2'-methylbiphenyl-3-ylcarbamoyl)-1-methyl-6,7-dihydro-1H-imidazo[4,5-c]pyridine-5(4H)-carboxylate

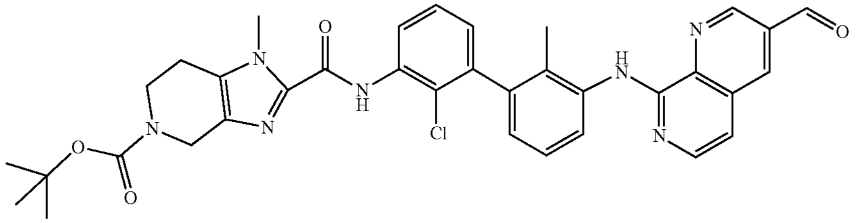 [SMILES: Cc1c(Nc2nccc3cc(C=O)cnc23)cccc1-c1cccc(NC(=O)c2nc3c(n2C)CCN(C(=O)OC(C)(C)C)C3)c1Cl]

A mixture of tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (0.35 g, 0.677 mmol), 8-((3-bromo-2-methylphenyl)amino)-1,7-naphthyridine-3-carbaldehyde (Example 9, Step 1: 0.255 g, 0.745 mmol), dichloro[1,1'-bis(dicyclohexylphosphino)ferrocene]-palladium(II) (0.051 g, 0.068 mmol) and cesium fluoride (0.514 g, 3.39 mmol) in t-BuOH (3.00 mL)/water (1.2 mL) was evacuated and backfilled with $N_2$ 3 times. The reaction was stirred at 105° C. for 2 h. The mixture was cooled to rt, diluted with ethyl acetate, and washed with water. The organic layers were washed with brine, dried over $MgSO_4$, filtered, and concentrated under reduced pressure. The product was purified by column chromatography eluting with $CH_2Cl_2$/EtOAc (7:3). LC-MS calculated for $C_{35}H_{35}ClN_7O_4(M+H)^+$: m/z=652.2; found 652.4.

Step 3: (R)-tert-butyl 2-(2-chloro-3'-(3-((3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridine-5(4H)-carboxylate

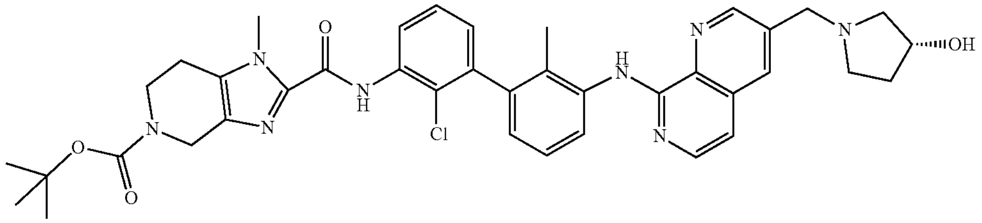 [SMILES: Cc1c(Nc2nccc3cc(CN4CC[C@@H](O)C4)cnc23)cccc1-c1cccc(NC(=O)c2nc3c(n2C)CCN(C(=O)OC(C)(C)C)C3)c1Cl]

(R)-pyrrolidin-3-ol (Combi-Blocks, cat #AM-2005: 0.072 g, 0.828 mmol) was added to a solution of tert-butyl 2-((2-chloro-3'-((3-formyl-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridine-5-carboxylate (0.180 g, 0.276 mmol) in $CH_2Cl_2$ (1.0 mL). Triethylamine (0.308 mL, 2.208 mmol) was then added and the mixture was stirred at rt for 1 h. At this time sodium triacetoxyborohydride (0.175 g, 0.828 mmol) was added and then stirred at rt for 2 h. The reaction was quenched with water, extracted with $CH_2Cl_2$, and the organic phase was dried over $MgSO_4$, filtered, and concentrated under reduced pressure. The product was purified by column chromatography eluting with $CH_2Cl_2$/MeOH (9:1). LC-MS calculated for $C_{39}H_{44}ClN_8O_4$ $(M+H)^+$: m/z=723.3; found 723.5.

Step 4: (R)-N-(2-chloro-3'-(3-((3-hydroxypyrrolidin-1-yl)methyl)-1,7-naphthyridin-8-ylamino)-2'-methylbiphenyl-3-yl)-1-methyl-4,5,6,7-tetrahydro-1H-imidazo[4,5-c]pyridine-2-carboxamide

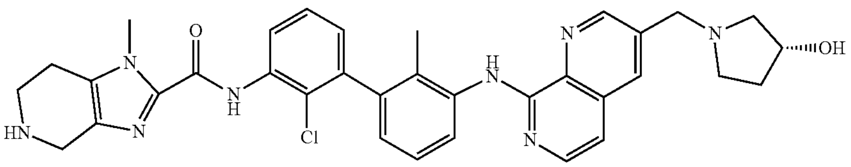 [SMILES: Cc1c(Nc2nccc3cc(CN4CC[C@@H](O)C4)cnc23)cccc1-c1cccc(NC(=O)c2nc3c(n2C)CCNC3)c1Cl]

4 N HCl in dioxane (2.0 mL) was added to a mixture of tert-butyl (R)-2-((2-chloro-3'-((3-((3-hydroxypyrrolidin-1-yl)methyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridine-5-carboxylate (0.18 g, 0.249 mmol) in $CH_2Cl_2$ (1.0 mL)/MeOH (1.0 mL) and the reaction was stirred at rt for 2 h. The solvent was removed and the crude HCl salt was used directly in the next step. LC-MS calculated for $C_{34}H_{36}ClN_8O_2(M+H)^+$: m/z=623.3; found 623.3.

Step 5: trans-4-((2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid To a mixture of (R)-N-(2-chloro-3'-((3-((3-hydroxypyrrolidin-1-yl)methyl)-1,7-naphthyridin-8-yl)amino)-2'-methyl-[1,1'-biphenyl]-3-yl)-1-methyl-4,5,6,7-tetrahydro-1H-imidazo[4,5-c]pyridine-2-carboxamide (0.025 g, 0.040 mmol) and methyl trans-4-formylcyclohexane-1-carboxylate (Ark Pharm, cat #AK-50935: 0.014 g, 0.080 mmol) in $CH_2Cl_2$ (1.0 mL) was added triethylamine (0.011 mL, 0.201 mmol) and the resulting mixture was stirred for 10 min. Sodium triacetoxyborohydride (0.026 g, 0.120 mmol) was added and the reaction was stirred at rt for 2 h. The solvent was removed and the crude residue was redissolved in methanol/THF/water (0.5/0.5/0.2 mL) and LiOH monohydrate (20 mg) was added. The mixture was then stirred at rt for 3 h. The mixture was diluted with acetonitrile/water, acidified to pH=2, and purified by prep HPLC (pH=2, acetonitrile/water+TFA) to provide the desired compound as its TFA salt. LC-MS calculated for $C_{42}H_{48}ClN_8O_4(M+H)^+$: m/z=763.3; found 763.3.

Example 48 cis-4-((2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid

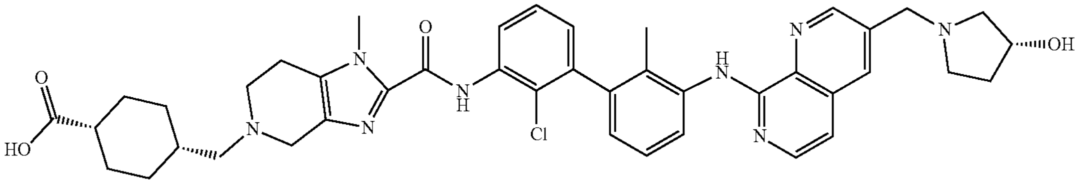 [SMILES: Cc1c(Nc2nccc3cc(CN4CC[C@@H](O)C4)cnc23)cccc1-c1cccc(NC(=O)c2nc3c(n2C)CCN(C[C@H]2CC[C@@H](C(=O)O)CC2)C3)c1Cl]

To a mixture of (R)-N-(2-chloro-3'-((3-((3-hydroxypyrrolidin-1-yl)methyl)-1,7-naphthyridin-8-yl)amino)-2'-methyl-[1,1'-biphenyl]-3-yl)-1-methyl-4,5,6,7-tetrahydro-1H-imidazo[4,5-c]pyridine-2-carboxamide (Example 47, Step 4: 85.0 mg, 0.136 mmol) in DMF (2.0 mL) was added methyl cis-4-(((methylsulfonyl)oxy)methyl)cyclohexane-1-carboxylate (Aldlab Chemicals, cat #JPM2-11253: 102 mg, 0.409 mmol), potassium carbonate (56.6 mg, 0.409 mmol), potassium iodide (22.64 mg, 0.136 mmol) and benzyltriethylammonium chloride (31.1 mg, 0.136 mmol). The mixture was then stirred at 75° C. overnight. The solvent was removed and the crude residue was redissolved in methanol/THF/water (0.5/0.5/0.2 mL). LiOH hydrate (20 mg) was added and the mixture was stirred at rt for 5 h. The mixture was diluted with acetonitrile/water, acidified to pH=2 and purified by prep HPLC (pH=2, acetonitrile/water+TFA) to provide the desired compound as its TFA salt. LC-MS calculated for $C_{42}H_{48}ClN_8O_4(M+H)^+$: m/z=763.3; found 763.4.

Example 49 cis-4-((2-(2-chloro-2'-methyl-3'-(3-(pyrrolidin-1-ylmethyl)-1,7-naphthyridin-8-ylamino)biphenyl-3-ylcarbamoyl)-1-methyl-6,7-dihydro-1H-imidazo[4,5-c]pyridin-5(4H)-yl)methyl)cyclohexanecarboxylic acid

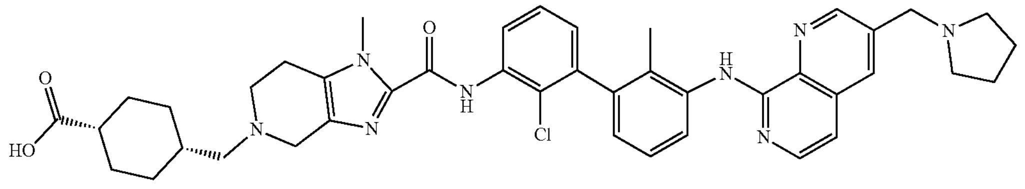 [SMILES: Cc1c(Nc2nccc3cc(CN4CCCC4)cnc23)cccc1-c1cccc(NC(=O)c2nc3c(n2C)CCN(C[C@H]2CC[C@@H](C(=O)O)CC2)C3)c1Cl]

Step 1: N-(3-bromo-2-methylphenyl)-3-(pyrrolidin-1-ylmethyl)-1,7-naphthyridin-8-amine

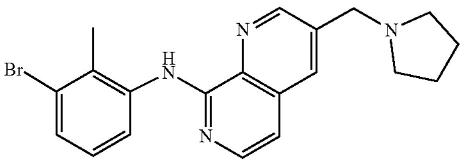 [SMILES: Cc1c(Br)cccc1Nc1nccc2cc(CN3CCCC3)cnc12]

A mixture of 8-((3-bromo-2-methylphenyl)amino)-1,7-naphthyridine-3-carbaldehyde (Example 9, Step 1: 0.342 g, 1.0 mmol) and pyrrolidine (0.107 g, 1.500 mmol) in $CH_2Cl_2$ (8.0 mL) was stirred at rt for 10 min. Sodium triacetoxyborohydride (0.424 g, 2.000 mmol) was then added and the mixture was stirred at rt for 2 h. The mixture was diluted with $CH_2Cl_2$, washed with 1 N NaOH, water, brine, and the organic phase was separated and dried over $Na_2SO_4$, filtered and concentrated under reduced pressure. The product was purified by column chromatography eluting with $CH_2Cl_2$/MeOH (9:1). LC-MS calculated for $C_{20}H_{22}BrN_4$ $(M+H)^+$: m/z=397.1; found 397.2.

Step 2: tert-butyl 2-(2-chloro-2'-methyl-3'-(3-(pyrrolidin-1-ylmethyl)-1,7-naphthyridin-8-ylamino)biphenyl-3-ylcarbamoyl)-1-methyl-6,7-dihydro-1H-imidazo[4,5-c]pyridine-5(4H)-carboxylate

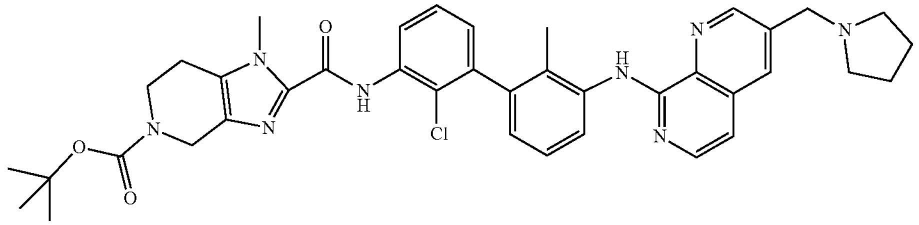 [SMILES: Cc1c(Nc2nccc3cc(CN4CCCC4)cnc23)cccc1-c1cccc(NC(=O)c2nc3c(n2C)CCN(C(=O)OC(C)(C)C)C3)c1Cl]

A mixture of tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 47, Step 1: 1.0 g, 1.935 mmol), N-(3-bromo-2-methylphenyl)-3-(pyrrolidin-1-ylmethyl)-1,7-naphthyridin-8-amine (0.846 g, 2.128 mmol), dichloro[1,1'-bis(dicyclohexylphosphino)ferrocene]palladium(II) (0.146 g, 0.193 mmol) and cesium fluoride (1.470 g, 9.67 mmol) in t-BuOH (3.00 mL)/water (1.2 mL) was evacuated and backfilled with $N_2$ 3 times. The reaction mixture was stirred at 105° C. for 2 h. The mixture was diluted with ethyl acetate and washed with water, dried over $Na_2SO_4$, filtered, and concentrated under reduced pressure. The product was purified by column chromatography eluting with $CH_2Cl_2$/MeOH (9:1). LC-MS calculated for $C_{39}H_{44}ClN_8O_3(M+H)^+$: m/z=707.3; found 707.5.

Step 3: N-(2-chloro-2'-methyl-3'-(3-(pyrrolidin-1-ylmethyl)-1,7-naphthyridin-8-ylamino)biphenyl-3-yl)-1-methyl-4,5,6,7-tetrahydro-1H-imidazo[4,5-c]pyridine-2-carboxamide

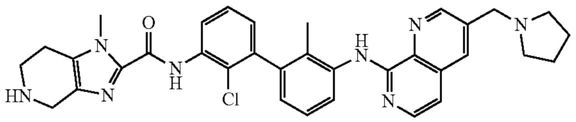 [SMILES: Cc1c(Nc2nccc3cc(CN4CCCC4)cnc23)cccc1-c1cccc(NC(=O)c2nc3c(n2C)CCNC3)c1Cl]

This compound was prepared using a similar procedure as described for Example 47, Step 4 with tert-butyl 2-(2-chloro-2'-methyl-3'-(3-(pyrrolidin-1-ylmethyl)-1,7-naphthyridin-8-ylamino)biphenyl-3-ylcarbamoyl)-1-methyl-6,7-dihydro-1H-imidazo[4,5-c]pyridine-5(4H)-carboxylate replacing tert-butyl (R)-2-((2-chloro-3'-((3-((3-hydroxypyrrolidin-1-yl)methyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridine-5-carboxylate. LC-MS calculated for $C_{34}H_{36}ClN_8O$ $(M+H)^+$: m/z=607.3; found 607.4.

Step 4: cis-4-((2-(2-chloro-2'-methyl-3'-(3-(pyrrolidin-1-ylmethyl)-1,7-naphthyridin-8-ylamino)biphenyl-3-ylcarbamoyl)-1-methyl-6,7-dihydro-1H-imidazo[4,5-c]pyridin-5(4H)-yl)methyl)cyclohexanecarboxylic acid This compound was prepared using a similar procedure as described for Example 48 with N-(2-chloro-2'-methyl-3'-(3-(pyrrolidin-1-ylmethyl)-1,7-naphthyridin-8-ylamino)biphenyl-3-yl)-1-methyl-4,5,6,7-tetrahydro-1H-imidazo[4,5-c]pyridine-2-carboxamide replacing (R)-N-(2-chloro-3'-((3-((3-hydroxypyrrolidin-1-yl)methyl)-1,7-naphthyridin-8-yl)amino)-2'-methyl-[1,1'-biphenyl]-3-yl)-1-methyl-4,5,6,7-tetrahydro-1H-imidazo[4,5-c]pyridine-2-carboxamide. LC-MS calculated for $C_{42}H_{48}ClN_8O_3(M+H)^+$: m/z=747.4; found 747.5.

Example 50 trans-4-((2-(2-chloro-3'-(3-(((S)-1-hydroxypropan-2-ylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid

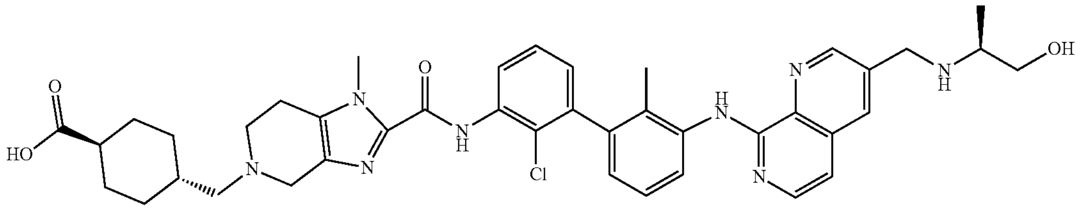 [SMILES: Cc1c(Nc2nccc3cc(CN[C@@H](C)CO)cnc23)cccc1-c1cccc(NC(=O)c2nc3c(n2C)CCN(C[C@H]2CC[C@H](C(=O)O)CC2)C3)c1Cl]

Step 1: tert-butyl 2-(2-chloro-3'-(3-(hydroxymethyl)-1,7-naphthyridin-8-ylamino)-2'-methylbiphenyl-3-ylcarbamoyl)-1-methyl-6,7-dihydro-1H-imidazo[4,5-c]pyridine-5(4H)-carboxylate

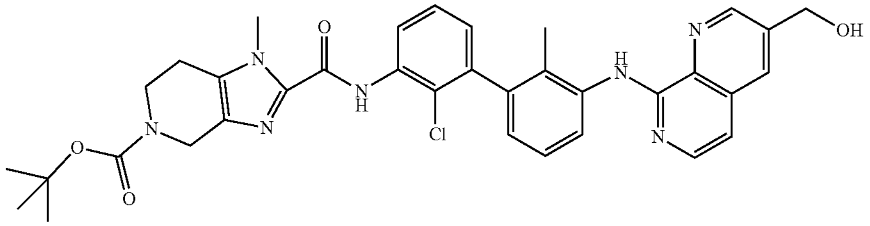 [SMILES: Cc1c(Nc2nccc3cc(CO)cnc23)cccc1-c1cccc(NC(=O)c2nc3c(n2C)CCN(C(=O)OC(C)(C)C)C3)c1Cl]

A mixture of tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 47, Step 1: 1.0 g, 1.935 mmol), (8-((3-bromo-2-methylphenyl)amino)-1,7-naphthyridin-3-yl)methanol (Affinity Research Chemicals, #ARI-0169: 0.733 g, 2.128 mmol), dichloro[1,1'-bis(dicyclohexylphosphino)ferrocene]palladium(II) (0.146 g, 0.193 mmol) and cesium fluoride (1.470 g, 9.67 mmol) in t-BuOH (3.00 mL)/water (1.2 mL) was evacuated and backfilled with $N_2$ 3 times. The reaction was stirred at 105° C. for 2 h. The mixture was diluted with ethyl acetate and washed with water, brine, dried over $Na_2SO_4$, and concentrated under reduced pressure. The product was purified by column chromatography eluting with $CH_2Cl_2$/EtOAc (1:1). LC-MS calculated for $C_{35}H_{37}ClN_7O_4$ $(M+H)^+$: m/z=654.2; found 654.2.

Step 2: N-(2-chloro-3'-(3-(hydroxymethyl)-1,7-naphthyridin-8-ylamino)-2'-methylbiphenyl-3-yl)-1-methyl-4,5,6,7-tetrahydro-1H-imidazo[4,5-c]pyridine-2-carboxamide

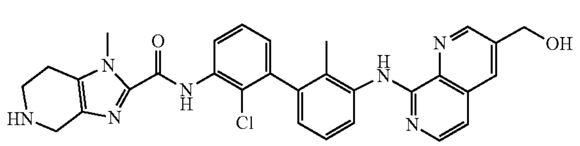 [SMILES: Cc1c(Nc2nccc3cc(CO)cnc23)cccc1-c1cccc(NC(=O)c2nc3c(n2C)CCNC3)c1Cl]

This compound was prepared using a similar procedure as described for Example 47, Step 4 with tert-butyl 2-(2-chloro-3'-(3-(hydroxymethyl)-1,7-naphthyridin-8-ylamino)-2'-methylbiphenyl-3-ylcarbamoyl)-1-methyl-6,7-dihydro-1H-imidazo[4,5-c]pyridine-5(4H)-carboxylate replacing tert-butyl (R)-2-((2-chloro-3'-((3-((3-hydroxypyrrolidin-1-yl)methyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridine-5-carboxylate. LC-MS calculated for $C_{30}H_{29}ClN_7O_2$ $(M+H)^+$: m/z=554.2; found 554.2.

Step 3: trans-methyl 4-((2-(2-chloro-3'-(3-(hydroxymethyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylate

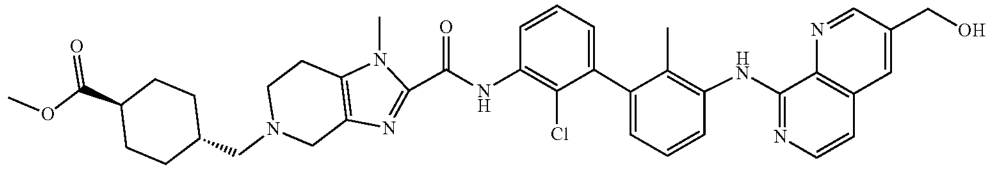 [SMILES: COC(=O)[C@H]1CC[C@H](CN2CCc3c(nc(C(=O)Nc4cccc(-c5cccc(Nc6nccc7cc(CO)cnc67)c5C)c4Cl)n3C)C2)CC1]

To a mixture of N-(2-chloro-3'-((3-(hydroxymethyl)-1,7-naphthyridin-8-yl)amino)-2'-methyl-[1,1'-biphenyl]-3-yl)-1-methyl-4,5,6,7-tetrahydro-1H-imidazo[4,5-c]pyridine-2-carboxamide (0.075 g, 0.135 mmol) and methyl trans-4-formylcyclohexane-1-carboxylate (Ark Pharm, cat #AK-50935: 0.046 g, 0.271 mmol) in $CH_2Cl_2$ (1.0 mL) was added triethylamine (0.039 mL, 0.677 mmol), and the resulting mixture was stirred at 40° C. for 30 min. Sodium triacetoxyborohydride (0.086 g, 0.406 mmol) was added and stirred at rt for 4 h. The mixture was diluted with $CH_2Cl_2$ and washed with 1 N NaOH, water, and brine. The organic phase was concentrated under reduced pressure and the crude product was purified by column chromatography eluting with $CH_2Cl_2$/MeOH (9:1). LC-MS calculated for $C_{39}H_{43}ClN_7O_4$ $(M+H)^+$: m/z=708.3; found 708.4.

Step 4: trans-methyl 4-((2-(2-chloro-3'-(3-formyl-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylate

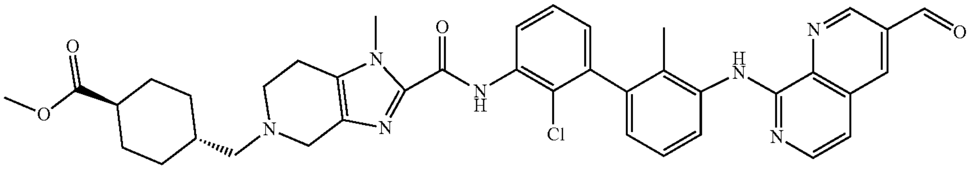 [SMILES: COC(=O)[C@H]1CC[C@H](CN2CCc3c(nc(C(=O)Nc4cccc(-c5cccc(Nc6nccc7cc(C=O)cnc67)c5C)c4Cl)n3C)C2)CC1]

Manganese dioxide (0.313 g, 3.60 mmol) was added to a solution of methyl trans 4-((2-((2-chloro-3'-((3-(hydroxymethyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate (0.17 g, 0.240 mmol) in $CH_2Cl_2$ (5.0 mL) and the mixture was stirred at 45° C. for 5 h. The mixture was diluted with $CH_2Cl_2$, filtered through Celite® and then concentrated under reduced pressure. The crude product which was purified by column chromatography eluting with $CH_2Cl_2$/MeOH (9:1). LC-MS calculated for $C_{39}H_{41}ClN_7O_4(M+H)^+$: m/z=706.3; found 706.4.

Step 5: trans-4-((2-(2-chloro-3'-(3-(((S)-1-hydroxypropan-2-ylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid A mixture of methyl trans 4-((2-((2-chloro-3'-((3-formyl-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate (0.010 g, 0.014 mmol) and (S)-2-aminopropan-1-ol (Aldrich, cat #A76206: 5.32 mg, 0.071 mmol) in $CH_2Cl_2$ (1.0 mL) was stirred for 30 min at rt. Sodium triacetoxyborohydride (9.0 mg, 0.042 mmol) was added and the mixture was stirred at rt overnight. The solvent was removed and the crude material was redissolved in methanol/THF/water (0.5/0.5/0.2 mL). LiOH monohydrate (40 mg) was added and the mixture was stirred at rt for 5 h. The mixture was diluted with acetonitrile/water, acidified to pH=2 and purified by prep HPLC (pH=2, acetonitrile/water+TFA) to provide the desired compound as its TFA salt. LC-MS calculated for $C_{41}H_{48}ClN_8O_4(M+H)^+$: m/z=751.3; found 751.4.

Example 51 trans-4-((2-(2-chloro-3'-(3-(((1S,2S)-2-hydroxycyclopentylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid

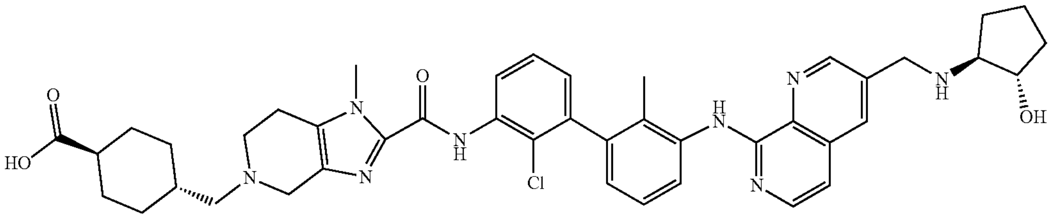 [SMILES: Cc1c(Nc2nccc3cc(CN[C@H]4CCC[C@@H]4O)cnc23)cccc1-c1cccc(NC(=O)c2nc3c(n2C)CCN(C[C@H]2CC[C@H](C(=O)O)CC2)C3)c1Cl]

This compound was prepared using a similar procedure as described for Example 50 with (1S,2S)-2-aminocyclopentan-1-ol (Ark Pharm, cat #AK-88109) replacing (S)-2-aminopropan-1-ol in Step 5. LC-MS calculated for $C_{43}H_{50}ClN_8O_4(M+H)^+$: m/z=777.4; found 777.4.

Example 52 trans 4-(2-(2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl) cyclohexanecarboxylic acid

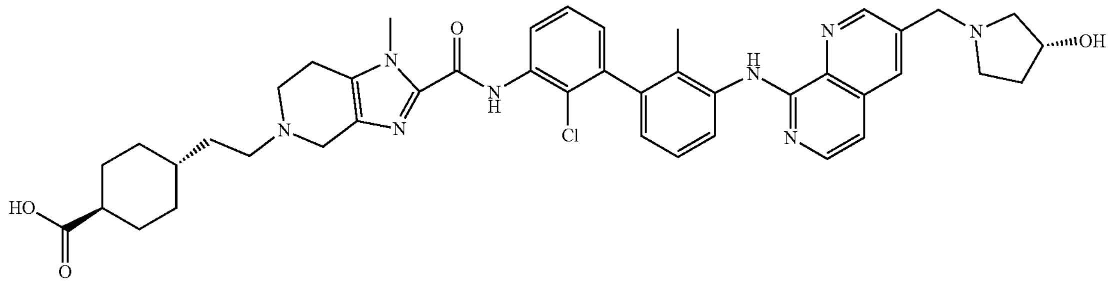 [SMILES: Cc1c(Nc2nccc3cc(CN4CC[C@@H](O)C4)cnc23)cccc1-c1cccc(NC(=O)c2nc3c(n2C)CCN(CC[C@H]2CC[C@H](C(=O)O)CC2)C3)c1Cl]

This compound was prepared using a similar procedure as described for Example 47 with methyl 4-(2-oxoethyl)cyclohexane-1-carboxylate (Enamine, cat #EN300-198655) replacing methyl trans-4-formylcyclohexane-1-carboxylate in Step 5 as a mixture of diastereomers. The diastereomers were separated using prep HPLC (pH=2, acetonitrile/water+TFA), with the trans isomer eluting first in the column, peak 1: retention time on analytical LCMS (pH=2, acetonitrile/water+TFA) $t_r$=0.80 min; LC-MS calculated for $C_{43}H_{50}ClN_8O_4(M+H)^+$: m/z=777.4; found 777.4.

Example 53 cis 4-(2-(2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl) cyclohexanecarboxylic acid

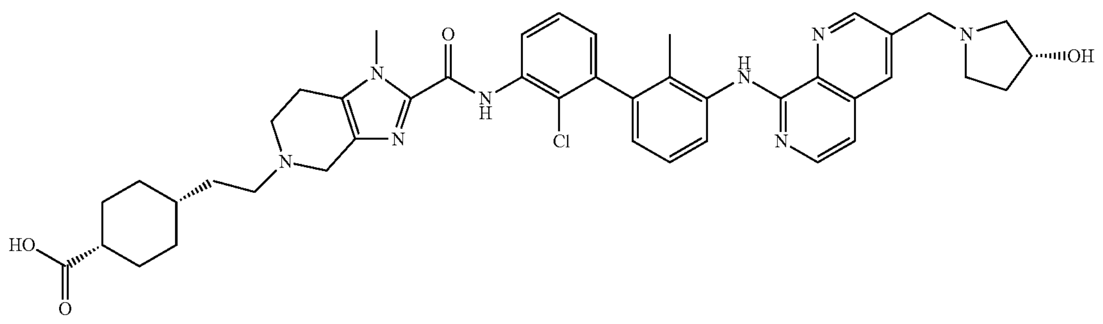 [SMILES: Cc1c(Nc2nccc3cc(CN4CC[C@@H](O)C4)cnc23)cccc1-c1cccc(NC(=O)c2nc3c(n2C)CCN(CC[C@H]2CC[C@@H](C(=O)O)CC2)C3)c1Cl]

This compound was prepared using a similar procedure as described for Example 52 The diastereomers were separated using prep HPLC (pH=2, acetonitrile/water+TFA), with the minor cis isomer eluting later in the column, peak 2: retention time on analytical LCMS (pH=2, acetonitrile/water+TFA) $t_r$=0.82 min; LC-MS calculated for $C_{43}H_{50}ClN_8O_4(M+H)^+$: m/z=777.4; found 777.4.

Example 54

3-(2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)butanoic acid

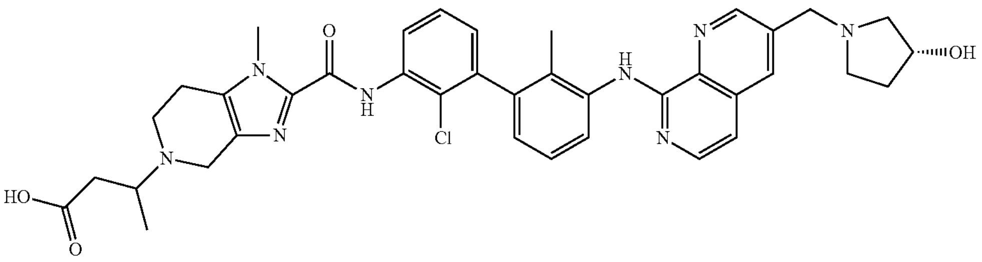 [SMILES: Cc1c(Nc2nccc3cc(CN4CC[C@@H](O)C4)cnc23)cccc1-c1cccc(NC(=O)c2nc3c(n2C)CCN(C(C)CC(=O)O)C3)c1Cl]

This compound was prepared using a similar procedure as described for Example 47 with methyl 3-oxobutanoate (Aldrich, cat #537365) replacing methyl trans-4-formylcyclohexane-1-carboxylate in Step 5. LC-MS calculated for $C_{38}H_{42}ClN_8O_4(M+H)^+$: m/z=709.3; found 709.2.

Example 55 cis 4-((2-(2-chloro-3'-(3-(((S)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid

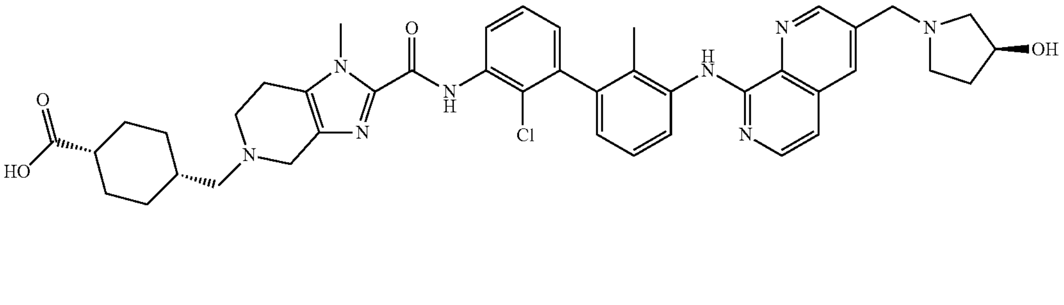 [SMILES: Cc1c(Nc2nccc3cc(CN4CC[C@H](O)C4)cnc23)cccc1-c1cccc(NC(=O)c2nc3c(n2C)CCN(C[C@H]2CC[C@@H](C(=O)O)CC2)C3)c1Cl]

Step 1: N-(2-chloro-3'-(3-formyl-1,7-naphthyridin-8-ylamino)-2'-methylbiphenyl-3-yl)-1-methyl-4,5,6,7-tetrahydro-1H-imidazo[4,5-c]pyridine-2-carboxamide

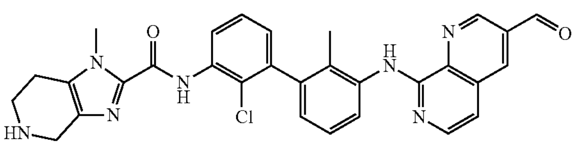 [SMILES: Cc1c(Nc2nccc3cc(C=O)cnc23)cccc1-c1cccc(NC(=O)c2nc3c(n2C)CCNC3)c1Cl]

TFA (2.0 mL, 26.0 mmol) was added to a solution of tert-butyl 2-((2-chloro-3'-((3-formyl-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridine-5-carboxylate (Example 45, Step 2: 0.20 g, 0.307 mmol) in $CH_2Cl_2$ (1.0 mL) at rt and the reaction was stirred for 30 min. The solvent was removed under vacuum and the crude TFA salt was used directly in the next step without further purification. LC-MS calculated for $C_{30}H_{27}ClN_7O_2(M+H)^+$: m/z=552.2; found 552.1.

Step 2: cis-methyl 4-((2-(2-chloro-3'-(3-formyl-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylate

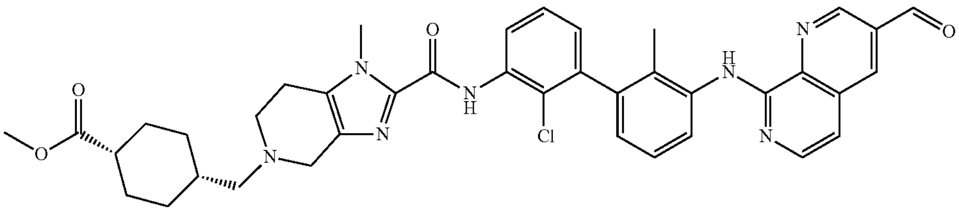 [SMILES: COC(=O)[C@H]1CC[C@@H](CN2CCc3c(nc(C(=O)Nc4cccc(-c5cccc(Nc6nccc7cc(C=O)cnc67)c5C)c4Cl)n3C)C2)CC1]

To a mixture of N-(2-chloro-3'-((3-formyl-1,7-naphthyridin-8-yl)amino)-2'-methyl-[1,1'-biphenyl]-3-yl)-1-methyl-4,5,6,7-tetrahydro-1H-imidazo[4,5-c]pyridine-2-carboxamide (150.0 mg, 0.272 mmol) in DMF (2.0 mL) was added methyl cis-4-(((methylsulfonyl)oxy)methyl)cyclohexane-1-carboxylate (Aldlab Chemicals, cat #JPM2-11253: 136 mg, 0.543 mmol), potassium carbonate (113 mg, 0.815 mmol), potassium iodide (45.1 mg, 0.272 mmol), and benzyltriethylammonium chloride (61.9 mg, 0.272 mmol). The resulting mixture was then stirred at 75° C. overnight. The mixture was diluted with $CH_2Cl_2$ and then washed with water and brine. The organic phase was dried over $MgSO_4$, filtered, and concentrated under reduced pressure. The product was purified by column chromatography eluting with $CH_2Cl_2$/MeOH (9:1). LC-MS calculated for $C_{39}H_{41}ClN_7O_4(M+H)^+$: m/z=706.3; found 706.4.

Step 3: cis-4-((2-(2-chloro-3'-(3-(((S)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid A mixture of methyl cis-4-((2-((2-chloro-3'-((3-formyl-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate (0.010 g, 0.014 mmol) and (S)-pyrrolidin-3-ol (Combi-Blocks, cat #SS-7948, 1.234 mg, 0.014 mmol) in $CH_2Cl_2$ (1.0 mL) was stirred for 30 min and then sodium triacetoxyborohydride (9.00 mg, 0.042 mmol) was added and stirred at rt overnight. The solvent was removed and the crude was redissolved in methanol/THF/water (0.5/0.5/0.2 mL). LiOH monohydrate (40 mg) was added and the mixture was stirred at rt for 5 h. The mixture was diluted with acetonitrile/water, acidified to pH=2 and purified by prep HPLC (pH=2, acetonitrile/water+TFA) to provide the desired compound as its TFA salt. LC-MS calculated for $C_{42}H_{48}ClN_8O_4(M+H)^+$: m/z=763.3; found 763.5.

Example 56 cis 4-((2-(2-chloro-3'-(3-(((R)-3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid

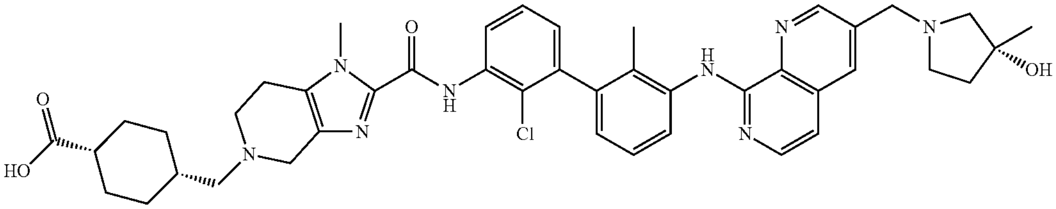 [SMILES: Cc1c(Nc2nccc3cc(CN4CC[C@@](C)(O)C4)cnc23)cccc1-c1cccc(NC(=O)c2nc3c(n2C)CCN(C[C@H]2CC[C@@H](C(=O)O)CC2)C3)c1Cl]

This compound was prepared using a similar procedure as described for Example 55 with (R)-3-methylpyrrolidin-3-ol (Ark Pharm, cat #AK100499) replacing (S)-pyrrolidin-3-ol in Step 3. LC-MS calculated for $C_{43}H_{50}ClN_8O_4(M+H)^+$: m/z=777.3; found 777.3.

Example 57

(R)-4-(2-(2-chloro-3'-(3-((3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)cyclohexanecarboxylic acid

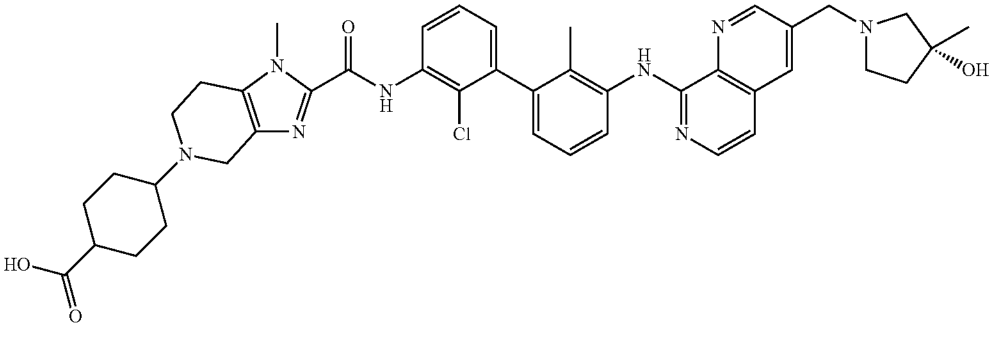 [SMILES: Cc1c(Nc2nccc3cc(CN4CC[C@@](C)(O)C4)cnc23)cccc1-c1cccc(NC(=O)c2nc3c(n2C)CCN(C2CCC(C(=O)O)CC2)C3)c1Cl]

Step 1: tert-butyl 4-(2-(2-chloro-3'-(3-(hydroxymethyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)cyclohexanecarboxylate

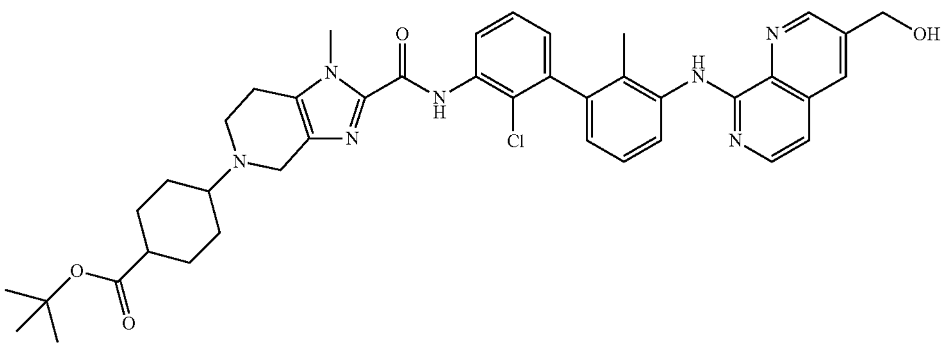 [SMILES: Cc1c(Nc2nccc3cc(CO)cnc23)cccc1-c1cccc(NC(=O)c2nc3c(n2C)CCN(C2CCC(C(=O)OC(C)(C)C)CC2)C3)c1Cl]

To a mixture of N-(2-chloro-3'-((3-(hydroxymethyl)-1,7-naphthyridin-8-yl)amino)-2'-methyl-[1,1'-biphenyl]-3-yl)-1-methyl-4,5,6,7-tetrahydro-1H-imidazo[4,5-c]pyridine-2-carboxamide (Example 50, Step 2: 0.275 g, 0.496 mmol) and tert-butyl 4-oxocyclohexane-1-carboxylate (Ark Pharm, cat #AK-40114: 0.197 g, 0.993 mmol) in $CH_2Cl_2$ (1.0 mL) was added triethylamine (0.142 mL, 2.482 mmol). The resulting mixture was stirred at 40° C. for 30 min and then sodium triacetoxyborohydride (0.316 g, 1.489 mmol) was added and stirred at rt overnight. The mixture was diluted with $CH_2Cl_2$ and washed with 1 N NaOH, water, and brine. The solvent was removed and the product was purified by column chromatography eluting with $CH_2Cl_2$/MeOH (9:1). LC-MS calculated for $C_{41}H_{47}ClN_7O_4(M+H)^+$: m/z=736.3; found 736.3.

Step 2: tert-butyl 4-(2-(2-chloro-2'-methyl-3'-(3-((methylsulfonyloxy)methyl)-1,7-naphthyridin-8-ylamino)biphenyl-3-ylcarbamoyl)-1-methyl-6,7-dihydro-1H-imidazo[4,5-c]pyridin-5(4H)-yl)cyclohexanecarboxylate

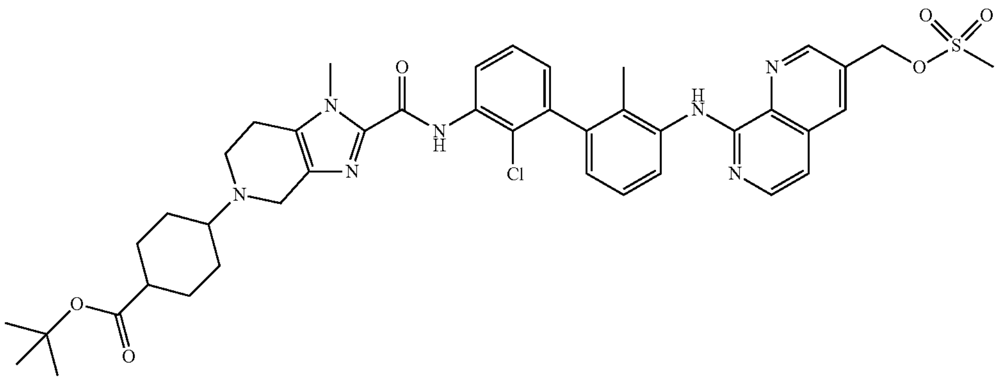 [SMILES: Cc1c(Nc2nccc3cc(COS(C)(=O)=O)cnc23)cccc1-c1cccc(NC(=O)c2nc3c(n2C)CCN(C2CCC(C(=O)OC(C)(C)C)CC2)C3)c1Cl]

Methanesulfonyl chloride (0.023 g, 0.204 mmol) was added to a solution of tert-butyl 4-(2-((2-chloro-3'-((3-(hydroxymethyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridin-5-yl)cyclohexane-1-carboxylate (0.10 g, 0.136 mmol) and triethylamine (0.057 mL, 0.407 mmol) in $CH_2Cl_2$ (2.0 mL) at 0° C. and then the reaction was stirred at this temperature for 30 min. The mixture was quenched by adding aqueous saturated $NaHCO_3$, and the aqueous phase was extracted with methylene chloride. The combined organic layers were dried over $Na_2SO_4$, filtered, and concentrated under reduced pressure, and the crude product was used directly in the next step. LC-MS calculated for $C_{42}H_{49}ClN_7O_6S$ $(M+H)^+$: m/z=814.3; found 814.3.

Step 3: (R)-4-(2-(2-chloro-3'-(3-((3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)cyclohexanecarboxylic acid (R)-3-methylpyrrolidin-3-ol (Ark Pharm, cat #AK100499: 2.484 mg, 0.025 mmol) was added to a solution of tert-butyl 4-(2-((2-chloro-2'-methyl-3'-((3-(((methylsulfonyl)oxy)methyl)-1,7-naphthyridin-8-yl)amino)-[1,1'-biphenyl]-3-yl)carbamoyl)-1-methyl-1,4,6,7-tetrahydro-5H-imidazo[4,5-c]pyridin-5-yl)cyclohexane-1-carboxylate (0.020 g, 0.025 mmol) and triethylamine (0.021 mL, 0.147 mmol) in $CH_2Cl_2$ (0.8 mL) at rt. The reaction was stirred at 30° C. for 1 h. The solvent was removed and the residue was treated with 4 N HCl in dioxane (1.0 mL) for 2 h. The mixture was diluted with acetonitrile/water, acidified to pH=2 and purified by prep HPLC (pH=2, acetonitrile/water+TFA) to provide the desired compound as its TFA salt. LC-MS calculated for $C_{42}H_{48}ClN_8O_4(M+H)^+$: m/z=763.3; found 763.3.

Example 58

(S)-4-(2-(2-chloro-3'-(3-((3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)cyclohexanecarboxylic acid

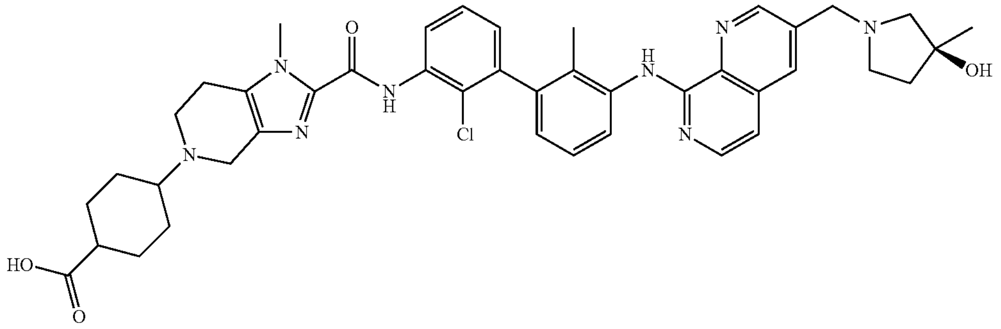 [SMILES: Cc1c(Nc2nccc3cc(CN4CC[C@](C)(O)C4)cnc23)cccc1-c1cccc(NC(=O)c2nc3c(n2C)CCN(C2CCC(C(=O)O)CC2)C3)c1Cl]

This compound was prepared using a similar procedure as described for Example 57 with (S)-3-methylpyrrolidin-3-ol (J&W Pharma, cat #75R0496) replacing (R)-3-methylpyrrolidin-3-ol in Step 3. LC-MS calculated for $C_{42}H_{48}ClN_8O_4$ $(M+H)^+$: m/z=763.3; found 763.3.

Example 59 trans 4-(2-(2-(2-chloro-3'-(3-(((R)-1-hydroxypropan-2-ylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl) cyclohexanecarboxylic acid

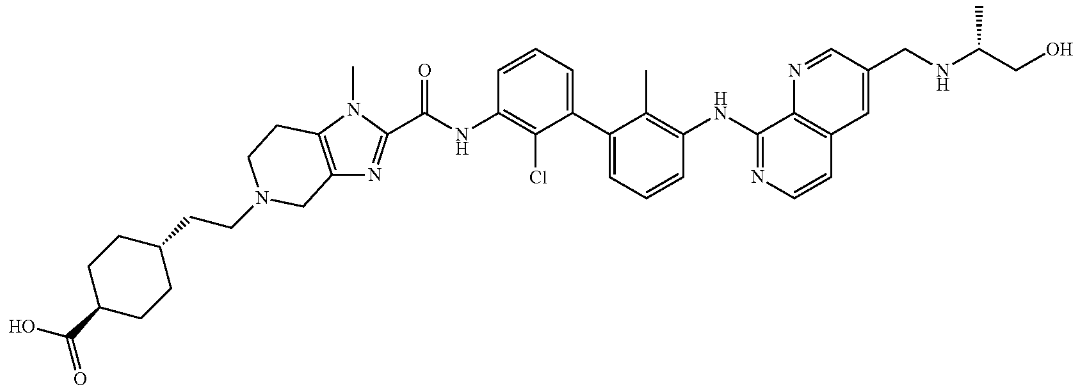 [SMILES: Cc1c(Nc2nccc3cc(CN[C@H](C)CO)cnc23)cccc1-c1cccc(NC(=O)c2nc3c(n2C)CCN(CC[C@H]2CC[C@H](C(=O)O)CC2)C3)c1Cl]

Step 1: trans methyl 4-(2-(2-(2-chloro-3'-(3-(hydroxymethyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl) cyclohexanecarboxylate

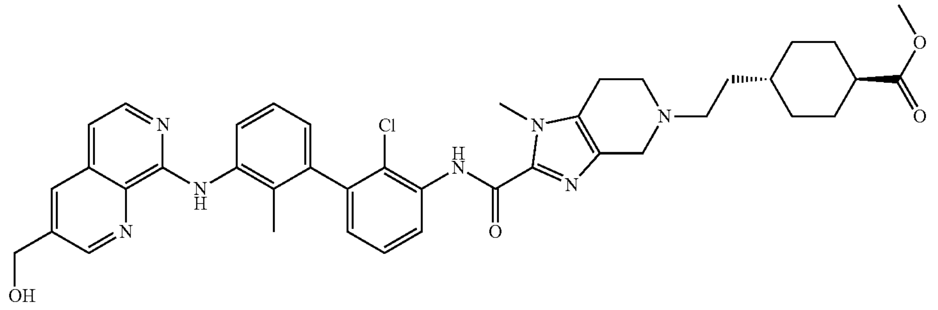 [SMILES: COC(=O)[C@H]1CC[C@H](CCN2CCc3c(nc(C(=O)Nc4cccc(-c5cccc(Nc6nccc7cc(CO)cnc67)c5C)c4Cl)n3C)C2)CC1]

To a mixture of N-(2-chloro-3'-((3-(hydroxymethyl)-1,7-naphthyridin-8-yl)amino)-2'-methyl-[1,1'-biphenyl]-3-yl)-1-methyl-4,5,6,7-tetrahydro-1H-imidazo[4,5-c]pyridine-2-carboxamide (Example 50, Step 2: 0.075 g, 0.135 mmol) and methyl trans 4-(2-oxoethyl)cyclohexane-1-carboxylate (Enamine, cat #EN300-198655: 0.050 g, 0.271 mmol) in $CH_2Cl_2$ (1.0 mL) was added triethylamine (0.039 mL, 0.677 mmol) and the resulting mixture was stirred at 40° C. for 30 min. Sodium triacetoxyborohydride (0.086 g, 0.406 mmol) was added and stirred at rt for 4 h. The mixture was diluted with $CH_2Cl_2$ and washed with 1 N NaOH, water, and brine. The solvent was removed and the product was purified by column chromatography eluting with $CH_2Cl_2$/MeOH (9:1). LC-MS calculated for $C_{40}H_{45}ClN_7O_4(M+H)^+$: m/z=722.3; found 722.4.

Step 2: trans methyl 4-(2-(2-(2-chloro-2'-methyl-3'-(3-((methylsulfonyloxy)methyl)-1,7-naphthyridin-8-ylamino)biphenyl-3-ylcarbamoyl)-1-methyl-6,7-dihydro-1H-imidazo[4,5-c]pyridin-5(4H)-yl)ethyl)cyclohexanecarboxylate

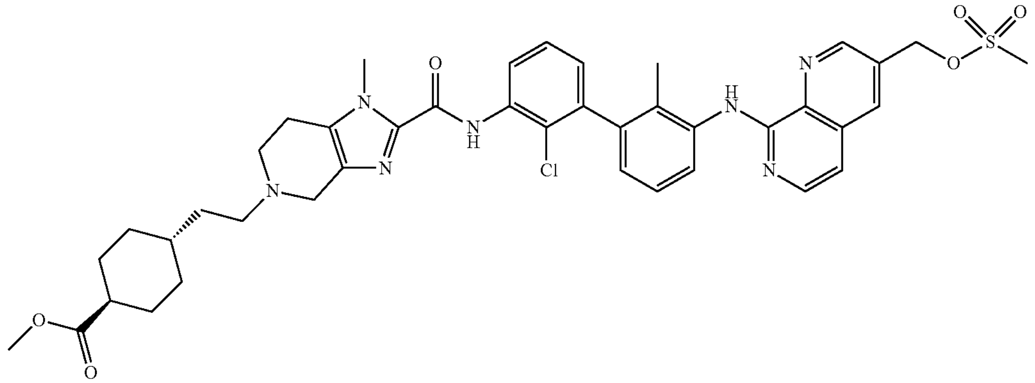

Methanesulfonyl chloride (0.024 g, 0.208 mmol) was added to a solution of trans methyl 4-(2-(2-((2-chloro-3'-((3-(hydroxymethyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridin-5-yl)ethyl) cyclohexane-1-carboxylate (0.10 g, 0.138 mmol) and triethylamine (0.058 mL, 0.415 mmol) in $CH_2Cl_2$ (2.0 mL) at 0° C. and then the reaction was stirred at this temperature for 30 min. The mixture was quenched by adding aqueous saturated $NaHCO_3$, and the reaction was extracted with methylene chloride. The combined organic layers were dried over $Na_2SO_4$, filtered, and concentrated under reduced pressure. The crude product was used directly in the next step. LC-MS calculated for $C_{41}H_{47}ClN_7O_6S$ $(M+H)^+$: m/z=800.3; found 800.3.

Step 3: trans-4-(2-(2-(2-chloro-3'-(3-(((R)-1-hydroxypropan-2-ylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl)cyclohexanecarboxylic acid (R)-2-aminopropan-1-ol (Aldrich, cat #297682: 1.9 mg, 0.025 mmol) was added to a solution of trans methyl 4-(2-(2-((2-chloro-2'-methyl-3'-((3-(((methylsulfonyl)oxy) methyl)-1,7-naphthyridin-8-yl)amino)-[1,1'-biphenyl]-3-yl) carbamoyl)-1-methyl-1,4,6,7-tetrahydro-5H-imidazo[4,5-c] pyridin-5-yl)ethyl)cyclohexane-1-carboxylate (20 mg, 0.025 mmol) and triethylamine (0.021 mL, 0.147 mmol) in $CH_2Cl_2$ (0.8 mL) at rt. The reaction was stirred at 30° C. for 1 h. The solvent was removed and the residue was dissolved in MeOH/THF/water (0.4/0.4/0.2 mL). LiOH monohydrate (40 mg) was added and stirred at rt for 4 h. The mixture was diluted with acetonitrile/water, acidified to pH=2 and purified by prep HPLC (pH=2, acetonitrile/water+TFA) to provide the desired compound as its TFA salt. LC-MS calculated for $C_{42}H_{50}ClN_8O_4(M+H)^+$: m/z=765.4; found 765.5.

Example 60 trans 4-(2-(2-(2-chloro-3'-(3-(((S)-1-hydroxypropan-2-ylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl) cyclohexanecarboxylic acid

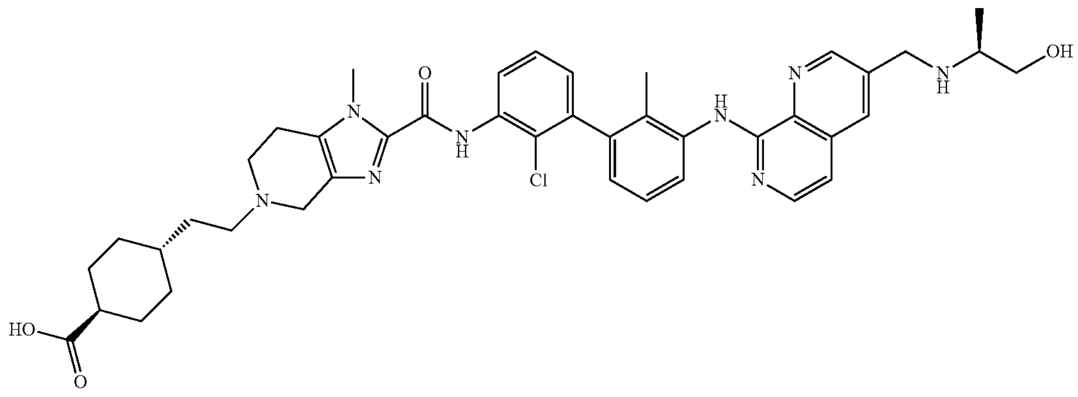 [SMILES: Cc1c(Nc2nccc3cc(CN[C@@H](C)CO)cnc23)cccc1-c1cccc(NC(=O)c2nc3c(n2C)CCN(CC[C@H]2CC[C@H](C(=O)O)CC2)C3)c1Cl]

This compound was prepared using a similar procedure as described for Example 59 with (S)-2-aminopropan-1-ol (Aldrich, cat #A76206) replacing (R)-2-aminopropan-1-ol in Step 3. LC-MS calculated for $C_{42}H_{50}ClN_8O_4(M+H)^+$: m/z=765.4; found 765.5.

Example 61 trans-4-(2-(2-(2-chloro-3'-(3-(((R)-3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl)cyclohexanecarboxylic acid

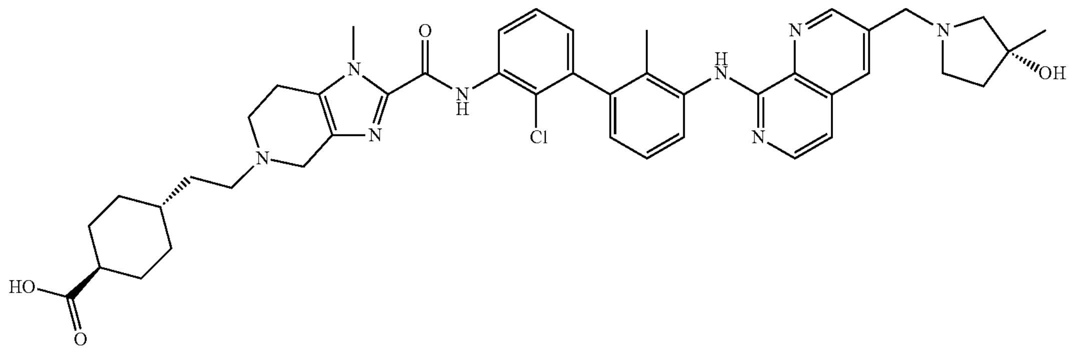 [SMILES: Cc1c(Nc2nccc3cc(CN4CC[C@@](C)(O)C4)cnc23)cccc1-c1cccc(NC(=O)c2nc3c(n2C)CCN(CC[C@H]2CC[C@H](C(=O)O)CC2)C3)c1Cl]

This compound was prepared using a similar procedure as described for Example 59 with (R)-3-methylpyrrolidin-3-ol (Ark Pharm, cat #AK100499) replacing (R)-2-aminopropan-1-ol in Step 3. LC-MS calculated for $C_{44}H_{52}ClN_8O_4$ $(M+H)^+$: m/z=791.4; found 791.4.

Example 62

(R)-4-(2-(3'-(3-((3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c]pyridin-5(4H)-yl)-1-methylcyclohexanecarboxylic acid

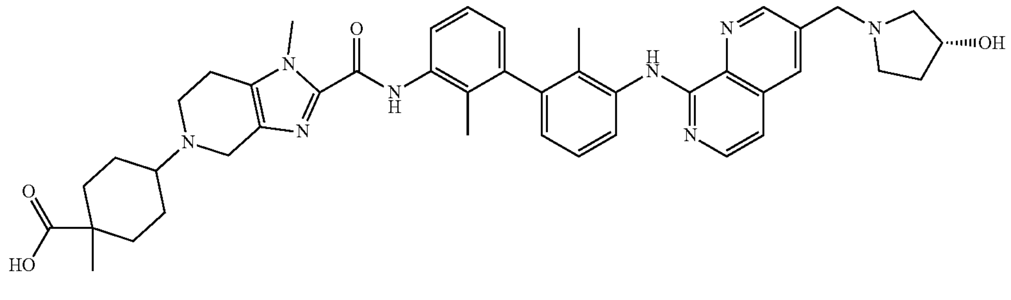 [SMILES: Cc1c(NC(=O)c2nc3c(n2C)CCN(C2CCC(C)(C(=O)O)CC2)C3)cccc1-c1cccc(Nc2nccc3cc(CN4CC[C@@H](O)C4)cnc23)c1C]

Step 1: (R)-tert-butyl 2-(3'-(3-((3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c]pyridine-5(4H)-carboxylate

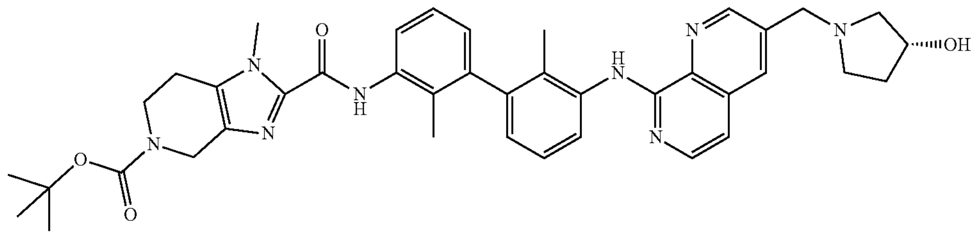 [SMILES: Cc1c(NC(=O)c2nc3c(n2C)CCN(C(=O)OC(C)(C)C)C3)cccc1-c1cccc(Nc2nccc3cc(CN4CC[C@@H](O)C4)cnc23)c1C]

A mixture of tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate (Example 14, Step 3: 0.25 g, 0.504 mmol), (R)-1-((8-((3-bromo-2-methylphenyl)amino)-1,7-naphthyridin-3-yl)methyl)pyrrolidin-3-ol (Example 9, Step 2: 0.229 g, 0.554 mmol), dichloro[1,1'-bis(dicyclohexylphosphino)ferrocene] palladium(II), (0.038 g, 0.050 mmol), and cesium fluoride (0.383 g, 2.52 mmol) in t-BuOH (8.00 mL)/water (3.0 mL) was evacuated and backfilled with $N_2$. The evacuation/backfill sequence was repeated two more times, and then the reaction was stirred at 105° C. for 2 h. The mixture was diluted with ethyl acetate and washed with water and brine. The organic phase was dried over $MgSO_4$, filtered, and concentrated. The product was purified by column chromatography eluting with $CH_2Cl_2$/MeOH (9:1). LC-MS calculated for $C_{40}H_{47}N_8O_4$ $(M+H)^+$: m/z=703.4; found 703.6.

Step 2: (R)-N-(3'-(3-((3-hydroxypyrrolidin-1-yl)methyl)-1,7-naphthyridin-8-ylamino)-2,2'-dimethylbiphenyl-3-yl)-1-methyl-4,5,6,7-tetrahydro-1H-imidazo[4,5-c]pyridine-2-carboxamide

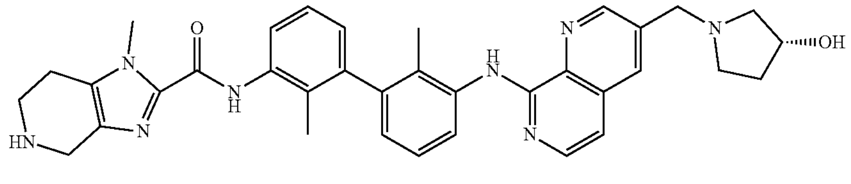 [SMILES: Cc1c(NC(=O)c2nc3c(n2C)CCNC3)cccc1-c1cccc(Nc2nccc3cc(CN4CC[C@@H](O)C4)cnc23)c1C]

This compound was prepared using a similar procedure as described for Example 47, Step 4 with (R)-tert-butyl 2-(3'-(3-((3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c]pyridine-5(4H)-carboxylate replacing tert-butyl (R)-2-((2-chloro-3'-((3-((3-hydroxypyrrolidin-1-yl)methyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridine-5-carboxylate. LC-MS calculated for $C_{35}H_{39}N_8O_2$ $(M+H)^+$: m/z=603.3; found 603.3.

Step 3: (R)-4-(2-(3'-(3-((3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c]pyridin-5(4H)-yl)-1-methylcyclohexanecarboxylic acid To a mixture of (R)-N-(3'-((3-((3-hydroxypyrrolidin-1-yl)methyl)-1,7-naphthyridin-8-yl)amino)-2,2'-dimethyl-[1,1'-biphenyl]-3-yl)-1-methyl-4,5,6,7-tetrahydro-1H-imidazo[4,5-c]pyridine-2-carboxamide (0.025 g, 0.041 mmol) and 1-methyl-4-oxocyclohexane-1-carboxylic acid (Aurum Pharmatech, cat #U31985: 6.48 mg, 0.041 mmol) in $CH_2Cl_2$ (1.0 mL) was added triethylamine (0.012 mL, 0.207 mmol), and the reaction was stirred for 30 min at 40° C. Sodium triacetoxyborohydride (0.026 g, 0.124 mmol) was added and stirred at 40° C. for 4 h. The mixture was diluted with acetonitrile/water, acidified to pH=2 and purified by prep HPLC (pH=2, acetonitrile/water+TFA) to provide the two desired compounds as TFA salts.

Peak 1: retention time on analytical LCMS (pH=2, acetonitrile/water+TFA) $t_r$=0.686 min; LC-MS calculated for $C_{43}H_{51}N_8O_4$ $(M+H)^+$: m/z=743.4; found 743.4.

Peak 2: retention time on analytical LCMS (pH=2, acetonitrile/water+TFA) $t_r$=0.700 min; LC-MS calculated for $C_{43}H_{51}N_8O_4$ $(M+H)^+$: m/z=743.4; found 743.4.

Example 63 trans-4-(2-(2-(3'-(3-(((R)-3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c]pyridin-5(4H)-yl)ethyl)cyclohexanecarboxylic acid

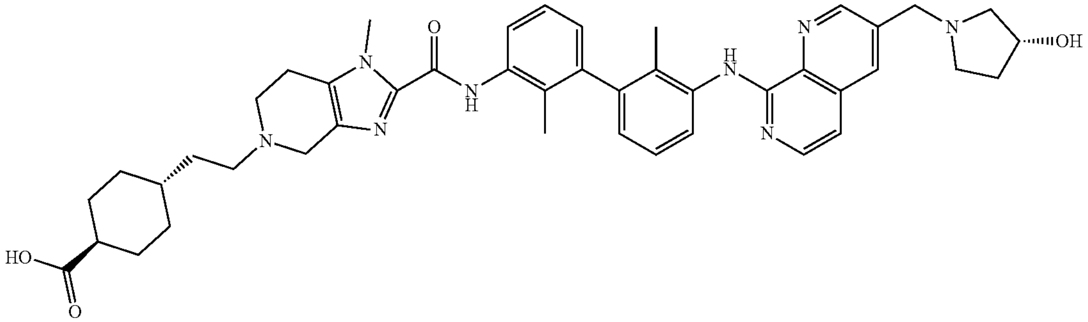 [SMILES: Cc1c(NC(=O)c2nc3c(n2C)CCN(CC[C@H]2CC[C@H](C(=O)O)CC2)C3)cccc1-c1cccc(Nc2nccc3cc(CN4CC[C@@H](O)C4)cnc23)c1C]

To a mixture of (R)-N-(3'-((3-((3-hydroxypyrrolidin-1-yl)methyl)-1,7-naphthyridin-8-yl)amino)-2,2'-dimethyl-[1,1'-biphenyl]-3-yl)-1-methyl-4,5,6,7-tetrahydro-1H-imidazo[4,5-c]pyridine-2-carboxamide (Example 62, Step 2: 0.025 g, 0.041 mmol) and methyl trans 4-(2-oxoethyl)cyclohexane-1-carboxylate (Enamine, cat #EN300-198655: 0.015 g, 0.083 mmol) in $CH_2Cl_2$ (1.0 mL) was added triethylamine (0.012 mL, 0.207 mmol). The resulting mixture was stirred for 10 min and then sodium triacetoxyborohydride (0.026 g, 0.124 mmol) was added and stirred at rt overnight. The solvent was removed and the crude was redissolved in methanol/THF/water (0.5/0.5/0.2 mL). LiOH monohydrate (20 mg) was added and the mixture was stirred at rt for 3 h. The mixture was diluted with acetonitrile/water, acidified to pH=2, and purified by prep HPLC (pH=2, acetonitrile/water+TFA) to provide the desired compound as its TFA salt. LC-MS calculated for $C_{44}H_{53}N_8O_4$ $(M+H)^+$: m/z=757.4; found 757.6.

Example 64

(R)-4-(2-(3'-(3-((3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c]pyridin-5(4H)-yl)cyclohexanecarboxylic acid

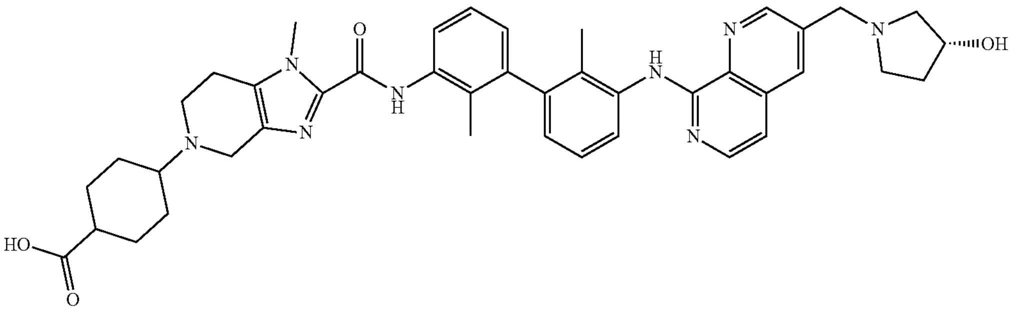 [SMILES: Cc1c(NC(=O)c2nc3c(n2C)CCN(C2CCC(C(=O)O)CC2)C3)cccc1-c1cccc(Nc2nccc3cc(CN4CC[C@@H](O)C4)cnc23)c1C]

To a mixture of (R)-N-(3'-((3-((3-hydroxypyrrolidin-1-yl)methyl)-1,7-naphthyridin-8-yl)amino)-2,2'-dimethyl-[1,1'-biphenyl]-3-yl)-1-methyl-4,5,6,7-tetrahydro-1H-imidazo[4,5-c]pyridine-2-carboxamide (Example 62, Step 2: 0.275 g, 0.456 mmol) and tert-butyl 4-oxocyclohexane-1-carboxylate (Ark Pharm, cat #AK-40114: 0.181 g, 0.912 mmol) in $CH_2Cl_2$ (1.0 mL) was added triethylamine (0.131 mL, 2.281 mmol). The mixture was stirred at 40° C. for 30 min and then sodium triacetoxyborohydride (0.290 g, 1.369 mmol) was added and stirred at rt overnight to provide (R)-tert-butyl 4-(2-(3'-(3-((3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c]pyridin-5(4H)-yl)cyclohexanecarboxylate as a mixture of cis & trans isomers which were separated by prep-HPLC (pH=10, acetonitrile/water+$NH_4OH$): Peak 1: retention time on analytical LCMS (pH=10, acetonitrile/water+$NH_4OH$), $t_r$=1.78 min; LC-MS calculated for $C_{46}H_{57}N_8O_4$ $(M+H)^+$: m/z=785.4; found 785.4. Peak 2: retention time on analytical LCMS (pH=10, acetonitrile/water+$NH_4OH$), $t_r$=1.82 min; LC-MS calculated for $C_{46}H_{57}N_8O_4$ $(M+H)^+$: m/z=785.4; found 785.4.

The fractions of each peak were combined, concentrated under reduced pressure, and the resulting residues were then treated with 4 N HCl (in dioxane) for 4 h. The respective mixtures were diluted with acetonitrile/water, acidified to pH=2 and purified by prep HPLC (pH=2, acetonitrile/water+TFA) to provide each isomer as its TFA salt.

Peak 1: retention time on analytical LCMS (pH=2, acetonitrile/water+TFA), $t_r$=0.656 min; LC-MS calculated for $C_{42}H_{49}N_8O_4$ $(M+H)^+$: m/z=729.4; found 729.4.

Peak 2: retention time on analytical LCMS (pH=2, acetonitrile/water+TFA), $t_r$=0.663 min; LC-MS calculated for $C_{42}H_{49}N_8O_4$ $(M+H)^+$: m/z=729.4; found 729.4.

Example 65

Trans-4-(2-(2-(2,2'-dichloro-3'-(3-(((R)-3-hydroxypyrrolidin-1-yl)methyl)-1,7-naphthyridin-8-ylamino)biphenyl-3-ylcarbamoyl)-1-methyl-6,7-dihydro-1H-imidazo[4,5-c]pyridin-5(4H)-yl)ethyl)cyclohexanecarboxylic acid

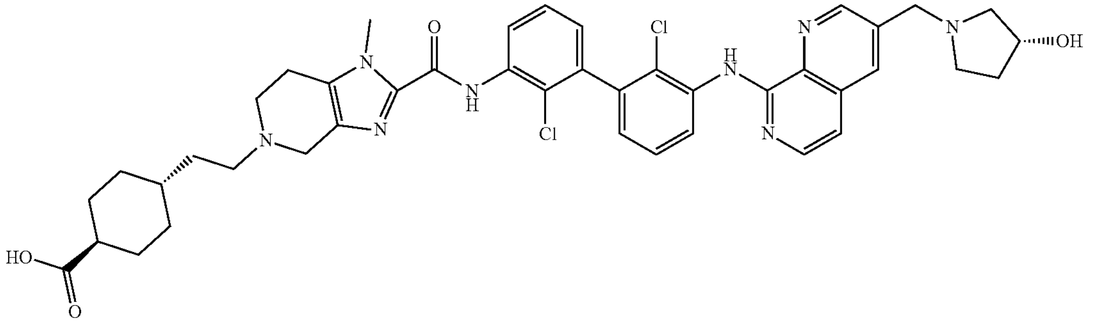 [SMILES: Cn1c(C(=O)Nc2cccc(-c3cccc(Nc4nccc5cc(CN6CC[C@@H](O)C6)cnc45)c3Cl)c2Cl)nc2c1CCN(CC[C@H]1CC[C@H](C(=O)O)CC1)C2]

Step 1: (R)-tert-butyl 2-(2,2'-dichloro-3'-(3-((3-hydroxypyrrolidin-1-yl)methyl)-1,7-naphthyridin-8-ylamino)biphenyl-3-ylcarbamoyl)-1-methyl-6,7-dihydro-1H-imidazo[4,5-c]pyridine-5(4H)-carboxylate

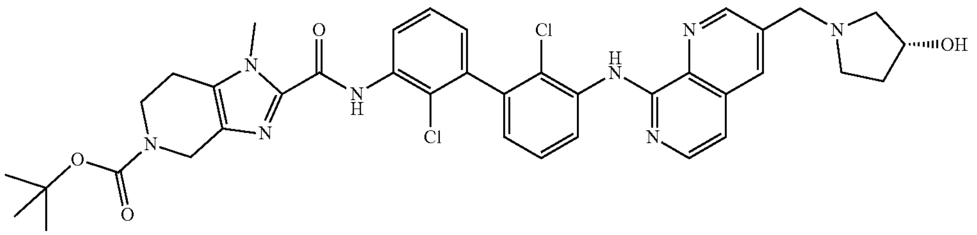 [SMILES: Cn1c(C(=O)Nc2cccc(-c3cccc(Nc4nccc5cc(CN6CC[C@@H](O)C6)cnc45)c3Cl)c2Cl)nc2c1CCN(C(=O)OC(C)(C)C)C2]

A mixture of tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 47, Step 1: 0.050 g, 0.097 mmol), (R)-1-((8-((3-bromo-2-chlorophenyl)amino)-1,7-naphthyridin-3-yl)methyl)pyrrolidin-3-ol (Example 22, Step 4: 0.046 g, 0.106 mmol), dichloro[1,1'-bis(dicyclohexylphosphino)ferrocene]palladium(II) (7.31 mg, 9.67 μmol) and cesium fluoride (0.073 g, 0.484 mmol) in t-BuOH (8.00 mL)/water (3.0 mL) was evacuated and flushed with $N_2$ 3 times. The reaction was stirred at 105° C. for 2 h. The mixture was diluted with ethyl acetate and washed with water and brine. The organic layer was separated, dried over $Na_2SO_4$, filtered, and concentrated under reduced pressure. The product was purified by column chromatography eluting with $CH_2Cl_2$/MeOH (9:1). LC-MS calculated for $C_{38}H_{41}C_{12}N_8O_4$ $(M+H)^+$: m/z=743.3; found 743.3.

Step 2: (R)-N-(2,2'-dichloro-3'-(3-((3-hydroxypyrrolidin-1-yl)methyl)-1,7-naphthyridin-8-ylamino)biphenyl-3-yl)-1-methyl-4,5,6,7-tetrahydro-1H-imidazo[4,5-c]pyridine-2-carboxamide

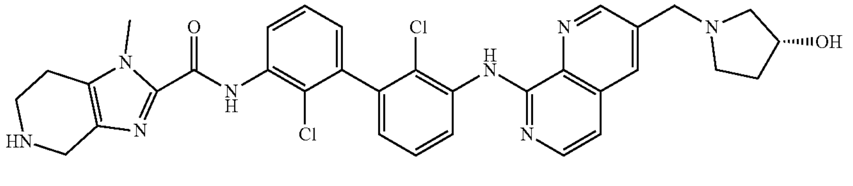 [SMILES: Cn1c(C(=O)Nc2cccc(-c3cccc(Nc4nccc5cc(CN6CC[C@@H](O)C6)cnc45)c3Cl)c2Cl)nc2c1CCNC2]

This compound was prepared using a similar procedure as described for Example 47, Step 4 with (R)-tert-butyl 2-(2,2'-dichloro-3'-(3-((3-hydroxypyrrolidin-1-yl)methyl)-1,7-naphthyridin-8-ylamino)biphenyl-3-ylcarbamoyl)-1-methyl-6,7-dihydro-1H-imidazo[4,5-c]pyridine-5(4H)-carboxylate replacing tert-butyl (R)-2-((2-chloro-3'-((3-((3-hydroxypyrrolidin-1-yl)methyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridine-5-carboxylate. LC-MS calculated for $C_{33}H_{33}Cl_2N_8O_2$ $(M+H)^+$: m/z=643.2; found 643.2.

Step 3: Trans 4-(2-(2-(2,2'-dichloro-3'-(3-(((R)-3-hydroxypyrrolidin-1-yl)methyl)-1,7-naphthyridin-8-ylamino)biphenyl-3-ylcarbamoyl)-1-methyl-6,7-dihydro-1H-imidazo[4,5-c]pyridin-5(4H)-yl)ethyl)cyclohexanecarboxylic acid This compound was prepared using a similar procedure as described for Example 63 with (R)-N-(2,2'-dichloro-3'-((3-((3-hydroxypyrrolidin-1-yl)methyl)-1,7-naphthyridin-8-yl)amino)-[1,1'-biphenyl]-3-yl)-1-methyl-4,5,6,7-tetrahydro-1H-imidazo[4,5-c]pyridine-2-carboxamide replacing (R)-N-(3'-((3-((3-hydroxypyrrolidin-1-yl)methyl)-1,7-naphthyridin-8-yl)amino)-2,2'-dimethyl-[1,1'-biphenyl]-3-yl)-1-methyl-4,5,6,7-tetrahydro-1H-imidazo[4,5-c]pyridine-2-carboxamide. LC-MS calculated for $C_{42}H_{47}Cl_2N_8O_4$ $(M+H)^+$: m/z=797.3; found 797.2.

Example 66 trans 4-(2-(2-(2'-chloro-3'-(3-(((R)-3-hydroxypyrrolidin-1-yl)methyl)-1,7-naphthyridin-8-ylamino)-2-methylbiphenyl-3-ylcarbamoyl)-1-methyl-6,7-dihydro-1H-imidazo[4,5-c]pyridin-5(4H)-yl)ethyl)cyclohexanecarboxylic acid

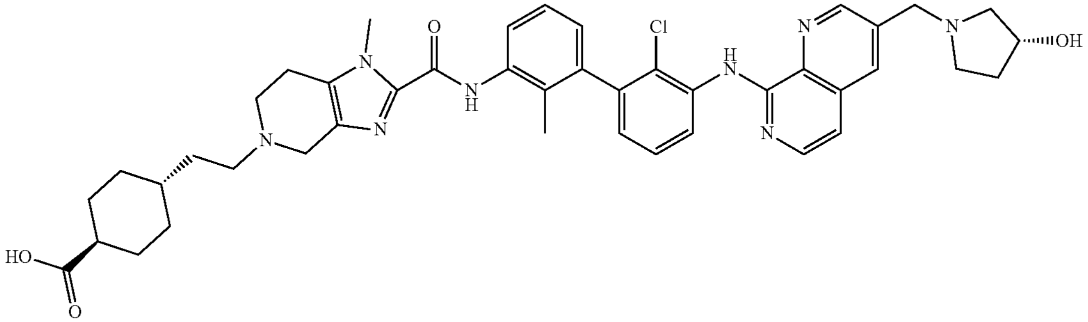 [SMILES: Cc1c(NC(=O)c2nc3c(n2C)CCN(CC[C@H]2CC[C@H](C(=O)O)CC2)C3)cccc1-c1cccc(Nc2nccc3cc(CN4CC[C@@H](O)C4)cnc23)c1Cl]

Step 1: (R)-tert-butyl 2-(2'-chloro-3'-(3-((3-hydroxypyrrolidin-1-yl)methyl)-1,7-naphthyridin-8-ylamino)-2-methylbiphenyl-3-ylcarbamoyl)-1-methyl-6,7-dihydro-1H-imidazo[4,5-c]pyridine-5(4H)-carboxylate

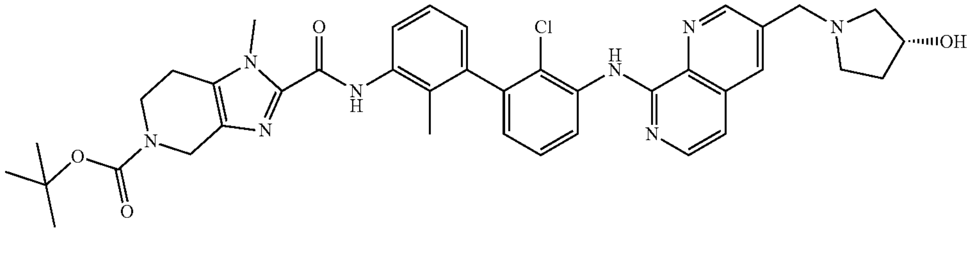 [SMILES: Cc1c(NC(=O)c2nc3c(n2C)CCN(C(=O)OC(C)(C)C)C3)cccc1-c1cccc(Nc2nccc3cc(CN4CC[C@@H](O)C4)cnc23)c1Cl]

This compound was prepared using a similar procedure as described for Example 65 with tert-butyl 1-methyl-2-(2-methyl-3-(4,4,5,5-tetramethyl-1,3,2-dioxaborolan-2-yl)phenylcarbamoyl)-6,7-dihydro-1H-imidazo[4,5-c]pyridine-5(4H)-carboxylate (Example 14, Step 3) replacing tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate in Step 1. LC-MS calculated for $C_{39}H_{44}ClN_8O_4(M+H)^+$: m/z=723.3; found 723.3.

Step 2: (R)-N-(2'-chloro-3'-(3-((3-hydroxypyrrolidin-1-yl)methyl)-1,7-naphthyridin-8-ylamino)-2-methylbiphenyl-3-yl)-1-methyl-4,5,6,7-tetrahydro-1H-imidazo[4,5-c]pyridine-2-carboxamide

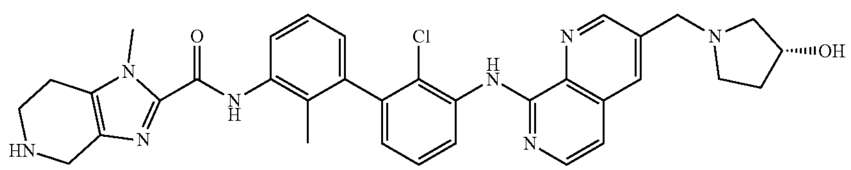 [SMILES: Cc1c(NC(=O)c2nc3c(n2C)CCNC3)cccc1-c1cccc(Nc2nccc3cc(CN4CC[C@@H](O)C4)cnc23)c1Cl]

This compound was prepared using a similar procedure as described for Example 47 with (R)-tert-butyl 2-(2'-chloro-3'-(3-((3-hydroxypyrrolidin-1-yl)methyl)-1,7-naphthyridin-8-ylamino)-2-methylbiphenyl-3-ylcarbamoyl)-1-methyl-6,7-dihydro-1H-imidazo[4,5-c]pyridine-5(4H)-carboxylate replacing tert-butyl (R)-2-((2-chloro-3'-((3-((3-hydroxypyrrolidin-1-yl)methyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridine-5-carboxylate in Step 4. LC-MS calculated for $C_{34}H_{36}ClN_8O_2(M+H)^+$: m/z=623.3; found 623.3.

Step 3: trans 4-(2-(2-(2'-chloro-3'-(3-(((R)-3-hydroxypyrrolidin-1-yl)methyl)-1,7-naphthyridin-8-ylamino)-2-methylbiphenyl-3-ylcarbamoyl)-1-methyl-6,7-dihydro-1H-imidazo[4,5-c]pyridin-5(4H)-yl)ethyl)cyclohexanecarboxylic acid This compound was prepared using a similar procedure as described for Example 63 with (R)-N-(2'-chloro-3'-(3-((3-hydroxypyrrolidin-1-yl)methyl)-1,7-naphthyridin-8-ylamino)-2-methylbiphenyl-3-yl)-1-methyl-4,5,6,7-tetrahydro-1H-imidazo[4,5-c]pyridine-2-carboxamide replacing (R)-N-(3'-((3-((3-hydroxypyrrolidin-1-yl)methyl)-1,7-naphthyridin-8-yl)amino)-2,2'-dimethyl-[1,1'-biphenyl]-3-yl)-1-methyl-4,5,6,7-tetrahydro-1H-imidazo[4,5-c]pyridine-2-carboxamide. LC-MS calculated for $C_{43}H_{50}ClN_8O_4(M+H)^+$: m/z=777.4; found 777.4.

Example 67

(R)-1-((4-(2'-chloro-3'-(1,5-dimethyl-4,5,6,7-tetrahydro-1H-imidazo[4,5-c]pyridine-2-carboxamido)-2-methylbiphenyl-3-ylamino)pyrido[3,2-d]pyrimidin-7-yl)methyl)-3-methylpyrrolidine-3-carboxylic acid

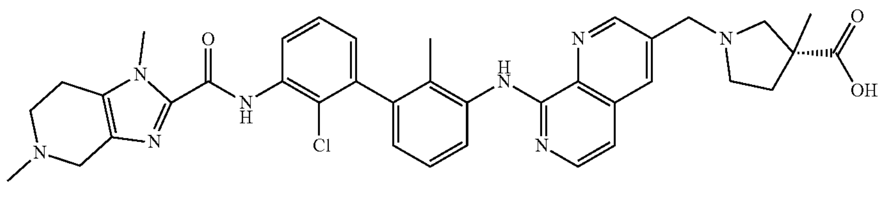 [SMILES: Cc1c(Nc2nccc3cc(CN4CC[C@@](C)(C(=O)O)C4)cnc23)cccc1-c1cccc(NC(=O)c2nc3c(n2C)CCN(C)C3)c1Cl]

Step 1: tert-butyl 2-(3'-amino-2-chloro-2'-methylbiphenyl-3-ylcarbamoyl)-1-methyl-6,7-dihydro-1H-imidazo[4,5-c]pyridine-5(4H)-carboxylate

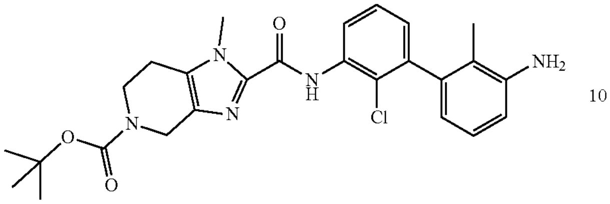

A mixture of tert-butyl 2-((3-bromo-2-chlorophenyl)carbamoyl)-1-methyl-1,4,6,7-tetrahydro-5H-imidazo[4,5-c]pyridine-5-carboxylate (Example 31, Step 3: 0.470 g, 1.0 mmol), 2-methyl-3-(4,4,5,5-tetramethyl-1,3,2-dioxaborolan-2-yl)aniline (Combi-Blocks, cat #PN-9127: 0.233 g, 1.000 mmol), dichloro[1,1'-bis(diphenylphosphino)ferrocene]palladium (II) dichloromethane adduct (0.082 g, 0.100 mmol) and sodium carbonate (0.212 g, 2.000 mmol) in dioxane (6 mL)/water (2 mL) was evacuated under vacuum and flushed with $N_2$ 3 times. The reaction was stirred at 110° C. overnight. The mixture was diluted with ethyl acetate and washed with saturated $NaHCO_3$, water, and brine. The organic phase was separated and dried over $Na_2SO_4$, filtered, and concentrated under reduced pressure. The product was purified by silica gel chromatography using $CH_2Cl_2$/EtOAc (1:1). LC-MS calculated for $C_{26}H_{31}ClN_5O_3(M+H)^+$: m/z=496.2; found 496.1.

Step 2: tert-butyl 2-(3'-(7-bromopyrido[3,2-d]pyrimidin-4-ylamino)-2-chloro-2'-methylbiphenyl-3-ylcarbamoyl)-1-methyl-6,7-dihydro-1H-imidazo[4,5-c]pyridine-5(4H)-carboxylate

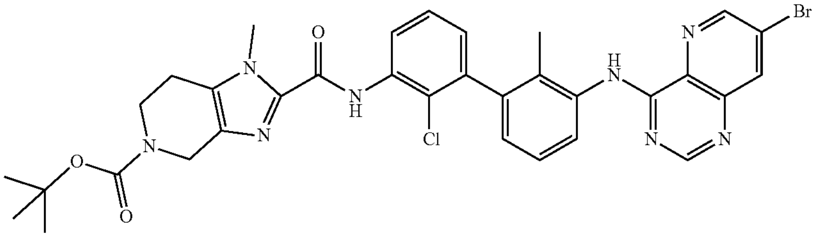 [SMILES: Cc1c(Nc2ncnc3cc(Br)cnc23)cccc1-c1cccc(NC(=O)c2nc3c(n2C)CCN(C(=O)OC(C)(C)C)C3)c1Cl]

7-Bromo-4-chloropyrido[3,2-d]pyrimidine (Synthonix, cat #B0473: 0.217 g, 0.887 mmol) was added to a mixture of tert-butyl 2-((3'-amino-2-chloro-2'-methyl-[1,1'-biphenyl]-3-yl)carbamoyl)-1-methyl-1,4,6,7-tetrahydro-5H-imidazo[4,5-c]pyridine-5-carboxylate (0.40 g, 0.806 mmol) and triethylamine (0.225 mL, 1.613 mmol) in 2-propanol (5.0 mL) at rt. The reaction was stirred at 100° C. for 2 h. Diethyl ether (5.0 mL) was added to the reaction mixture and the resulting precipitate was filtered and dried to provide the crude product which was used directly in the next step without further purification. LC-MS calculated for $C_{33}H_{33}BrClN_8O_3(M+H)^+$: m/z=703.2; found 703.3.

Step 3: tert-butyl 2-(2-chloro-2'-methyl-3'-(7-vinylpyrido[3,2-d]pyrimidin-4-ylamino)biphenyl-3-ylcarbamoyl)-1-methyl-6,7-dihydro-1H-imidazo[4,5-c]pyridine-5(4H)-carboxylate

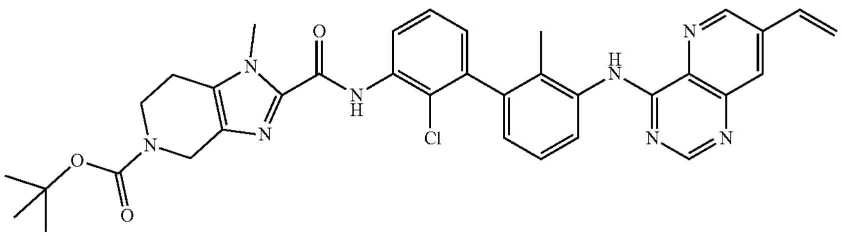 [SMILES: C=Cc1cnc2c(Nc3cccc(-c4cccc(NC(=O)c5nc6c(n5C)CCN(C(=O)OC(C)(C)C)C6)c4Cl)c3C)ncnc2c1]

A mixture of tert-butyl 2-((3'-((7-bromopyrido[3,2-d]pyrimidin-4-yl)amino)-2-chloro-2'-methyl-[1,1'-biphenyl]-3-yl)carbamoyl)-1-methyl-1,4,6,7-tetrahydro-5H-imidazo[4,5-c]pyridine-5-carboxylate (0.35 g, 0.497 mmol), 4,4,5,5-tetramethyl-2-vinyl-1,3,2-dioxaborolane (Aldrich, cat #663348: 0.115 g, 0.746 mmol), dichloro[1,1'-bis(diphenylphosphino)ferrocene]-palladium (II) dichloromethane adduct (0.041 g, 0.050 mmol) and sodium carbonate (0.105 g, 0.994 mmol) in dioxane (6 mL)/water (2 mL) was evacuated under vacuum and flushed with $N_2$ 3 times. The reaction was stirred at 110° C. for 2 h. The mixture was diluted with ethyl acetate and washed with saturated $NaHCO_3$, water, and brine. The organic phase was separated, dried over $Na_2SO_4$, and concentrated under reduced pressure. The product was purified by column chromatography using $CH_2Cl_2$/EtOAc (7:3). LC-MS calculated for $C_{35}H_{36}ClN_8O_3(M+H)^+$: m/z=651.3; found 651.2.

Step 4: tert-butyl 2-(2-chloro-3'-(7-formylpyrido[3,2-d]pyrimidin-4-ylamino)-2'-methylbiphenyl-3-ylcarbamoyl)-1-methyl-6,7-dihydro-1H-imidazo[4,5-c]pyridine-5(4H)-carboxylate

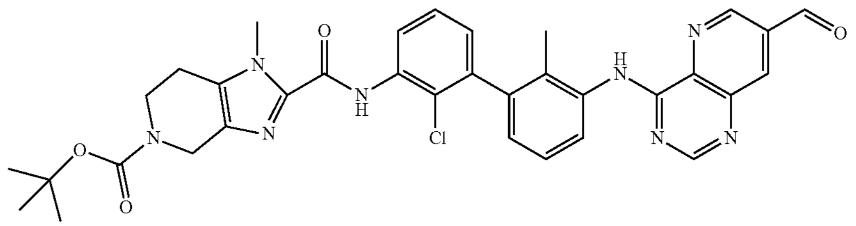 [SMILES: Cc1c(Nc2ncnc3cc(C=O)cnc23)cccc1-c1cccc(NC(=O)c2nc3c(n2C)CCN(C(=O)OC(C)(C)C)C3)c1Cl]

A vial was charged with tert-butyl 2-((2-chloro-2'-methyl-3'-((7-vinylpyrido[3,2-d]pyrimidin-4-yl)amino)-[1,1'-biphenyl]-3-yl)carbamoyl)-1-methyl-1,4,6,7-tetrahydro-5H-imidazo[4,5-c]pyridine-5-carboxylate (10.0 mg, 0.015 mmol), a stir bar, THF (2.0 mL) and water (0.8 mL). To this suspension was added a 4% w/w mixture of osmium tetroxide in water (12.0 μL, 1.529 μmol). The reaction was stirred for 5 min then sodium periodate (16.42 mg, 0.077 mmol) was added. After stirring at rt for 1 h, the reaction was quenched with a saturated aqueous solution of sodium thiosulfate. The mixture was then extracted with ethyl acetate (2×10 mL), and the combined organic layers were washed with brine, dried over $Na_2SO_4$, filtered, and concentrated in vacuo. The crude residue was used directly in the next step. LC-MS calculated for $C_{34}H_{34}ClN_8O_4(M+H)^+$: m/z=653.2; found 653.2.

Step 5: (R)-1-((4-(2'-chloro-2-methyl-3'-(1-methyl-4,5,6,7-tetrahydro-1H-imidazo[4,5-c]pyridine-2-carboxamido)biphenyl-3-ylamino)pyrido[3,2-d]pyrimidin-7-yl)methyl)-3-methylpyrrolidine-3-carboxylic acid

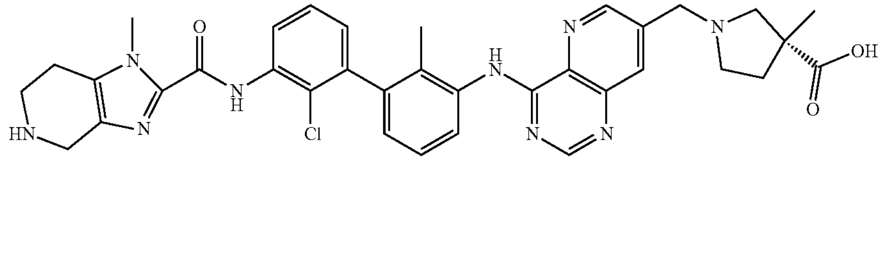 [SMILES: Cc1c(Nc2ncnc3cc(CN4CC[C@@](C)(C(=O)O)C4)cnc23)cccc1-c1cccc(NC(=O)c2nc3c(n2C)CCNC3)c1Cl]

(R)-3-methylpyrrolidine-3-carboxylic acid (J&W Pharm-Lab, cat #75R0495: 0.015 g, 0.115 mmol) was added to a suspension of tert-butyl 2-((2-chloro-3'-((7-formylpyrido[3,2-d]pyrimidin-4-yl)amino)-2'-methyl-[1,1'-biphenyl]-3-yl)carbamoyl)-1-methyl-1,4,6,7-tetrahydro-5H-imidazo[4,5-c]pyridine-5-carboxylate (0.025 g, 0.038 mmol) in $CH_2Cl_2$ (1.0 mL). Triethylamine (0.043 mL, 0.306 mmol) was added and the mixture was stirred at rt for 1 h. At this time sodium triacetoxyborohydride (0.024 g, 0.115 mmol) was added and then stirred at rt for 2 h. The reaction was quenched with water, extracted with $CH_2Cl_2$/iPrOH, and the layers were separated. The organic phase was dried over $Na_2SO_4$, filtered, and concentrated under reduced pressure. The resulting crude residue was redissolved in $CH_2Cl_2$ (0.2 mL) and then TFA (0.5 mL) was added and the reaction was stirred at rt for 30 min. The solvent was removed and the crude product was used directly in the next step. LC-MS calculated for $C_{35}H_{37}ClN_9O_3$ $(M+H)^+$: m/z=666.3; found 666.5.

Step 6: (R)-1-((4-(2'-chloro-3'-(1,5-dimethyl-4,5,6,7-tetrahydro-1H-imidazo[4,5-c]pyridine-2-carboxamido)-2-methylbiphenyl-3-ylamino)pyrido[3,2-dl]pyrimidin-7-yl)methyl)-3-methylpyrrolidine-3-carboxylic acid Formaldehyde (4.5 mg, 0.15 mmol) was added to a mixture of (R)-1-((4-(2'-chloro-2-methyl-3'-(1-methyl-4,5,6,7-tetrahydro-1H-imidazo[4,5-c]pyridine-2-carboxamido)biphenyl-3-ylamino)pyrido[3,2-d]pyrimidin-7-yl)methyl)-3-methylpyrrolidine-3-carboxylic acid (20. mg, 0.03 mmol) in $CH_2Cl_2$ (1.0 mL) followed by the addition of triethylamine (0.021 mL, 0.15 mmol). The mixture was stirred at rt for 10 min. At this time sodium triacetoxyborohydride (19 mg, 0.09 mmol) was added and then stirred at rt for 30 min. The mixture was diluted with acetonitrile/water, acidified to pH=2 and purified by prep HPLC (pH=2, acetonitrile/water+TFA) to provide the desired compound as its TFA salt. LC-MS calculated for $C_{36}H_{39}ClN_9O_3(M+H)^+$: m/z=680.3; found 680.4.

Example 68

(R)-4-(2-(2-chloro-3'-(7-((3-hydroxypyrrolidin-1-yl)methyl)pyrido[3,2-d]pyrimidin-4-ylamino)-2'-methylbiphenyl-3-ylcarbamoyl)-1-methyl-6,7-dihydro-1H-imidazo[4,5-c]pyridin-5(4H)-yl)-1-methylcyclohexanecarboxylic acid

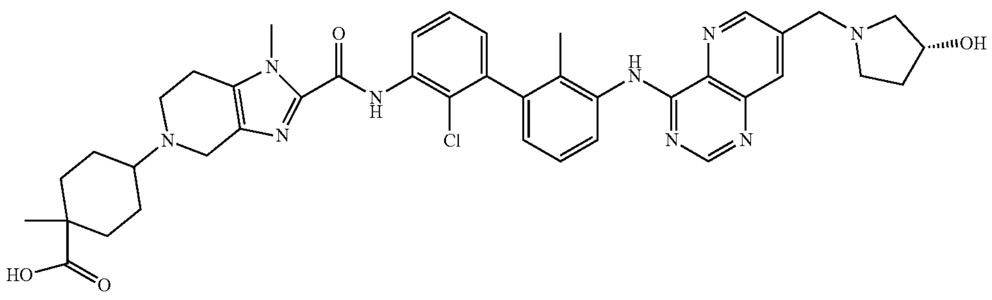 [SMILES: Cc1c(Nc2ncnc3cc(CN4CC[C@@H](O)C4)cnc23)cccc1-c1cccc(NC(=O)c2nc3c(n2C)CCN(C2CCC(C)(C(=O)O)CC2)C3)c1Cl]

Step 1: (R)-tert-butyl 2-(2-chloro-3'-(7-((3-hydroxypyrrolidin-1-yl)methyl)pyrido[3,2-d]pyrimidin-4-ylamino)-2'-methylbiphenyl-3-ylcarbamoyl)-1-methyl-6,7-dihydro-1H-imidazo[4,5-c]pyridine-5(4H)-carboxylate

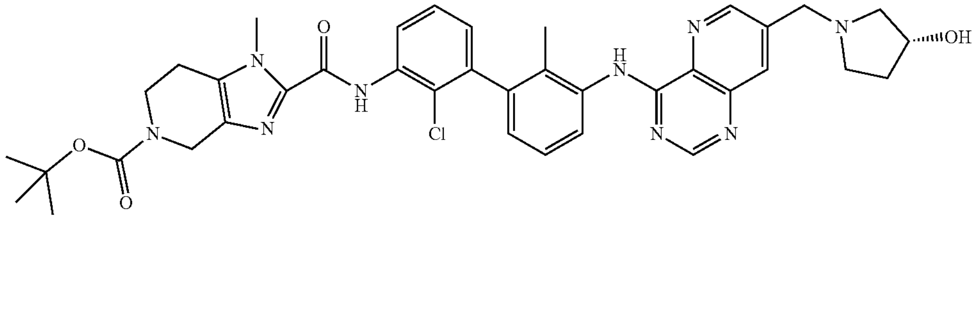 [SMILES: Cc1c(Nc2ncnc3cc(CN4CC[C@@H](O)C4)cnc23)cccc1-c1cccc(NC(=O)c2nc3c(n2C)CCN(C(=O)OC(C)(C)C)C3)c1Cl]

A mixture of tert-butyl 2-((2-chloro-3'-((7-formylpyrido[3,2-d]pyrimidin-4-yl)amino)-2'-methyl-[1,1'-biphenyl]-3-yl)carbamoyl)-1-methyl-1,4,6,7-tetrahydro-5H-imidazo[4,5-c]pyridine-5-carboxylate (Example 67, Step 4: 0.10 g, 0.153 mmol) and (R)-pyrrolidin-3-ol (Combi-Blocks, cat #AM-2005: 0.027 g, 0.306 mmol) in $CH_2Cl_2$ (8.0 mL) was stirred at rt for 10 min. Sodium triacetoxyborohydride (0.097 g, 0.459 mmol) was then added and the mixture was stirred at rt for 2 h. The mixture was diluted with $CH_2Cl_2$, washed with 1 N NaOH, water, and brine. The organic phase was dried over $Na_2SO_4$, filtered and concentrated. The product was purified by silica gel chromatography eluting with $CH_2Cl_2$/MeOH (9:1). LC-MS calculated for $C_{38}H_{43}ClN_9O_4(M+H)^+$: m/z=724.3; found 724.5.

Step 2: (R)-N-(2-chloro-3'-(7-((3-hydroxypyrrolidin-1-yl)methyl)pyrido[3,2-d]pyrimidin-4-ylamino)-2'-methylbiphenyl-3-yl)-1-methyl-4,5,6,7-tetrahydro-1H-imidazo[4,5-c]pyridine-2-carboxamide

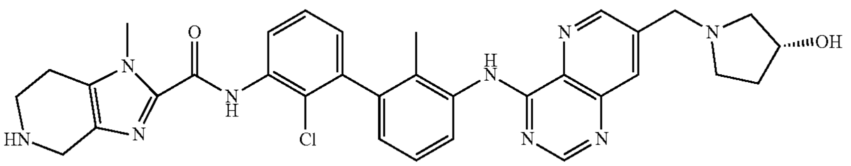 [SMILES: Cc1c(Nc2ncnc3cc(CN4CC[C@@H](O)C4)cnc23)cccc1-c1cccc(NC(=O)c2nc3c(n2C)CCNC3)c1Cl]

This compound was prepared using a similar procedure as described for Example 47 with (R)-tert-butyl 2-(2-chloro-3'-(7-((3-hydroxypyrrolidin-1-yl)methyl)pyrido[3,2-d]pyrimidin-4-ylamino)-2'-methylbiphenyl-3-ylcarbamoyl)-1-methyl-6,7-dihydro-1H-imidazo[4,5-c]pyridine-5(4H)-carboxylate replacing tert-butyl (R)-2-((2-chloro-3'-((3-((3-hydroxypyrrolidin-1-yl)methyl)-1,7-naphthyridin-8-yl)amino)-2'-methyl-[1,1'-biphenyl]-3-yl)carbamoyl)-1-methyl-1,4,6,7-tetrahydro-5H-imidazo[4,5-c]pyridine-5-carboxylate in Step 4. LC-MS calculated for $C_{33}H_{35}ClN_9O_2$ $(M+H)^+$: m/z=624.3; found 624.2.

Step 3: (R)-4-(2-(2-chloro-3'-(7-((3-hydroxypyrrolidin-1-yl)methyl)pyrido[3,2-d]pyrimidin-4-ylamino)-2'-methylbiphenyl-3-ylcarbamoyl)-1-methyl-6,7-dihydro-1H-imidazo[4,5-c]pyridin-5(4H)-yl)-1-methylcyclohexanecarboxylic acid This compound was prepared using a similar procedure as described for Example 62 with (R)-N-(2-chloro-3'-(7-((3-hydroxypyrrolidin-1-yl)methyl)pyrido[3,2-d]pyrimidin-4-ylamino)-2'-methylbiphenyl-3-yl)-1-methyl-4,5,6,7-tetrahydro-1H-imidazo[4,5-c]pyridine-2-carboxamide replacing (R)-N-(3'-((3-((3-hydroxypyrrolidin-1-yl)methyl)-1,7-naphthyridin-8-yl)amino)-2,2'-dimethyl-[1,1'-biphenyl]-3-yl)-1-methyl-4,5,6,7-tetrahydro-1H-imidazo[4,5-c]pyridine-2-carboxamide in Step 3.

Peak 1: retention time on analytical LCMS (pH=2, acetonitrile/water+TFA) $t_r$=0.796 min; LC-MS calculated for $C_{41}H_{47}ClN_9O_4(M+H)^+$: m/z=764.3; found 764.4.

Peak 2: retention time on analytical LCMS (pH=2, acetonitrile/water+TFA) $t_r$=0.805 min; LC-MS calculated for $C_{41}H_{47}ClN_9O_4(M+H)^+$: m/z=764.3; found 764.4.

Example 69 trans 4-((2-(2-chloro-3'-(7-(((R)-3-hydroxypyrrolidin-1-yl)methyl)pyrido[3,2-d]pyrimidin-4-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid

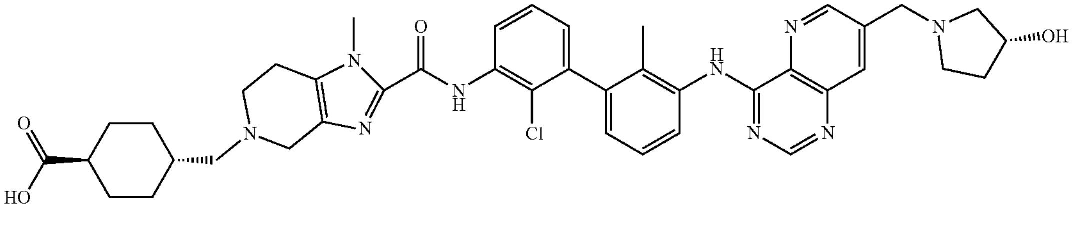 [SMILES: Cc1c(Nc2ncnc3cc(CN4CC[C@@H](O)C4)cnc23)cccc1-c1cccc(NC(=O)c2nc3c(n2C)CCN(C[C@H]2CC[C@H](C(=O)O)CC2)C3)c1Cl]

This compound was prepared using a similar procedure as described for Example 47 with (R)-N-(2-chloro-3'-(7-((3-hydroxypyrrolidin-1-yl)methyl)pyrido[3,2-d]pyrimidin-4-ylamino)-2'-methylbiphenyl-3-yl)-1-methyl-4,5,6,7-tetrahydro-1H-imidazo[4,5-c]pyridine-2-carboxamide (Example 68, Step 2) replacing (R)-N-(2-chloro-3'-((3-((3-hydroxypyrrolidin-1-yl)methyl)-1,7-naphthyridin-8-yl)amino)-2'-methyl-[1,1'-biphenyl]-3-yl)-1-methyl-4,5,6,7-tetrahydro-1H-imidazo[4,5-c]pyridine-2-carboxamide in Step 5. LC-MS calculated for $C_{41}H_{47}ClN_9O_4(M+H)^+$: m/z=764.3; found 764.5.

Example 70

(R)-1-((5-(3'-(3-(((R)-3-hydroxypyrrolidin-1-yl)methyl)-1,7-naphthyridin-8-ylamino)-2,2'-dimethylbiphenyl-3-ylamino)pyrido[4,3-b]pyrazin-2-yl)methyl)pyrrolidine-3-carboxylic acid

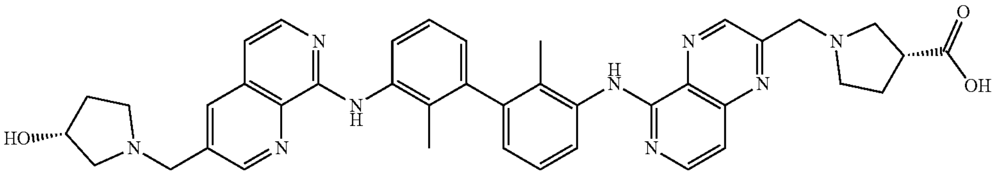

Step 1: 5-(3-chloro-2-methylphenylamino)pyrido[4,3-b]pyrazin-2(1H)-one

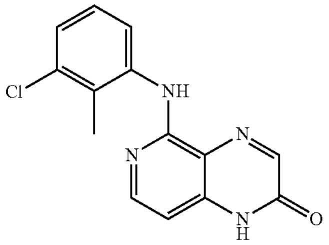 [SMILES: Cc1c(Cl)cccc1Nc1nccc2[nH]c(=O)cnc12]

In a vial was combined 3-chloro-2-methylaniline (Aldrich, cat #101621: 351 mg, 2.478 mmol), 5-chloropyrido[3,4-b]pyrazin-2(1H)-one (Ark Pharm, cat #AK329687: 500 mg, 2.75 mmol), isopropanol (5.0 mL), and sulfuric acid (0.147 mL, 2.75 mmol). The vial was sealed, then the reaction was heated to 100° C. for 1 hour. The mixture was cooled to rt, quenched with sat. $NaHCO_3$, diluted with ethyl acetate and the layers were separated. The aqueous layer was further extracted with ethyl acetate, and the combined organic layers were washed with brine, dried over $MgSO_4$, and filtered. The filtrate was concentrated in vacuo and the crude residue was purified by silica gel chromatography (50% EtOAc/hexanes) to provide the desired compound as a yellow oil. LC-MS calculated for $C_{14}H_{12}ClN_4O$ $(M+H)^+$: m/z=287.1; found 287.1.

Step 2: 2-bromo-N-(3-chloro-2-methylphenyl)pyrido[4,3-b]pyrazin-5-amine

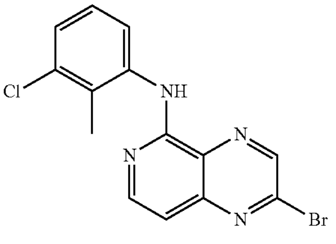 [SMILES: Cc1c(Cl)cccc1Nc1nccc2nc(Br)cnc12]

In a vial, a mixture of 5-(3-chloro-2-methylphenylamino)pyrido[4,3-b]pyrazin-2(1H)-one (200 mg, 0.698 mmol), phosphorus (V) oxybromide (1000 mg, 3.49 mmol), and MeCN (6.0 mL) was stirred at 80° C. for 4 hours. The mixture was cooled to rt, quenched with sat. $NaHCO_3$, diluted with ethyl acetate and the layers were separated. The aqueous layer was further extracted with ethyl acetate, and the combined organic layers were washed with brine, dried over $MgSO_4$, and filtered. The filtrate was concentrated in vacuo and the crude residue was purified by silica gel chromatography (20% EtOAc/hexanes) to provide the desired compound as a brown oil. LC-MS calculated for $C_{14}H_{11}ClBrN_4$ $(M+H)^+$: m/z=349.0; found 349.0.

Step 3: N-(3-chloro-2-methylphenyl)-2-vinylpyrido[4,3-b]pyrazin-5-amine

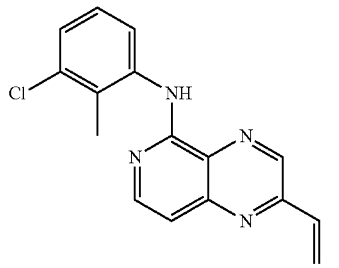 [SMILES: C=Cc1cnc2c(Nc3cccc(Cl)c3C)nccc2n1]

In a vial, a mixture of 2-bromo-N-(3-chloro-2-methylphenyl)pyrido[4,3-b]pyrazin-5-amine (30 mg, 0.086 mmol), 4,4,5,5-tetramethyl-2-vinyl-1,3,2-dioxaborolane (Aldrich, cat #663348: 29.1 μL, 0.172 mmol), sodium carbonate (27.3 mg, 0.257 mmol), palladiumtetrakis (9.92 mg, 8.58 μmol) and 1,4-dioxane (2.0 mL) was stirred at 90° C. for 2 hours. The mixture was cooled to rt, diluted with ethyl acetate and washed with water and brine, dried over $MgSO_4$, and filtered. The filtrate was concentrated in vacuo and the crude residue was purified by silica gel chromatography (20% EtOAc/hexanes) to provide the desired compound as a brown oil. LC-MS calculated for $C_{16}H_{14}ClN_4$ $(M+H)^+$: m/z=297.1; found 297.1.

Step 4: 5-(3-chloro-2-methylphenylamino)pyrido[4,3-b]pyrazine-2-carbaldehyde

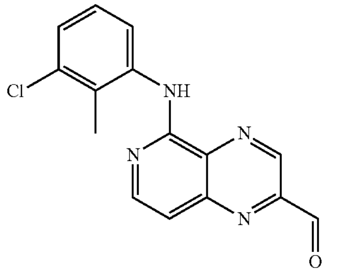 [SMILES: Cc1c(Cl)cccc1Nc1nccc2nc(C=O)cnc12]

A 10 mL vial was charged with N-(3-chloro-2-methylphenyl)-2-vinylpyrido[4,3-b]pyrazin-5-amine (25.6 mg, 0.086 mmol) 1,4-dioxane (2 mL) and water (2 mL). A 4% osmium tetroxide solution in water (38.2 μL, 6.01 μmol) was added to the reaction mixture. After 5 min, sodium periodate (147 mg, 0.686 mmol) was added. The reaction was stirred at rt for 2 hours before being quenched with sat. $NaHCO_3$. The resulting mixture was extracted with DCM, and the combined organic layers were washed with water and brine, dried over $MgSO_4$, and filtered. The filtrate was concentrated in vacuo and the crude residue was used directly in next step without further purification. LC-MS calculated for $C_{15}H_{12}ClN_4O$ $(M+H)^+$: m/z=299.1; found 299.1.

Step 5: (R)-1-((5-(3-chloro-2-methylphenylamino)pyrido[4,3-b]pyrazin-2-yl)methyl)pyrrolidine-3-carboxylic acid

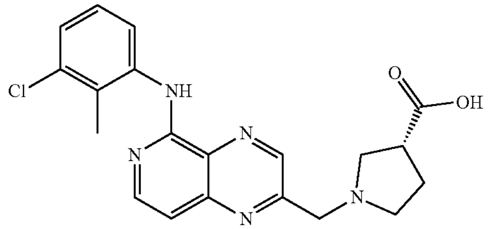 [SMILES: Cc1c(Cl)cccc1Nc1nccc2nc(CN3CC[C@@H](C(=O)O)C3)cnc12]

A 10 mL vial was charged with 5-(3-chloro-2-methylphenylamino)pyrido[4,3-b]pyrazine-2-carbaldehyde (10.0 mg, 0.033 mmol), (R)-pyrrolidine-3-carboxylic acid (Combi-Blocks, cat #ST-7698: 5.8 mg, 0.050 mmol) and DCM (1 mL). Triethylamine (9.3 μl, 0.067 mmol) and sodium triacetoxyborohydride (14.2 mg, 0.067 mmol) were added subsequently. The resulting reaction mixture was stirred at rt overnight before being quenched with sat. $NaHCO_3$. The resulting mixture was extracted with a 3:1 DCM/IPA mixture, and the combined organic layers were washed with water and brine, dried over $MgSO_4$, and filtered. The filtrate was concentrated in vacuo and the crude residue was used directly in next step without further purification. LC-MS calculated for $C_{20}H_{21}ClN_5O_2$ $(M+H)^+$: m/z=398.1; found 398.1.

Step 6: (R)-1-((5-(3'-(3-(((R)-3-hydroxypyrrolidin-1-yl)methyl)-1,7-naphthyridin-8-ylamino)-2,2'-dimethylbiphenyl-3-ylamino)pyrido[4,3-b]pyrazin-2-yl)methyl)pyrrolidine-3-carboxylic acid A mixture of (R)-1-((5-(3-chloro-2-methylphenylamino)pyrido[4,3-b]pyrazin-2-yl)methyl)pyrrolidine-3-carboxylic acid (10.0 mg, 0.025 mmol), (R)-1-((8-((2-methyl-3-(4,4,5,5-tetramethyl-1,3,2-dioxaborolan-2-yl)phenyl)amino)-1,7-naphthyridin-3-yl)methyl)pyrrolidin-3-ol (Example 37, step 9: 23.14 mg, 0.050 mmol), XPhos Pd G2 (2.0 mg, 2.51 μmol), and sodium carbonate (5.3 mg, 0.050 mmol) in 1,4-dioxane (1 mL) and water (0.2 mL) was degassed and sealed. It was stirred at 90° C. overnight. The reaction mixture was cooled then diluted with methanol, then purified with prep-LC-MS (pH=2, acetonitrile/water+TFA) to give the desired product as its TFA salt. LC-MS calculated for $C_{40}H_{42}N_9O_3$ $(M+H)^+$: m/z=696.3; found 696.3.

Example 71

(3R)-1-((8-(2,2'-dimethyl-3'-(3-(pyrrolidin-2-yl)-1,7-naphthyridin-8-ylamino)biphenyl-3-ylamino)-1,7-naphthyridin-3-yl)methyl)pyrrolidine-3-carboxylic acid

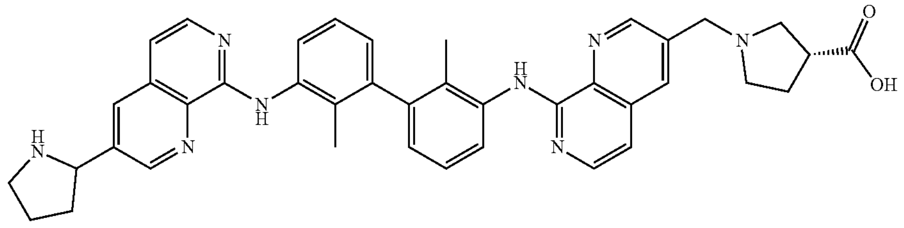 [SMILES: Cc1c(Nc2nccc3cc(CN4CC[C@@H](C(=O)O)C4)cnc23)cccc1-c1cccc(Nc2nccc3cc(C4CCCN4)cnc23)c1C]

Step 1: tert-butyl 4-(8-chloro-1,7-naphthyridin-3-yl)-4-oxobutylcarbamate

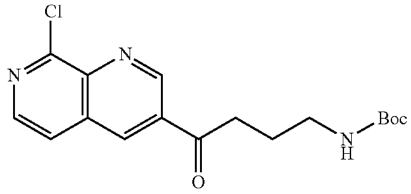 [SMILES: CC(C)(C)OC(=O)NCCCC(=O)c1cnc2c(Cl)nccc2c1]

To a solution of 3-bromo-8-chloro-1,7-naphthyridine (PharmaBlock, cat #PBLJ2743: 100.2 mg, 0.411 mmol) in THF (10 mL) was added n-butyllithium (1.6 M, 0.26 mL, 0.411 mmol) dropwise at −78° C. After stirring at this temperature for 1 hour, tert-butyl 2-oxopyrrolidine-1-carboxylate (0.14 mL, 0.821 mmol) was added. The reaction was further stirred at −78° C. for 2 hours. After completion, the reaction mixture was quenched by adding sat. $NH_4Cl$, which was then extracted with EtOAc. The combined organic layers were washed with water and brine, dried over $MgSO_4$, and filtered. The filtrate was concentrated in vacuo and the crude residue was purified by silica gel chromatography (80% EtOAc/hexanes) to provide the desired compound as a brown oil. LC-MS calculated for $C_{17}H_{21}ClN_3O_3$ $(M+H)^+$: m/z=350.1; found 350.1.

Step 2: tert-butyl 2-(8-(3-bromo-2-methylphenylamino)-1,7-naphthyridin-3-yl)pyrrolidine-1-carboxylate

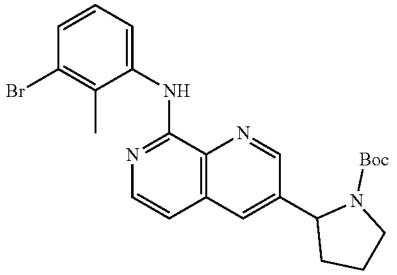 [SMILES: Cc1c(Br)cccc1Nc1nccc2cc(C3CCCN3C(=O)OC(C)(C)C)cnc12]

In a vial was combined 3-bromo-2-methylaniline (Aldrich, cat #530018: 51.1 mg, 0.274 mmol), tert-butyl (4-(8-chloro-1,7-naphthyridin-3-yl)-4-oxobutyl)carbamate (80.0 mg, 0.229 mmol), isopropanol (2.0 mL), and sulfuric acid (13.4 μl, 0.252 mmol). The vial was sealed, then the reaction was heated to 100° C. for 1 hour. The mixture was cooled to rt, quenched with solid $NaHCO_3$, diluted with ethyl acetate and filtered. The filtrate was concentrated in vacuo and the crude residue was dissolved in DCM (2.0 mL). Triethylamine (63.8 μl, 0.457 mmol) and sodium triacetoxyborohydride (72.7 mg, 0.343 mmol) were added to the above solution. The reaction was stirred at rt overnight before being quenched with sat. $NaHCO_3$. The resulting mixture was extracted with 3:1 DCM/IPA mixture, and the combined organic layers were washed with water and brine, dried over $MgSO_4$, and filtered. The filtrate was concentrated in vacuo and the crude residue was dissolved in dry DCM (4.0 mL) followed by addition of triethylamine (0.064 mL, 0.458 mmol) and Boc-anhydride (0.10 g, 0.458 mmol). The reaction mixture was stirred at rt for 2 hours before being quenched with sat. $NaHCO_3$. The resulting mixture was extracted with DCM, and the combined organic layers were washed with water and brine, dried over $MgSO_4$, and filtered. The filtrate was concentrated in vacuo and the residue was purified by silica gel chromatography (50% EtOAc/hexanes) to provide the desired compound as a yellow oil. LC-MS calculated for $C_{2-4}H_{28}BrN_4O_2(M+H)^+$: m/z=483.1; found 483.1.

Step 3: tert-butyl 2-(8-(3'-(3-(hydroxymethyl)-1,7-naphthyridin-8-ylamino)-2,2'-dimethylbiphenyl-3-ylamino)-1,7-naphthyridin-3-yl)pyrrolidine-1-carboxylate

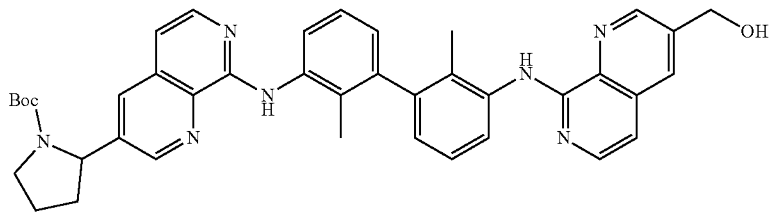 [SMILES: Cc1c(Nc2nccc3cc(CO)cnc23)cccc1-c1cccc(Nc2nccc3cc(C4CCCN4C(=O)OC(C)(C)C)cnc23)c1C]

A mixture of tert-butyl 2-(8-(3-bromo-2-methylphenylamino)-1,7-naphthyridin-3-yl)pyrrolidine-1-carboxylate (200 mg, 0.414 mmol), (8-(2-methyl-3-(4,4,5,5-tetramethyl-1,3,2-dioxaborolan-2-yl)phenylamino)-1,7-naphthyridin-3-yl)methanol (Example 20, step 3 23.1 mg, 0.050 mmol), tetrakis(triphenylphosphine)palladium(0) (47.8 mg, 0.041 mmol), and sodium carbonate (88 mg, 0.827 mmol) in 1,4-dioxane (10 mL) and water (2 mL) was degassed and sealed. It was stirred at 100° C. overnight. The reaction mixture was cooled and then diluted with EtOAc. The organic layer was washed with water and brine, dried over $MgSO_4$, and filtered. The filtrate was concentrated in vacuo and the crude residue was purified by silica gel chromatography (90% EtOAc/hexanes) to provide the desired compound as a brown oil. LC-MS calculated for $C_{40}H_{42}N_7O_3$ $(M+H)^+$: m/z=668.3; found 668.3.

Step 4: tert-butyl 2-(8-(3'-(3-formyl-1,7-naphthyridin-8-ylamino)-2,2'-dimethylbiphenyl-3-ylamino)-1,7-naphthyridin-3-yl)pyrrolidine-1-carboxylate

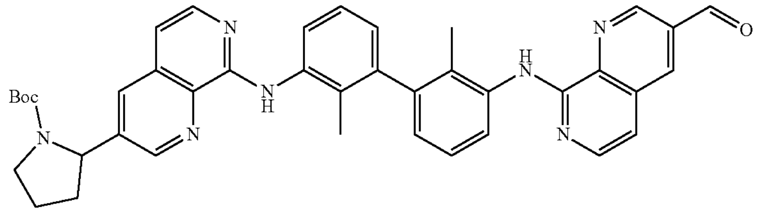 [SMILES: Cc1c(Nc2nccc3cc(C=O)cnc23)cccc1-c1cccc(Nc2nccc3cc(C4CCCN4C(=O)OC(C)(C)C)cnc23)c1C]

To a stirred solution of tert-butyl 2-(8-(3'-(3-(hydroxymethyl)-1,7-naphthyridin-8-ylamino)-2,2'-dimethylbiphenyl-3-ylamino)-1,7-naphthyridin-3-yl)pyrrolidine-1-carboxylate (276 mg, 0.414 mmol) in DCM (10.0 mL) was added manganese dioxide (719 mg, 8.27 mmol). The resulted mixture was stirred at 45° C. for 2 hours, then filtered. The filtrate was concentrated under reduced pressure. The residue was used in the next step directly without further purification. LC-MS calculated for $C_{40}H_{40}N_7O_3$ $(M+H)^+$: m/z=666.3; found 666.3.

Step 5: (3R)-1-((8-(2,2'-dimethyl-3'-(3-(pyrrolidin-2-yl)-1,7-naphthyridin-8-ylamino)biphenyl-3-ylamino)-1,7-naphthyridin-3-yl)methyl)pyrrolidine-3-carboxylic acid To a solution of tert-butyl 2-(8-(3'-(3-formyl-1,7-naphthyridin-8-ylamino)-2,2'-dimethylbiphenyl-3-ylamino)-1,7-naphthyridin-3-yl)pyrrolidine-1-carboxylate (20 mg, 0.030 mmol) in DCM (1 mL) was added (R)-pyrrolidine-3-carboxylic acid (Combi-Blocks, cat #ST-7698: 3.5 mg, 0.030 mmol) and triethylamine (8.4 μl, 0.060 mmol). The mixture was stirred at rt for 60 min, then sodium triacetoxyborohydride (9.6 mg, 0.045 mmol) was added. The resulting mixture was stirred at rt overnight before 1 mL of TFA was added. The reaction mixture was further stirred for 1 h. The reaction mixture was concentrated then purified with prep-LC-MS (pH 2, acetonitrile/water+TFA) to give the desired product as its TFA salt. LC-MS calculated for $C_{40}H_{41}N_8O_2$ $(M+H)^+$: m/z=665.3; found 665.3.

Example 72

(R)-1-((8-(2,2'-dichloro-3'-(3-((2-hydroxyethylamino)methyl)imidazo[1,2-a]pyrazin-8-ylamino)biphenyl-3-ylamino)-1,7-naphthyridin-3-yl)methyl)pyrrolidin-3-ol

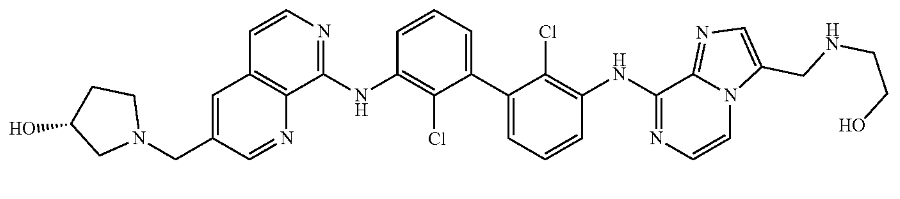 [SMILES: OCCNCc1cnc2c(Nc3cccc(-c4cccc(Nc5nccc6cc(CN7CC[C@@H](O)C7)cnc56)c4Cl)c3Cl)nccn12]

Step 1: (R)-1-((8-(3'-amino-2,2'-dichlorobiphenyl-3-ylamino)-1,7-naphthyridin-3-yl)methyl)pyrrolidin-3-ol

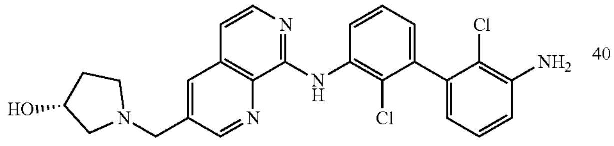

In a vial was combined 2-chloro-3-(4,4,5,5-tetramethyl-1,3,2-dioxaborolan-2-yl)aniline (Example 5, step 1: 0.474 g, 1.870 mmol), (R)-1-((8-((3-bromo-2-chlorophenyl)amino)-1,7-naphthyridin-3-yl)methyl)pyrrolidin-3-ol (Example 22, step 4: 0.676 g, 1.559 mmol), sodium carbonate (0.330 g, 3.12 mmol), (1,1'-bis(di-cyclohexylphosphino)ferrocene)-dichloropalladium(II) (Aldrich, cat #701998: 0.023 g, 0.031 mmol), 1,4-dioxane (2.92 mL) and water (0.974 mL). The mixture was degassed, sealed, and heated to 90° C. whilst stirring for 2 h. The mixture was cooled, diluted with EtOAc and filtered through celite. The filtrate was concentrated and purified using flash chromatography (0→15% MeOH/DCM). LC-MS calculated for $C_{25}H_{24}C_{12}N_5O$ $(M+H)^+$: m/z=480.1; found 480.2.

Step 2: (R)-1-((8-(3'-(3-bromoimidazo[1,2-a]pyrazin-8-ylamino)-2,2'-dichlorobiphenyl-3-ylamino)-1,7-naphthyridin-3-yl)methyl)pyrrolidin-3-ol

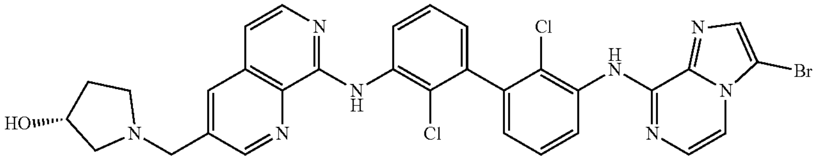 [SMILES: O[C@@H]1CCN(Cc2cnc3c(Nc4cccc(-c5cccc(Nc6nccn7c(Br)cnc67)c5Cl)c4Cl)nccc3c2)C1]

In a vial was combined (R)-1-((8-((3'-amino-2,2'-dichloro-[1,1'-biphenyl]-3-yl)amino)-1,7-naphthyridin-3-yl)methyl)pyrrolidin-3-ol (497 mg, 1.035 mmol) and 3-bromo-8-chloroimidazo[1,2-a]pyrazine (Combi-Blocks, cat #QA-2223: 361 mg, 1.552 mmol). The reactants were diluted with 2-propanol (5173 μl). To this was then added sulfuric acid (83 μl, 1.552 mmol) drop-wise. The reaction mixture was heated to 100° C. overnight. The solvent was removed under reduced pressure. The crude residue was taken back up in a 3:1 chloroform/IPA mixture and was neutralized with a saturated solution of sodium bicarbonate. The aqueous layer was extracted once more with 3:1 chloroform/IPA. The combined organic layers were washed with brine, dried over magnesium sulfate and filtered. The filtrate was concentrated and purified using flash chromatography (0→40% MeOH/DCM). LC-MS calculated for $C_{31}H_{26}BrCl_2N_8O$ $(M+H)^+$: m/z=675.1; found 675.1.

Step 3: (R)-1-((8-(2,2'-dichloro-3'-(3-vinylimidazo[1,2-a]pyrazin-8-ylamino)biphenyl-3-ylamino)-1,7-naphthyridin-3-yl)methyl)pyrrolidin-3-ol

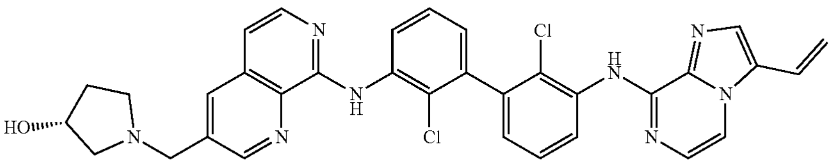 [SMILES: C=Cc1cnc2c(Nc3cccc(-c4cccc(Nc5nccc6cc(CN7CC[C@@H](O)C7)cnc56)c4Cl)c3Cl)nccn12]

A mixture of (R)-1-((8-((3'-((3-bromoimidazo[1,2-a]pyrazin-8-yl)amino)-2,2'-dichloro-[1,1'-biphenyl]-3-yl)amino)-1,7-naphthyridin-3-yl)methyl)pyrrolidin-3-ol (458 mg, 0.677 mmol), 4,4,5,5-tetramethyl-2-vinyl-1,3,2-dioxaborolane (Sigma-Aldrich, cat #633348: 126 μl, 0.745 mmol), sodium carbonate (2.031 mmol) and [1,1'-bis(dicyclohexylphosphino)ferrocene]dichloropalladium(II) (Aldrich, cat #701998: 25.7 mg, 0.034 mmol) in 1,4-dioxane (3224 μL) and water (1290 μL) was degassed and sealed. It was stirred at 90° C. for 1.5 h. The crude reaction mixture was diluted with water and extracted with ethyl acetate. The combined organic layers were washed with brine, dried over magnesium sulfate and filtered. The filtrate was concentrated under reduced pressure and used without further purification. LC-MS calculated for $C_{33}H_{29}Cl_2N_8O$ $(M+H)^+$: m/z=623.2; found 623.4.

Step 4: (R)-8-(2,2'-dichloro-3'-(3-((3-hydroxypyrrolidin-1-yl)methyl)-1,7-naphthyridin-8-ylamino)biphenyl-3-ylamino)imidazo[1,2-a]pyrazine-3-carbaldehyde

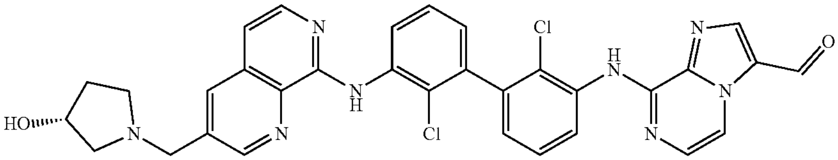 [SMILES: O=Cc1cnc2c(Nc3cccc(-c4cccc(Nc5nccc6cc(CN7CC[C@@H](O)C7)cnc56)c4Cl)c3Cl)nccn12]

In a vial was combined (R)-1-((8-((2,2'-dichloro-3'-((3-vinylimidazo[1,2-a]pyrazin-8-yl)amino)-[1,1'-biphenyl]-3-yl)amino)-1,7-naphthyridin-3-yl)methyl)pyrrolidin-3-ol (200 mg, 0.321 mmol) and THF (2053 μl). The material was sonicated until it was fully in solution. To this, in order, was then added water (513 μl), 2,6-lutidine (191 μl, 1.636 mmol), sodium periodate (343 mg, 1.604 mmol) and potassium osmate dihydrate (17.73 mg, 0.048 mmol). The reaction was allowed to stir at rt for 30 min. The reaction was diluted with water and was extracted with ethyl acetate. The combined organic layers were washed with brine, dried over magnesium sulfate, and was filtered. The filtrate was concentrated and purified using flash chromatography (0→40% MeOH/DCM). LC-MS calculated for $C_{32}H_{27}Cl_2N_8O_2$ (M+H)$^+$: m/z=625.2; found 625.2.

Step 5: (R)-1-((8-(2,2'-dichloro-3'-(3-((2-hydroxyethylamino)methyl)imidazo[1,2-a]pyrazin-8-ylamino)biphenyl-3-ylamino)-1,7-naphthyridin-3-yl)methyl)pyrrolidin-3-ol In a vial (R)-8-((2,2'-dichloro-3'-((3-((3-hydroxypyrrolidin-1-yl)methyl)-1,7-naphthyridin-8-yl)amino)-[1,1'-biphenyl]-3-yl)amino)imidazo[1,2-a]pyrazine-3-carbaldehyde (10 mg, 0.016 mmol) was combined with ethanolamine (9.67 μl, 0.160 mmol) and was diluted with methanol (160 μl). To this was then added acetic acid (13.73 μl, 0.240 mmol) followed by sodium cyanoborohydride (2.009 mg, 0.032 mmol) as a solution in methanol (160 μl). The reaction was allowed to stir at room temperature for 15 minutes after which time the reaction mixture was further diluted to a final volume of 5 mL with methanol and purified by prep HPLC (pH=2, acetonitrile/water+TFA) to provide the desired compound as the TFA salt. LC-MS calculated for $C_{34}H_{34}Cl_2N_9O_2$ (M+H)$^+$: m/z=670.2; found 670.5.

Example 73

(R)-1-((8-((2,2'-dimethyl-3'-((3-(pyrrolidin-1-ylmethyl)-1,7-naphthyridin-8-yl)amino)-[1,1'-biphenyl]-3-yl)amino)-1,7-naphthyridin-3-yl)methyl)pyrrolidin-3-ol

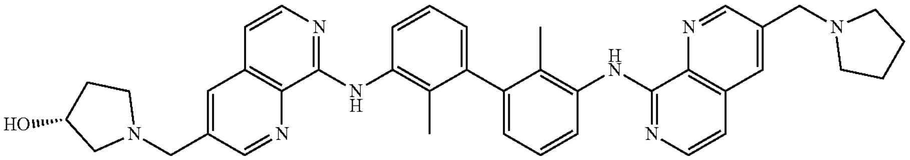 [SMILES: Cc1c(Nc2nccc3cc(CN4CCCC4)cnc23)cccc1-c1cccc(Nc2nccc3cc(CN4CC[C@@H](O)C4)cnc23)c1C]

This compound was prepared using similar procedures as described for Example 20 with pyrrolidine (Aldrich, cat #394238) replacing (R)-pyrrolidin-3-ol in Step 6. The reaction mixture was diluted with methanol and purified by prep HPLC (pH=2, acetonitrile/water+TFA) to provide the desired compound as its TFA salt. LC-MS calculated for $C_{40}H_{43}N_8O$ (M+H)$^+$: m/z=651.4; found 651.3.

Example 74

(S)-1-((8-((2'-chloro-3'-((3-(((R)-3-hydroxypyrrolidin-1-yl)methyl)-1,7-naphthyridin-8-yl)amino)-2-methyl-[1,1'-biphenyl]-3-yl)amino)-1,7-naphthyridin-3-yl)methyl)pyrrolidin-3-ol

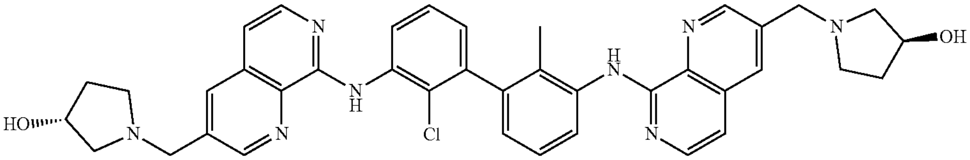 [SMILES: Cc1c(Nc2nccc3cc(CN4CC[C@H](O)C4)cnc23)cccc1-c1cccc(Nc2nccc3cc(CN4CC[C@@H](O)C4)cnc23)c1Cl]

Step 1: (R)-1-((8-((2-chloro-3'-((3-(hydroxymethyl)-1,7-naphthyridin-8-yl)amino)-2'-methyl-[1,1'-biphenyl]-3-yl)amino)-1,7-naphthyridin-3-yl)methyl)pyrrolidin-3-ol

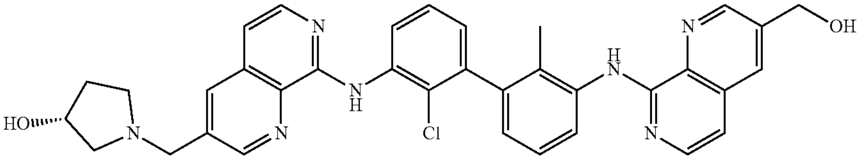

To a vial was added (8-((2-methyl-3-(4,4,5,5-tetramethyl-1,3,2-dioxaborolan-2-yl)phenyl)amino)-1,7-naphthyridin-3-yl)methanol (Example 9, Step 3: 0.166 g, 0.424 mmol), (R)-1-((8-((3-bromo-2-chlorophenyl)amino)-1,7-naphthyridin-3-yl)methyl)pyrrolidin-3-ol (Example 22, Step 4: 0.184 g, 0.424 mmol), 1 M aqueous sodium carbonate (0.848 mmol), tetrakis (0.049 g, 0.042 mmol), and 1,4-dioxane (3.74 mL). The mixture was degassed, sealed, and heated to 110° C. whilst stirring for 4 h. The mixture was cooled, diluted with EtOAc and filtered through celite. The filtrate was concentrated and purified by silica gel chromatography (15% MeOH/DCM) to provide the desired product as a yellow solid. LC-MS calculated for $C_{35}H_{33}ClN_7O_2(M+H)^+$: m/z=618.2; found 618.3.

Step 2: (R)-8-((2'-chloro-3'-((3-((3-hydroxypyrrolidin-1-yl)methyl)-1,7-naphthyridin-8-yl)amino)-2-methyl-[1,1'-biphenyl]-3-yl)amino)-1,7-naphthyridine-3-carbaldehyde

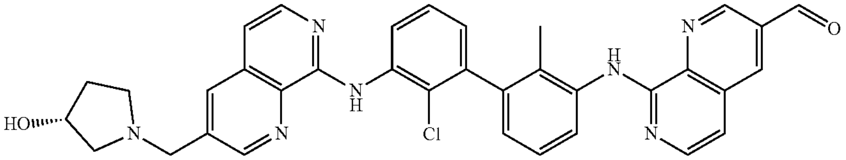 [SMILES: Cc1c(Nc2nccc3cc(C=O)cnc23)cccc1-c1cccc(Nc2nccc3cc(CN4CC[C@@H](O)C4)cnc23)c1Cl]

This compound was prepared using similar procedures as described for Example 9 with (R)-1-((8-((2-chloro-3'-((3-(hydroxymethyl)-1,7-naphthyridin-8-yl)amino)-2'-methyl-[1,1'-biphenyl]-3-yl)amino)-1,7-naphthyridin-3-yl)methyl) pyrrolidin-3-ol replacing (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol in Step 5. LC-MS calculated for $C_{35}H_{31}ClN_7O_2(M+H)^+$: m/z=616.2; found 616.3.

Step 3: (S)-1-((8-((2'-chloro-3'-((3-(((R)-3-hydroxypyrrolidin-1-yl)methyl)-1,7-naphthyridin-8-yl) amino)-2-methyl-[1,1'-biphenyl]-3-yl)amino)-1,7-naphthyridin-3-yl)methyl)pyrrolidin-3-ol To a vial was added (R)-8-((2'-chloro-3'-((3-((3-hydroxypyrrolidin-1-yl)methyl)-1,7-naphthyridin-8-yl)amino)-2-methyl-[1,1'-biphenyl]-3-yl)amino)-1,7-naphthyridine-3-carbaldehyde (0.015 g, 0.024 mmol), (S)-pyrrolidin-3-ol (Combi-Blocks, cat #SS-7948: 6.4 mg, 0.073 mmol), a stir bar, and 1,2-dichloroethane (0.122 mL). The mixture was stirred for 5 min, then sodium triacetoxyborohydride (0.015 g, 0.073 mmol) and acetic acid (0.011 mL, 0.195 mmol) were added. The mixture was stirred for 1 h, then was diluted with methanol and purified by prep HPLC (pH=2, acetonitrile/water+TFA) to provide the desired compound as its TFA salt. LC-MS calculated for $C_{39}H_{40}ClN_8O_2(M+H)^+$: m/z=687.3; found 687.4.

Example 75

(R)-1-((8-((2'-chloro-3'-((3-((3-hydroxypyrrolidin-1-yl)methyl)-1,7-naphthyridin-8-yl)amino)-2-methyl-[1,1'-biphenyl]-3-yl)amino)-1,7-naphthyridin-3-yl) methyl)azetidine-3-carboxylic acid

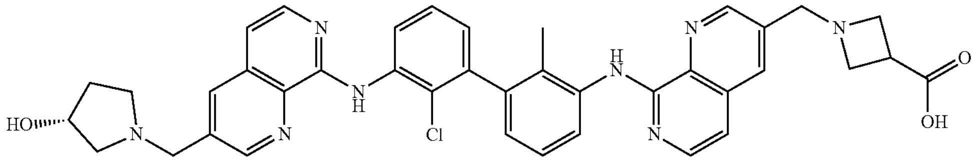 [SMILES: Cc1c(Nc2nccc3cc(CN4CC(C(=O)O)C4)cnc23)cccc1-c1cccc(Nc2nccc3cc(CN4CC[C@@H](O)C4)cnc23)c1Cl]

This compound was prepared using similar procedures as described for Example 74 with azetidine-3-carboxylic acid (Aldrich, cat #391131) replacing (S)-pyrrolidin-3-ol in Step 3. The reaction mixture was diluted with methanol and purified by prep HPLC (pH=2, acetonitrile/water+TFA) to provide the desired compound as its TFA salt. LC-MS calculated for $C_{39}H_{38}ClN_8O_3(M+H)^+$: m/z=701.3; found 701.3.

Example 76

(R)-1-((8-((2,2'-dichloro-3'-((3-(((R)-3-hydroxypyrrolidin-1-yl)methyl)-1,7-naphthyridin-8-yl)amino)-[1,1'-biphenyl]-3-yl)amino)-1,7-naphthyridin-3-yl)methyl)-3-methylpyrrolidin-3-ol

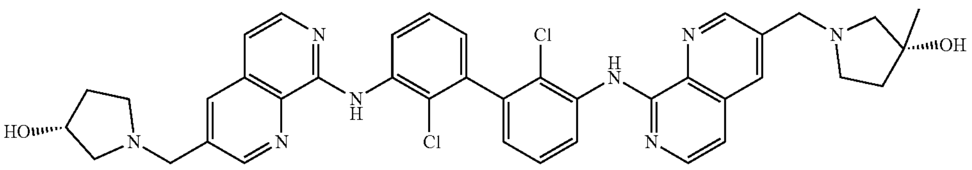 [SMILES: C[C@@]1(O)CCN(Cc2cnc3c(Nc4cccc(-c5cccc(Nc6nccc7cc(CN8CC[C@@H](O)C8)cnc67)c5Cl)c4Cl)nccc3c2)C1]

Step 1: (8-((3-bromo-2-chlorophenyl)amino)-1,7-naphithyridin-3-yl)methanol

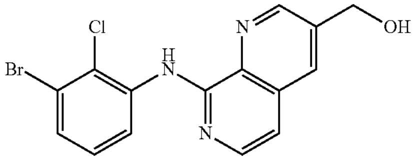 [SMILES: OCc1cnc2c(Nc3cccc(Br)c3Cl)nccc2c1]

A flask was charged with 8-((3-bromo-2-chlorophenyl)amino)-1,7-naphthyridine-3-carbaldehyde (Example 14, Step 6: 0.586 g, 1.625 mmol), methanol (6.7 mL), and a stir bar. The mixture was cooled to 0° C., and sodium borohydride (0.255 g, 6.74 mmol) was added portionwise over 1 h. After the final addition, the mixture was warmed to rt and stirred for 1 h. Another portion of sodium borohydride (0.050 g, 1.349 mmol) was added and stirred for 30 min. Saturated aqueous sodium bicarbonate was added (5 mL), and the mixture was diluted with DCM (10 mL). The layers were separated, and the aqueous layer was further extracted with DCM (2×10 mL). The combined organic extracts were dried over $MgSO_4$, filtered, and concentrated in vacuo. The crude product was purified by silica gel chromatography (0→46% EtOAc/hexanes). LC-MS calculated for $C_{15}H_{12}BrClN_3O$ $(M+H)^+$: m/z=364.0; found 364.0.

Step 2: (8-((2-chloro-3-(4,4,5,5-tetramethyl-1,3,2-dioxaborolan-2-yl)phenyl)amino)-1,7-naphthyridin-3-yl)methanol

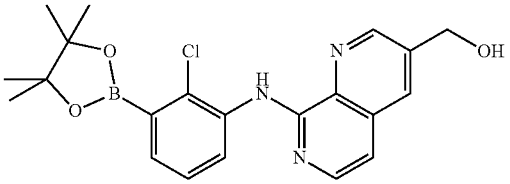 [SMILES: CC1(C)OB(c2cccc(Nc3nccc4cc(CO)cnc34)c2Cl)OC1(C)C]

This compound was prepared using similar procedures as described for Example 9 with (8-((3-bromo-2-chlorophenyl)amino)-1,7-naphthyridin-3-yl)methanol replacing (8-((3-bromo-2-methylphenyl)amino)-1,7-naphthyridin-3-yl)methanol in Step 3. LC-MS calculated for $C_{21}H_{24}BClN_3O_3$ $(M+H)^+$: m/z=412.2; found 412.2.

Step 3: (R)-1-((8-((2,2'-dichloro-3'-((3-(hydroxymethyl)-1,7-naphthyridin-8-yl)amino)-[1,1'-biphenyl]-3-yl)amino-1,7-naphthyridin-3-yl)methyl)pyrrolidin-3-ol

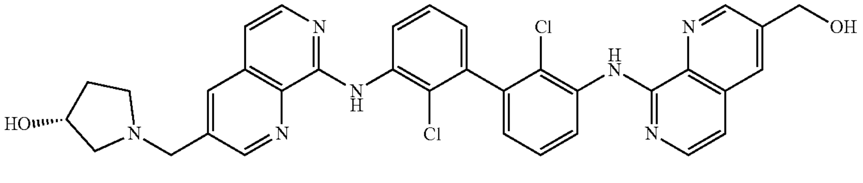

This compound was prepared using similar procedures as described for Example 74 with (8-((2-chloro-3-(4,4,5,5-tetramethyl-1,3,2-dioxaborolan-2-yl)phenyl)amino)-1,7-naphthyridin-3-yl)methanol replacing (8-((2-methyl-3-(4,4,5,5-tetramethyl-1,3,2-dioxaborolan-2-yl)phenyl)amino)-1,7-naphthyridin-3-yl)methanol in Step 1. LC-MS calculated for $C_{34}H_{30}C_{12}N_7O_2$ $(M+H)^+$: m/z=638.2; found 638.2.

Step 4: (R)-8-((2,2'-dichloro-3'-((3-((3-hydroxypyrrolidin-1-yl)methyl)-1,7-naphthyridin-8-yl)amino)-[1,1'-biphenyl]-3-yl)amino)-1,7-naphthyridine-3-carbaldehyde

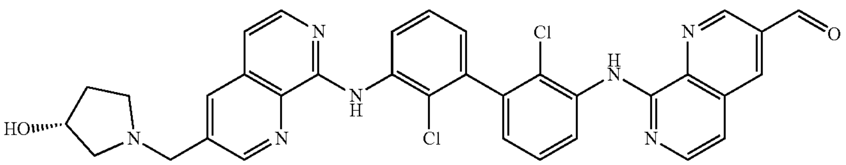

This compound was prepared using similar procedures as described for Example 9 with (R)-1-((8-((2,2'-dichloro-3'-((3-(hydroxymethyl)-1,7-naphthyridin-8-yl)amino)-[1,1'-biphenyl]-3-yl)amino)-1,7-naphthyridin-3-yl)methyl)pyrrolidin-3-ol replacing (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol in Step 5. LC-MS calculated for $C_{34}H_{28}Cl_2N_7O_2$ $(M+H)^+$: m/z=636.2; found 636.2.

Step 5: (R)-1-((8-((2,2'-dichloro-3'-((3-(((R)-3-hydroxypyrrolidin-1-yl)methyl)-1,7-naphthyridin-8-yl)amino)-[1,1'-biphenyl]-3-yl)amino)-1,7-naphthyridin-3-yl)methyl)-3-methylpyrrolidin-3-ol To a vial was added (R)-8-((2,2'-dichloro-3'-((3-((3-hydroxypyrrolidin-1-yl)methyl)-1,7-naphthyridin-8-yl)amino)-[1,1'-biphenyl]-3-yl)amino)-1,7-naphthyridine-3-carbaldehyde (0.0150 g, 0.024 mmol), (R)-3-methylpyrrolidin-3-ol (Ark Pharm, cat #AK100499: 7.15 mg, 0.071 mmol), a stir bar, and 1,2-dichloroethane (0.236 mL). The mixture was stirred for 5 min, then sodium triacetoxyborohydride (0.015 g, 0.071 mmol) and acetic acid (4.05 μl, 0.071 mmol) were added. The reaction was stirred for 1 h, and the mixture was diluted with methanol and purified by prep HPLC (pH=2, acetonitrile/water+TFA) to provide the desired compound as its TFA salt. LC-MS calculated for $C_{39}H_{39}Cl_2N_8O_2$ $(M+H)^+$: m/z=721.3; found 721.3.

Example 77

(R)-1-((8-((2,2'-dichloro-3'-((3-(((2-hydroxyethyl)amino)methyl)-1,7-naphthyridin-8-yl)amino)-[1,1'-biphenyl]-3-yl)amino)-1,7-naphthyridin-3-yl)methyl)pyrrolidin-3-ol

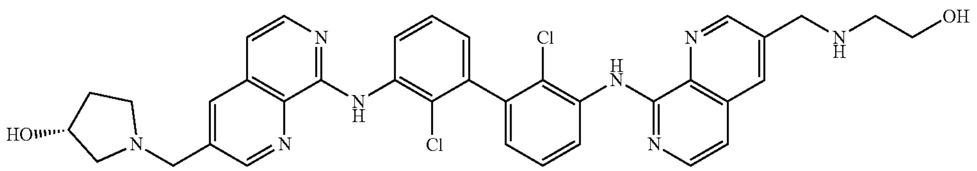

This compound was prepared using similar procedures as described for Example 76 with ethanolamine (Aldrich, cat #411000) replacing (R)-3-methylpyrrolidin-3-ol in Step 5. LC-MS calculated for $C_{36}H_{35}Cl_2N_8O_2$ $(M+H)^+$: m/z=681.2; found 681.2.

Example 78

(R)-1-((8-((2,2'-dichloro-3'-((3-(((R)-3-hydroxypyrrolidin-1-yl)methyl)-1,7-naphthyridin-8-yl)amino)-[1,1'-biphenyl]-3-yl)amino)-1,7-naphthyridin-3-yl)methyl)pyrrolidine-3-carboxylic acid

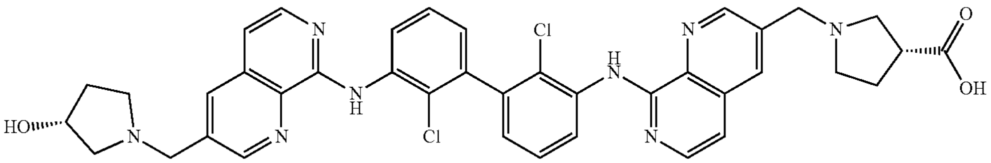 [SMILES: O=C(O)[C@@H]1CCN(Cc2cnc3c(Nc4cccc(-c5cccc(Nc6nccc7cc(CN8CC[C@@H](O)C8)cnc67)c5Cl)c4Cl)nccc3c2)C1]

This compound was prepared using similar procedures as described for Example 76 with (R)-pyrrolidine-3-carboxylic acid (Combi-Blocks, cat #ST-7698) replacing (R)-3-methylpyrrolidin-3-ol in Step 5. LC-MS calculated for $C_{39}H_{37}C_2N_8O_3$ $(M+H)^+$: m/z=735.2; found 735.2.

Example 79

(R)-1-((8-((2-chloro-3'-((3-(((R)-3-hydroxypyrrolidin-1-yl)methyl)-1,7-naphthyridin-8-yl)amino)-2'-methyl-[1,1'-biphenyl]-3-yl)amino)-1,7-naphthyridin-3-yl)methyl)pyrrolidine-3-carboxylic acid

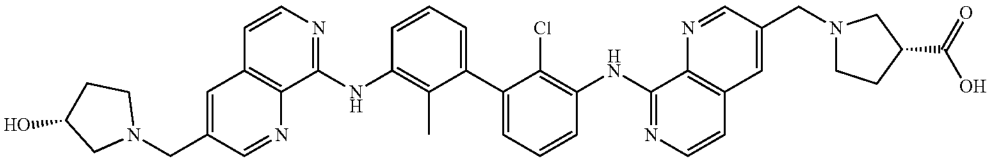 [SMILES: Cc1c(Nc2nccc3cc(CN4CC[C@@H](O)C4)cnc23)cccc1-c1cccc(Nc2nccc3cc(CN4CC[C@@H](C(=O)O)C4)cnc23)c1Cl]

Step 1: (R)-1-((8-((2'-chloro-2-methyl-3'-((3-vinyl-1,7-naphthyridin-8-yl)amino)-[1,1'-biphenyl]-3-yl)amino)-1,7-naphthyridin-3-yl)methyl)pyrrolidin-3-ol

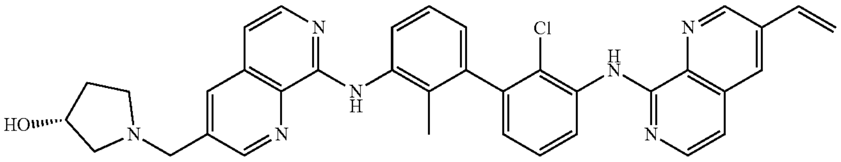 [SMILES: C=Cc1cnc2c(Nc3cccc(-c4cccc(Nc5nccc6cc(CN7CC[C@@H](O)C7)cnc56)c4C)c3Cl)nccc2c1]

To a vial was added N-(3-bromo-2-chlorophenyl)-3-vinyl-1,7-naphthyridin-8-amine (Example 14, Step 5: 0.141 g, 0.391 mmol), (R)-1-((8-((2-methyl-3-(4,4,5,5-tetramethyl-1,3,2-dioxaborolan-2-yl)phenyl)amino)-1,7-naphthyridin-3-yl)methyl)pyrrolidin-3-ol (Example 37, Step 9: 0.150 g, 0.326 mmol), sodium carbonate (0.069 g, 0.652 mmol), tetrakis (0.038 g, 0.033 mmol), 1,4-dioxane (2.444 mL), and water (0.815 mL). The mixture was degassed, sealed, and heated to 110° C. whilst stirring for 4 h. The mixture was cooled, diluted with EtOAc and filtered through celite. The filtrate was concentrated and purified using flash chromatography (0→15% MeOH/DCM). LC-MS calculated for $C_{36}H_{33}ClN_7O$ $(M+H)^+$: m/z=614.2; found 614.4.

Step 2: (R)-8-((2-chloro-3'-((3-((3-hydroxypyrrolidin-1-yl)methyl)-1,7-naphthyridin-8-yl)amino)-2'-methyl-[1,1'-biphenyl]-3-yl)amino)-1,7-naphthyridine-3-carbaldehyde

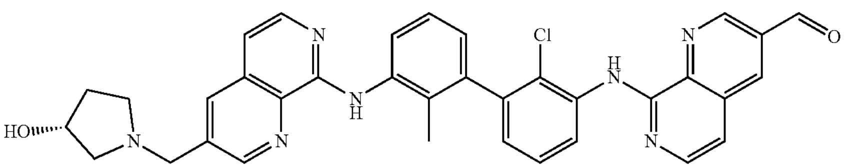

To a vial was added (R)-1-((8-((2'-chloro-2-methyl-3'-((3-vinyl-1,7-naphthyridin-8-yl)amino)-[1,1'-biphenyl]-3-yl)amino)-1,7-naphthyridin-3-yl)methyl)pyrrolidin-3-ol (0.108 g, 0.176 mmol), tetrahydrofuran (1.125 mL), water (0.281 mL), 2,6-lutidine (0.107 mL, 0.914 mmol), sodium periodate (0.188 g, 0.879 mmol), then potassium osmate dihydrate (9.72 mg, 0.026 mmol). The mixture was stirred for 30 min at rt. The mixture was diluted with 3:1 $CHCl_3$/IPA (5 mL) and water (2 mL), and the layers were separated. The aqueous layer was further extracted with 3:1 $CHCl_3$/IPA, dried over $MgSO_4$, filtered and concentrated under reduced pressure. The solid was slurried with 5:1 $Et_2O$/DCM, and filtered to provide the desired product as a beige solid. LC-MS calculated for $C_{35}H_{31}ClN_7O_2(M+H)^+$: m/z=616.2; found 616.2.

Step 3: (R)-1-((8-((2-chloro-3'-((3-(((R)-3-hydroxypyrrolidin-1-yl)methyl)-1,7-naphthyridin-8-yl)amino)-2'-methyl-[1,1'-biphenyl]-3-yl)amino)-1,7-naphthyridin-3-yl)methyl)pyrrolidine-3-carboxylic acid To a vial was added (R)-8-((2-chloro-3'-((3-((3-hydroxypyrrolidin-1-yl)methyl)-1,7-naphthyridin-8-yl)amino)-2'-methyl-[1,1'-biphenyl]-3-yl)amino)-1,7-naphthyridine-3-carbaldehyde (0.0350 g, 0.057 mmol), (R)-pyrrolidine-3-carboxylic acid (Combi-Blocks, cat #ST-7698: 0.020 g, 0.170 mmol), a stir bar, and 1,2-dichloroethane (0.568 mL). The mixture was stirred for 5 min, then sodium triacetoxyborohydride (0.036 g, 0.170 mmol) and acetic acid (0.020 mL, 0.341 mmol) were added. The reaction was stirred for 1 h, and the mixture was diluted with methanol and purified by prep HPLC (pH=2, acetonitrile/water+TFA) to provide the desired compound as its TFA salt. LC-MS calculated for $C_{40}H_{40}ClN_8O_3(M+H)^+$: m/z=715.3; found 715.3.

Example 80

(R)-1-((8-((2-chloro-3'-((3-((3-hydroxypyrrolidin-1-yl)methyl)-1,7-naphthyridin-8-yl)amino)-2'-methyl-[1,1'-biphenyl]-3-yl)amino)-1,7-naphthyridin-3-yl)methyl)azetidine-3-carboxylic acid

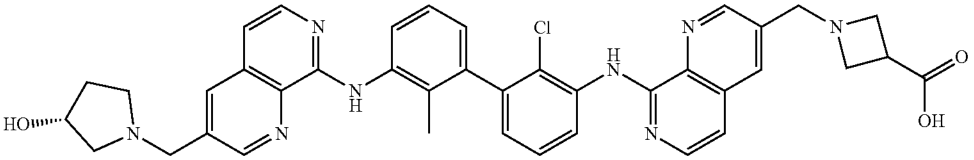 [SMILES: Cc1c(Nc2nccc3cc(CN4CC[C@@H](O)C4)cnc23)cccc1-c1cccc(Nc2nccc3cc(CN4CC(C(=O)O)C4)cnc23)c1Cl]

This compound was prepared using similar procedures as described for Example 79 with azetidine-3-carboxylic acid (Aldrich, cat #391131) replacing (R)-pyrrolidine-3-carboxylic acid in Step 3. LC-MS calculated for $C_{39}H_{38}ClN_8O_3$ $(M+H)^+$: m/z=701.3; found 701.3.

Example 81

(R)-3-(((8-((2-chloro-3'-((3-((3-hydroxypyrrolidin-1-yl)methyl)-1,7-naphthyridin-8-yl)amino)-2'-methyl-[1,1'-biphenyl]-3-yl)amino)-1,7-naphthyridin-3-yl)methyl)amino)propanoic acid

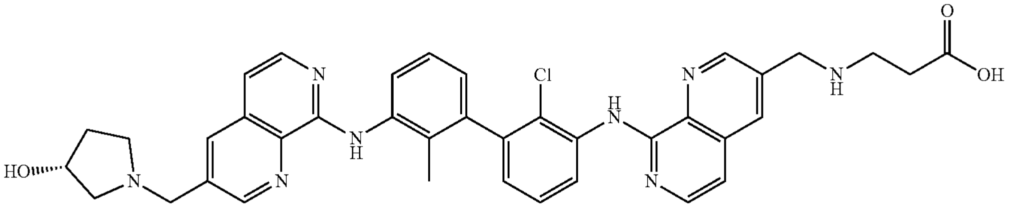 [SMILES: Cc1c(Nc2nccc3cc(CN4CC[C@@H](O)C4)cnc23)cccc1-c1cccc(Nc2nccc3cc(CNCCC(=O)O)cnc23)c1Cl]

This compound was prepared using similar procedures as described for Example 79 with β-alanine (Aldrich, cat #146064) replacing (R)-pyrrolidine-3-carboxylic acid in Step 3. LC-MS calculated for $C_{38}H_{38}ClN_8O_3(M+H)^+$: m/z=689.3; found 689.3.

Example 82

(R)-1-((8-((2,2'-dichloro-3'-((3-(((S)-3-hydroxypyrrolidin-1-yl)methyl)-1,7-naphthyridin-8-yl)amino)-[1,1'-biphenyl]-3-yl)amino)-1,7-naphthyridin-3-yl)methyl)pyrrolidine-3-carboxylic acid

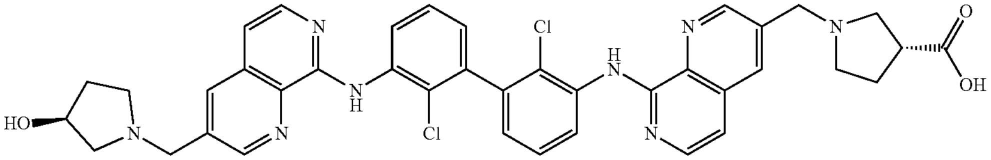 [SMILES: O=C(O)[C@@H]1CCN(Cc2cnc3c(Nc4cccc(-c5cccc(Nc6nccc7cc(CN8CC[C@H](O)C8)cnc67)c5Cl)c4Cl)nccc3c2)C1]

Step 1: (S)-1-((8-((3-bromo-2-chlorophenyl)amino)-1,7-naphthyridin-3-yl)methyl)pyrrolidin-3-ol

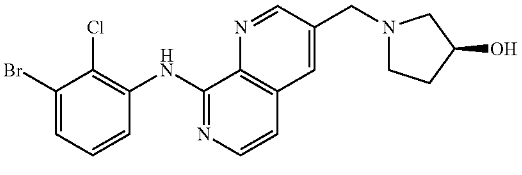 [SMILES: O[C@H]1CCN(Cc2cnc3c(Nc4cccc(Br)c4Cl)nccc3c2)C1]

To a vial was added 8-((3-bromo-2-chlorophenyl)amino)-1,7-naphthyridine-3-carbaldehyde (Example 14, Step 6: 0.200 g, 0.552 mmol), (S)-3-hydroxypyrrolidine (Combi-Blocks, cat #SS-7948: 0.144 g, 1.655 mmol), DCE (2.76 mL), and a stir bar. The mixture was stirred at rt for 15 min, then sodium cyanoborohydride (0.104 g, 1.655 mmol) and acetic acid (0.120 mL, 2.096 mmol) were added. The mixture was stirred at rt for 1 h, then the reaction was quenched with aqueous saturated sodium bicarbonate (5 mL). 3:1 $CHCl_3$/IPA was added (5 mL), and the layers were separated. The aqueous layer was further extracted with 3:1 $CHCl_3$/IPA (2×5 mL), and the combined organic layers were dried over $MgSO_4$, filtered, and concentrated under reduced pressure. The resulting brown residue was purified by silica gel chromatography (0→15% MeOH/DCM) to provide the desired product as a brown solid. LC-MS calculated for $C_{19}H_{19}BrClN_4O$ $(M+H)^+$: m/z=433.0; found 433.2.

Step 2: (S)-1-((8-((2,2'-dichloro-3'-((3-(hydroxymethyl)-1,7-naphthyridin-8-yl)amino)-[1,1'-biphenyl]-3-yl)amino)-1,7-naphthyridin-3-yl)methyl)pyrrolidin-3-ol

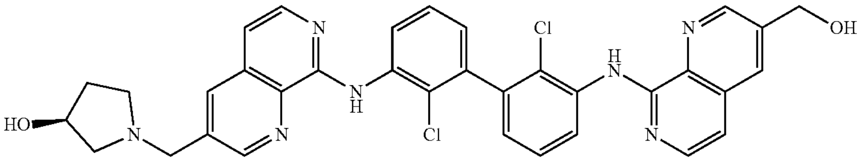 [SMILES: OCc1cnc2c(Nc3cccc(-c4cccc(Nc5nccc6cc(CN7CC[C@H](O)C7)cnc56)c4Cl)c3Cl)nccc2c1]

To a vial was added (8-((2-chloro-3-(4,4,5,5-tetramethyl-1,3,2-dioxaborolan-2-yl)phenyl)amino)-1,7-naphthyridin-3-yl)methanol (Example 76, Step 2: 0.163 g, 0.396 mmol), (S)-1-((8-((3-bromo-2-chlorophenyl)amino)-1,7-naphthyridin-3-yl)methyl)pyrrolidin-3-ol (0.172 g, 0.396 mmol), 1 M aqueous sodium carbonate (0.792 mmol), tetrakis (0.046 g, 0.040 mmol), and 1,4-dioxane (2.97 mL). The mixture was degassed, sealed, and heated to 110° C. whilst stirring for 4 h. The mixture was cooled, diluted with EtOAc and filtered through celite. The filtrate was concentrated and purified by silica gel chromatography (15% MeOH/DCM) to provide the desired product as a yellow solid. LC-MS calculated for $C_{34}H_{30}Cl_2N_7O_2$ $(M+H)^+$: m/z=638.2; found 638.2.

Step 3: (S)-8-((2,2'-dichloro-3'-((3-((3-hydroxypyrrolidin-1-yl)methyl)-1,7-naphthyridin-8-yl)amino)-[1,1'-biphenyl]-3-yl)amino)-1,7-naphthyridine-3-carbaldehyde

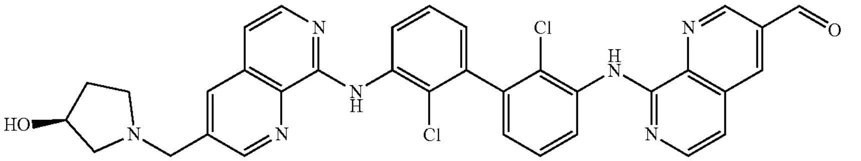 [SMILES: O=Cc1cnc2c(Nc3cccc(-c4cccc(Nc5nccc6cc(CN7CC[C@H](O)C7)cnc56)c4Cl)c3Cl)nccc2c1]

This compound was prepared using similar procedures as described for Example 9 with (S)-1-((8-((2,2'-dichloro-3'-((3-(hydroxymethyl)-1,7-naphthyridin-8-yl)amino)-[1,1'-biphenyl]-3-yl)amino)-1,7-naphthyridin-3-yl)methyl)pyrrolidin-3-ol replacing (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol in Step 5. LC-MS calculated for $C_{34}H_{28}C_{12}N_7O_2$ $(M+H)^+$: m/z=636.2; found 636.2.

Step 4: (R)-1-((8-((2,2'-dichloro-3'-((3-(((S)-3-hydroxypyrrolidin-1-yl)methyl)-1,7-naphthyridin-8-yl)amino)-[1,1'-biphenyl]-3-yl)amino)-1,7-naphthyridin-3-yl)methyl)pyrrolidine-3-carboxylic acid To a vial was added (S)-8-((2,2'-dichloro-3'-((3-((3-hydroxypyrrolidin-1-yl)methyl)-1,7-naphthyridin-8-yl)amino)-[1,1'-biphenyl]-3-yl)amino)-1,7-naphthyridine-3-carbaldehyde (0.009 g, 0.014 mmol), (R)-pyrrolidine-3-carboxylic acid (Combi-Blocks, cat #ST-7698: 4.88 mg, 0.042 mmol), a stir bar, N,N-dimethylformamide (0.141 mL), and DIPEA (7.41 μl, 0.042 mmol). The mixture was stirred for 5 min, then sodium cyanoborohydride (2.67 mg, 0.042 mmol) and was added. The reaction was stirred for 1 h, then the mixture was diluted with methanol and purified by prep HPLC (pH=2, acetonitrile/water+TFA) to provide the desired compound as its TFA salt. LC-MS calculated for $C_{39}H_{37}C_2N_8O_3$ $(M+H)^+$: m/z=735.2; found 735.2.

Example 83

(S)-1-((8-((2,2'-dichloro-3'-((3-(((S)-3-hydroxypyrrolidin-1-yl)methyl)-1,7-naphthyridin-8-yl)amino)-[1,1'-biphenyl]-3-yl)amino)-1,7-naphthyridin-3-yl)methyl)pyrrolidine-3-carboxylic acid

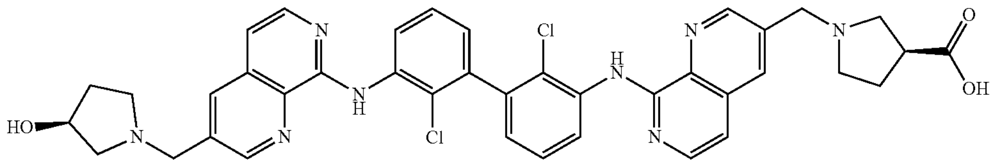 [SMILES: O=C(O)[C@H]1CCN(Cc2cnc3c(Nc4cccc(-c5cccc(Nc6nccc7cc(CN8CC[C@H](O)C8)cnc67)c5Cl)c4Cl)nccc3c2)C1]

This compound was prepared using similar procedures as described for Example 82 with (S)-pyrrolidine-3-carboxylic acid (Combi-Blocks, cat #ST-1381) replacing (R)-pyrrolidine-3-carboxylic acid in Step 4. LC-MS calculated for $C_{39}H_{37}C_2N_8O_3$ $(M+H)^+$: m/z=735.2; found 735.2.

Example 84

(R)-1-((8-((3'-(5-(dimethylglycyl)-5,6-dihydro-4H-pyrrolo[3,4-d]oxazol-2-yl)-2,2'-dimethyl-[1,1'-biphenyl]-3-yl)amino)-1,7-naphthyridin-3-yl)methyl)pyrrolidine-3-carboxylic acid

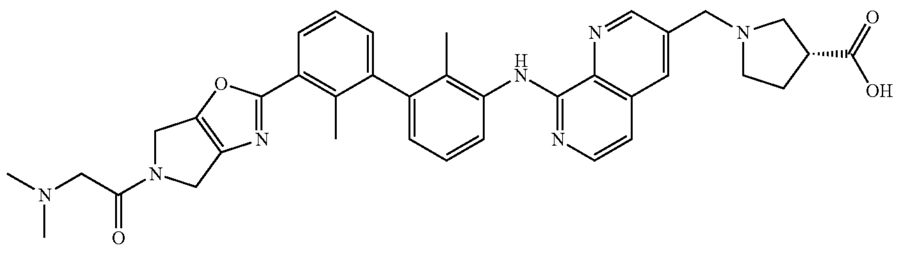 [SMILES: Cc1c(Nc2nccc3cc(CN4CC[C@@H](C(=O)O)C4)cnc23)cccc1-c1cccc(-c2nc3c(o2)CN(C(=O)CN(C)C)C3)c1C]

Step 1: 2-(dimethylamino)-1-(2-(3'-((3-(hydroxymethyl)-1,7-naphthyridin-8-yl)amino)-2,2'-dimethyl-[1,1'-biphenyl]-3-yl)-4,6-dihydro-5H-pyrrolo[3,4-d]oxazol-5-yl)ethan-1-one

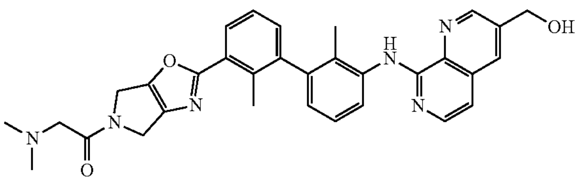 [SMILES: Cc1c(Nc2nccc3cc(CO)cnc23)cccc1-c1cccc(-c2nc3c(o2)CN(C(=O)CN(C)C)C3)c1C]

A mixture of 1-(2-(3-bromo-2-methylphenyl)-4,6-dihydro-5H-pyrrolo[3,4-d]oxazol-5-yl)-2-(dimethylamino)ethan-1-one (Example 37, Step 7:112 mg, 0.307 mmol), (8-((2-methyl-3-(4,4,5,5-tetramethyl-1,3,2-dioxaborolan-2-yl)phenyl)amino)-1,7-naphthyridin-3-yl)methanol (Example 9, Step 3: 120 mg, 0.307 mmol), dicyclohexyl(2',4',6'-triisopropylbiphenyl-2-yl)phosphine-(2'-aminobiphenyl-2-yl)(chloro)palladium (1:1) (24.13 mg, 0.031 mmol) and tripotassium phosphate hydrate (155 mg, 0.675 mmol) in 1,4-dioxane (3 mL)/water (1 mL) was stirred at 80° C. for 1 h. The residue was dissolved in methanol and 1 N HCl and purified with prep-LCMS (pH 2, acetonitrile/water+TFA) to give the desired compound as light yellow solid. LC-MS calculated for $C_{32}H_{33}N_6O_3$ $(M+H)^+$: m/z=549.3; found 549.3.

Step 2: 8-((3'-(5-(dimethylglycyl)-5,6-dihydro-4H-pyrrolo[3,4-d]oxazol-2-yl)-2,2'-dimethyl-[1,1'-biphenyl]-3-yl)amino)-1,7-naphthyridine-3-carbaldehyde

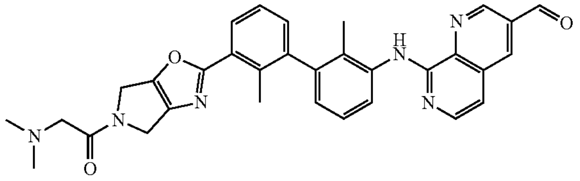 [SMILES: Cc1c(Nc2nccc3cc(C=O)cnc23)cccc1-c1cccc(-c2nc3c(o2)CN(C(=O)CN(C)C)C3)c1C]

This compound was prepared using similar procedures as described for Example 34, with 2-(dimethylamino)-1-(2-(3'-((3-(hydroxymethyl)-1,7-naphthyridin-8-yl)amino)-2,2'-dimethyl-[1,1'-biphenyl]-3-yl)-4,6-dihydro-5H-pyrrolo[3,4-d]oxazol-5-yl)ethan-1-one replacing tert-butyl 2-(3'-((3-(hydroxymethyl)-1,7-naphthyridin-8-yl)amino)-2,2'-dimethyl-[1,1'-biphenyl]-3-yl)-6,7-dihydrothiazolo[5,4-c]pyridine-5(4H)-carboxylate in Step 2. LC-MS calculated for $C_{32}H_{31}N_6O_3$ $(M+H)^+$: m/z=547.2; found 547.3.

Step 3. (R)-1-((8-((3'-(5-(dimethylglycyl)-5,6-dihydro-4H-pyrrolo[3,4-d]oxazol-2-yl)-2,2'-dimethyl-[1,1'-biphenyl]-3-yl)amino)-1,7-naphthyridin-3-yl)methyl)pyrrolidine-3-carboxylic acid This compound was prepared using similar procedures as described for Example 31 with 8-((3'-(5-(dimethylglycyl)-5,6-dihydro-4H-pyrrolo[3,4-d]oxazol-2-yl)-2,2'-dimethyl-[1,1'-biphenyl]-3-yl)amino)-1,7-naphthyridine-3-carbaldehyde replacing N-(2-chloro-3'-((3-formyl-1,7-naphthyridin-8-yl)amino)-2'-methyl-[1,1'-biphenyl]-3-yl)-1,5-dimethyl-4,5,6,7-tetrahydro-1H-imidazo[4,5-c]pyridine-2-carboxamide in Step 7. LC-MS calculated for $C_{37}H_{40}N_7O_4$ $(M+H)^+$: m/z=646.3; found 646.3.

Example 85

(R)-1-((8-((3'-(5-(dimethylglycyl)-5,6-dihydro-4H-pyrrolo[3,4-d]thiazol-2-yl)-2,2'-dimethyl-[1,1'-biphenyl]-3-yl)amino)-1,7-naphthyridin-3-yl)methyl)pyrrolidine-3-carboxylic acid

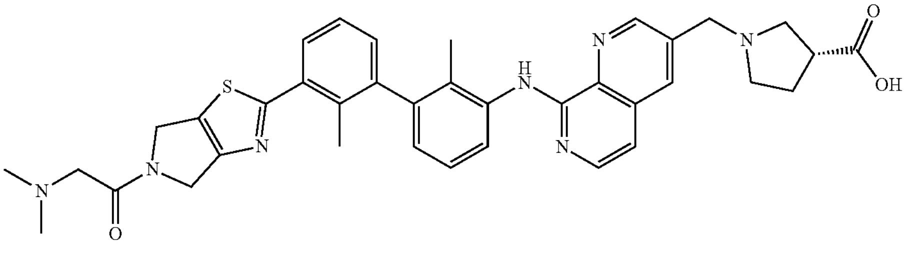 [SMILES: Cc1c(Nc2nccc3cc(CN4CC[C@@H](C(=O)O)C4)cnc23)cccc1-c1cccc(-c2nc3c(s2)CN(C(=O)CN(C)C)C3)c1C]

Step 1: tert-butyl 2-bromo-4H-pyrrolo[3,4-d]thiazole-5(6H)-carboxylate

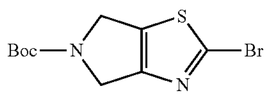 [SMILES: CC(C)(C)OC(=O)N1Cc2nc(Br)sc2C1]

To a stirred solution of 2-bromo-5,6-dihydro-4H-pyrrolo[3,4-d]thiazole, HBr salt (Aurum Pharm, cat #MR22320: 220.0 mg, 0.769 mmol) and N,N-diisopropylethylamine (0.269 mL, 1.539 mmol) in DCM (5.0 mL), Boc-anhydride (201 mg, 0.923 mmol) was added at room temperature. After 1 hour, the reaction mixture was diluted with EtOAc (100 mL), and washed with water (3×15 mL). The organic layer was dried over $Na_2SO_4$, filtered and the filtrate was concentrated to afford crude tert-butyl 2-bromo-4H-pyrrolo[3,4-d]thiazole-5(6H)-carboxylate (220 mg, 0.724 mmol, 93.6% yield), which was used directly in the next step without further purification. LC-MS calculated for $C_{10}H_{14}BrN_2O_2S$ $(M+H)^+$: m/z=305.0/307.0; found 305.0/307.0.

Step 2: tert-butyl 2-(3-chloro-2-methylphenyl)-4,6-dihydro-5H-pyrrolo[3,4-d]thiazole-5-carboxylate

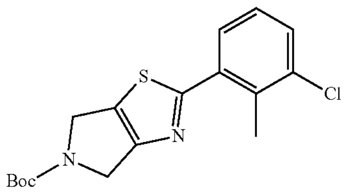 [SMILES: Cc1c(Cl)cccc1-c1nc2c(s1)CN(C(=O)OC(C)(C)C)C2]

(3-Chloro-2-methylphenyl)boronic acid (344 mg, 2.02 mmol) (Combi-blocks, cat #BB-2035), tert-butyl 2-bromo-4,6-dihydro-5H-pyrrolo[3,4-d]thiazole-5-carboxylate (616 mg, 2.02 mmol), sodium carbonate (428 mg, 4.04 mmol) in 1,4-dioxane (8 mL) and water (2 mL) was added palladiumtetrakis (233 mg, 0.202 mmol). The resulting mixture was purged with $N_2$, then heated at 100° C. After 3 h, the reaction was concentrated, and diluted with DCM. The crude product was added to a silica gel column and was eluted with ethyl acetate/hexane from 0% to 40% to give tert-butyl 2-(3-chloro-2-methylphenyl)-4,6-dihydro-5H-pyrrolo[3,4-d]thiazole-5-carboxylate (541 mg, 76% yield). LC-MS calculated for $C_{17}H_{20}ClN_2O_2S$ $(M+H)^+$: m/z=351.1; found 351.0.

Step 3: tert-butyl 2-(2-methyl-3-(4,4,5,5-tetramethyl-1,3,2-dioxaborolan-2-yl)phenyl)-4,6-dihydro-5H-pyrrolo[3,4-d]thiazole-5-carboxylate

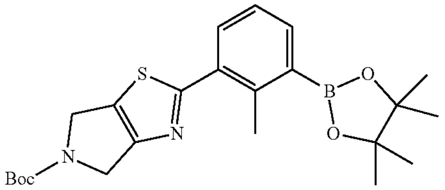 [SMILES: Cc1c(B2OC(C)(C)C(C)(C)O2)cccc1-c1nc2c(s1)CN(C(=O)OC(C)(C)C)C2]

A mixture of tert-butyl 2-(3-chloro-2-methylphenyl)-4,6-dihydro-5H-pyrrolo[3,4-d]thiazole-5-carboxylate (261 mg, 0.715 mmol), 4,4,5,5,4',4',5',5'-octamethyl-[2,2']bi[[1,3,2]dioxaborolanyl] (Aldrich, cat #473294: 545 mg, 2.14 mmol), palladium acetate (6.42 mg, 0.0286 mmol), $K_3PO_4$ (455 mg, 2.14 mmol) and 2-(dicyclohexylphosphino)-2',6'-dimethoxy-1,1'-biphenyl (Strem Chemicals, cat #15-1143: 29.4 mg, 0.0715 mmol) in 1,4-dioxane was degassed and stirred at rt for 16 h. The mixture was diluted with DCM, and washed with water. The organic layer was concentrated in vacuo and purified by silica-gel chromatography (5% EtOAc/DCM). LC-MS calculated for $C_{23}H_{32}BN_2O_4S$ $(M+H)^+$: m/z=443.2; found 443.3.

Step 4: tert-butyl 2-(3'-((3-formyl-1,7-naphthyridin-8-yl)amino)-2,2'-dimethyl-[1,1'-biphenyl]-3-yl)-4,6-dihydro-5H-pyrrolo[3,4-d]thiazole-5-carboxylate

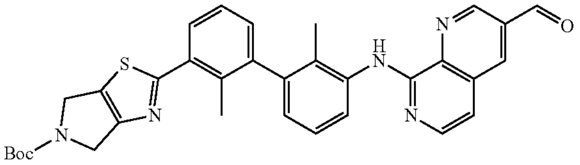 [SMILES: Cc1c(Nc2nccc3cc(C=O)cnc23)cccc1-c1cccc(-c2nc3c(s2)CN(C(=O)OC(C)(C)C)C3)c1C]

To a vial was added tert-butyl 2-(2-methyl-3-(4,4,5,5-tetramethyl-1,3,2-dioxaborolan-2-yl)phenyl)-4,6-dihydro-5H-pyrrolo[3,4-d]thiazole-5-carboxylate (0.013 g, 0.029 mmol), 8-((3-bromo-2-methylphenyl)amino)-1,7-naphthyridine-3-carbaldehyde (Example 15, Step 2: 7 mg, 0.020 mmol), sodium carbonate (6.24 mg, 0.059 mmol), [1,1'-bis(diphenylphosphino)ferrocene]dichloropalladium(II) (1.436 mg, 1.962 µmol), 1,4-dioxane (0.346 mL), and water (0.046 mL). The mixture was degassed, sealed, and heated to 90° C. whilst stirring for 4 h. After cooling, the mixture was diluted with DCM and water. The layers were separated and the aqueous layer was further extracted. The combined organic layers were dried over magnesium sulfate, filtered, concentrated in vacuo, and purified by silica gel chromatography (MeOH/DCM). LC-MS calculated for $C_{33}H_{32}N_5O_3S$ $(M+H)^+$: m/z=578.2; found 578.4.

Step 5: (R)-1-((8-((3'-(5-(tert-butoxycarbonyl)-5,6-dihydro-4H-pyrrolo[3,4-d]thiazol-2-yl)-2,2'-dimethyl-[1,1'-biphenyl]-3-yl)amino)-1,7-naphthyridin-3-yl)methyl)pyrrolidine-3-carboxylic acid

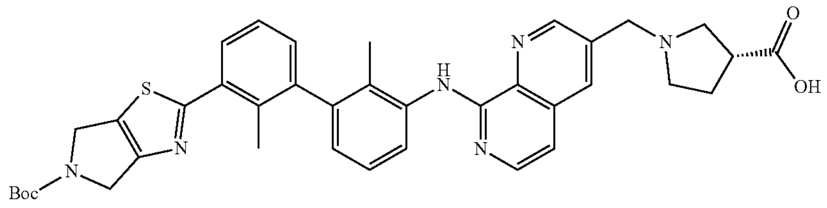 [SMILES: Cc1c(Nc2nccc3cc(CN4CC[C@@H](C(=O)O)C4)cnc23)cccc1-c1cccc(-c2nc3c(s2)CN(C(=O)OC(C)(C)C)C3)c1C]

To a vial was added tert-butyl 2-(3'-((3-formyl-1,7-naphthyridin-8-yl)amino)-2,2'-dimethyl-[1,1'-biphenyl]-3-yl)-4,6-dihydro-5H-pyrrolo[3,4-d]thiazole-5-carboxylate (9 mg, 0.02 mmol), (R)-pyrrolidine-3-carboxylic acid (Combi-Blocks, cat #ST-7698: 0.017 g, 0.152 mmol), dichloromethane (0.829 mL) and triethylamine (0.016 mL, 0.115 mmol). The reaction was stirred at rt for 2 h, then sodium triacetoxyborohydride (0.054 g, 0.253 mmol) and acetic acid (8.7 μl, 0.15 mmol) were added. The reaction was stirred at rt for 2 h, then quenched with a saturated aqueous solution of sodium bicarbonate. The mixture was then extracted with a 3:1 mixture of chloroform/isopropanol. The combined organic layers were dried over sodium sulfate, then concentrated in vacuo to provide the desired compound. LC-MS calculated for $C_{38}H_{41}N_6O_4S$ $(M+H)^+$: m/z=677.3; found 677.2.

Step 6: (R)-1-((8-((3'-(5,6-dihydro-4H-pyrrolo[3,4-d]thiazol-2-yl)-2,2'-dimethyl-[1,1'-biphenyl]-3-yl)amino)-1,7-naphthyridin-3-yl)methyl)pyrrolidine-3-carboxylic acid

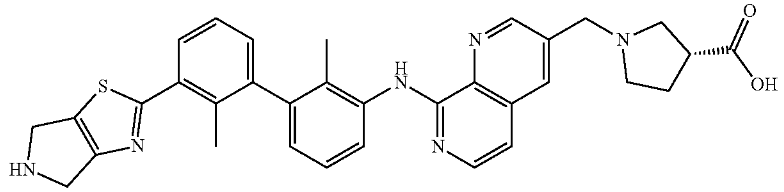 [SMILES: Cc1c(Nc2nccc3cc(CN4CC[C@@H](C(=O)O)C4)cnc23)cccc1-c1cccc(-c2nc3c(s2)CNC3)c1C]

To a solution of (R)-1-((8-((3'-(5-(tert-butoxycarbonyl)-5,6-dihydro-4H-pyrrolo[3,4-d]thiazol-2-yl)-2,2'-dimethyl-[1,1'-biphenyl]-3-yl)amino)-1,7-naphthyridin-3-yl)methyl)pyrrolidine-3-carboxylic acid (7 mg, 0.02 mmol) in DCM (0.5 mL) was added TFA (0.2 mL). After 2 h, the reaction mixture was concentrated, and then the crude product was used directly in the next step. LC-MS calculated for $C_{33}H_{33}N_6O_2S$ $(M+H)^+$: m/z=577.2; found 577.3.

Step 7: (R)-1-((8-((3'-(5-(dimethylglycyl)-5,6-dihydro-4H-pyrrolo[3,4-d]thiazol-2-yl)-2,2'-dimethyl-[1,1'-biphenyl]-3-yl)amino)-1,7-naphthyridin-3-yl)methyl)pyrrolidine-3-carboxylic acid In a 1 dram vial (R)-1-((8-((3'-(5,6-dihydro-4H-pyrrolo[3,4-d]thiazol-2-yl)-2,2'-dimethyl-[1,1'-biphenyl]-3-yl)amino)-1,7-naphthyridin-3-yl)methyl)pyrrolidine-3-carboxylic acid (6 mg, 0.02 mmol) and N,N-Dimethylglycine (6 mg, 0.06 mmol) were dissolved in DMF (0.2 mL). DIPEA (14 μl, 0.08 mmol) and HATU (18 mg, 0.05 mmol) were added to the reaction mixture in one portion. After 5 h, the reaction mixture was diluted with MeOH then purified by prep-HPLC (pH=10, acetonitrile/water+$NH_4OH$) to give the desired product. LC-MS calculated for $C_{37}H_{40}N_7O_3S$ $(M+H)^+$: m/z=662.3; found 662.2. $^1H$ NMR (600 MHz, DMSO-$d_6$) δ 9.30 (s, 1H), 8.85 (d, J=2.0 Hz, 1H), 8.43 (d, J=8.1 Hz, 1H), 8.17 (d, J=1.7 Hz, 1H), 8.05 (d, J=5.8 Hz, 1H), 7.66 (d, J=7.8 Hz, 1H), 7.42 (td, J=7.6, 2.4 Hz, 1H), 7.32 (t, J=7.8 Hz, 1H), 7.28 (d, J=7.7 Hz, 1H), 7.17 (d, J=5.8 Hz, 1H), 6.89 (d, J=7.5 Hz, 1H), 5.06-4.96 (m, 1H), 4.88 (t, J=2.8 Hz, 1H), 4.77-4.68 (m, 1H), 4.63-4.54 (m, 1H), 3.81 (q, J=13.8 Hz, 2H), 3.16 (d, J=1.9 Hz, 2H), 2.97-2.85 (m, 1H), 2.75 (t, J=8.7 Hz, 1H), 2.66 (dd, J=9.1, 6.5 Hz, 1H), 2.61-2.52 (m, 2H), 2.25 (s, 6H), 2.21 (s, 3H), 2.08 (s, 3H), 1.96 (q, J=7.2 Hz, 2H).

Example 86
2-((R)-3-hydroxypyrrolidin-1-yl)-1-(2-(3'-((3-(((R)-3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]thiazol-5-yl)ethan-1-one
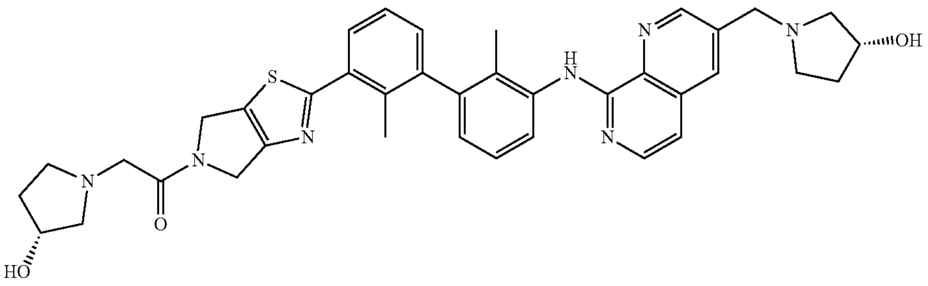 [SMILES: Cc1c(Nc2nccc3cc(CN4CC[C@@H](O)C4)cnc23)cccc1-c1cccc(-c2nc3c(s2)CN(C(=O)CN2CC[C@@H](O)C2)C3)c1C]
Step 1: tert-butyl (R)-2-(3'-((3-((3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]thiazole-5-carboxylate
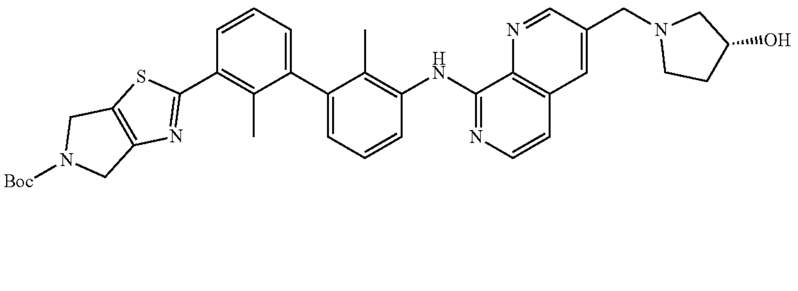 [SMILES: Cc1c(Nc2nccc3cc(CN4CC[C@@H](O)C4)cnc23)cccc1-c1cccc(-c2nc3c(s2)CN(C(=O)OC(C)(C)C)C3)c1C]

This compound was prepared using a similar procedure as described for Example 85, Step 4 with (R)-1-((8-((3-bromo-2-methylphenyl)amino)-1,7-naphthyridin-3-yl)methyl)pyrrolidin-3-ol (Example 20, Step 2) replacing 8-((3-bromo-2-methylphenyl)amino)-1,7-naphthyridine-3-carbaldehyde. The crude compound was diluted with DCM and water. The layers were separated and the aqueous layer was further extracted. The combined organic layers were dried over magnesium sulfate, filtered, and concentrated in vacuo. LC-MS calculated for $C_{37}H_{41}N_6O_3S$ $(M+H)^+$: m/z=649.3; found 649.2.

Step 2: (R)-1-((8-((3'-(5,6-dihydro-4H-pyrrolo[3,4-d]thiazol-2-yl)-2,2'-dimethyl-[1,1'-biphenyl]-3-yl)amino)-1,7-naphthyridin-3-yl)methyl)pyrrolidin-3-ol

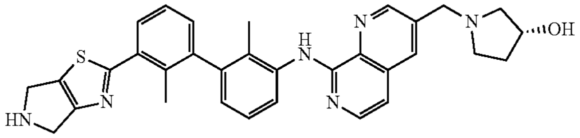 [SMILES: Cc1c(Nc2nccc3cc(CN4CC[C@@H](O)C4)cnc23)cccc1-c1cccc(-c2nc3c(s2)CNC3)c1C]

To a solution of tert-butyl (R)-2-(3'-((3-((3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]thiazole-5-carboxylate (147 mg, 0.226 mmol) in DCM (3 mL) was added TFA (1 mL). After 2 h, the reaction mixture was concentrated, and then the crude product was used directly in the next step. LC-MS calculated for $C_{32}H_{33}N_{60}S$ $(M+H)^+$: m/z=549.2; found 549.3.

Step 3: (R)-2-chloro-1-(2-(3'-((3-((3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]thiazol-5-yl)ethan-1-one

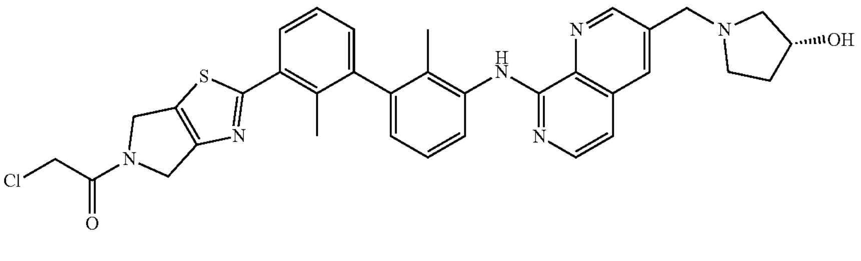 [SMILES: Cc1c(Nc2nccc3cc(CN4CC[C@@H](O)C4)cnc23)cccc1-c1cccc(-c2nc3c(s2)CN(C(=O)CCl)C3)c1C]

To a solution of the above crude product and DIPEA (118 uL, 0.678 mmol) in DCM (3 mL) was added chloroacetyl chloride (20 uL, 0.25 mmol) at −78° C. After 15 min, the reaction mixture was warmed to room temperature slowly. After 30 min, the reaction mixture was concentrated and diluted with MeOH then purified by prep-HPLC (pH=2, acetonitrile/water+TFA) to give the desired product as the TFA salt. LC-MS calculated for $C_{34}H_{34}ClN_6O_2S$ $(M+H)^+$: m/z=625.2; found 625.2.

Step 4: 2-((R)-3-hydroxypyrrolidin-1-yl)-1-(2-(3'-((3-(((R)-3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]thiazol-5-yl)ethan-1-one In a 1 dram vial (R)-2-chloro-1-(2-(3'-((3-((3-hydroxypyrrolidin-1-yl)methyl)-1,7-naphthyridin-8-yl)amino)-2,2'-dimethyl-[1,1'-biphenyl]-3-yl)-4,6-dihydro-5H-pyrrolo[3,4-d]thiazol-5-yl)ethan-1-one (5 mg, 8.00 μmol) was dissolved in acetonitrile (400 μL) to give a yellow solution. (R)-pyrrolidin-3-ol (Combi-Blocks, cat #AM-2005: 5 mg) and DIPEA (1.5 μl, 8.0 μmol) were added to the reaction mixture. The reaction mixture was heated to 60° C. After 12 h, the reaction mixture was diluted with MeOH then purified by prep-HPLC (pH=2, acetonitrile/water+TFA) to give the desired product as the TFA salt. LC-MS calculated for $C_{38}H_{42}N_7O_3S$ $(M+H)^+$: m/z=676.3; found 676.3.

Example 87

(R)-1-((8-((3'-(5-(dimethylglycyl)-5,6-dihydro-4H-pyrrolo[3,4-d]thiazol-2-yl)-2,2'-dimethyl-[1,1'-biphenyl]-3-yl)amino)-1,7-naphthyridin-3-yl)methyl)-3-methylpyrrolidine-3-carboxylic acid

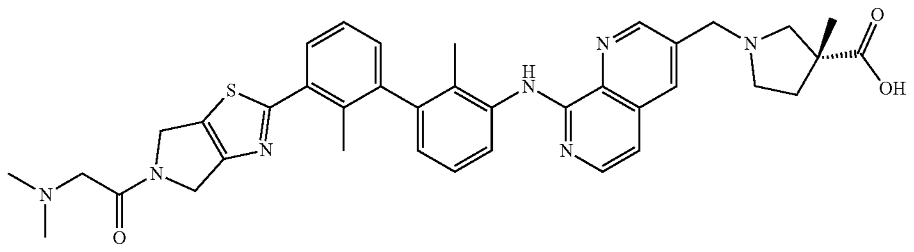 [SMILES: Cc1c(Nc2nccc3cc(CN4CC[C@@](C)(C(=O)O)C4)cnc23)cccc1-c1cccc(-c2nc3c(s2)CN(C(=O)CN(C)C)C3)c1C]

This compound was prepared using a similar procedure as described for Example 85, Step 5 with (R)-3-methylpyrrolidine-3-carboxylic acid (J&W PharmLab, cat #75R0495) replacing (R)-pyrrolidine-3-carboxylic acid. LC-MS calculated for $C_{38}H_{42}N_7O_3S$ $(M+H)^+$: m/z=676.3; found 676.3.

Example 88

1-((8-((3'-(5-(dimethylglycyl)-5,6-dihydro-4H-pyrrolo[3,4-d]thiazol-2-yl)-2,2'-dimethyl-[1,1'-biphenyl]-3-yl)amino)-1,7-naphthyridin-3-yl)methyl)azetidine-3-carboxylic acid

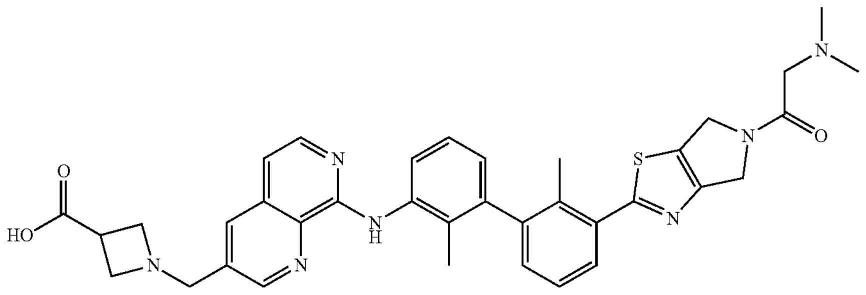 [SMILES: Cc1c(Nc2nccc3cc(CN4CC(C(=O)O)C4)cnc23)cccc1-c1cccc(-c2nc3c(s2)CN(C(=O)CN(C)C)C3)c1C]

This compound was prepared using a similar procedure as described for Example 85, Step 5 with azetidine-3-carboxylic acid (Aldrich, cat #391131) replacing (R)-pyrrolidine-3-carboxylic acid. LC-MS calculated for $C_{36}H_{38}N_7O_3S$ $(M+H)^+$: m/z=648.3; found 648.3.

Example 89

(R)-1-((8-((2-chloro-3'-(5-(dimethylglycyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid

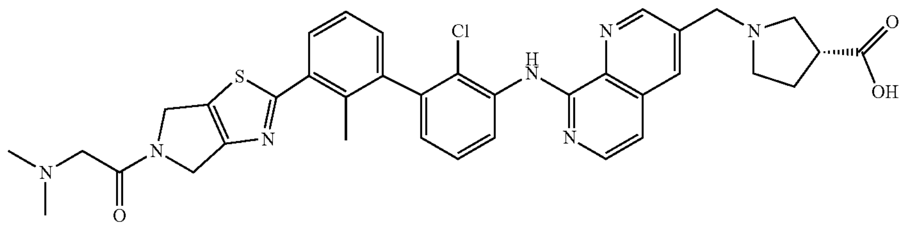 [SMILES: Cc1c(-c2nc3c(s2)CN(C(=O)CN(C)C)C3)cccc1-c1cccc(Nc2nccc3cc(CN4CC[C@@H](C(=O)O)C4)cnc23)c1Cl]

Step 1: tert-butyl 2-(2'-chloro-3'-((3-formyl-1,7-naphthyridin-8-yl)amino)-2-methyl-[1,1'-biphenyl]-3-yl)-4,6-dihydro-5H-pyrrolo[3,4-d]thiazole-5-carboxylate

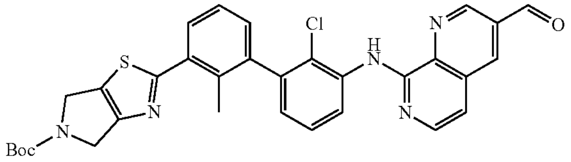 [SMILES: Cc1c(-c2nc3c(s2)CN(C(=O)OC(C)(C)C)C3)cccc1-c1cccc(Nc2nccc3cc(C=O)cnc23)c1Cl]

This compound was prepared using a similar procedure as described for Example 85, Step 4 with 8-((3-bromo-2-chlorophenyl)amino)-1,7-naphthyridine-3-carbaldehyde (Example 14, Step 6) replacing 8-((3-bromo-2-methylphenyl)amino)-1,7-naphthyridine-3-carbaldehyde. The crude compound was diluted with DCM and water. The layers were separated and the aqueous layer was further extracted. The combined organic layers were dried over magnesium sulfate, filtered, and concentrated in vacuo. LC-MS calculated for $C_{32}H_{29}ClN_5O_3S$ $(M+H)^+$: m/z=598.2; found 598.3.

Step 2: (R)-1-((8-((2-chloro-3'-(5-(dimethylglycyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid This compound was prepared using a similar procedure as described for Example 85, Steps 5-7 with tert-butyl 2-(2'-chloro-3'-((3-formyl-1,7-naphthyridin-8-yl)amino)-2-methyl-[1,1'-biphenyl]-3-yl)-4,6-dihydro-5H-pyrrolo[3,4-d]thiazole-5-carboxylate replacing tert-butyl 2-(3'-((3-formyl-1,7-naphthyridin-8-yl)amino)-2,2'-dimethyl-[1,1'-biphenyl]-3-yl)-4,6-dihydro-5H-pyrrolo[3,4-d]thiazole-5-carboxylate. LC-MS calculated for $C_{36}H_{37}ClN_7O_3S$ $(M+H)^+$: m/z=682.2; found 682.3.

Example 90

(R)-1-((8-((2-chloro-3'-(5-(N-ethyl-N-methylglycyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid

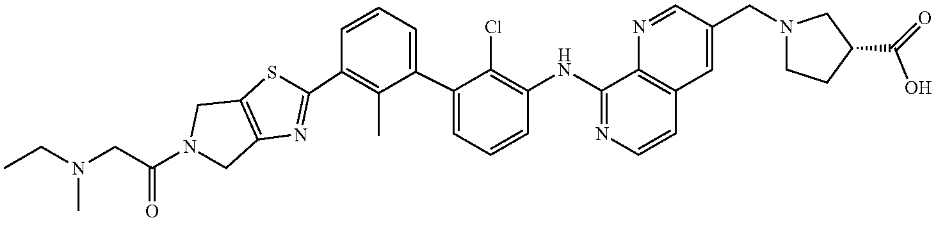 [SMILES: CCN(C)CC(=O)N1Cc2nc(-c3cccc(-c4cccc(Nc5nccc6cc(CN7CC[C@@H](C(=O)O)C7)cnc56)c4Cl)c3C)sc2C1]

This compound was prepared using a similar procedure as described for Example 85 with 8-((3-bromo-2-chlorophenyl)amino)-1,7-naphthyridine-3-carbaldehyde (Example 14, Step 6) replacing 8-((3-bromo-2-methylphenyl)amino)-1,7-naphthyridine-3-carbaldehyde in Step 4 and N-ethyl-N-methylglycine replacing N,N-dimethylglycine in Step 7. LC-MS calculated for $C_{37}H_{39}ClN_7O_3S$ $(M+H)^+$: m/z=696.2; found 696.3.

Example 91

(R)-2-(1-((8-((2-chloro-3'-(5-(dimethylglycyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidin-3-yl)acetic acid

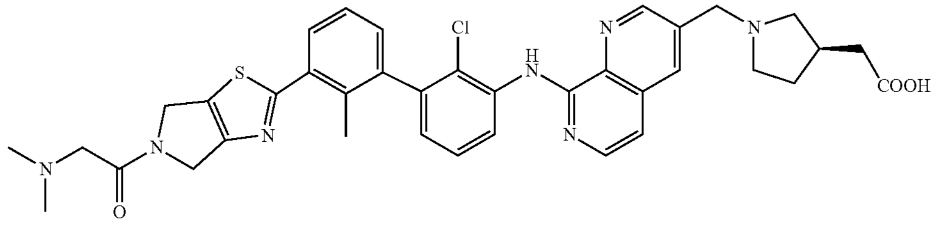 [SMILES: Cc1c(-c2nc3c(s2)CN(C(=O)CN(C)C)C3)cccc1-c1cccc(Nc2nccc3cc(CN4CC[C@H](CC(=O)O)C4)cnc23)c1Cl]

This compound was prepared using a similar procedure as described for Example 85 with 8-((3-bromo-2-chlorophenyl)amino)-1,7-naphthyridine-3-carbaldehyde (Example 14, Step 6) replacing 8-((3-bromo-2-methylphenyl)amino)-1,7-naphthyridine-3-carbaldehyde in Step 4 and (R)-2-(pyrrolidin-3-yl)acetic acid (Combi-Blocks, cat #QE6116) replacing (R)-pyrrolidine-3-carboxylic acid in Step 5. LC-MS calculated for $C_{37}H_{39}ClN_7O_3S$ $(M+H)^+$: m/z=696.2; found 696.3.

Example 92

2-((8-((2-chloro-3'-(5-(dimethylglycyl)-5,6-dihydro-4H-pyrrolo[3,4-d]thiazol-2-yl)-2'-methyl-[1,1'-biphenyl]-3-yl)amino)-1,7-naphthyridin-3-yl)methyl)-2-azabicyclo[2.2.1]heptane-5-carboxylic acid

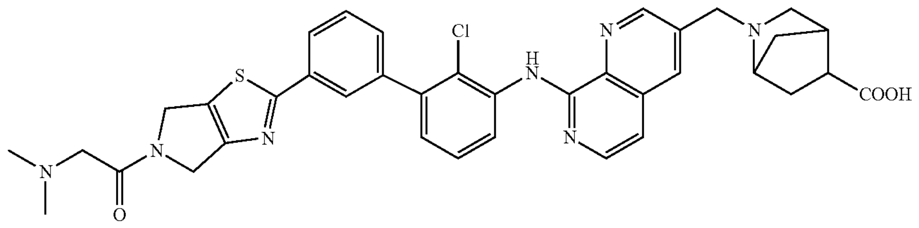 [SMILES: CN(C)CC(=O)N1Cc2nc(-c3cccc(-c4cccc(Nc5nccc6cc(CN7CC8CC7CC8C(=O)O)cnc56)c4Cl)c3)sc2C1]

This compound was prepared using a similar procedure as described for Example 85 with 8-((3-bromo-2-chlorophenyl)amino)-1,7-naphthyridine-3-carbaldehyde (Example 14, Step 6) replacing 8-((3-bromo-2-methylphenyl)amino)-1,7-naphthyridine-3-carbaldehyde in Step 4 and 2-azabicyclo[2.2.1]heptane-5-carboxylic acid (Aurora Fine Chemicals, cat #A30.309.242) replacing (R)-pyrrolidine-3-carboxylic acid in Step 5. LC-MS calculated for $C_{38}H_{39}ClN_7O_3S$ $(M+H)^+$: m/z=708.2; found 708.3.

Example 93

(R)-2-(1-((8-(2-chloro-3'-(5-(2-(ethyl(methyl)amino)acetyl)-5,6-dihydro-4H-pyrrolo[3,4-d]thiazol-2-yl)-2'-methylbiphenyl-3-ylamino)-1,7-naphthyridin-3-yl)methyl)pyrrolidin-3-yl)acetic acid

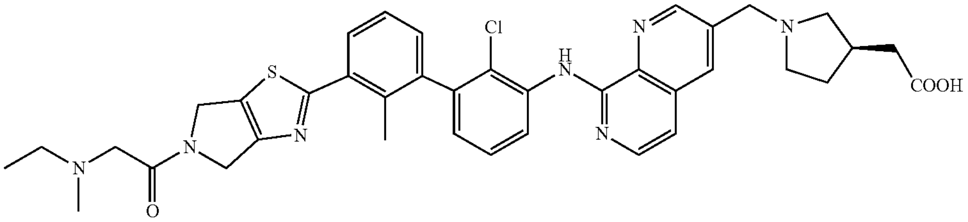 [SMILES: CCN(C)CC(=O)N1Cc2nc(-c3cccc(-c4cccc(Nc5nccc6cc(CN7CC[C@H](CC(=O)O)C7)cnc56)c4Cl)c3C)sc2C1]

This compound was prepared using a similar procedure as described for Example 85 with 8-((3-bromo-2-chlorophenyl)amino)-1,7-naphthyridine-3-carbaldehyde (Example 14, Step 6) replacing 8-((3-bromo-2-methylphenyl)amino)-1,7-naphthyridine-3-carbaldehyde in Step 4, (R)-2-(pyrrolidin-3-yl)acetic acid (Combi-Blocks, cat #QE6116) replacing (R)-pyrrolidine-3-carboxylic acid in Step 5 and N-ethyl-N-methylglycine replacing N,N-dimethylglycine in Step 7. LC-MS calculated for $C_{38}H_{41}ClN_7O_3S$ $(M+H)^+$: m/z=710.3; found 710.3.

Example 94

2-((8-(2-chloro-3'-(5-(2-(ethyl(methyl)amino)acetyl)-5,6-dihydro-4H-pyrrolo[3,4-d]thiazol-2-yl)-2'-methylbiphenyl-3-ylamino)-1,7-naphthyridin-3-yl)methyl)-2-azabicyclo[2.2.1]heptane-5-carboxylic acid

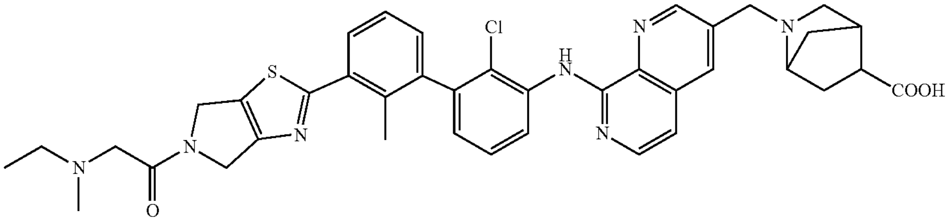 [SMILES: CCN(C)CC(=O)N1Cc2nc(-c3cccc(-c4cccc(Nc5nccc6cc(CN7CC8CC7CC8C(=O)O)cnc56)c4Cl)c3C)sc2C1]

This compound was prepared using a similar procedure as described for Example 85 with 8-((3-bromo-2-chlorophenyl)amino)-1,7-naphthyridine-3-carbaldehyde (Example 14, Step 6) replacing 8-((3-bromo-2-methylphenyl)amino)-1,7-naphthyridine-3-carbaldehyde in Step 4, 2-azabicyclo[2.2.1]heptane-5-carboxylic acid (Aurora Fine Chemicals, cat #A30.309.242) replacing (R)-pyrrolidine-3-carboxylic acid in Step 5 and N-ethyl-N-methylglycine replacing N,N-dimethylglycine in Step 7. LC-MS calculated for $C_{39}H_{41}ClN_7O_3S$ $(M+H)^+$: m/z=722.3; found 722.3.

Example 95

(R)-1-((8-((2-chloro-3'-(5-(2-((R)-3-hydroxypyrrolidin-1-yl)acetyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid

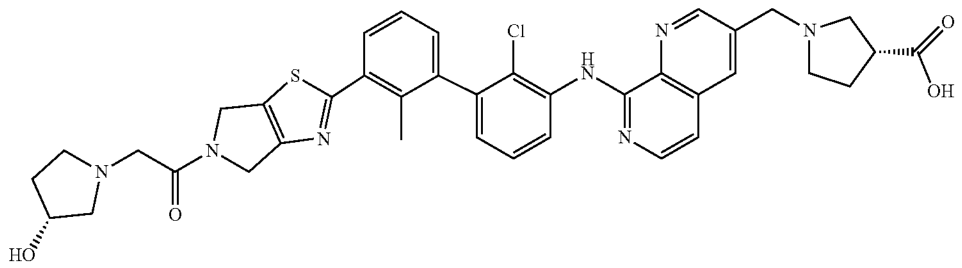 [SMILES: Cc1c(-c2nc3c(s2)CN(C(=O)CN2CC[C@@H](O)C2)C3)cccc1-c1cccc(Nc2nccc3cc(CN4CC[C@@H](C(=O)O)C4)cnc23)c1Cl]

Step 1: (R)-1-((8-((2-chloro-3'-(5-(2-chloroacetyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid

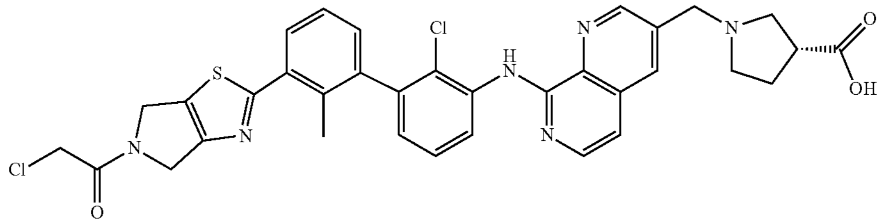 [SMILES: Cc1c(-c2nc3c(s2)CN(C(=O)CCl)C3)cccc1-c1cccc(Nc2nccc3cc(CN4CC[C@@H](C(=O)O)C4)cnc23)c1Cl]

This compound was prepared using a similar procedure as described for Example 90 with chloracetyl acid replacing N-ethyl-N-methylglycine. The reaction mixture was diluted with MeOH then purified by prep-HPLC (pH=2, acetonitrile/water+TFA) to give the desired product as the TFA salt. LC-MS calculated for $C_{34}H_{31}Cl_2N_6O_3S$ $(M+H)^+$: m/z=673.2; found 673.3.

Step 2: (R)-1-((8-((2-chloro-3'-(5-(2-((R)-3-hydroxypyrrolidin-1-yl)acetyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid In a 1 dram vial (R)-1-((8-((2-chloro-3'-(5-(2-chloroacetyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid (5 mg, 8.00 μmol) was dissolved in acetonitrile (400 μL) to give a yellow solution. (R)-pyrrolidin-3-ol (Combi-Blocks, cat #AM-2005: 5 mg) and DIPEA (1.5 μl, 8.0 μmol) were added to the reaction mixture. The reaction mixture was heated to 60° C. After 12 h, the reaction mixture was diluted with MeOH then purified by prep-HPLC (pH=2, acetonitrile/water+TFA) to give the desired product as the TFA salt. LC-MS calculated for $C_{38}H_{39}ClN_7O_4S$ $(M+H)^+$: m/z=724.3; found 724.2.

Example 96

(R)-1-((8-((2-chloro-3'-(5-(N-(2-hydroxyethyl)-N-methylglycyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid

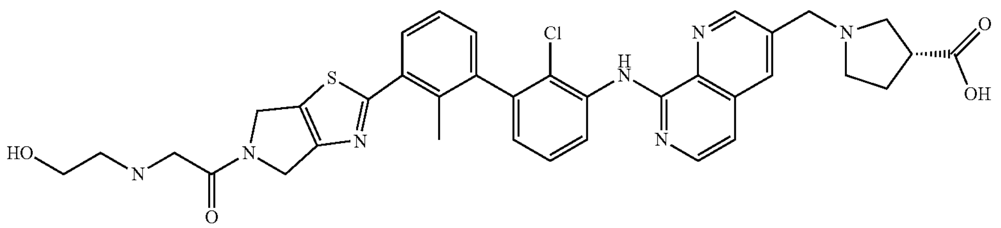 [SMILES: Cc1c(-c2nc3c(s2)CN(C(=O)CNCCO)C3)cccc1-c1cccc(Nc2nccc3cc(CN4CC[C@@H](C(=O)O)C4)cnc23)c1Cl]

This compound was prepared using a similar procedure as described for Example 95 with N-(2-hydroxyethyl)-N-methylamine replacing (R)-pyrrolidin-3-ol in Step 2. LC-MS calculated for $C_{37}H_{39}ClN_7O_4S$ $(M+H)^+$: m/z=712.3; found 712.3.

Example 97

(R)-1-((8-((2-chloro-3'-(5-(2-((S)-3-hydroxypyrrolidin-1-yl)acetyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid

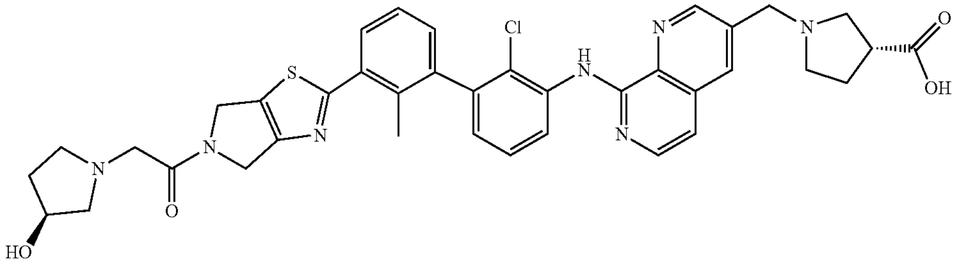 [SMILES: Cc1c(-c2nc3c(s2)CN(C(=O)CN2CC[C@H](O)C2)C3)cccc1-c1cccc(Nc2nccc3cc(CN4CC[C@@H](C(=O)O)C4)cnc23)c1Cl]

This compound was prepared using a similar procedure as described for Example 95 with (S)-pyrrolidin-3-ol (Combi-Blocks, cat #SS-7948) replacing (R)-pyrrolidin-3-ol in Step 2. LC-MS calculated for $C_{38}H_{39}ClN_7O_4S$ $(M+H)^+$: m/z=724.3; found 724.3.

Example 98

(R)-1-((8-((2-chloro-3'-(5-(2-(3-hydroxyazetidin-1-yl)acetyl)-5,6-dihydro-4H-pyrrolo[3,4-d]thiazol-2-yl)-2'-methyl-[1,1'-biphenyl]-3-yl)amino)-1,7-naphthyridin-3-yl)methyl)pyrrolidine-3-carboxylic acid

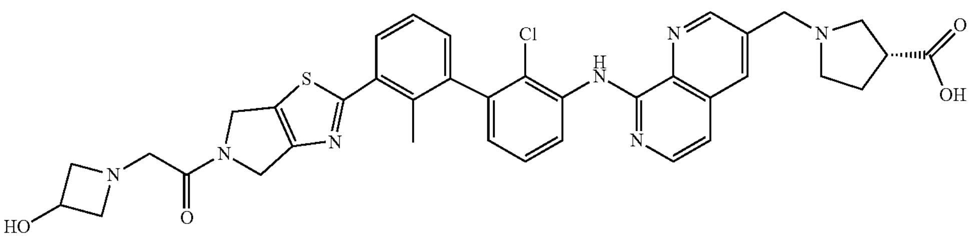 [SMILES: Cc1c(-c2nc3c(s2)CN(C(=O)CN2CC(O)C2)C3)cccc1-c1cccc(Nc2nccc3cc(CN4CC[C@@H](C(=O)O)C4)cnc23)c1Cl]

This compound was prepared using a similar procedure as described for Example 95 with 3-hydroxyazetidine hydrochloride (Ark Pharm, cat #AK-25536) replacing (R)-pyrrolidin-3-ol in Step 2. LC-MS calculated for $C_{37}H_{37}ClN_7O_4S$ $(M+H)^+$: m/z=710.3; found 710.3.

Example 99

Cis-4-((2-(3'-(3-(((R)-3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c]pyridin-5(4H)-yl)methyl)cyclohexanecarboxylic acid

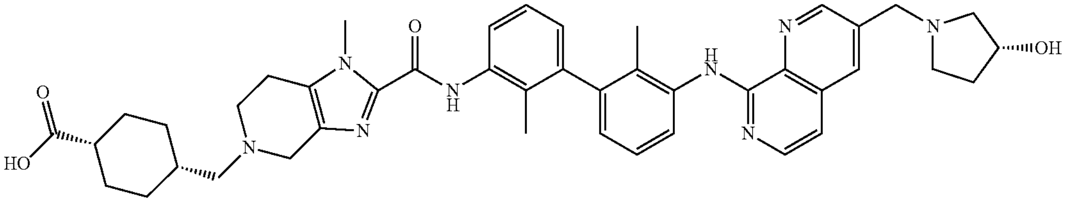 [SMILES: Cc1c(NC(=O)c2nc3c(n2C)CCN(C[C@H]2CC[C@@H](C(=O)O)CC2)C3)cccc1-c1cccc(Nc2nccc3cc(CN4CC[C@@H](O)C4)cnc23)c1C]

This compound was prepared using a similar procedure as described for Example 48 with (R)-N-(3'-(3-((3-hydroxypyrrolidin-1-yl)methyl)-1,7-naphthyridin-8-ylamino)-2,2'-dimethylbiphenyl-3-yl)-1-methyl-4,5,6,7-tetrahydro-1H-imidazo[4,5-c]pyridine-2-carboxamide (Example 62, Step 2) replacing (R)-N-(2-chloro-3'-((3-((3-hydroxypyrrolidin-1-yl)methyl)-1,7-naphthyridin-8-yl)amino)-2'-methyl-[1,1'-biphenyl]-3-yl)-1-methyl-4,5,6,7-tetrahydro-1H-imidazo[4,5-c]pyridine-2-carboxamide. The reaction mixture was purified by prep HPLC (pH=2, acetonitrile/water+TFA) to give the desired compound as its TFA salt. LC-MS calculated for $C_{43}H_{51}N_8O_4(M+H)^+$: m/z=743.4; found 743.4.

Example A. PD-1/PD-L1 Homogeneous Time-Resolved Fluorescence (HTRF) Binding Assay The assays were conducted in a standard black 384-well polystyrene plate with a final volume of 20 μL. Inhibitors were first serially diluted in DMSO and then added to the plate wells before the addition of other reaction components. The final concentration of DMSO in the assay was 1%. The assays were carried out at 25° C. in the PBS buffer (pH 7.4) with 0.05% Tween-20 and 0.1% BSA. Recombinant human PD-L1 protein (19-238) with a His-tag at the C-terminus was purchased from AcroBiosystems (PD1-H5229). Recombinant human PD-1 protein (25-167) with Fc tag at the C-terminus was also purchased from AcroBiosystems (PD1-H5257). PD-L1 and PD-1 proteins were diluted in the assay buffer and 10 μL was added to the plate well. Plates were centrifuged and proteins were preincubated with inhibitors for 40 minutes. The incubation was followed by the addition of 10 μL of HTRF detection buffer supplemented with Europium cryptate-labeled anti-human IgG (PerkinElmer-AD0212) specific for Fc and anti-His antibody conjugated to SureLight®-Allophycocyanin (APC, PerkinElmer-AD0059H). After centrifugation, the plate was incubated at 25° C. for 60 min. before reading on a PHERAstar FS plate reader (665 nm/620 nm ratio). Final concentrations in the assay were −3 nM PD1, 10 nM PD-L1, 1 nM europium anti-human IgG and 20 nM anti-His-Allophycocyanin. $IC_{50}$ determination was performed by fitting the curve of percent control activity versus the log of the inhibitor concentration using the GraphPad Prism 5.0 software.

Compounds of the present disclosure, as exemplified in the Examples, showed $IC_{50}$ values in the following ranges: $+=IC_{50}\leq 10$ nM; $++=10$ nM$<IC_{50}\leq 100$ nM; $+++=100$ nM$<IC_{50}\leq 1000$ nM.

Data obtained for the Example compounds using the PD-1/PD-L1 homogenous time-resolved fluorescence (HTRF) binding assay described in Example A is provided in Table 1.

TABLE 1

| Example | PD-1/PD-L1 HTRF $IC_{50}$ (nM) |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |

TABLE 1-continued

| Example | PD-1/PD-L1 HTRF $IC_{50}$ (nM) |
|---|---|
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62-peak1 | + |
| 62-peak2 | + |
| 63 | + |
| 64-peak1 | + |
| 64-peak2 | + |
| 65 | + |
| 66 | + |
| 67 | + |
| 68-peak1 | + |
| 68-peak2 | + |
| 69 | + |
| 70 | + |
| 71 | + |
| 72 | + |
| 73 | + |
| 74 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | ++ |
| 94 | + |
| 95 | + |
| 96 | + |
| 97 | + |
| 98 | + |
| 99 | + |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound of Formula (IIa):

(IIa)

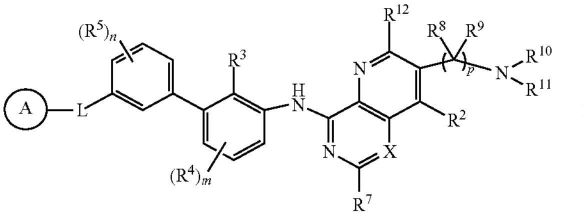

or a pharmaceutically acceptable salt or a stereoisomer thereof, wherein:

ring A is selected from:

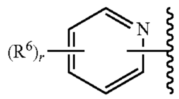, 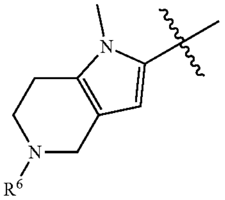, 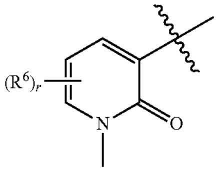, 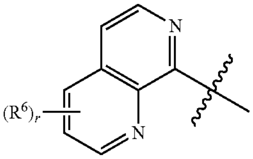, 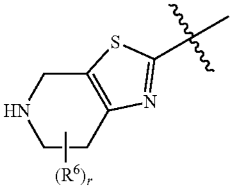, 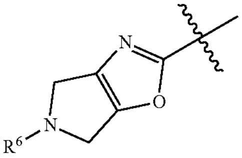, 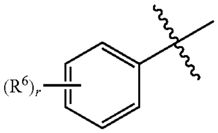 and 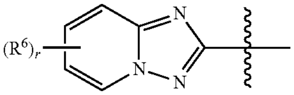;

wherein each subscript r is an integer of 1, 2, or 3;

L is —C(O)$NR^{13}$—, wherein the carbonyl group is attached to ring A;

X is N or $CR^{17}$;

$R^2$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$, wherein the $C_{1-4}$ alkyl and $C_{1-4}$ alkoxy of $R^2$ is optionally substituted with 1 or 2 substituents independently selected from $C_{1-4}$ alkoxy, $C_{1-4}$ haloalkyl, $C_{1-4}$ haloalkoxy, CN, halo, OH, —COOH, —C(O)$NH_2$, $NH_2$, —$NHC_{1-4}$ alkyl, and —N($C_{1-4}$ alkyl)$_2$;

$R^3$ is methyl, halo, CN or $C_{1-4}$ haloalkyl;

$R^4$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^5$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —N($C_{1-4}$ alkyl)$_2$;

$R^6$ is selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, C(O)$R^a$, C(O)$NR^aR^a$, C(O)$OR^a$, OC(O)$R^a$, OC(O)$NR^aR^a$, $NHR^a$, $NR^aR^a$, $NR^a$C(O)$R^a$, $NR^a$C(O)$OR^a$, $NR^a$C(O)$NR^aR^a$, C(=$NR^a$)$R^a$, C(=$NR^a$)$NR^aR^a$, $NR^a$C(=$NR^a$)$NR^aR^a$, $NR^a$S(O)$R^a$, $NR^a$S(O)$_2R^a$, $NR^a$S(O)$_2NR^aR^a$, S(O)$R^a$, S(O)$NR^aR^a$, S(O)$_2R^a$, and S(O)$_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl- and (4-10 membered heterocycloalkyl)-$C_{1-4}$ alkyl- of $R^6$ is optionally substituted with 1, 2, 3, 4 or 5 $R^b$ substituents;

$R^7$ is H, halo, CN, $C_{1-4}$ alkyl, $C_{1-4}$ alkoxy or $C_{1-4}$ haloalkoxy, wherein the $C_{1-4}$ alkyl and $C_{1-4}$ alkoxy of $R^7$ are each optionally substituted with CN;

or two $R^6$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

$R^8$ and $R^9$ are each independently selected from H, halo, CN, OH, —COOH, $C_{1-4}$ alkyl, $C_{1-4}$ alkoxy, —$NHC_{1-4}$ alkyl, —N($C_{1-4}$ alkyl)$_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^8$ or $R^9$ are each optionally substituted with 1, 2 or 3 independently selected $R^9$ substituents;

or $R^8$ and $R^9$ taken together with the carbon atom to which they are attached form 3-, 4-, 5- or 6-membered cycloalkyl or 4-, 5-, 6- or 7-membered heterocycloalkyl, each of which is optionally substituted with 1 or 2 $R^q$ substituents;

or $R^8$ and $R^{10}$ taken together with the atoms to which they are attached form 4-, 5-, 6- or 7-membered heterocycloalkyl, having zero to one additional heteroatoms as ring members selected from O, N or S, wherein the 4-, 5-, 6- or 7-membered heterocycloalkyl formed by $R^8$ and $R^{10}$ are each optionally substituted with 1 or 2 $R^q$ substituents;

$R^{10}$ and $R^{11}$ are each independently selected from H, $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-6}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, —C(O)$R^g$, —C(O)$OR^g$, —C(O)$NR^gR^g$, —$SO_2R^g$ and —$SO_2NR^gR^g$, wherein the $C_{1-6}$ alkyl, $C_{1-6}$ haloalkyl, $C_{3-6}$ cycloalkyl, $C_{6-10}$ aryl, 5-10 membered heteroaryl, 4-10 membered heterocycloalkyl, $C_{6-10}$ aryl-$C_{1-4}$ alkyl-, $C_{3-6}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^{10}$ or $R^{11}$ are each optionally substituted with 1, 2, or 3 independently selected $R^d$ substituents;

or $R^{10}$ and $R^{11}$ taken together with the nitrogen atom to which they are attached form 4-, 5-, 6-, 7-, 8-, 9-, 10-, or 11-membered heterocycloalkyl, wherein the 4-11 membered heterocycloalkyl is each optionally substituted with 1, 2 or 3 $R^f$ substituents;

$R^{12}$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl and —$N(C_{1-4}$ alkyl$)_2$;

$R^{14}$ and $R^{15}$ are each independently selected from H, halo, CN, OH, —COOH, $C_{1-4}$ alkyl, $C_{1-4}$ alkoxy, —$NHC_{1-4}$ alkyl, —$N(C_{1-4}$ alkyl$)_2$, $C_{1-4}$ haloalkyl, $C_{1-4}$ haloalkoxy, $C_{3-6}$ cycloalkyl, phenyl, 5-6 membered heteroaryl and 4-6 membered heterocycloalkyl, wherein the $C_{1-4}$ alkyl, $C_{1-4}$ alkoxy, $C_{1-4}$ haloalkyl, $C_{1-4}$ haloalkoxy, $C_{3-6}$ cycloalkyl, phenyl, 5-6 membered heteroaryl and 4-6 membered heterocycloalkyl of $R^{14}$ or $R^{15}$ are each optionally substituted with 1, 2, or 3 independently selected $R^q$ substituents;

or $R^{14}$ and $R^{15}$ taken together with the carbon atom to which they are attached form 3-, 4-, 5- or 6-membered cycloalkyl or 3-, 4-, 5- or 6-membered heterocycloalkyl, each of which is optionally substituted with 1 or 2 $R^q$ substituents;

$R^{17}$ is H, $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$, wherein the $C_{1-4}$ alkyl and $C_{1-4}$ alkoxy are each optionally substituted with 1 or 2 substituents independently selected from CN, halo and —C(O)$NH_2$;

each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 $R^d$ substituents;

each $R^d$ is independently selected from $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_{1-6}$ alkyl, $C_{1-6}$ haloalkyl, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 $R^n$ substituents;

each $R^n$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, and S(O)$_2$NR$^o$R$^o$, wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of R$^n$ are each optionally substituted with 1, 2 or 3 independently selected R$^q$ substituents;

each R$^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^g$ are each optionally substituted with 1, 2, or 3 R$^p$ substituents;

each R$^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O) R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ and S(O)$_2$NR$^r$R$^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^p$ is optionally substituted with 1, 2 or 3 R$^q$ substituents;

or any two R$^a$ substituents together with the nitrogen atom to which they are attached form a 4-, 5-, 6-, 7-, 8-, 9- or 10-membered heterocycloalkyl group optionally substituted with 1, 2 or 3 R$^h$ substituents;

each R$^h$ is independently selected from $C_{1-6}$ alkyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{1-6}$ haloalkoxy, $C_{2-6}$ alkenyl, $C_{2-6}$ alkynyl, halo, CN, OR$^i$, SR$^i$, NHOR$^i$, C(O)R$^i$, C(O)NR$^i$R$^i$, C(O)OR$^i$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR$^i$)NR$^i$R$^i$, S(O)R$^i$, S(O)NR$^i$R$^i$, S(O)$_2$R$^i$, NRiS(O)$_2$R$^i$, NRiS(O)$_2$NR$^i$R$^i$, and S(O)$_2$NR$^i$R$^i$, wherein the $C_{1-6}$ alkyl, $C_{2-6}$ alkenyl, $C_{2-6}$ alkynyl, $C_{3-10}$ cycloalkyl, 4-7 membered heterocycloalkyl, $C_{6-10}$ aryl, 5-6 membered heteroaryl, $C_{6-10}$ aryl-$C_{1-4}$ alkyl-, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of R$^h$ are each further optionally substituted by 1, 2, or 3 R$^i$ substituents;

each R$^i$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$, wherein the $C_{1-4}$ alkyl, $C_{3-6}$ cycloalkyl, $C_{6-10}$ aryl, 5- or 6-membered heteroaryl, 4-6 membered heterocycloalkyl, $C_{2-4}$ alkenyl, $C_{2-4}$ alkynyl, $C_{1-4}$ haloalkyl, and $C_{1-4}$ haloalkoxy of R$^i$ are each optionally substituted with 1, 2 or 3 independently selected R$^q$ substituents;

or two R$^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two R$^c$ substituents together with the nitrogen atom to which they are attached form a 4-, 5-, 6-, or 7-membered heterocycloalkyl group optionally substituted with 1, 2, or 3 independently selected R$^h$ substituents;

or any two R$^e$ substituents together with the nitrogen atom to which they are attached form a 4-, 5-, 6-, or 7-membered heterocycloalkyl group optionally substituted with 1, 2, or 3 independently selected R$^h$ substituents;

or any two R$^g$ substituents together with the nitrogen atom to which they are attached form a 4-, 5-, 6-, or 7-membered heterocycloalkyl group optionally substituted with 1, 2, or 3 independently selected R$^h$ substituents;

or any two R$^o$ substituents together with the nitrogen atom to which they are attached form a 4-, 5-, 6-, or 7-membered heterocycloalkyl group optionally substituted with 1, 2, or 3 independently selected R$^h$ substituents;

or any two R$^r$ substituents together with the nitrogen atom to which they are attached form a 4-, 5-, 6-, or 7-membered heterocycloalkyl group optionally substituted with 1, 2, or 3 independently selected R$^h$ substituents;

each R$^i$, R$^k$, R$^o$ or R$^r$ is independently selected from H, $C_{1-4}$ alkyl, $C_{3-6}$ cycloalkyl, $C_{6-10}$ aryl, 5 or 6-membered heteroaryl, 4-7 membered heterocycloalkyl, $C_{1-6}$ haloalkyl, $C_{1-6}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of R$^i$, R$^k$, R$^o$ or R$^r$ are each optionally substituted with 1, 2 or 3 R$^q$ substituents;

each R$^q$ is independently selected from halo, OH, CN, —COOH, $NH_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of R$^q$ are each optionally substituted with 1, 2, or 3 substituents selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

each subscript q is independently an integer of 1, 2, 3 or 4; and the subscript p is an integer of 1, 2, 3 or 4.

2. The compound of claim 1, having Formula (IIb):

(IIb)

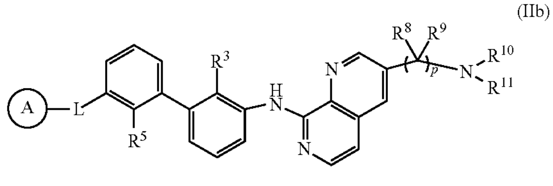

or a pharmaceutically acceptable salt or a stereoisomer thereof.

3. The compound of claim 1, or a pharmaceutically acceptable salt or a stereoisomer thereof, wherein $R^6$ is H, $C_{1-6}$ alkyl, (3-carboxypyrrolidin-1-yl)methyl, (R)-(3-carboxypyrrolidin-1-yl)methyl, (S)-(3-carboxypyrrolidin-1-yl) methyl, (3-hydroxypyrrolidin-1-yl)methyl, (R)-(3-hydroxypyrrolidin-1-yl)methyl, (S)-(3-hydroxypyrrolidin-1-yl) methyl, (2-hydroxyethylamino)methyl, (2-hydroxy-2-methylpropylamino)methyl, 2-(dimethylamino)ethanoyl, 2-(3-carboxyazetidin-1-yl)ethanoyl, (R)-2-(3-carboxyazetidin-1-yl)ethanoyl, (S)-2-(3-carboxyazetidin-1-yl)ethanoyl, 2-(2-carboxypiperidin-1-yl)ethanoyl, (R)-2-(2-carboxypiperidin-1-yl)ethanoyl, (S)-2-(2-carboxypiperidin-1-yl)ethanoyl, 2-(3-carboxypyrrolidin-1-yl)ethanoyl, (S)-2-(3-carboxypyrrolidin-1-yl)ethanoyl, (R)-2-(3-carboxypyrrolidin-1-yl)ethanoyl, (5-cyanopyridin-3-yl) methoxy, halo or CN.

4. The compound of claim 1, or a pharmaceutically acceptable salt or a stereoisomer thereof, wherein $R^6$ is (4-carboxycyclohexyl)methyl, trans-(4-carboxycyclohexyl) methyl, cis-(4-carboxycyclohexyl)methyl, 1-carboxy-2-propyl, (R)-1-carboxy-2-propyl, (S)-1-carboxy-2-propyl, (4-carboxy-4-methylcyclohexyl)methyl, 2-pyrrolidinyl, 2-(3-hydroxypyrrolidin-1-yl)acetyl, 2-((R)-3-hydroxypyrrolidin-1-yl)acetyl, 2-((S)-3-hydroxypyrrolidin-1-yl)acetyl, 2-(3-hydroxyazetidin-1-yl)acetyl, 2-((2-hydroxyethyl) (methyl)amino)acetyl, (4-carboxycyclohexyl)ethyl, 4-carboxycyclohexyl, 4-carboxy-4-methylcyclohexyl, dimethylglycyl, or N-ethyl-N-methylglycyl.

5. The compound of claim 1, or a pharmaceutically acceptable salt or a stereoisomer thereof, wherein L is —C(O)NH—, wherein the carbonyl group in the —C(O) NH— linkage is attached to ring A.

6. The compound of claim 1, or a pharmaceutically acceptable salt or a stereoisomer thereof, wherein the subscript m is 0.

7. The compound of claim 1, or a pharmaceutically acceptable salt or a stereoisomer thereof, wherein the subscript n is 1 and $R^5$ is halo or $C_{1-4}$ alkyl.

8. The compound of claim 1, or a pharmaceutically acceptable salt or a stereoisomer thereof, wherein $R^3$ is methyl, CN or $C_1$.

9. The compound of claim 1, or a pharmaceutically acceptable salt or a stereoisomer thereof, wherein $R^{12}$ is H, halo, CN, $C_{1-4}$ alkyl or $C_{1-4}$ alkoxy.

10. The compound of claim 1, or a pharmaceutically acceptable salt or a stereoisomer thereof, wherein $R^2$ is H.

11. The compound of claim 1, or a pharmaceutically acceptable salt or a stereoisomer thereof, wherein the subscript p is 1.

12. The compound of claim 1, or a pharmaceutically acceptable salt or a stereoisomer thereof, wherein $R^8$ and $R^9$ are each H.

13. The compound of claim 1, or a pharmaceutically acceptable salt or a stereoisomer thereof, wherein $R^{10}$ is H.

14. The compound of claim 1, or a pharmaceutically acceptable salt or a stereoisomer thereof, wherein $R^{11}$ is 2-hydroxyethyl, [1-(hydroxymethyl)cyclopropyl]methyl, [1-(hydroxymethyl)cyclobutyl]methyl or 2-(dimethylamino)-2-oxo-ethyl.

15. The compound of claim 1, or a pharmaceutically acceptable salt or a stereoisomer thereof, wherein —$NR^{10}R^{11}$ is (2-hydroxyethyl)amino, 3-hydroxypyrrolidin-1-yl, 3-carboxypyrrolidin-1-yl, 3-carboxyazetidin-1-yl, (S)-3-carboxyazetidin-1-yl, (R)-3-carboxyazetidin-1-yl, 2-carboxy-1-piperidinyl, 2-oxooxazolidin-3-yl, [1-(hydroxymethyl)cyclopropyl]methylamino, [1-(hydroxymethyl)cyclobutyl]methylamino or [2-(dimethylamino)-2-oxo-ethyl]amino.

16. The compound of claim 1, or a pharmaceutically acceptable salt or a stereoisomer thereof, wherein ring A is 2-pyridyl, optionally substituted with 1, 2, 3, or 4 independently selected $R^6$ substituents.

17. The compound of claim 1, or a pharmaceutically acceptable salt or a stereoisomer thereof, wherein X is N or CH.

18. The compound of claim 1 selected from:

1-(((6-(2-fluoro-3'-(3-((2-hydroxyethylamino)methyl)-1,7-naphthyridin-8-ylamino)-2'-methylbiphenyl-3-ylcarbamoyl)pyridin-3-yl)methyl)amino)cyclobutanecarboxylic acid;

(S)-1-((6-((2-fluoro-3'-((3-(((2-hydroxyethyl)amino) methyl)-1,7-naphthyridin-8-yl)amino)-2'-methyl-[1,1'-biphenyl]-3-yl) carbamoyl)pyridin-3-yl)methyl) piperidine-2-carboxylic acid;

N-(2-fluoro-3'-((3-(((2-hydroxyethyl)amino)methyl)-1,7-naphthyridin-8-yl)amino)-2'-methyl-[1,1'-biphenyl]-3-yl)-5-(((2-hydroxyethyl)amino)methyl)picolinamide;

N-(2-chloro-3'-((3-(((2-hydroxyethyl)amino)methyl)-1,7-naphthyridin-8-yl)amino)-2'-methyl-[1,1'-biphenyl]-3-yl)-5-(((2-hydroxyethyl)amino)methyl)picolinamide;

N-(2-chloro-3'-((3-(((R)-3-hydroxypyrrolidin-1-yl) methyl)-1,7-naphthyridin-8-yl)amino)-2'-methyl-[1,1'-biphenyl]-3-yl)-5-(((R)-3-hydroxypyrrolidin-1-yl) methyl)picolinamide;

(R)-1-((8-((2'-chloro-3'-(5-(((R)-3-hydroxypyrrolidin-1-yl)methyl)picolinamido)-2-methyl-[1,1'-biphenyl]-3-yl)amino)-1,7-naphthyridin-3-yl)methyl)pyrrolidine-3-carboxylic acid; and (R)-1-((8-((2'-chloro-3'-(5-((3-hydroxypyrrolidin-1-yl) methyl)picolinamido)-2-methyl-[1,1'-biphenyl]-3-yl) amino)-1,7-naphthyridin-3-yl)methyl)azetidine-3-carboxylic acid;

or a pharmaceutically acceptable salt thereof.

19. The compound of claim 1 selected from:

1-((8-(2-chloro-3'-(1,5-dimethyl-4,5,6,7-tetrahydro-1H-imidazo[4,5-c]pyridine-2-carboxamido)-2'-methylbiphenyl-3-ylamino)-1,7-naphthyridin-3-yl)methyl)azetidine-3-carboxylic acid;

(R)-1-((5-(2-chloro-3'-(3-(((R)-3-hydroxypyrrolidin-1-yl) methyl)-1,7-naphthyridin-8-ylamino)-2'-methylbiphenyl-3-ylcarbamoyl)-1-methyl-6-oxo-1,6-dihydropyridin-3-yl)methyl)pyrrolidine-3-carboxylic acid;

(R)-1-((8-(2,2'-dichloro-3'-(5-((3-hydroxypyrrolidin-1-yl)methyl)-1-methyl-2-oxo-1,2-dihydropyridine-3-carboxamido) biphenyl-3-ylamino)-1,7-naphthyridin-3-yl)methyl)azetidine-3-carboxylic acid;

1-((8-(2,2'-dichloro-3'-(5-((2-hydroxyethylamino) methyl)-1-methyl-2-oxo-1,2-dihydropyridine-3-carboxamido) biphenyl-3-ylamino)-1,7-naphthyridin-3-yl)methyl)azetidine-3-carboxylic acid;

1-((8-(2,2'-dichloro-3'-(5-((2-hydroxy-2-methylpropylamino)methyl)-1-methyl-2-oxo-1,2-dihydropyridine-3-carboxamido) biphenyl-3-ylamino)-1,7-naphthyridin-3-yl)methyl)azetidine-3-carboxylic acid;

(R)-1-((8-(3'-(5-(((R)-3-hydroxypyrrolidin-1-yl)methyl)-1-methyl-2-oxo-1,2-dihydropyridine-3-carboxamido)-2,2'-dimethylbiphenyl-3-ylamino)-1,7-naphthyridin-3-yl)methyl)pyrrolidine-3-carboxylic acid;

(R)-1-((8-(2'-chloro-3'-(1,5-dimethyl-4,5,6,7-tetrahydro-1H-imidazo[4,5-c]pyridine-2-carboxamido)-2-methylbiphenyl-3-ylamino)-1,7-naphthyridin-3-yl)methyl) pyrrolidine-3-carboxylic acid;

(S)-N-(2-chloro-3'-(3-((3-hydroxypyrrolidin-1-yl) methyl)-1,7-naphthyridin-8-ylamino)-2'-methylbiphenyl-3-yl)-1,5-dimethyl-4,5,6,7-tetrahydro-1H-imidazo [4,5-c]pyridine-2-carboxamide; and (R)-1-((8-(2'-chloro-3'-(1,5-dimethyl-4,5,6,7-tetrahydro-1H-imidazo[4,5-c]pyridine-2-carboxamido)-2-methylbiphenyl-3-ylamino)-1,7-naphthyridin-3-yl)methyl)-3-methylpyrrolidine-3-carboxylic acid;

or a pharmaceutically acceptable salt thereof.

20. The compound of claim 1 selected from:

(R)-1-((8-(2'-Chloro-2-methyl-3'-(1-methyl-4,5,6,7-tetrahydro-1H-imidazo[4,5-c]pyridine-2-carboxamido) biphenyl-3-ylamino)-1,7-naphthyridin-3-yl)methyl)-3-methylpyrrolidine-3-carboxylic acid;

(R)-1-((8-(3'-(1,5-dimethyl-4,5,6,7-tetrahydro-1H-imidazo[4,5-c]pyridine-2-carboxamido)-2,2'-dimethylbiphenyl-3-ylamino)-1,7-naphthyridin-3-yl)methyl)pyrrolidine-3-carboxylic acid;

trans-4-((2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl) cyclohexanecarboxylic acid;

cis-4-((2-(2-chloro-3'-(3-(((R)-3-hydroxypyrrolidin-1-yl) methyl)-1,7-naphthyridin-8-ylamino)-2'-methylbiphenyl-3-ylcarbamoyl)-1-methyl-6,7-dihydro-1H-imidazo [4,5-c]pyridin-5(4H)-yl)methyl) cyclohexanecarboxylic acid;

cis-4-((2-(2-chloro-2'-methyl-3'-(3-(pyrrolidin-1-ylmethyl)-1,7-naphthyridin-8-ylamino) biphenyl-3-ylcarbamoyl)-1-methyl-6,7-dihydro-1H-imidazo[4,5-c] pyridin-5(4H)-yl)methyl)cyclohexanecarboxylic acid;

trans-4-((2-(2-chloro-3'-(3-(((S)-1-hydroxypropan-2-ylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl) cyclohexanecarboxylic acid;

trans-4-((2-(2-chloro-3'-(3-(((1S,2S)-2-hydroxycyclopentylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl) cyclohexanecarboxylic acid;

trans 4-(2-(2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl) cyclohexanecarboxylic acid;

cis 4-(2-(2-(2-chloro-3'-(3-(((R)-3-hydroxypyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl) cyclohexanecarboxylic acid;

3-(2-(2-chloro-3'-(3-(((R)-3-hydroxypyrrolidin-1-yl) methyl)-1,7-naphthyridin-8-ylamino)-2'-methylbiphenyl-3-ylcarbamoyl)-1-methyl-6,7-dihydro-1H-imidazo [4,5-c]pyridin-5(4H)-yl)butanoic acid;

cis 4-((2-(2-chloro-3'-(3-(((S)-3-hydroxypyrrolidin-1-yl) methyl)-1,7-naphthyridin-8-ylamino)-2'-methylbiphenyl-3-ylcarbamoyl)-1-methyl-6,7-dihydro-1H-imidazo [4,5-c]pyridin-5(4H)-yl)methyl) cyclohexanecarboxylic acid;

cis 4-((2-(2-chloro-3'-(3-(((R)-3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)methyl) cyclohexanecarboxylic acid;

(R)-4-(2-(2-chloro-3'-(3-((3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl) cyclohexanecarboxylic acid;

(S)-4-(2-(2-chloro-3'-(3-((3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl) cyclohexanecarboxylic acid;

trans 4-(2-(2-(2-chloro-3'-(3-(((R)-1-hydroxypropan-2-ylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl) cyclohexanecarboxylic acid;

trans 4-(2-(2-(2-chloro-3'-(3-(((S)-1-hydroxypropan-2-ylamino)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl) cyclohexanecarboxylic acid;

trans-4-(2-(2-(2-chloro-3'-(3-(((R)-3-hydroxy-3-methylpyrrolidin-1-yl)methyl)-1,7-naphthyridin-8-ylamino)-2'-methylbiphenyl-3-ylcarbamoyl)-1-methyl-6,7-dihydro-1H-imidazo[4,5-c]pyridin-5(4H)-yl)ethyl)cyclohexanecarboxylic acid;

(R)-4-(2-(3'-(3-((3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c] pyridin-5(4H)-yl)-1-methylcyclohexanecarboxylic acid;

trans-4-(2-(2-(3'-(3-(((R)-3-hydroxypyrrolidin-1-yl) methyl)-1,7-naphthyridin-8-ylamino)-2,2'-dimethylbiphenyl-3-ylcarbamoyl)-1-methyl-6,7-dihydro-1H-imidazo[4,5-c]pyridin-5(4H)-yl)ethyl) cyclohexanecarboxylic acid;

(R)-4-(2-(3'-(3-((3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c] pyridin-5(4H)-yl)cyclohexanecarboxylic acid;

Trans-4-(2-(2-(2,2'-dichloro-3'-(3-(((R)-3-hydroxypyrrolidin-1-yl)methyl)-1,7-naphthyridin-8-ylamino) biphenyl-3-ylcarbamoyl)-1-methyl-6,7-dihydro-1H-imidazo [4,5-c] pyridin-5(4H)-yl)ethyl)cyclohexanecarboxylic acid;

trans 4-(2-(2-(2'-chloro-3'-(3-(((R)-3-hydroxypyrrolidin-1-yl)methyl)-1,7-naphthyridin-8-ylamino)-2-methylbiphenyl-3-ylcarbamoyl)-1-methyl-6,7-dihydro-1H-imidazo[4,5-c]pyridin-5(4H)-yl)ethyl) cyclohexanecarboxylic acid;

(R)-1-((4-(2'-chloro-3'-(1,5-dimethyl-4,5,6,7-tetrahydro-1H-imidazo[4,5-c]pyridine-2-carboxamido)-2-methylbiphenyl-3-ylamino)pyrido[3,2-d]pyrimidin-7-yl) methyl)-3-methylpyrrolidine-3-carboxylic acid (R)-4-(2-(2-chloro-3'-(7-((3-hydroxypyrrolidin-1-yl)methyl)pyrido[3,2-d]pyrimidin-4-ylamino)-2'-methylbiphenyl-3-ylcarbamoyl)-1-methyl-6,7-dihydro-1H-imidazo[4,5-c]pyridin-5(4H)-yl)-1-methylcyclohexanecarboxylic acid;

trans 4-((2-(2-chloro-3'-(7-(((R)-3-hydroxypyrrolidin-1-yl)methyl)pyrido[3,2-d]pyrimidin-4-ylamino)-2'-methylbiphenyl-3-ylcarbamoyl)-1-methyl-6,7-dihydro-1H-imidazo[4,5-c]pyridin-5(4H)-yl)methyl)cyclohexanecarboxylic acid; and Cis-4-((2-(3'-(3-(((R)-3-hydroxypyrrolidin-1-yl)methyl)-1,7-naphthyridin-8-ylamino)-2,2'-dimethylbiphenyl-3-ylcarbamoyl)-1-methyl-6,7-dihydro-1H-imidazo[4,5-c]pyridin-5(4H)-yl)methyl)cyclohexanecarboxylic acid;

or a pharmaceutically acceptable salt thereof.

21. The compound of claim 1, or a pharmaceutically acceptable salt or a stereoisomer thereof, wherein:

X is N or $CR^{17}$, wherein $R^{17}$ is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy are each optionally substituted with 1 or 2 substituents independently selected from CN, halo and —$C(O)NH_2$;

$R^2$ is H, $C_{1-4}$ alkyl, $C_{1-4}$ alkoxy, $C_{1-4}$ haloalkyl, $C_{1-4}$ haloalkoxy, CN, halo, or OH, wherein the $C_{1-4}$ alkyl and $C_{1-4}$ alkoxy of $R^1$ or $R^2$ is optionally substituted with 1 or 2 substituents independently selected from $C_{1-4}$ alkoxy, $C_{1-4}$ haloalkyl, $C_{1-4}$ haloalkoxy, CN, halo, and OH;

$R^4$ is $C_{1-4}$ alkyl, $C_{1-4}$ alkoxy, or $C_{1-4}$ haloalkyl;

$R^5$ is $C_{1-4}$ alkyl, $C_{1-4}$ alkoxy, $C_{1-4}$ haloalkyl, $C_{1-4}$ haloalkoxy, CN, halo, or OH;

each $R^6$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, 5-14 membered heteroaryl, 4-10 membered heterocycloalkyl, (5-14 membered heteroaryl)-$C_{1-4}$ alkyl-, (4-10 membered heterocycloalkyl)-$C_{1-4}$ alkyl-, CN, $NO_2$, $OR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, or $NR^aC(O)OR^a$, wherein the $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl- and (4-10 membered heterocycloalkyl)-$C_{1-4}$ alkyl- of $R^6$ are each optionally substituted with 1, 2, or 3 $R^b$ substituents;

$R^7$ is H, $C_{1-4}$ alkyl, $C_{1-4}$ alkoxy, $C_{1-4}$ haloalkoxy, CN, halo, or OH;

$R^8$ and $R^9$ are each independently selected from H, halo, CN, OH, —COOH, $C_{1-4}$ alkyl, $C_{1-4}$ alkoxy, —$NHC_{1-4}$ alkyl, —$N(C_{1-4}\ alkyl)_2$, and $C_{1-4}$ haloalkyl;

$R^{10}$ and $R^{11}$ are each independently selected from H, $C_{1-6}$ alkyl, $C_{1-6}$ haloalkyl, —$C(O)R^8$, —$C(O)OR^8$, and —$C(O)NR^8R^8$, wherein the $C_{1-6}$ alkyl and $C_{1-6}$ haloalkyl of $R^{10}$ or $R^{11}$ are each optionally substituted with 1 or 2 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents;

$R^{12}$ is H, $C_{1-4}$ alkyl, $C_{1-4}$ alkoxy, $C_{1-4}$ haloalkyl, $C_{1-4}$ haloalkoxy, CN, halo, or OH;

each $R^{13}$ is independently H, $C_{1-6}$ haloalkyl or $C_{1-6}$ alkyl;

each $R^a$ is independently selected from H, CN, $C_{1-6}$ alkyl, $C_{1-4}$ haloalkyl, $C_{2-6}$ alkenyl, and $C_{2-6}$ alkynyl;

each $R^d$ is independently selected from $C_{1-6}$ alkyl, $C_{1-6}$ haloalkyl, halo, CN, $NH_2$, $OR^e$, $C(O)R^e$, $C(O)NR^eR^e$, $C(O)OR^e$, $OC(O)R^e$, $OC(O)NR^eR^e$, $NHR^e$, $NR^eR^e$, and $NR^eC(O)R^e$;

each $R^e$ is independently selected from H, $C_{1-6}$ alkyl, $C_{1-6}$ haloalkyl, $C_{2-6}$ alkenyl, and $C_{2-6}$ alkynyl;

each $R^b$ substituent is independently selected from halo, $C_{1-6}$ alkyl, $C_{1-6}$ haloalkyl, $C_{1-6}$ haloalkoxy, CN, OH, $NH_2$, $NO_2$, $OR^c$, $C(O)R^c$, $C(O)NR^cR^c$, $C(O)OR^c$, $OC(O)R^c$, $OC(O)NR^cR^c$, $C({=}NR^c)NR^cR^c$, $NR^cC({=}NR^c)NR^cR^c$, $NHR^c$, $NR^cR^c$, $NR^cC(O)R^c$, and $NR^cC(O)OR^c$; wherein the $C_{1-4}$ alkyl, $C_{1-4}$ haloalkyl, and $C_{1-4}$ haloalkoxy of $R^b$ are each further optionally substituted with 1 or 2 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, $C_{6-10}$ aryl-$C_{1-4}$ alkyl-, and $C_{3-10}$ cycloalkyl-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, $C_{6-10}$ aryl-$C_{1-4}$ alkyl-, and $C_{3-10}$ cycloalkyl-$C_{1-4}$ alkyl- of $R^c$ are each optionally substituted with 1, 2, or 3 $R^f$ substituents;

each $R^f$ is independently selected from $C_{1-4}$ alkyl, $C_{1-4}$ haloalkyl, $C_{2-6}$ alkenyl, $C_{2-6}$ alkynyl, halo, CN, $OR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, and $NR^gC(O)OR^g$;

each $R^g$ is independently selected from H, $C_{1-6}$ alkyl, $C_{1-4}$ haloalkyl, $C_{2-6}$ alkenyl, and $C_{2-6}$ alkynyl;

each $R^h$ is independently selected from $C_{1-6}$ alkyl, $C_{1-6}$ haloalkyl, $C_{1-6}$ haloalkoxy, $C_{2-6}$ alkenyl, $C_{2-6}$ alkynyl, halo, CN, $OR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, and $NR^iC(O)OR^i$, wherein the $C_{1-6}$ alkyl, $C_{2-6}$ alkenyl, and $C_{2-6}$ alkynyl of $R^h$ are each further optionally substituted by 1, 2, or 3 $R^j$ substituents;

each $R^j$ is independently selected from $C_{2-4}$ alkenyl, $C_{2-4}$ alkynyl, halo, $C_{1-4}$ alkyl, $C_{1-4}$ haloalkyl, and CN;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

each $R^i$ is independently selected from H, $C_{1-4}$ alkyl, $C_{1-6}$ haloalkyl, $C_{1-6}$ haloalkoxy, $C_{2-4}$ alkenyl, and $C_{2-4}$ alkynyl;

the subscript m is an integer of 0, 1, or 2;

the subscript n is an integer of 0, 1, or 2; and the subscript p is an integer of 1, 2, or 3.

22. The compound of claim 1, or a pharmaceutically acceptable salt or a stereoisomer thereof, wherein:

X is $CR^{17}$, wherein $R^{17}$ is H or $C_{1-4}$ alkyl;

one of $R^1$ and $R^2$ is —$(CR^8R^9)_p$—$NR^{10}R^{11}$ and the other is H, $C_{1-4}$ alkyl, or $C_{1-4}$ alkoxy;

$R^3$ is methyl or halo;

$R^4$ is $C_{1-4}$ alkyl or $C_{1-4}$ alkoxy;

$R^5$ is $C_{1-4}$ alkyl, $C_{1-4}$ alkoxy, or halo;

each $R^6$ is independently selected from H, halo, $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, 5-14 membered heteroaryl, 4-10 membered heterocycloalkyl, (5-14 membered heteroaryl)-$C_{1-4}$ alkyl- and (4-10 membered heterocycloalkyl)-$C_{1-4}$ alkyl- of $R^6$ are each optionally substituted with 1, 2, or 3 $R^b$ substituents;

$R^7$ is H or $C_{1-4}$ alkyl;

$R^8$ and $R^9$ are each independently selected from H and $C_{1-4}$ alkyl;

$R^{10}$ and $R^{11}$ are each independently selected from H and $C_{1-6}$ alkyl optionally substituted with 1 or 2 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents;

$R^{12}$ is H or $C_{1-4}$ alkyl;

each $R^{13}$ is independently H or $C_{1-6}$ alkyl;

each $R^b$ substituent is independently selected from halo, $C_{1-6}$ alkyl, OH, $NH_2$, $C(O)OR^c$, $NHR^c$, and $NR^cR^c$;

each $R^c$ is independently selected from H, $C_{1-6}$ alkyl, $C_{2-6}$ alkenyl, $C_{2-6}$ alkynyl, $C_{3-10}$ cycloalkyl, and $C_{3-10}$ cycloalkyl-$C_{1-4}$ alkyl-, wherein the $C_{1-6}$ alkyl, $C_{2-6}$ alkenyl, $C_{2-6}$ alkynyl, $C_{3-10}$ cycloalkyl, and $C_{3-10}$ cycloalkyl-$C_{1-4}$ alkyl- of $R^c$ are each optionally substituted with 1 or 2 $R^f$ substituents;

each $R^f$ is independently selected from $C_{1-4}$ alkyl, $C_{2-6}$ alkenyl, $C_{2-6}$ alkynyl, halo, $OR^g$, and $C(O)OR^g$;

each $R^g$ is independently selected from H and $C_{1-6}$ alkyl;

each $R^h$ is independently selected from $C_{1-6}$ alkyl, $C_{2-6}$ alkenyl, $C_{2-6}$ alkynyl, halo, CN, $OR^i$, and $C(O)OR^i$, or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

each $R^i$ is independently selected from H and $C_{1-4}$ alkyl;

the subscript m is an integer of 0 or 1;

the subscript n is an integer of 0 or 1; and the subscript p is an integer of 1 or 2.

23. The compound of claim 1, or a pharmaceutically acceptable salt or a stereoisomer thereof, wherein:

X is $CR^{17}$, wherein $R^{17}$ is H;

one of $R^1$ and $R^2$ is $-(CR^8R^9)_p-NR^{10}R^{11}$ and the other is H;

$R^3$ is methyl or halo;

$R^4$ is $C_{1-4}$ alkyl or $C_{1-4}$ alkoxy;

$R^5$ is $C_{1-4}$ alkyl or halo;

each $R^6$ is independently selected from H, $C_{1-6}$ alkyl, and (4-10 membered heterocycloalkyl)-$C_{1-4}$ alkyl-, wherein the $C_{1-6}$ alkyl and (4-10 membered heterocycloalkyl)-$C_{1-4}$ alkyl- of $R^6$ are each optionally substituted with 1 or 2 $R^b$ substituents;

$R^7$ is H;

$R^8$ and $R^9$ are each independently selected from H and $C_{1-4}$ alkyl;

$R^{10}$ and $R^{11}$ are each independently selected from H and $C_{1-6}$ alkyl optionally substituted with 1 or 2 independently selected $R^f$ substituents;

or $R^{10}$ and $R^{11}$ taken together with the nitrogen atom to which they are attached form 4-, 5-, 6- or 7-membered heterocycloalkyl, wherein the 4-, 5-, 6- or 7-membered heterocycloalkyl is optionally substituted with 1, 2 or 3 $R^h$ substituents;

$R^{12}$ is H;

$R^{13}$ is H;

each $R^b$ substituent is independently selected from OH, $C(O)OR^c$, $NHR^c$, and $NR^cR^c$;

each $R^c$ is independently selected from H, $C_{1-6}$ alkyl, and $C_{3-10}$ cycloalkyl, wherein the $C_{1-6}$ alkyl, and $C_{3-10}$ cycloalkyl of $R^c$ are each optionally substituted with 1 or 2 $R^f$ substituents;

each $R^f$ is independently selected from $OR^g$, and $C(O)OR^g$;

$R^g$ is H;

each $R^h$ is independently selected from $OR^i$ and $C(O)OR^i$;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

$R^i$ is H;

the subscript m is an integer of 0 or 1;

the subscript n is an integer of 0 or 1; and the subscript p is an integer of 1 or 2.

24. A pharmaceutical composition comprising a compound of claim 1, or a pharmaceutically acceptable salt or a stereoisomer thereof, and one or more pharmaceutically acceptable excipient or carrier.

25. A method of inhibiting PD-1/PD-L1 interaction, said method comprising administering to a patient a compound of claim 1, or a pharmaceutically acceptable salt or a stereoisomer thereof.

26. A method of treating a disease or disorder associated with inhibition of PD-1/PD-L1 interaction, said method comprising administering to a patient in need thereof a therapeutically effective amount of a compound of claim 1, or a pharmaceutically acceptable salt or a stereoisomer thereof, wherein the disease or disorder is cancer.

27. The method according to claim 26, wherein the cancer is selected from urothelial cancer, cancers with high microsatellite instability ($MSI^{high}$), genitourinary tract cancers, liver cancers, nervous system cancers, gynecological cancers, acute promyelocytic leukemia (APL), myeloproliferative diseases, primary myelofibrosis (PMF), polycythemia vera (PV), essential thrombocytosis (ET), myelodysplasia syndrome (MDS), T-cell acute lymphoblastic lymphoma (T-ALL), osteosarcoma, angiosarcoma, fibrosarcoma, liposarcoma, myxoma, rhabdomyoma, rhabdosarcoma, fibroma, lipoma, teratoma, bronchogenic carcinoma, squamous cell carcinoma, undifferentiated small cell carcinoma, undifferentiated large cell carcinoma, adenocarcinoma, alveolar (bronchiolar) carcinoma, bronchial adenoma, chondromatous hamartoma, carcinoma, ductal adenocarcinoma, insulinoma, glucagonoma, gastrinoma, carcinoid tumors, vipoma, cancers of the small bowel, leiomyoma, hemangioma, cancers of the large bowel, tubular adenoma, villous adenoma, hamartoma, colorectal cancer, Wilm's tumor [nephroblastoma], transitional cell carcinoma, seminoma, embryonal carcinoma, teratocarcinoma, choriocarcinoma, sarcoma, interstitial cell carcinoma, fibroadenoma, adenomatoid tumors, hepatoma, hepatoblastoma, hepatocellular adenoma, malignant fibrous histiocytoma, malignant lymphoma, reticulum cell sarcoma, malignant giant cell tumor chordoma, osteochronfroma, osteocartilaginous exostoses, benign chondroma, chondroblastoma, chondromyxofibroma, osteoid osteoma, giant cell tumors, cancers of the skull, osteoma, granuloma, xanthoma, osteitis deformans, cancers of the meninges, meningioma, meningiosarcoma, gliomatosis, meduoblastoma, glioma, ependymoma, germinoma, pinealoma, glioblastoma multiform, oligodendroglioma, schwannoma, retinoblastoma, congenital tumors, cancers of the spinal cord, Lhermitte-Duclos disease, endometrial carcinoma, cancers of the cervix, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, cancers of the vulva, intraepithelial carcinoma, cancers of the vagina, botryoid sarcoma, embryonal rhabdomyosarcoma, moles dysplastic nevi, angioma, dermatofibroma, keloids, and urothelial carcinoma.

28. The method according to claim 26, wherein the cancer is selected from a metastatic cancer that expresses PD-L1, lung cancer, non-small cell lung cancer, kidney cancer, hepatic cancer, melanoma, cancer of the bladder, cancer of the urethra, renal cancer, and renal cell carcinoma.

* * * * *